(12) United States Patent
Dai et al.

(10) Patent No.: US 11,673,930 B2
(45) Date of Patent: Jun. 13, 2023

(54) IL10 AGONISTS AND METHODS OF USE THEREOF

(71) Applicant: Regeneron Pharmaceuticals, Inc., Tarrytown, NY (US)

(72) Inventors: Jie Dai, Yorktown Heights, NY (US); Maria del Pilar Molina-Portela, Bronx, NY (US); Ella Ioffe, Bronx, NY (US); Markus Mohrs, Pleasantville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 85 days.

(21) Appl. No.: 17/317,475

(22) Filed: May 11, 2021

(65) Prior Publication Data

US 2021/0355184 A1 Nov. 18, 2021

Related U.S. Application Data

(60) Provisional application No. 63/023,703, filed on May 12, 2020.

(51) Int. Cl.
| | |
|---|---|
| *A61K 38/20* | (2006.01) |
| *A61K 47/68* | (2017.01) |
| *C07K 14/54* | (2006.01) |
| *C07K 19/00* | (2006.01) |
| *A61P 35/00* | (2006.01) |
| *C07K 1/22* | (2006.01) |

(Continued)

(52) U.S. Cl.
CPC ...... *C07K 14/5428* (2013.01); *A61K 38/2066* (2013.01); *A61K 47/68* (2017.08); *A61K 47/6889* (2017.08); *A61P 35/00* (2018.01); *C07K 1/22* (2013.01); *C07K 16/42* (2013.01); *A61K 38/00* (2013.01); *C07K 2317/524* (2013.01); *C07K 2317/526* (2013.01); *C07K 2317/53* (2013.01); *C07K 2319/30* (2013.01)

(58) Field of Classification Search
CPC ................ A61K 38/2066; A61K 47/68; A61K 47/6889; A61P 35/00; C07K 14/5428; C07K 2319/30
See application file for complete search history.

(56) References Cited

U.S. PATENT DOCUMENTS

| | | |
|---|---|---|
| 6,410,008 B1 | 6/2002 | Strom et al. |
| 7,018,626 B2 | 3/2006 | Strom et al. |

(Continued)

FOREIGN PATENT DOCUMENTS

| | | |
|---|---|---|
| EP | 2882774 B1 | 6/2015 |
| WO | 2012/045334 A1 | 4/2012 |

(Continued)

OTHER PUBLICATIONS

Guo et al., 2012, "Purification and characterization of human IL-10/Fc fusion protein expressed in *Pichia pastoris*" ScienceDirect 83(2): 152-156.

(Continued)

*Primary Examiner* — Jeffrey E. Russel
(74) *Attorney, Agent, or Firm* — Biospark Intellectual Property Law

(57) ABSTRACT

The present disclosure relates to IL10 agonists with improved anti-tumor therapeutic efficacy. IL10 agonists disclosed herein comprise an IgG Fc domain, a linker moiety, and an IL10 moiety.

24 Claims, 60 Drawing Sheets

Specification includes a Sequence Listing.

(51) Int. Cl.
  *C07K 16/42* (2006.01)
  *A61K 38/00* (2006.01)

(56) References Cited

U.S. PATENT DOCUMENTS

| | | | |
|---|---|---|---|
| 7,261,882 B2 | 8/2007 | Watkins | |
| 7,939,056 B2 | 5/2011 | Horwitz et al. | |
| 9,346,872 B2 | 5/2016 | Duerner et al. | |
| 9,447,159 B2 | 9/2016 | Ast et al. | |
| 10,040,843 B2* | 8/2018 | Duerner | A61P 1/00 |
| 10,143,726 B2 | 12/2018 | Oft | |
| 10,195,274 B2 | 2/2019 | Mumm et al. | |
| 10,335,459 B2 | 7/2019 | Moustakas et al. | |
| 10,357,545 B2 | 7/2019 | Oft | |
| 2007/0179094 A1* | 8/2007 | Faulds | A61P 1/00 435/325 |
| 2010/0093076 A1* | 4/2010 | Moore | C07K 14/7155 530/391.1 |
| 2015/0218244 A1 | 8/2015 | Emrich et al. | |
| 2016/0243196 A1 | 8/2016 | Mumm et al. | |
| 2017/0313781 A1* | 11/2017 | Govindan | A61P 1/18 |
| 2017/0340708 A1 | 11/2017 | Xu et al. | |
| 2018/0289825 A1 | 10/2018 | Alvarez et al. | |
| 2019/0070262 A1* | 3/2019 | Ring | A61P 35/00 |
| 2019/0290688 A1 | 9/2019 | Bar-Sagi et al. | |
| 2019/0336582 A1 | 11/2019 | Moustakas et al. | |
| 2021/0171596 A1* | 6/2021 | Moore | C07K 14/5428 |
| 2021/0214411 A1* | 7/2021 | Eijkelkamp | A61P 25/04 |
| 2021/0230272 A1* | 7/2021 | Liu | C07K 14/7051 |
| 2022/0227827 A1* | 7/2022 | Xu | A61P 37/06 |

FOREIGN PATENT DOCUMENTS

| | | |
|---|---|---|
| WO | 2017/087768 A1 | 5/2017 |
| WO | 2019/242505 A1 | 12/2019 |
| WO | 2020/097946 A1 | 5/2020 |
| WO | 2020/172631 A2 | 8/2020 |

OTHER PUBLICATIONS

Josephson et al., 2000 "Design and Analysis of an Engineered Human Interleukin 10 Monomer" The Journal of Biological Chemistry 275(18): 13552-13557.

Notification of Transmittal of the International Search Report and Written Opinion of the International Searching Authority for International Application No. PCT/US2021/031806 dated Aug. 16, 2021, including International Search report and Written Opinion.

Shouval et al., 2014 "Interleukin 10 Receptor Signaling: Master Regulator of Intestinal Mucosal Homeostasis in Mice and Humans" Adv Immunol. 122:177-210.

Vazquez-Lombari et al., 2013, "Molecular Engineering of Therapeutic Cytokines," Antibodies 2: 426-451.

Zdanov et al., 1995 "Crystal structure of interleukin-10 reveals the functional dimer with an unexpected topological similarity to interferon γ" Structure 3:591-601.

Zheng et al., 1997 "A noncytolytic IL-10/Fc fusion protein prevents diabetes, blocks autoimmunity, and promotes suppressor phenomena in NOD mice" J. Immunol. 158(9): 4507-13.

* cited by examiner

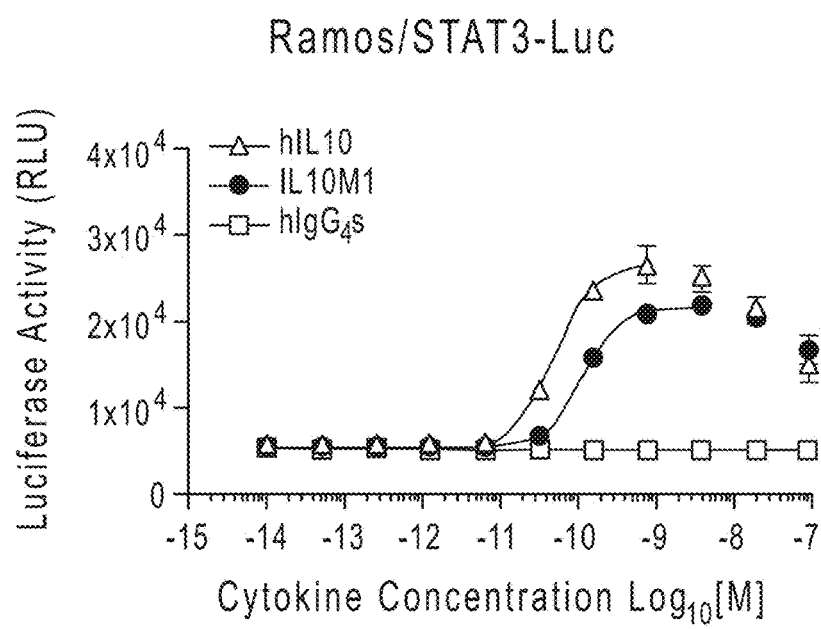
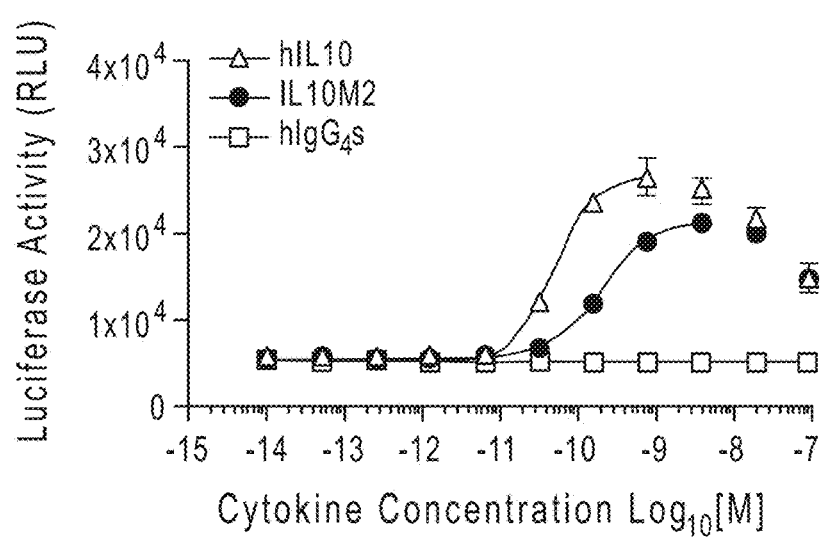
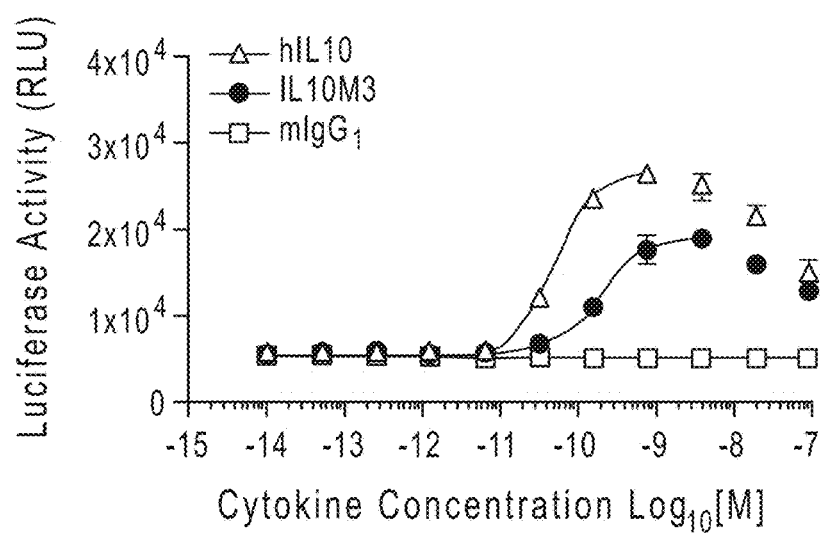

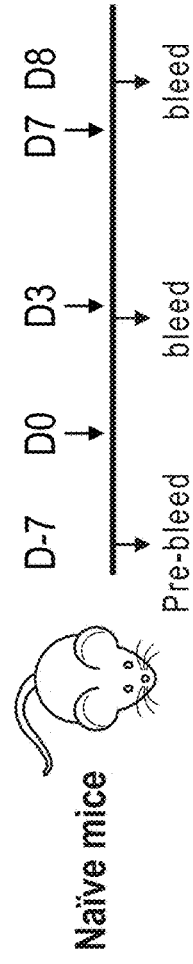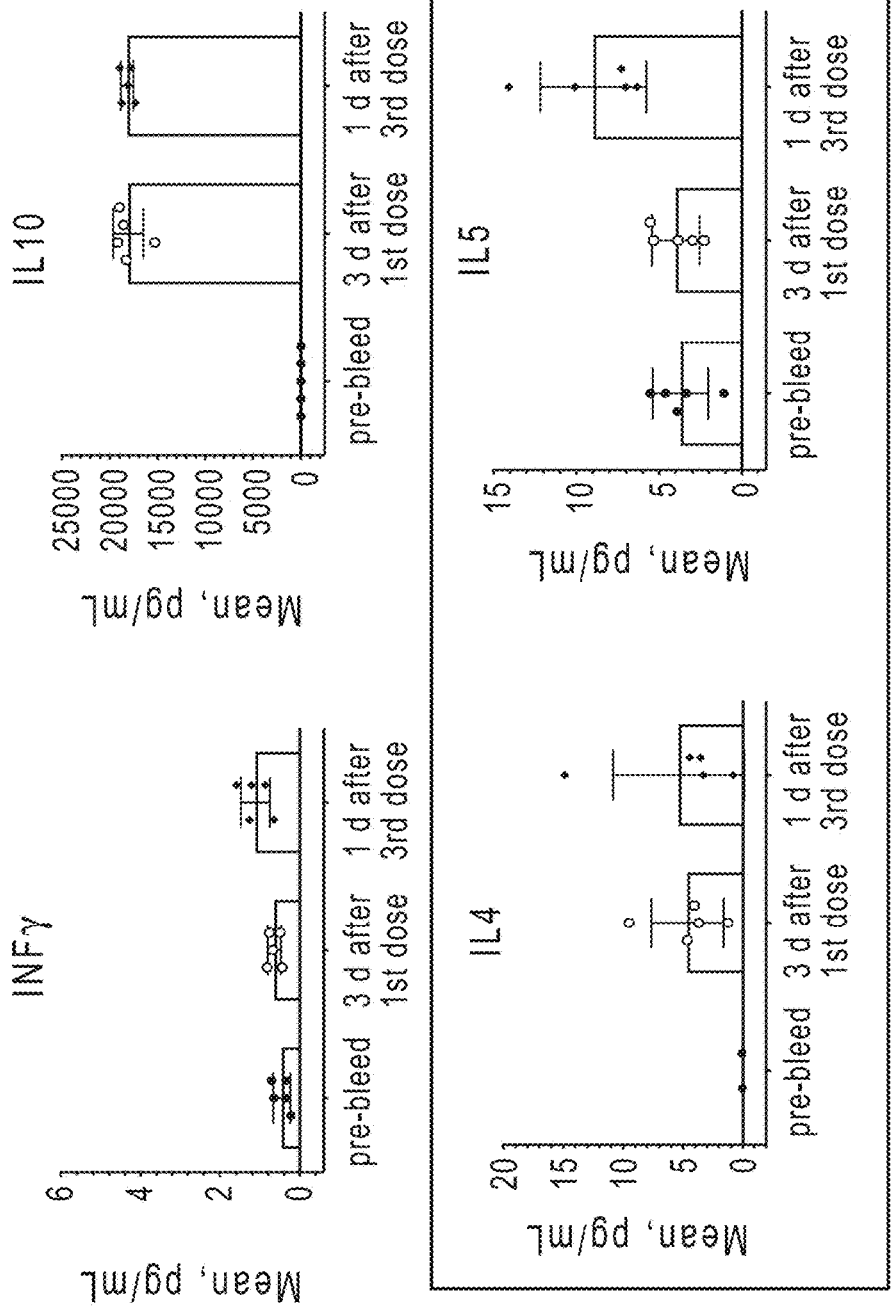
FIG. 19A
FIG. 19B

IL10 AGONISTS AND METHODS OF USE THEREOF

1. CROSS-REFERENCE TO RELATED APPLICATIONS

This application claims the priority benefit of U.S. provisional application No. 63/023,703, filed May 12, 2020, the contents of which are incorporated herein in their entireties by reference thereto.

2. SEQUENCE LISTING

The instant application contains a Sequence Listing which has been submitted electronically in ASCII format and is hereby incorporated by reference in its entirety. Said ASCII copy, created on May 7, 2021, is named RGN-002US_SL.txt and is 94,668 bytes in size.

3. BACKGROUND

The cytokine interleukin-10 (IL-10 or IL10), also known as human cytokine synthesis inhibitory factor (CSIF), is a pleiotropic cytokine that regulates multiple immune responses through actions on T cells, B cells, macrophages, and antigen presenting cells (APC). Although IL10 is predominantly expressed in macrophages, expression has also been detected in activated T cells, B cells, mast cells, and monocytes. IL10 was first reported as inhibiting immune response due to its suppression of antigen presentation (by lowering expression of the major histocompatibility complex type II (MHC-II) and the costimulatory ligands CD80/CD86), repression of pro-inflammatory cytokine release by myeloid cells, and inhibition of T cell priming (via repression of CD28 signaling). However, more recent studies also described immunostimulatory roles of IL10 through co-stimulation of B cells, enhancement of NK cells cytolytic activity and enhancement of cytolytic T cells proliferation, cytokine release and cytolytic activity (reviewed by Mosser and Zhang, 2008, Immunol Rev. 226:205-18).

Human IL10 is a non-covalently linked homodimer and its receptor is heterotetramer complex comprising two IL10Rα (also referred to as IL10R1) molecules and two IL10Rβ (also referred to as IL10R2) molecules. IL10Rα is expressed on all IL10-responsive cells, while IL10Rβ is constitutively expressed in most cell types. Upon binding to IL10, IL10Rα induces a conformational change in IL10Rβ, permitting IL10Rβ to also bind IL10. Once the IL10/IL10Ra/IL10Rβ complex is assembled, tyrosine kinases Jak1 and Tyk2 are activated and phosphorylate specific tyrosine residues in the intracellular domain of IL10Ra, leading to the recruitment of signal transducer and activator of transcription 3 (STAT3), which mediate signaling downstream of IL10. Unlike IL10Ra, which is unique to IL10, the IL10Rβ subunit is shared by receptors for other type-II cytokines including IL22, IL26, and INFλ (reviewed by Shouval et al., 2014, Adv. Immunol. 122:177-210).

As a result of its pleiotropic activity, IL10 has been linked to a broad range of diseases, disorders and conditions, including inflammatory conditions, immune-related disorders, fibrotic disorders and cancer.

One drawback of using IL10 and particularly any form of recombinant IL10 in therapy is its short serum half-life. The loss of IL10 activity in vivo may be due to several factors, including renal clearance and proteolytic degradation.

It would be an advantage to have an IL10 agonist that is better able to tolerate systemic exposure during treatment, by enhancing the circulating life (delayed clearance), solubility and stability of IL10. The present disclosure addresses this and other related needs in the art.

4. SUMMARY

The present disclosure stems from the discovery of IL10 agonists that have surprisingly improved in vivo therapeutic efficacy, particularly anti-tumor activity.

IL10 moieties that can be used in the IL10 agonists of the disclosure are described in Section 6.3.

Fc domains that that can be used in the IL10 agonists of the disclosure are described in Section 6.4.

Targeting moieties that can be used in the IL10 agonists of the disclosure are described in Section 6.5.

Stabilization moieties that can be used in the IL10 agonists of the disclosure are described in Section 6.6.

Various exemplary configurations of the IL10 agonists of the disclosure are described in specific embodiments 260 to 77, infra.

Linkers that can be used to connect different components of the IL10 agonists of the disclosures are described in Section 6.7.

The disclosure further provides nucleic acids encoding the IL10 agonists of the disclosure. The nucleic acids encoding the IL10 agonists can be a single nucleic acid (e.g., a vector encoding all polypeptide chains of an IL10 agonist) or a plurality of nucleic acids (e.g., two or more vectors encoding the different polypeptide chains of an IL10 agonist). The disclosure further provides host cells and cell lines engineered to express the nucleic acids and IL10 agonists of the disclosure. The disclosure further provides methods of producing an IL10 agonist of the disclosure. Exemplary nucleic acids, host cells, and cell lines, and methods of producing an IL10 agonist are described in Section 6.8 and specific embodiments 199 to 204, infra.

The disclosure further provides pharmaceutical compositions comprising the IL10 agonists of the disclosure. Exemplary pharmaceutical compositions are described in Section 6.8.3 and specific embodiments 211 to 223, infra.

Further provided herein are methods of using the IL10 agonists and the pharmaceutical compositions of the disclosure, e.g., for treating cancer and immune disorders. Exemplary methods are described in Section 6.10. The IL10 agonists of the disclosure are useful in combination therapy, for example as an adjunct to CART therapy. Exemplary combination therapy methods are disclosed in 6.11. Specific embodiments of the methods of treatment of the disclosure are described in specific embodiments 224 to 280, infra.

5. BRIEF DESCRIPTION OF THE FIGURES

FIG. 1A-1B illustrate the differential effects of IL10 on priming vs effector function of CD8 T cells.

FIG. 2A-2B illustrate IL10 agonists of the disclosure. FIG. 2A illustrates the general format of the IL10 agonists and FIG. 2B illustrates specific embodiments of IL10 agonists of the disclosure. The illustrations are intended to depict the N- to C-terminal order of domains included in the IL10 agonists and are not intended to convey scale or three dimensional configuration. IL10M11 (not pictured) is similar to IL10M3, but has a murine IL10 moiety in place of the human IL10 moiety of IL10M3.

FIGS. 3A-3F illustrate the activity of IL10 muteins on STAT3-mediated luciferase reporter activity. Recombinant IL10 and IL10 muteins increase STAT3-response element driven luciferase activity in engineered Ramos/STAT3-Luc (FIG. 3A-FIG. 3C) and TF-1/STAT3-Luc (FIG. 3D-3F) reporter cells. Graphs are separated by the IL10 agonist used, with black filled circles representing IL10M1 (FIG. 3A, FIG. 3D), IL10M2 (FIG. 3B, FIG. 3E), or IL10M3 (FIG. 3C, FIG. 3F), open filled squares representing the isotype control (human IgG4 stealth for FIG. 3A, FIG. 3B, FIG. 3D, and FIG. 3E, mouse IgG1 for FIG. 3C and FIG. 3F), and triangles representing commercially available human IL10 (purchased from Peptrotech).

FIGS. 4A-4I illustrate that IL10 muteins suppress cytokine release from primary human T-cells from donor 5500Y to similar levels as recombinant human IL10. IL2 (FIG. 4A, FIG. 4D, FIG. 4G), TNFα (FIG. 4B, FIG. 4E, FIG. 4H) and IFNγ (FIG. 4C, FIG. 4F, FIG. 4I) release from T-cells from donor 5500Y co-incubated with allogeneic mitomycin C treated PBMC and IL10M1 (FIG. 4A-FIG. 4C), IL10M2 (FIG. 4D-FIG. 4F) or IL10M3 (FIG. 4G-FIG. 4I). Graphs are separated by the IL10 mutein used with black filled circles representing the IL10 mutein, open squares representing the isotype control (hIgG4s for IL10M1 and IL10M2, mIgG1 for IL10M3), and grey triangles representing the recombinant human IL10.

FIGS. 5A-5I illustrate that IL10 muteins suppress cytokine release from primary human T-cells from donor 6900M to similar levels as recombinant human IL10. IL2 (FIG. 5A, FIG. 5D, FIG. 5G), TNFα (FIG. 5B, FIG. 5E, FIG. 5H) and IFNγ (FIG. 5C, FIG. 5F, FIG. 5I) release from T-cells from donor 6900M co-incubated with allogeneic mitomycin C treated PBMC and IL10M1 (FIG. 5A-FIG. 5C), IL10M2 (FIG. 5D-FIG. 5F) or IL10M3 (FIG. 5G-FIG. 5I). Graphs are separated by the IL10 mutein used with black filled circles representing the IL10 mutein, open squares representing the isotype control (hIgG4s for IL10M1 and IL10M2, mIgG1 for IL10M3), and grey triangles representing the recombinant human IL10.

Figure 8A:
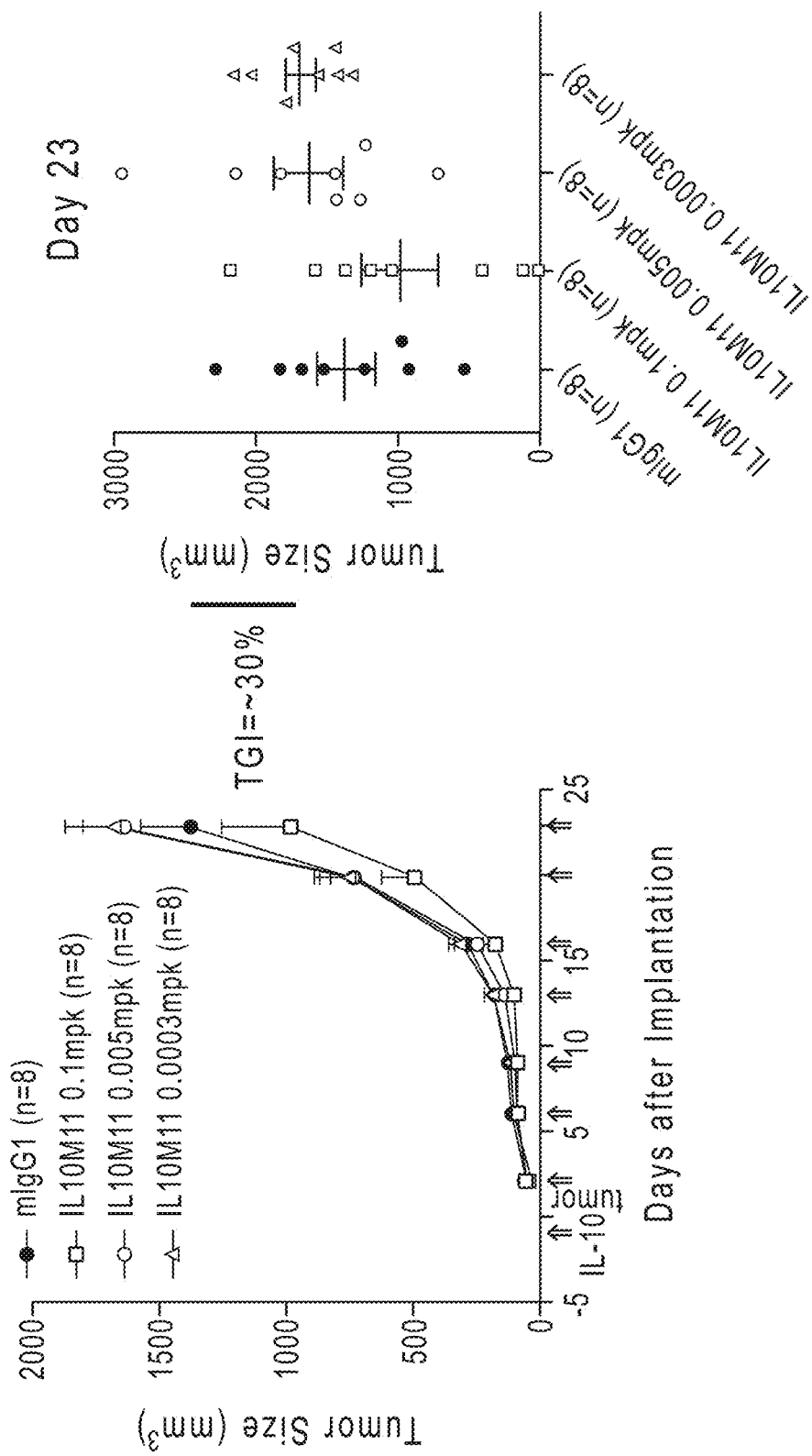
Figure 8B:
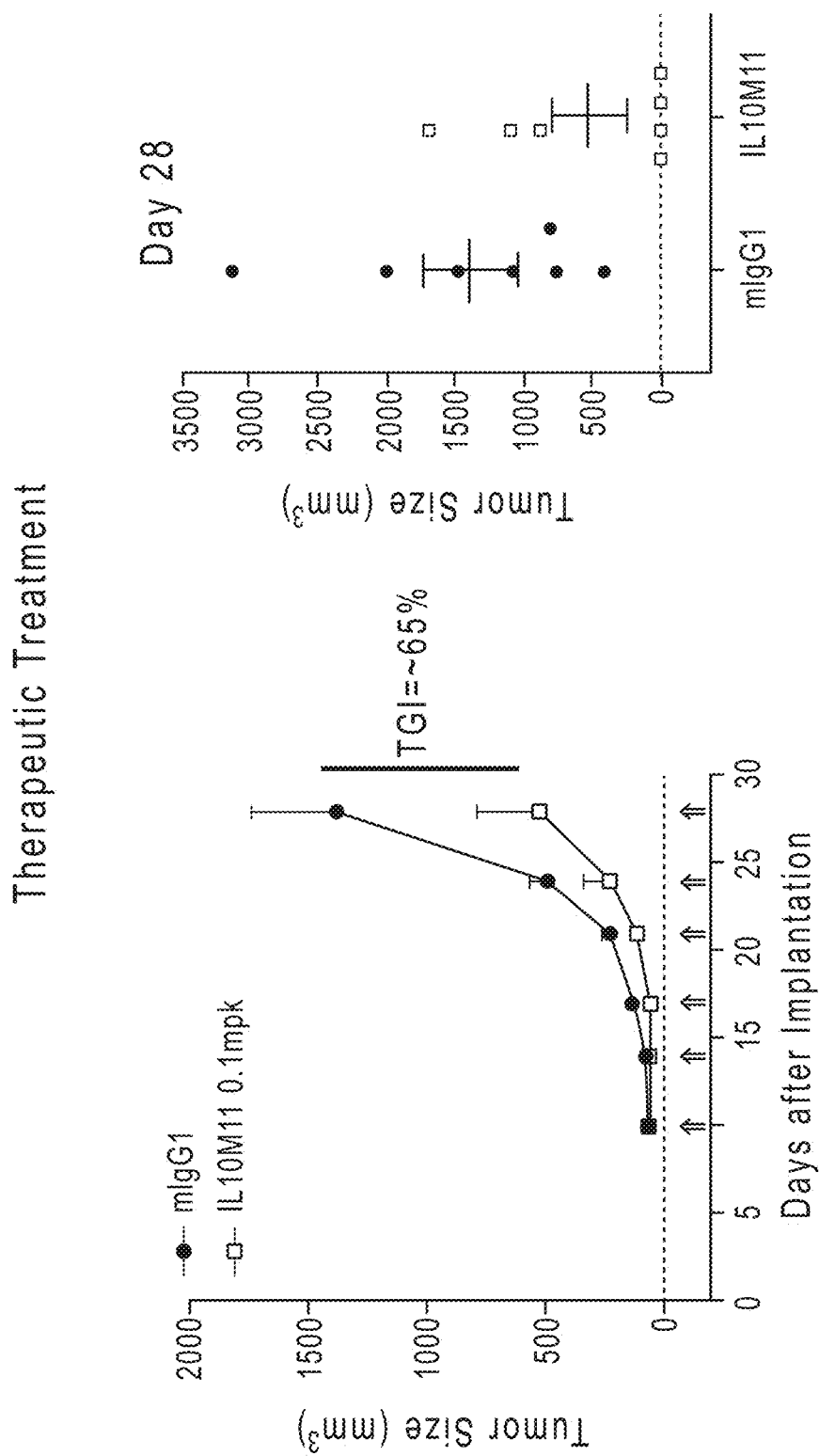
Figure 8C:
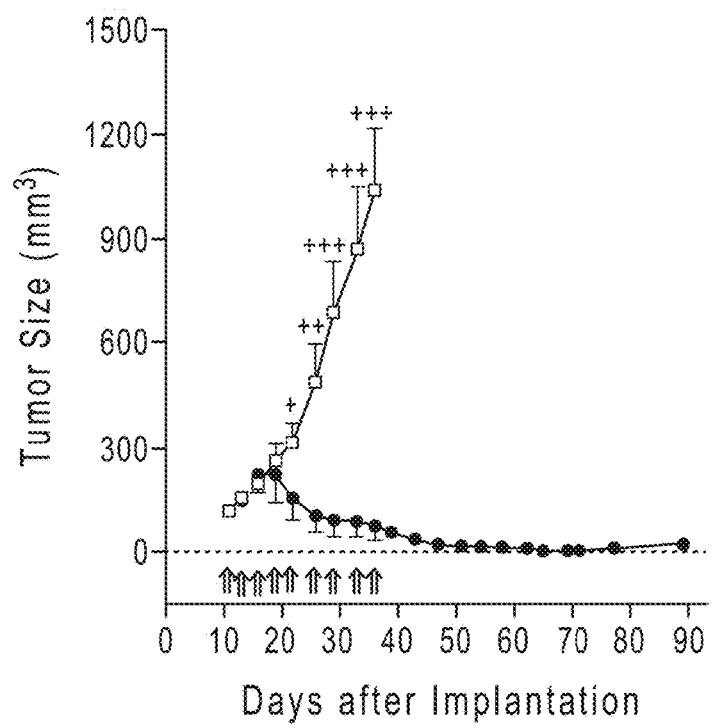
Figure 8C:
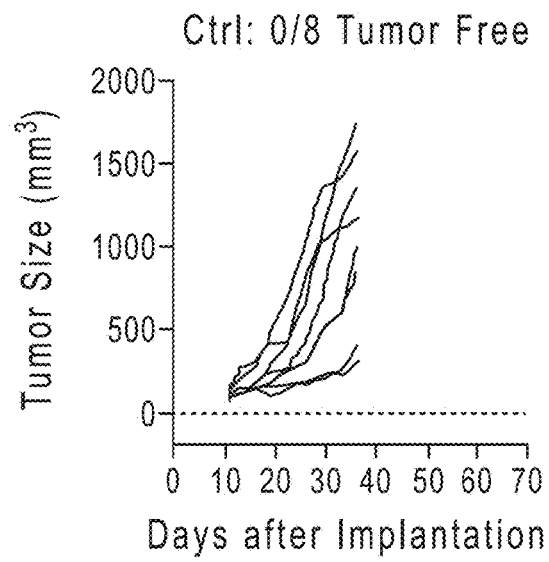
Figure 8C:
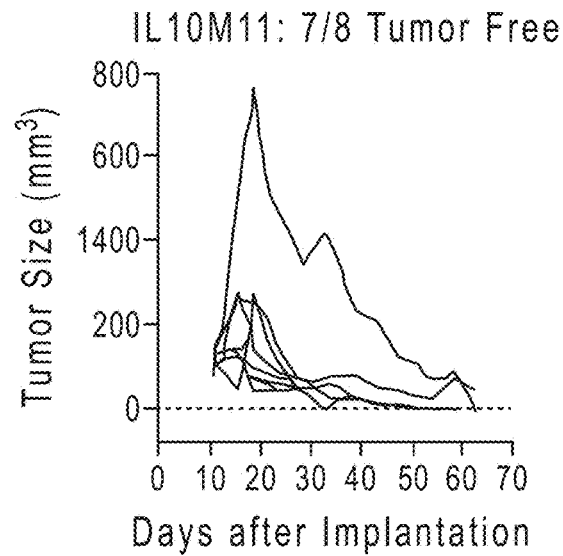
Figure 8D:
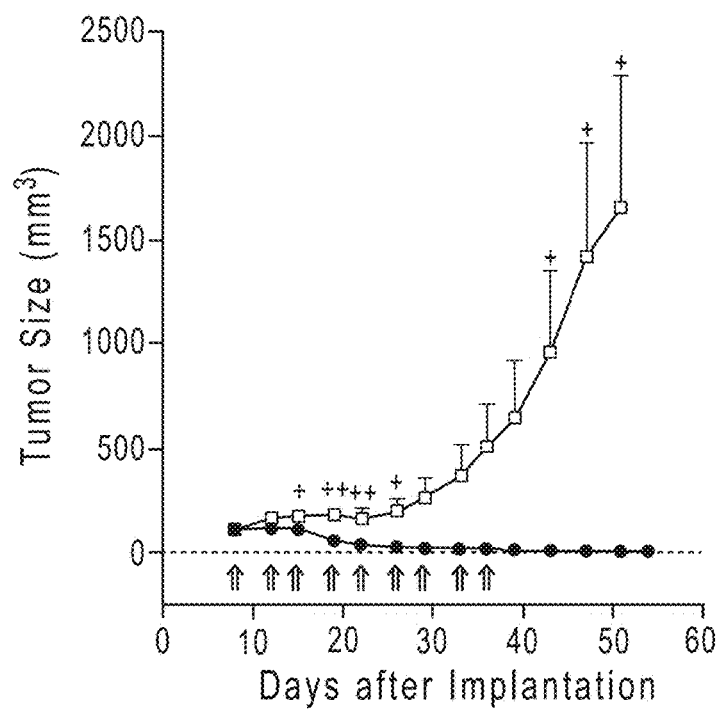
Figure 8D:
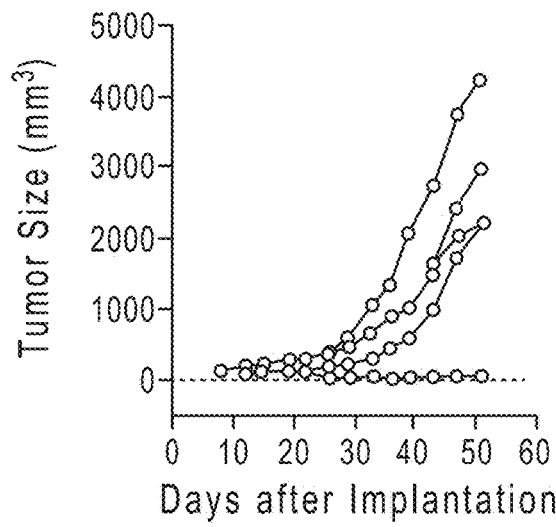
Figure 8D:
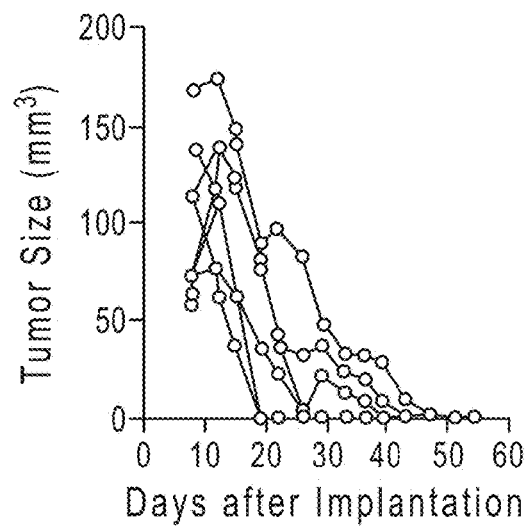
Figures 1, 8E:
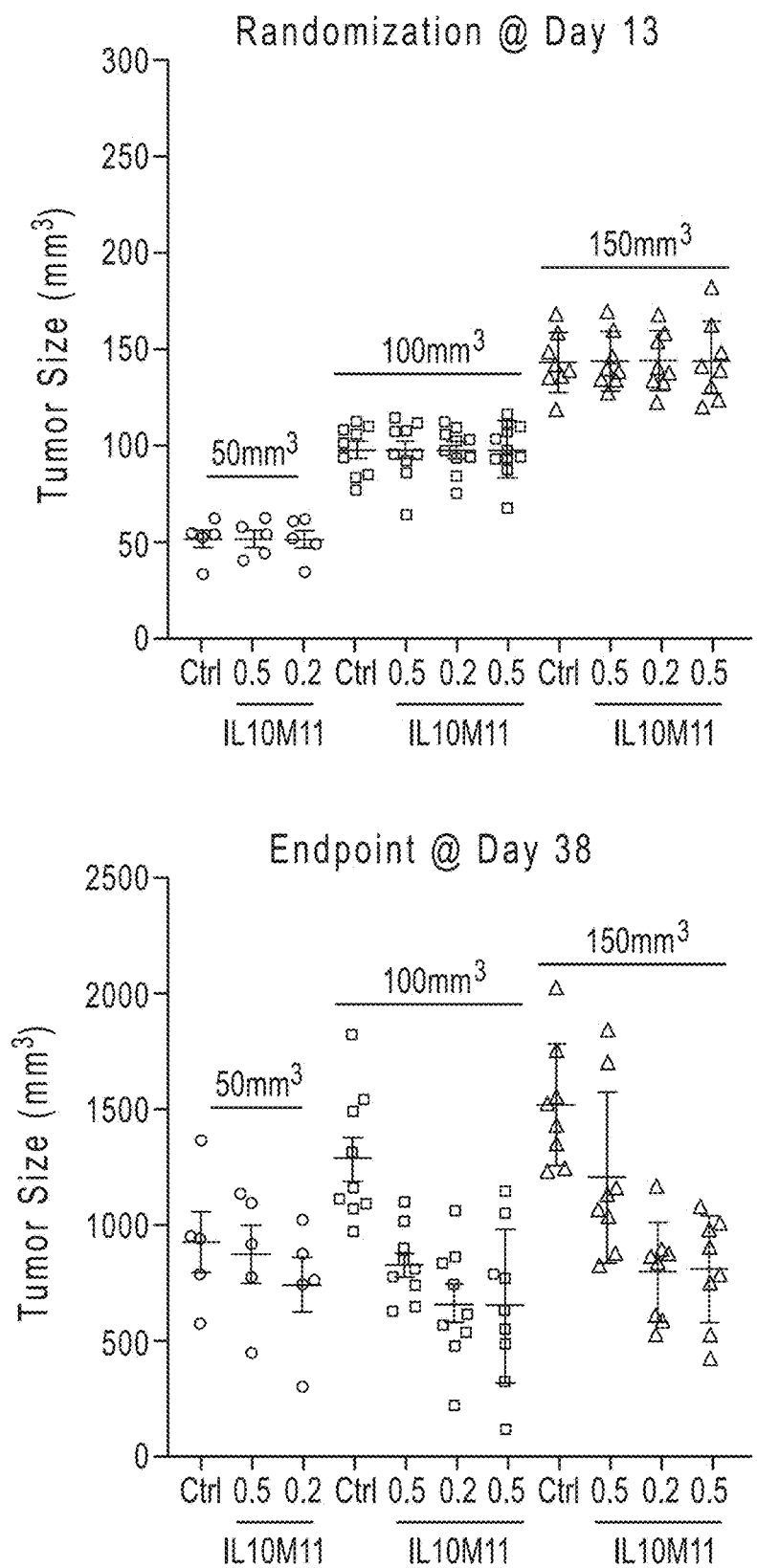
Figures 2, 8E:
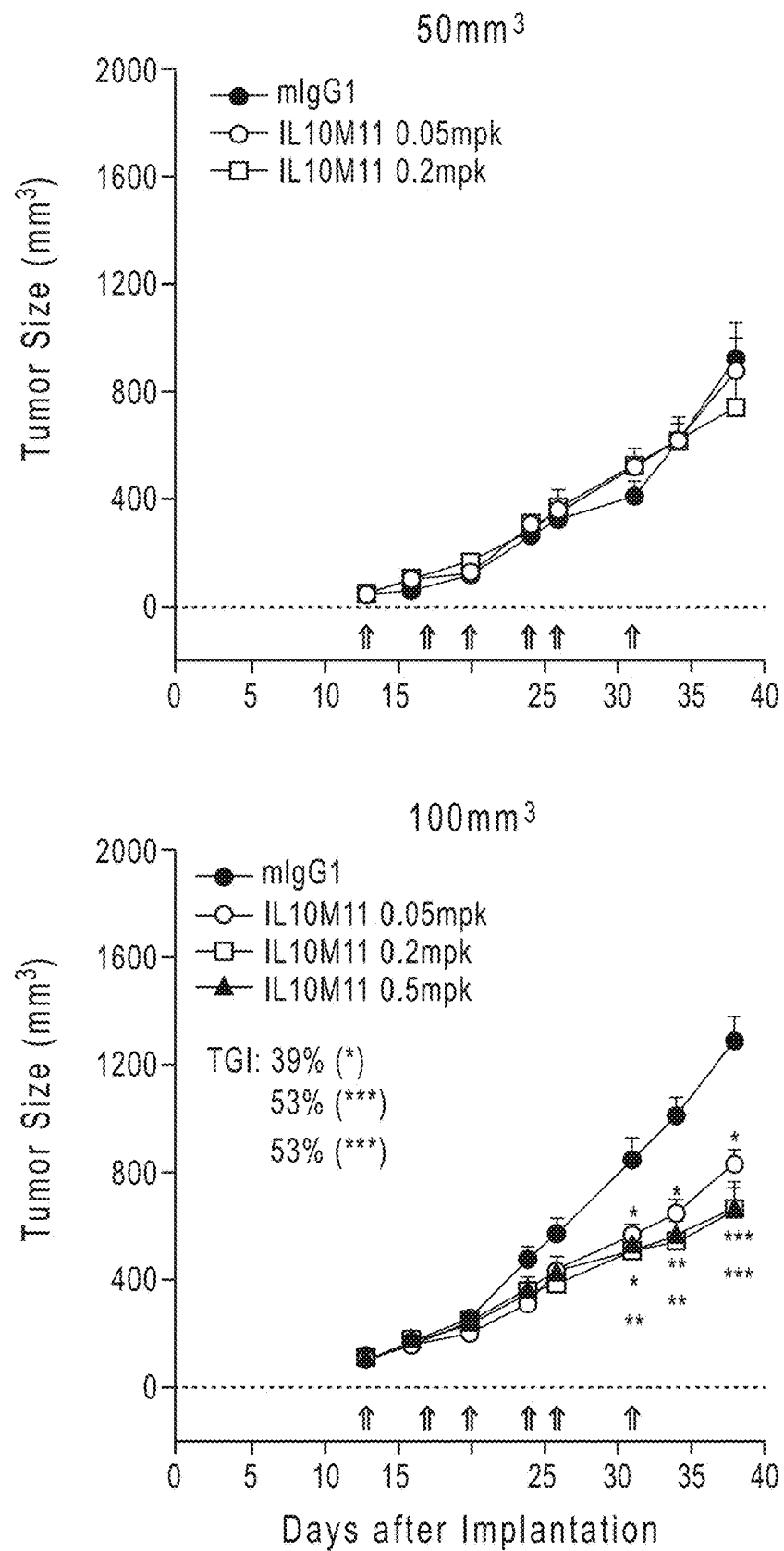
Figures 3, 8E:
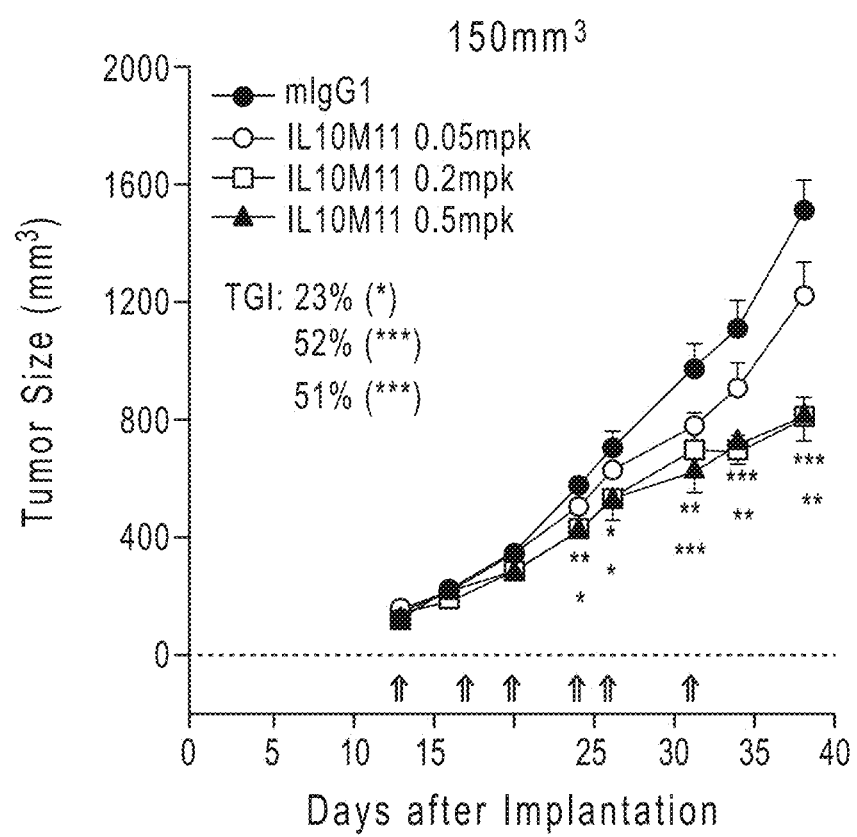
Figure 8F:
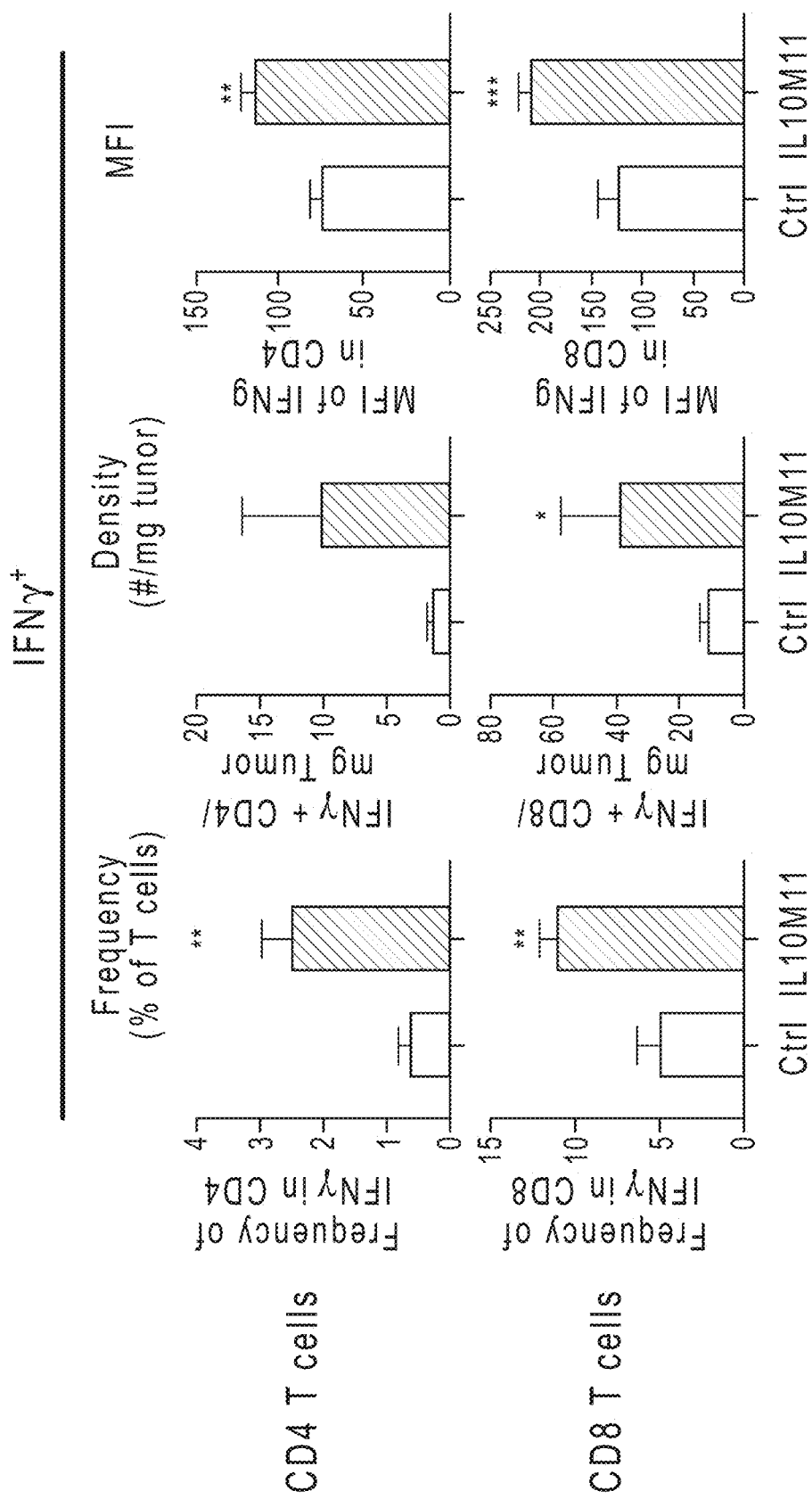
Figure 8G:
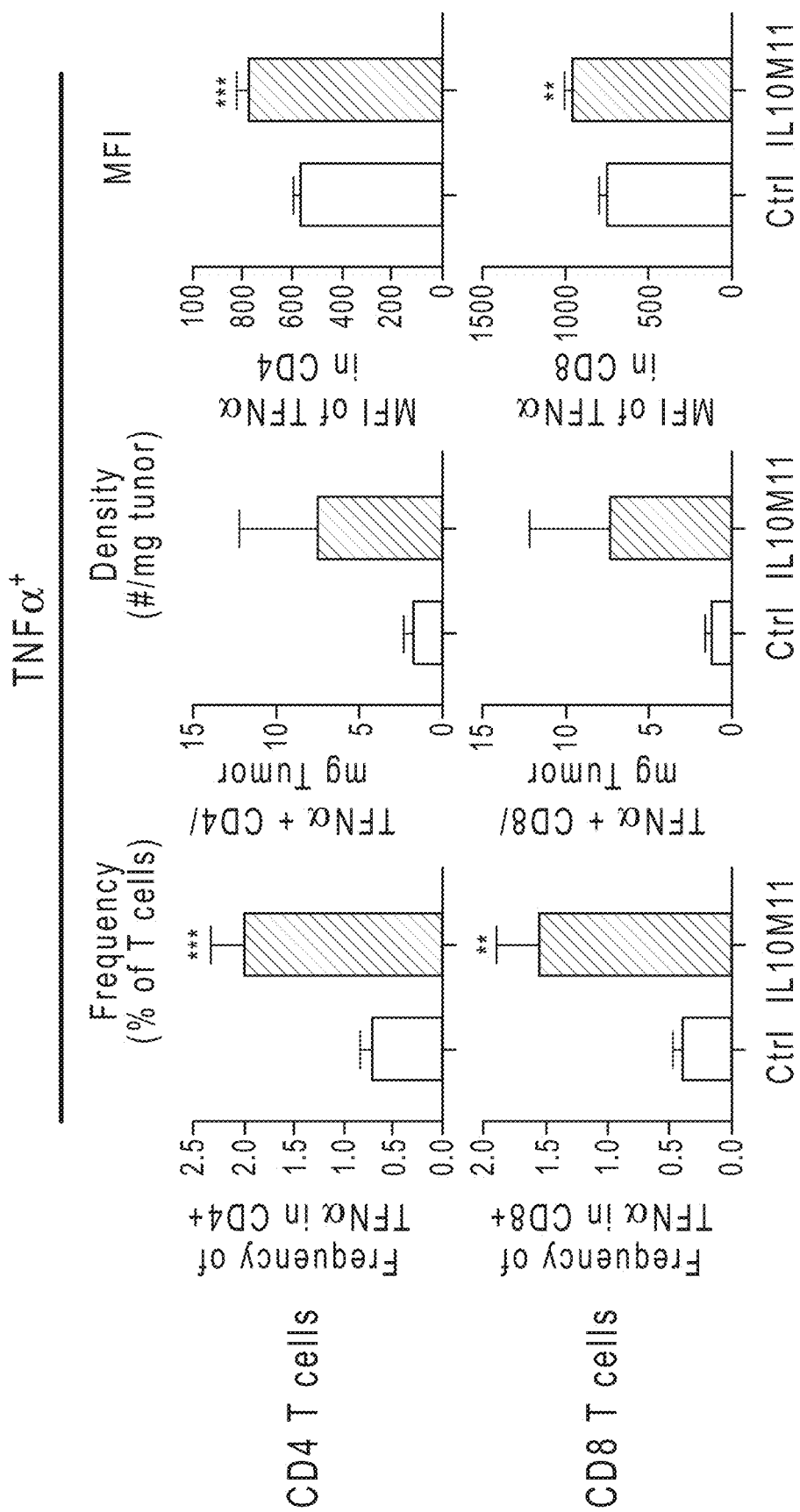
Figure 8H:
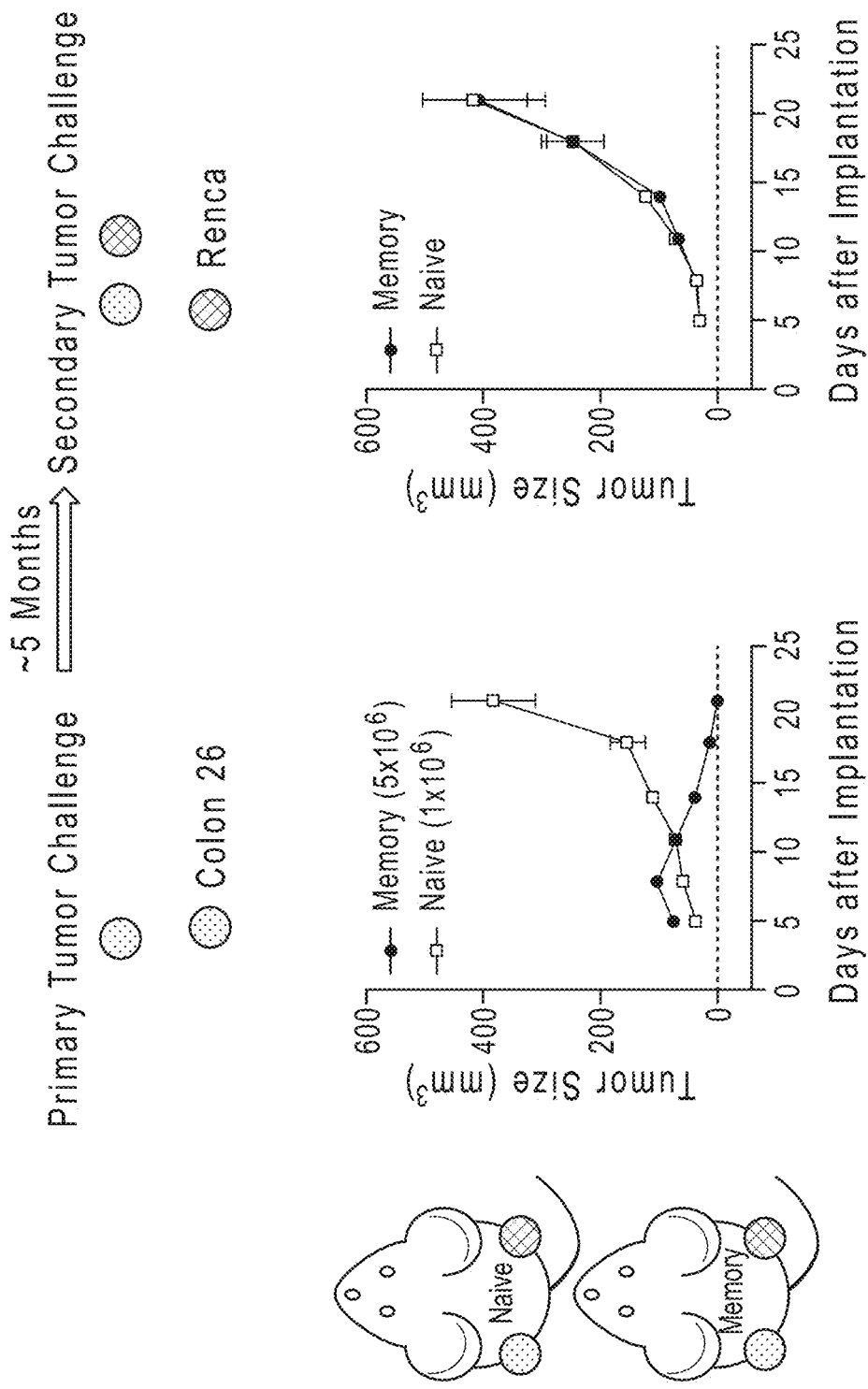
Figure 8I:
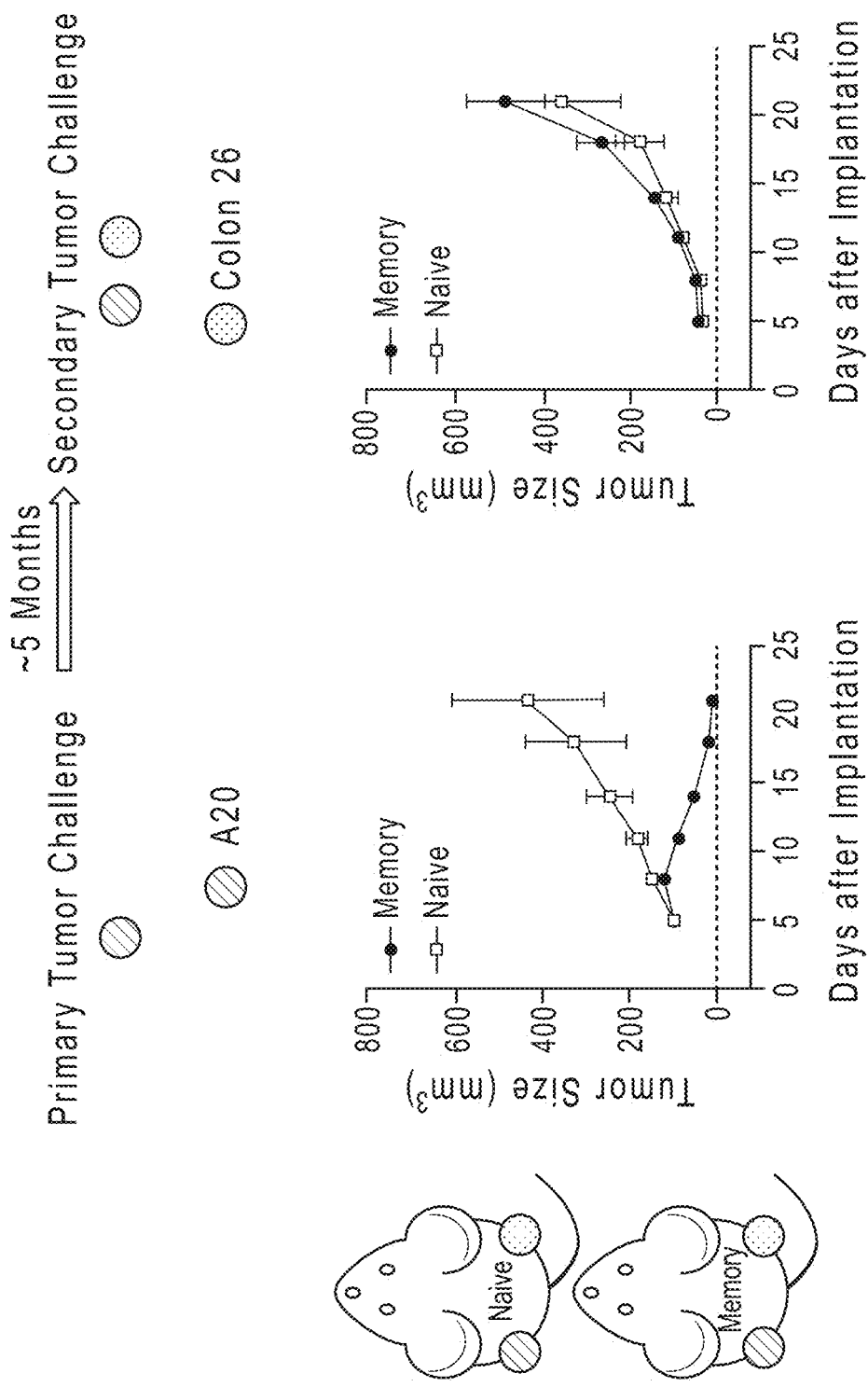

FIGS. 8A-8I show the anti-tumor activity of IL10M11. IL10M11 has anti-tumor activity against a variety of tumor cell lines following prophylactic or therapeutic administration (FIGS. 8A-8E-3). IL10M11 administration results in increased frequencies of TNFα- and IFN-γ producing CD4 and CD8 T cells (FIGS. 8F and 8G, respectively). IL10M11 induces long-term memory and rejection of secondary tumor challenges (FIGS. 8H and 8I, respectively).

Figure 9A:
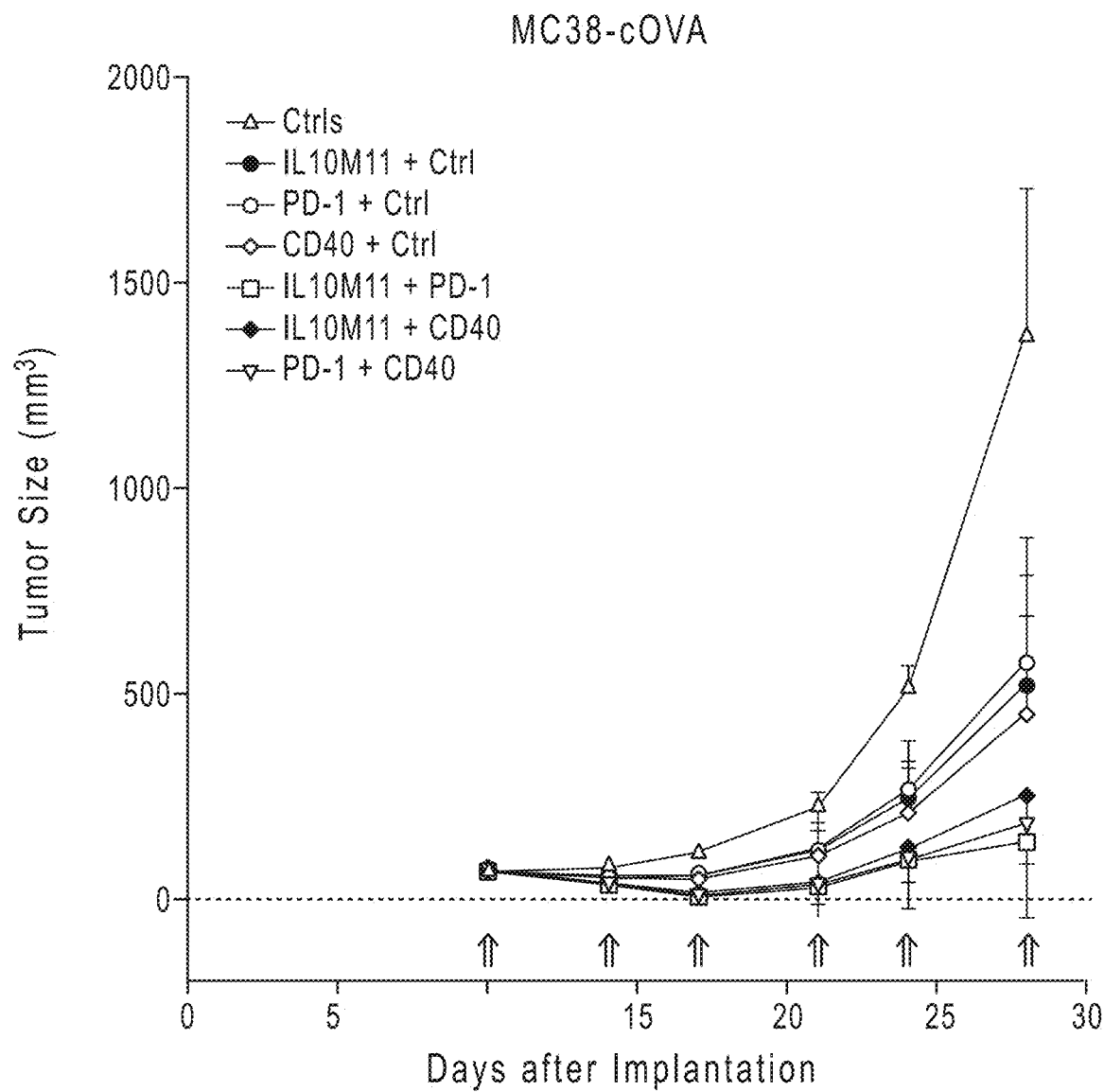
Figure 9C:
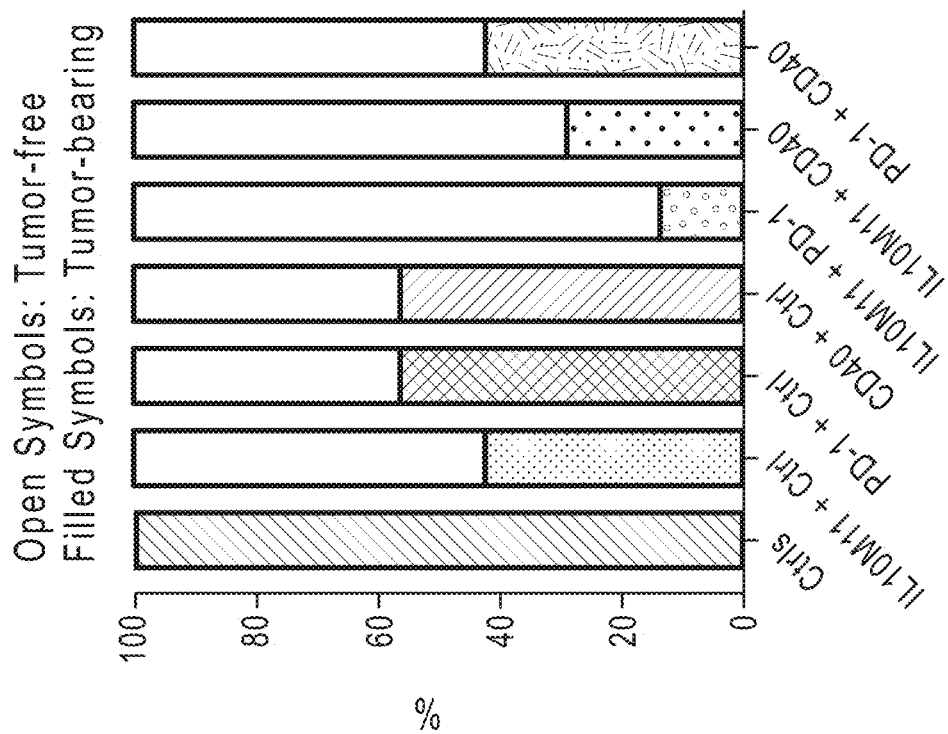
Figure 9B:
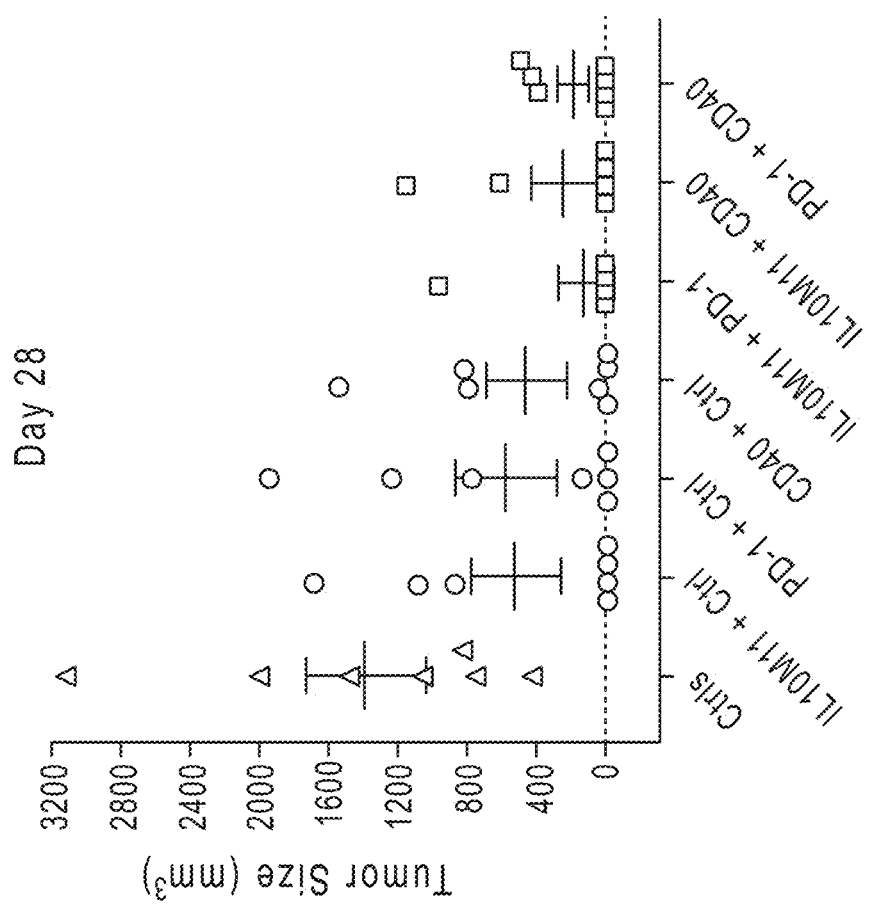
Figure 10A:
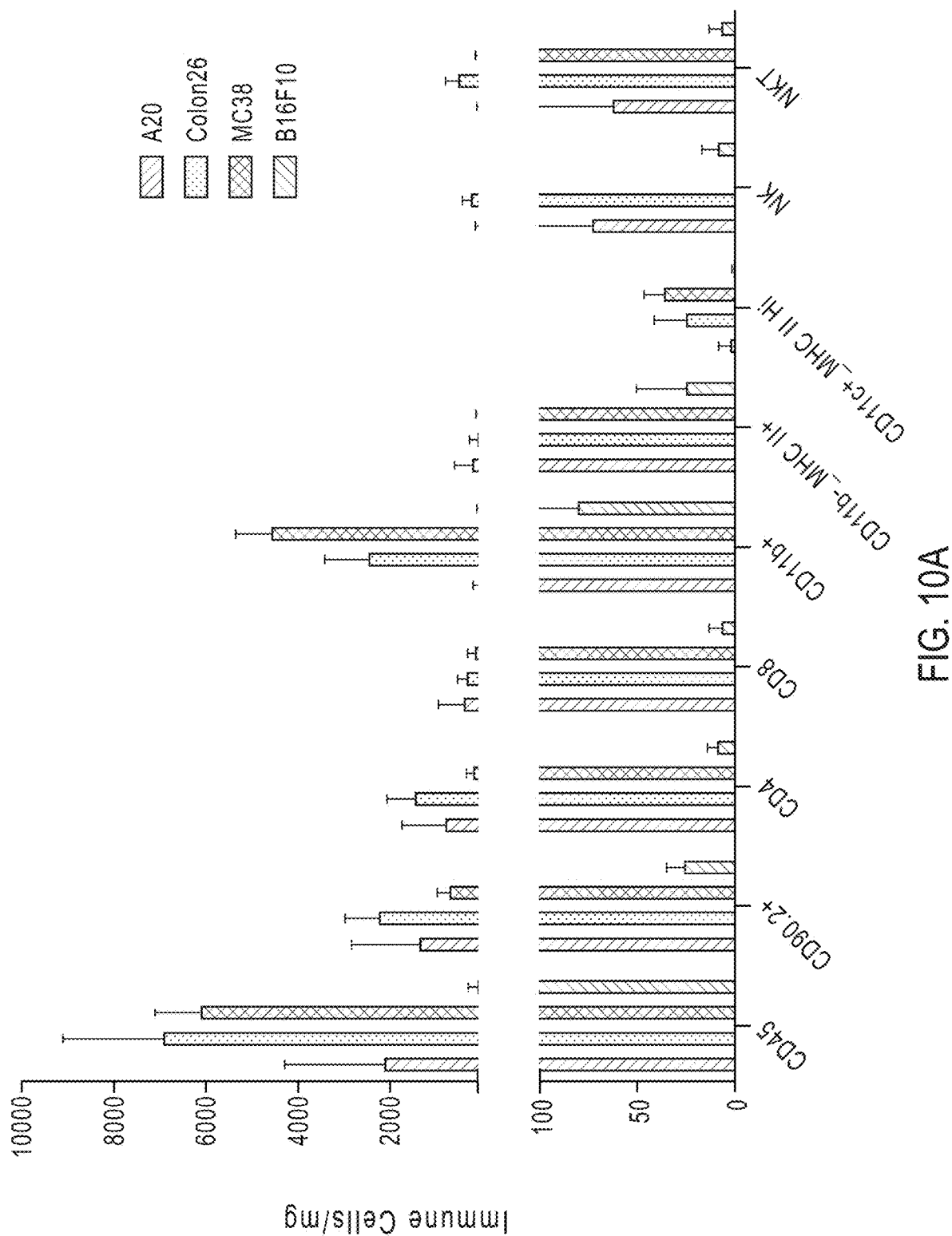
Figure 10B:
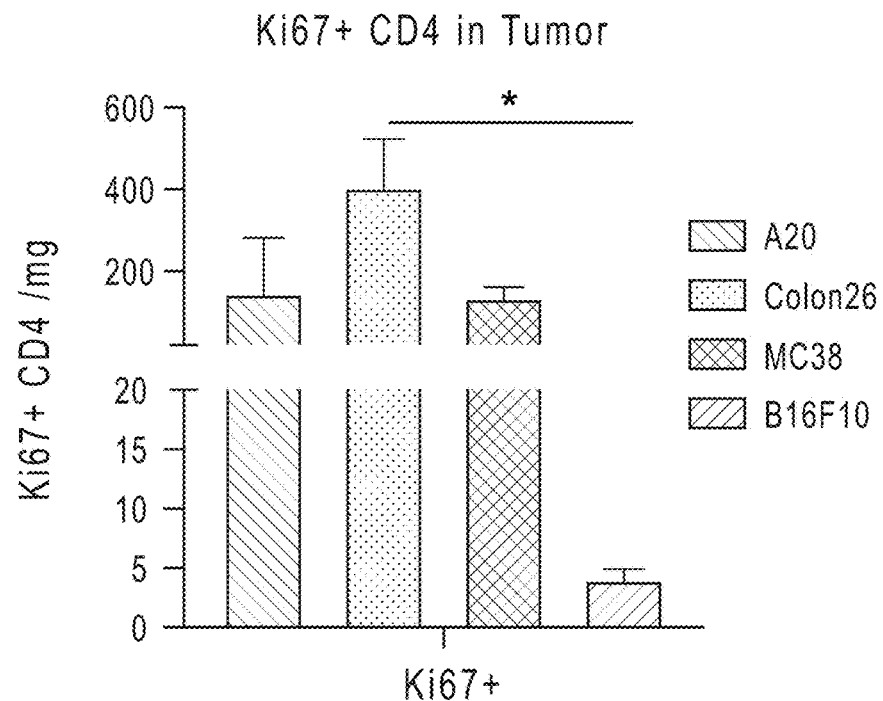
Figure 10C:
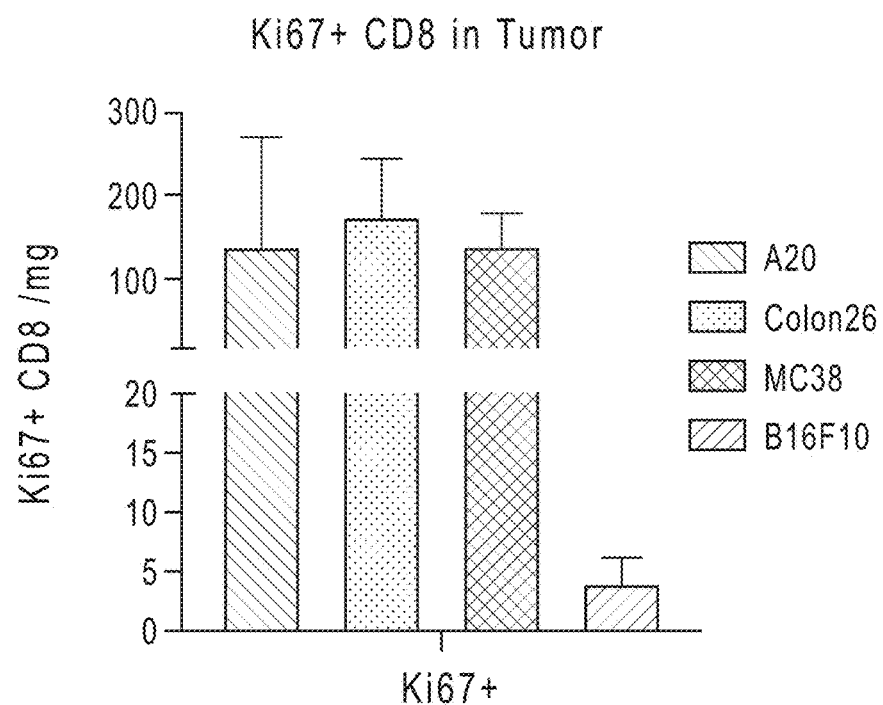
Figure 10D:
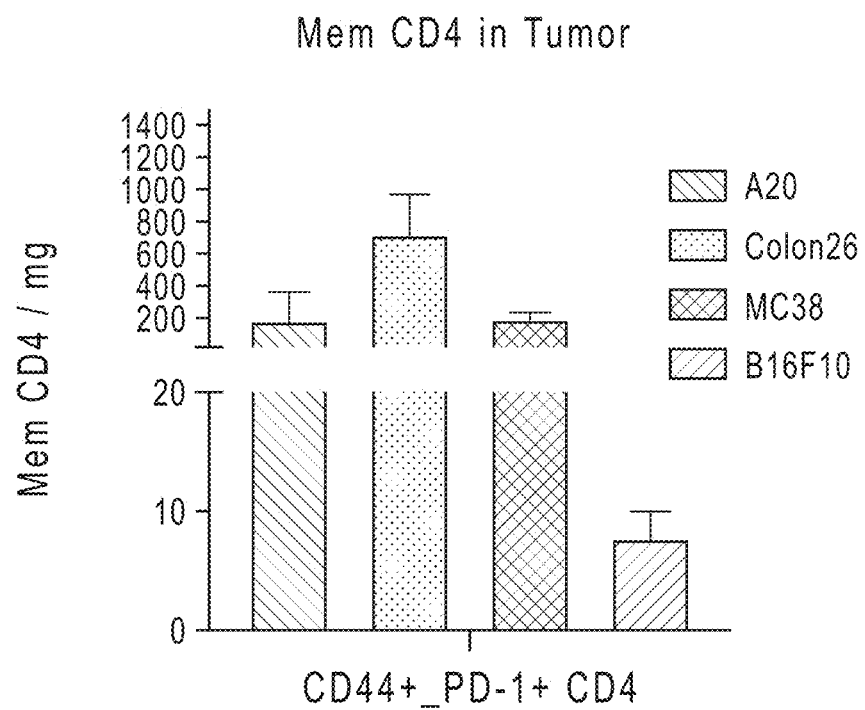
Figure 10E:
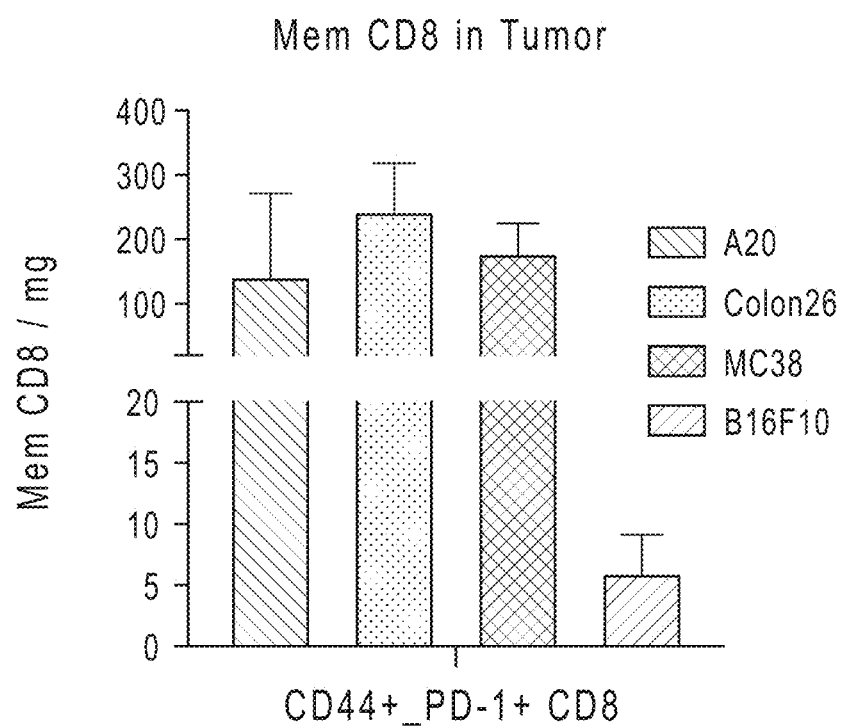

FIGS. 9A-9C show the results of administration of IL10M11 in combination with a PD-1 antagonist and a CD40 agonist. These results show that modulating these pathways enhances the durable primary and memory anti-tumor responses elicited by IL10M11.

FIGS. 10A-10E show the density of total CD45+ immune cells and the analyzed immune cell subsets in A20, Colon25, MC38, and B16F10 tumors. These results show that the density of total CD45+ immune cells was much higher in A20, Colon26, and MC38 cells than in B16F10 tumors, and that B16F10 tumors had less Ki67 proliferating CD4 and CD8 T cells and or memory phenotype.

Figures 1, 11A:
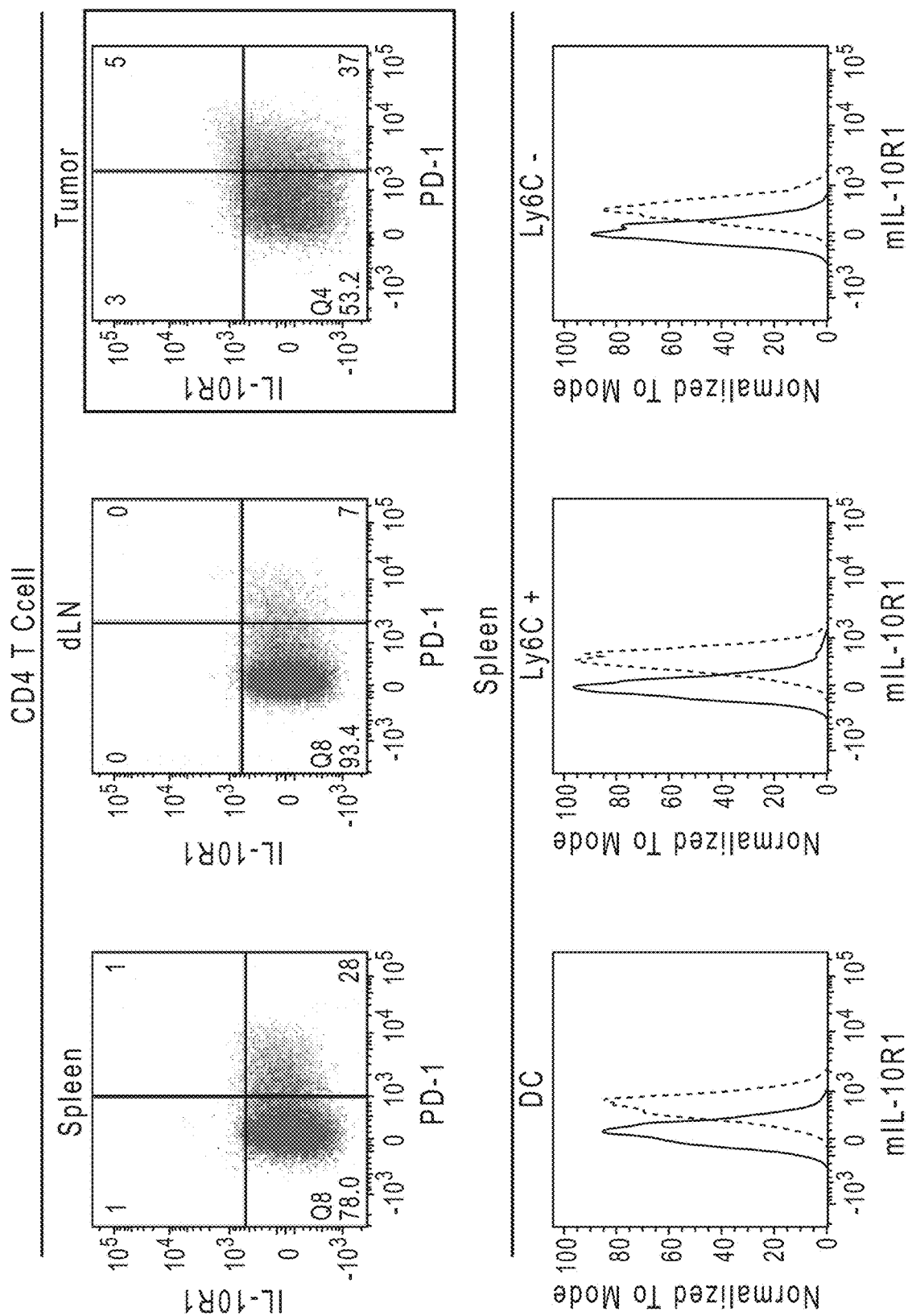
Figures 2, 11A:
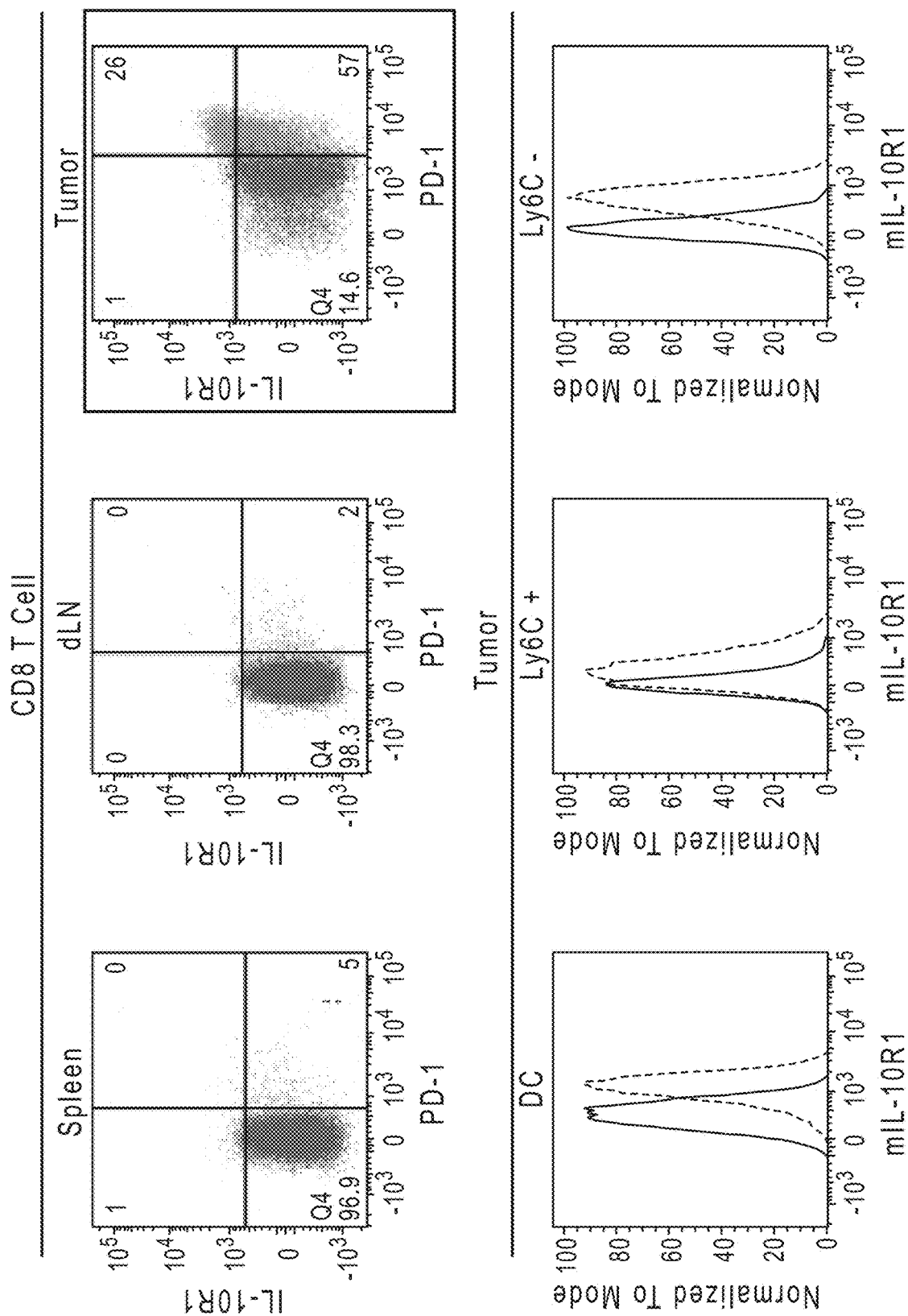
Figure 11C:
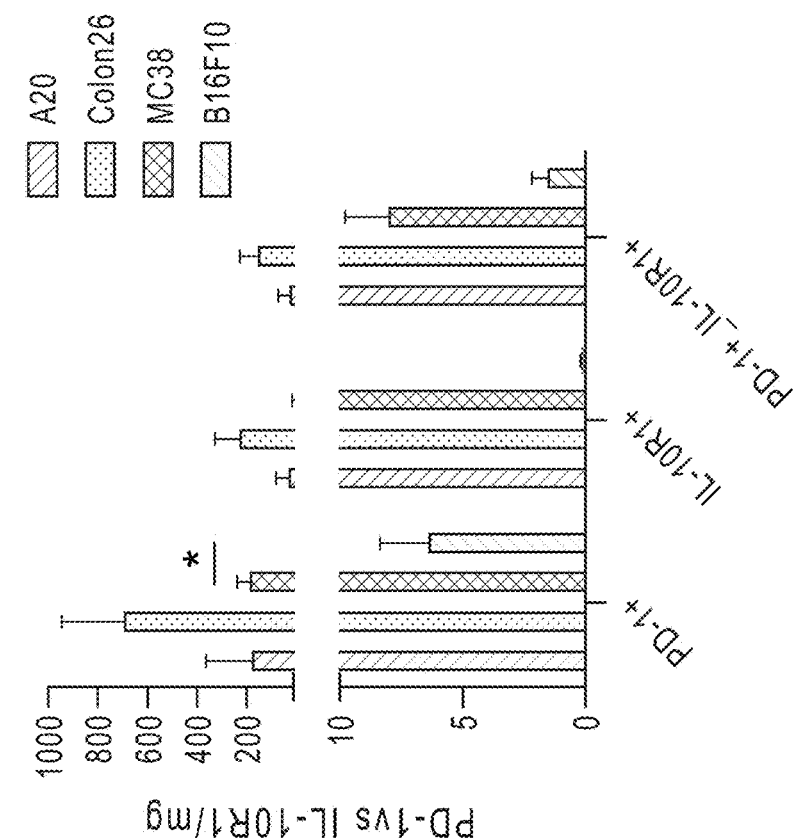
Figure 11B:
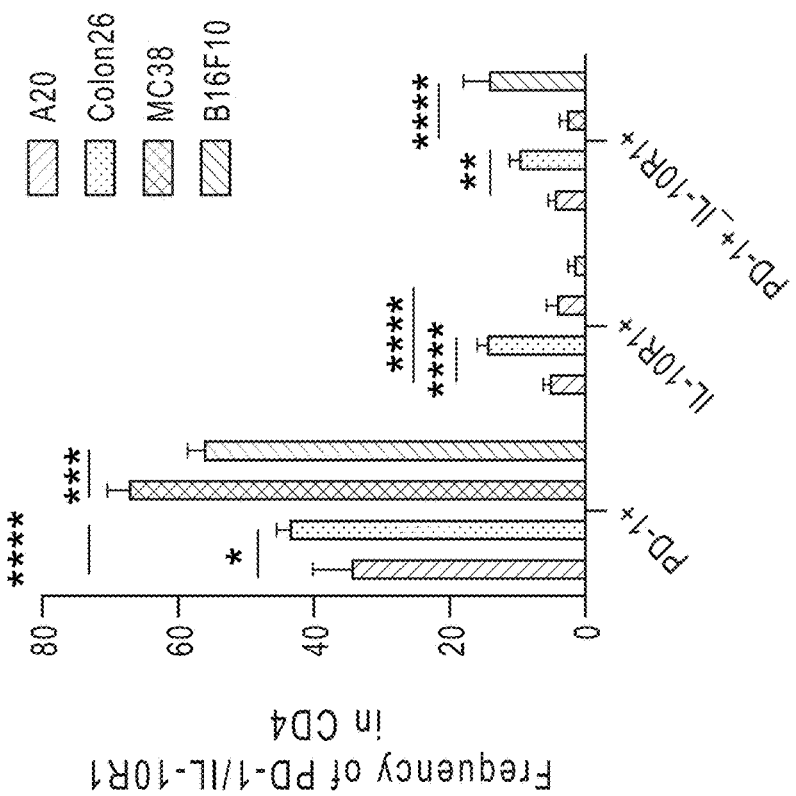
Figure 11E:
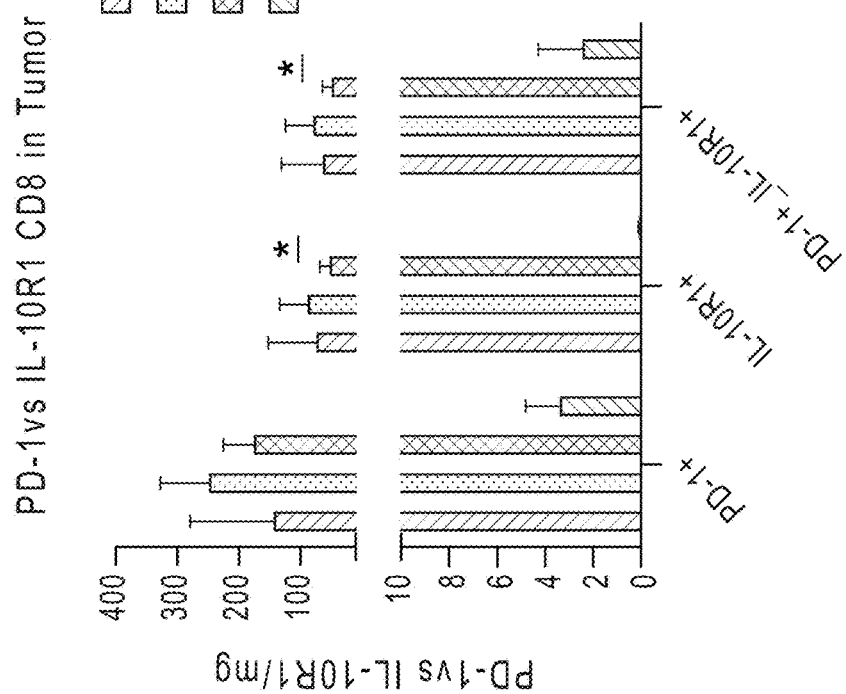
Figure 11D:
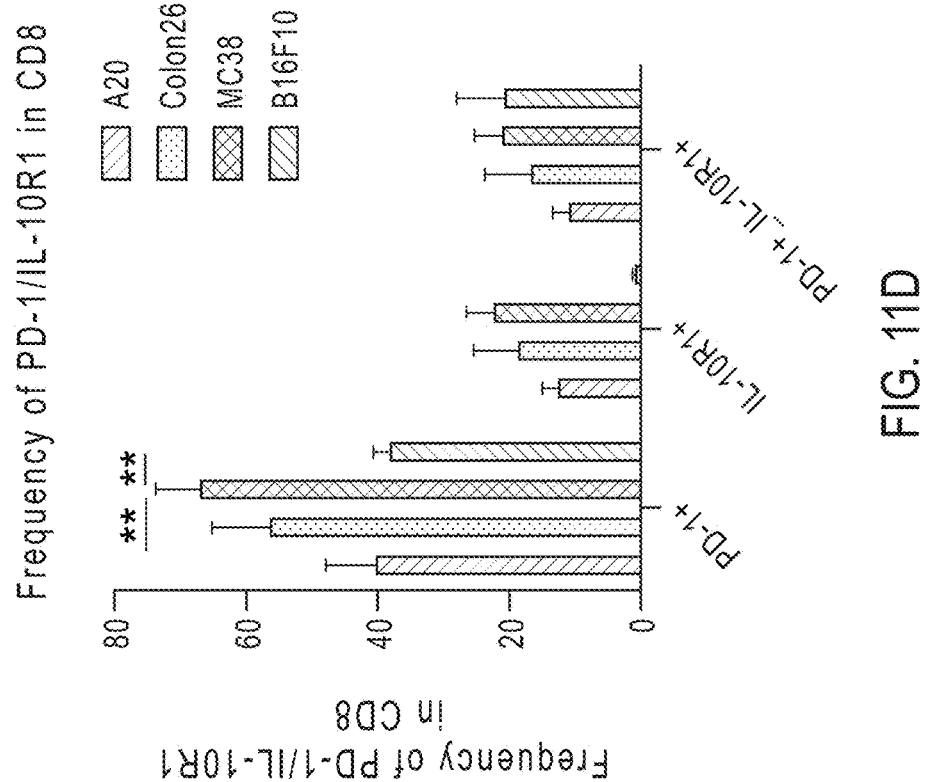
Figure 11F:
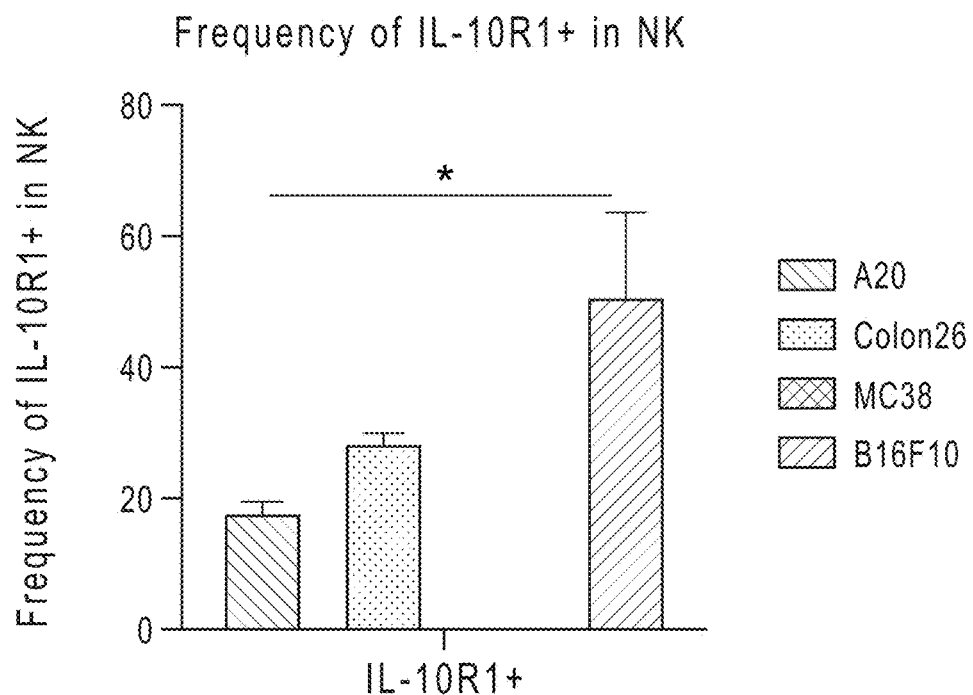
Figure 11G:
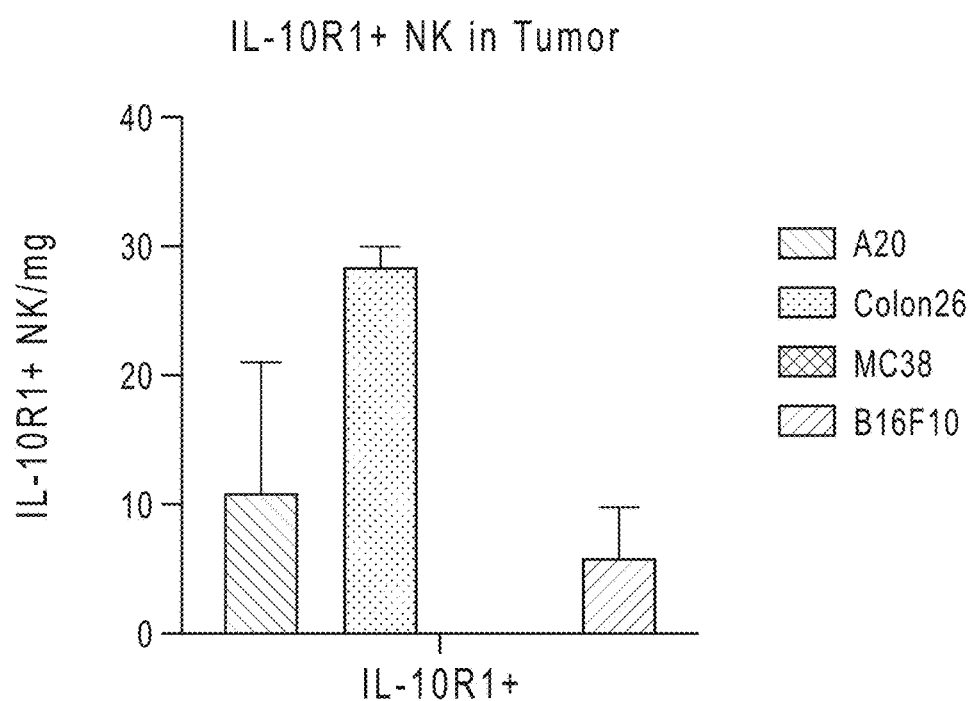
Figure 11H:
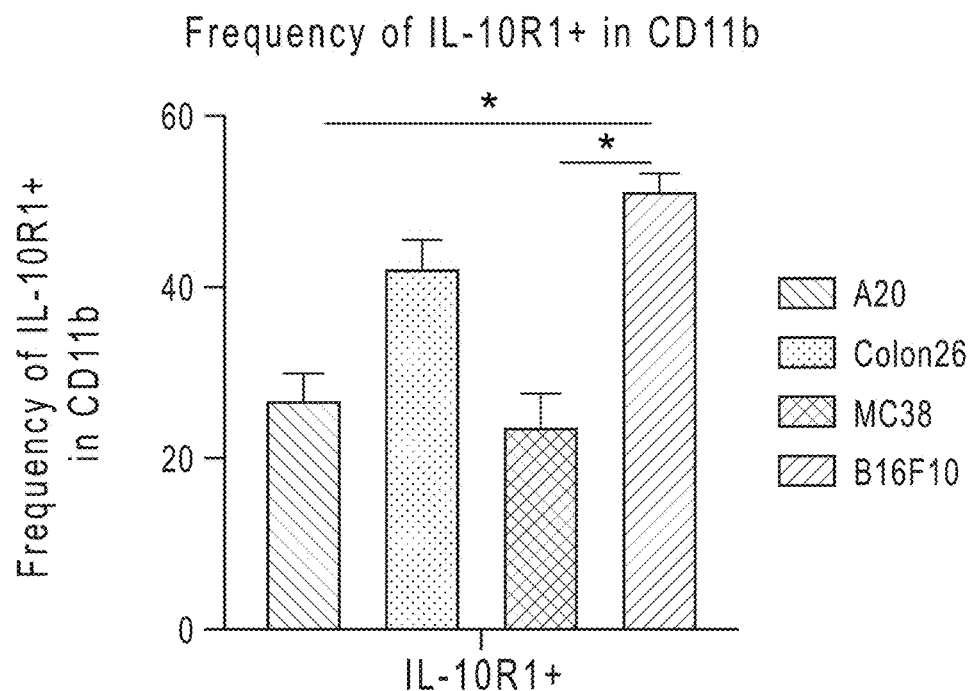
Figure 11I:
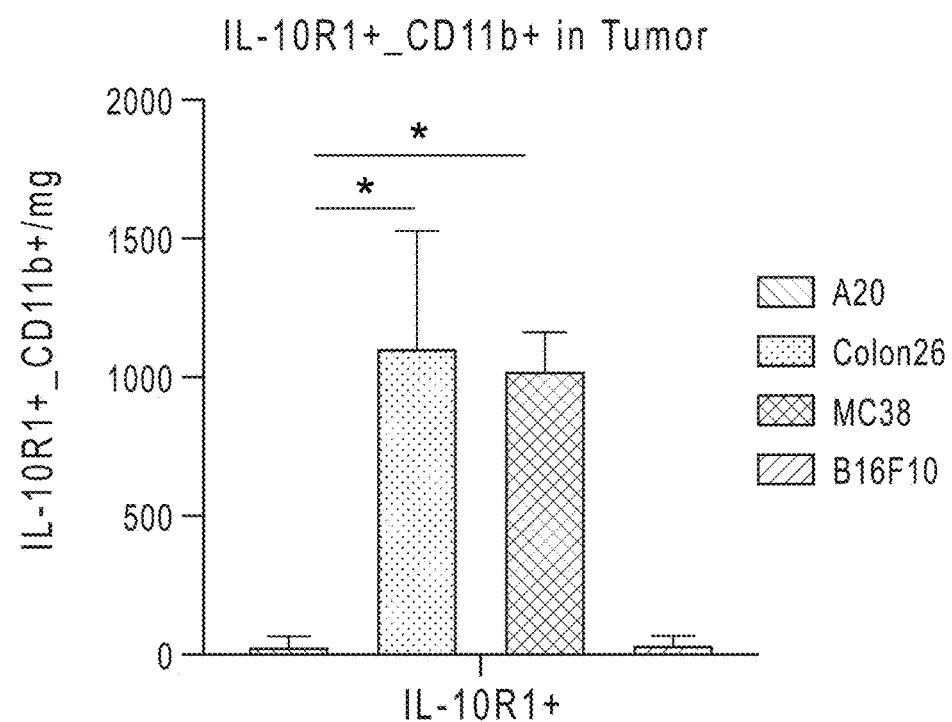
Figure 12A:
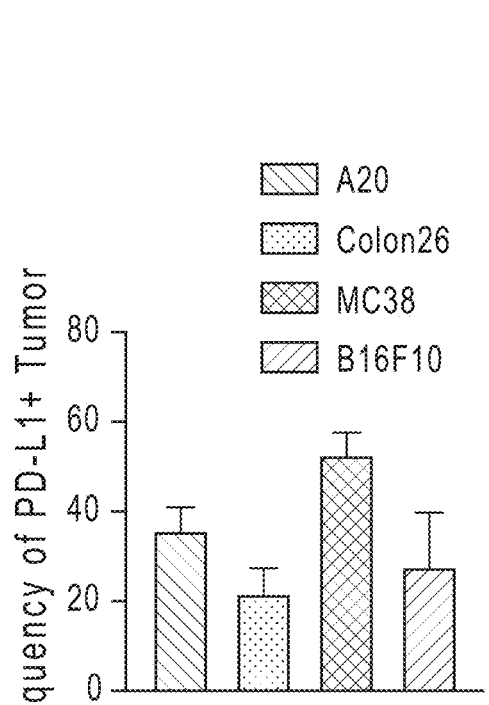
Figure 12B:
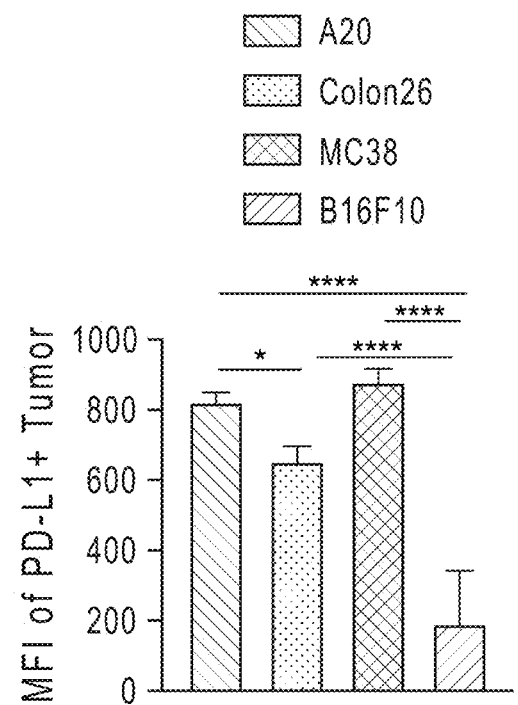
Figure 12C:
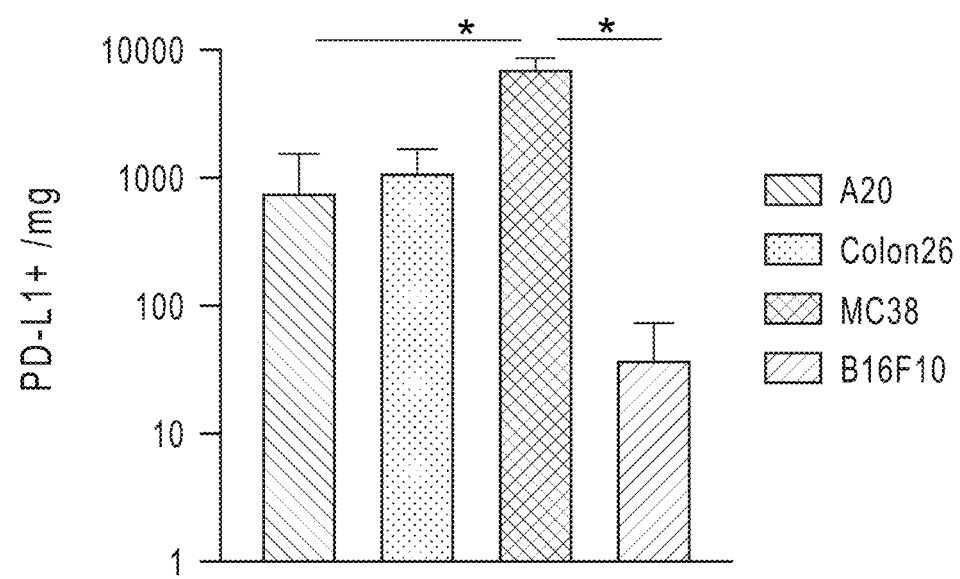
Figure 12D:
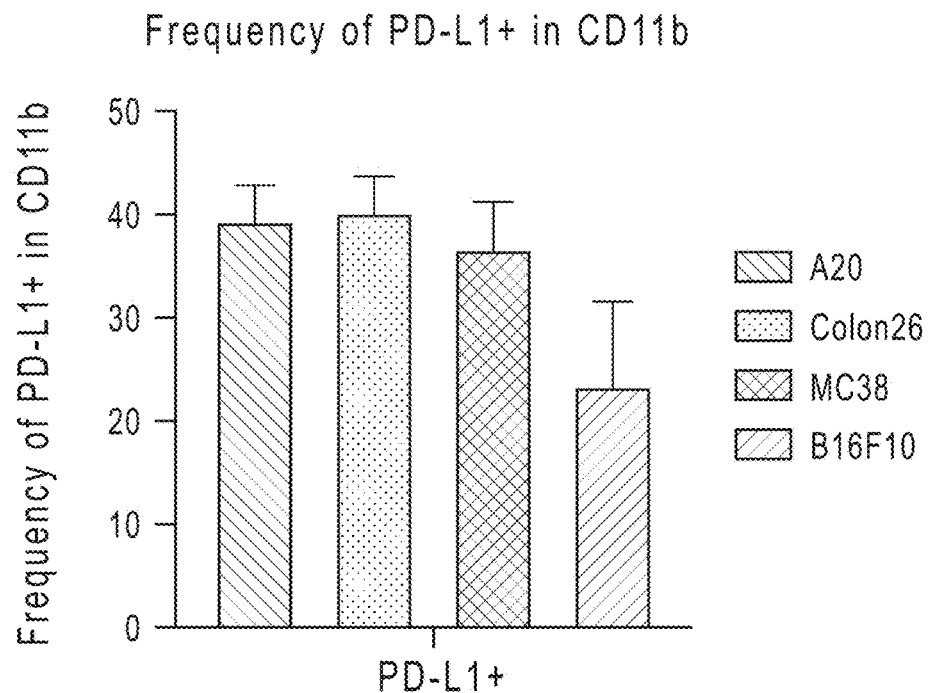
Figure 12E:
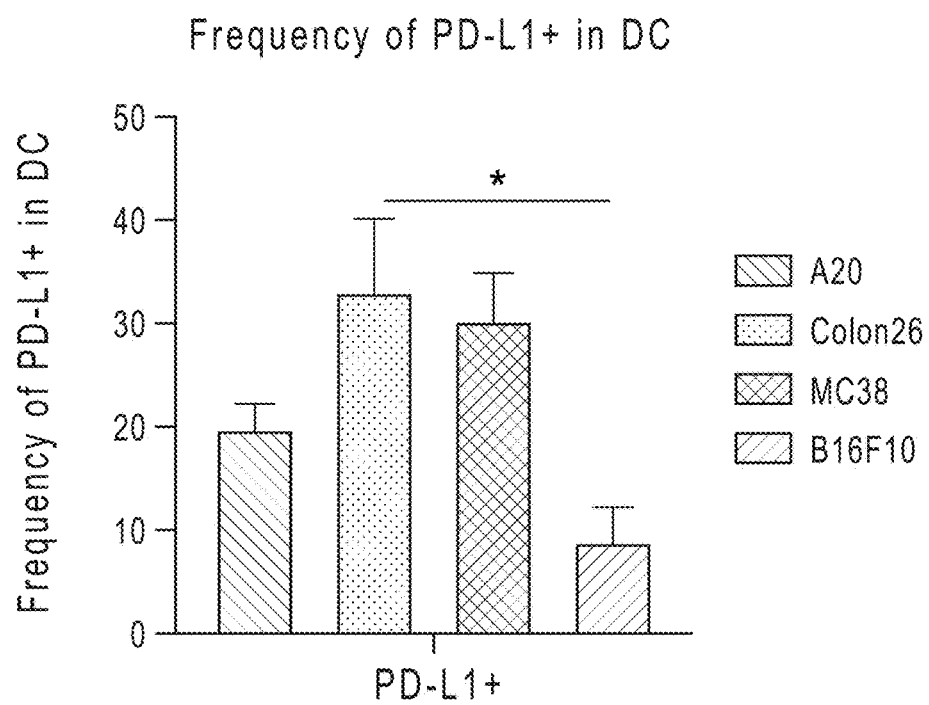
Figure 12F:
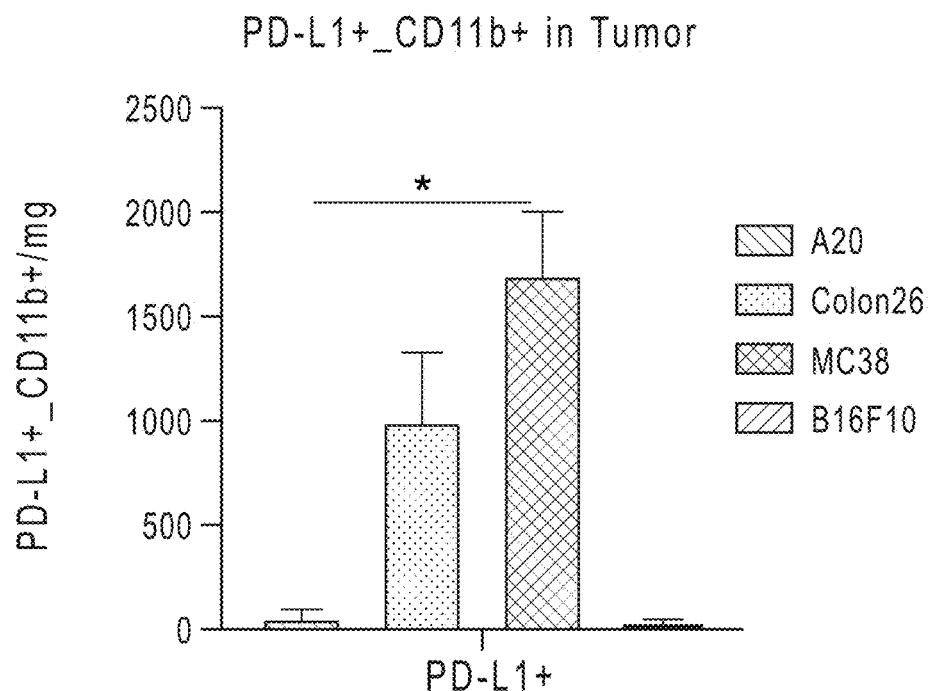
Figure 12G:
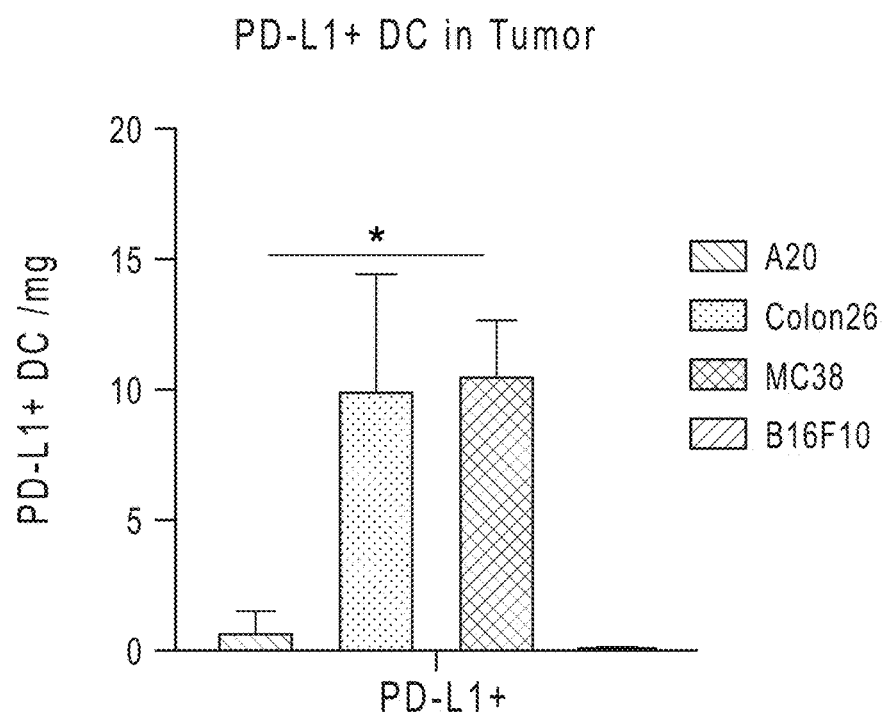

FIGS. 11A-1-11I show the expression of PD-1 and IL10R1 I a variety of myeloid cells in spleen, draining lymph node (dLN), and tumors. Expression of IL10R1 on T cells, CD8 T cells in particular, was very much restricted to tumor-infiltrating CD8 T cells, with little expression on T cells of secondary lymphoid tissues, such as spleen and draining LNs of MC38-cOVA and Colon26. almost all the IL10R1+CD8 T cells expressed PD1 molecules.

FIGS. 12A-12G show the expression of PD-L1 in four different tumor types (A20, Colon26, MC38, and B16F10). The results show that PD-L1 expression was variable among the tumor types.

Figure 13A:
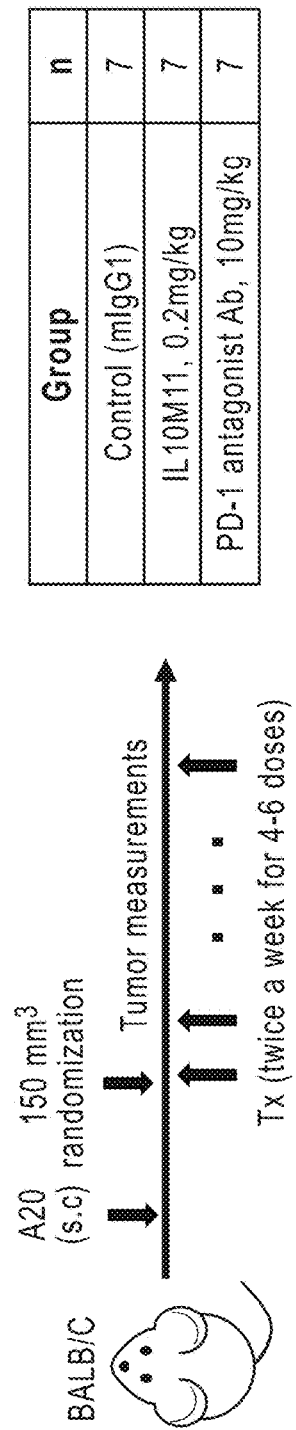
Figure 13B:
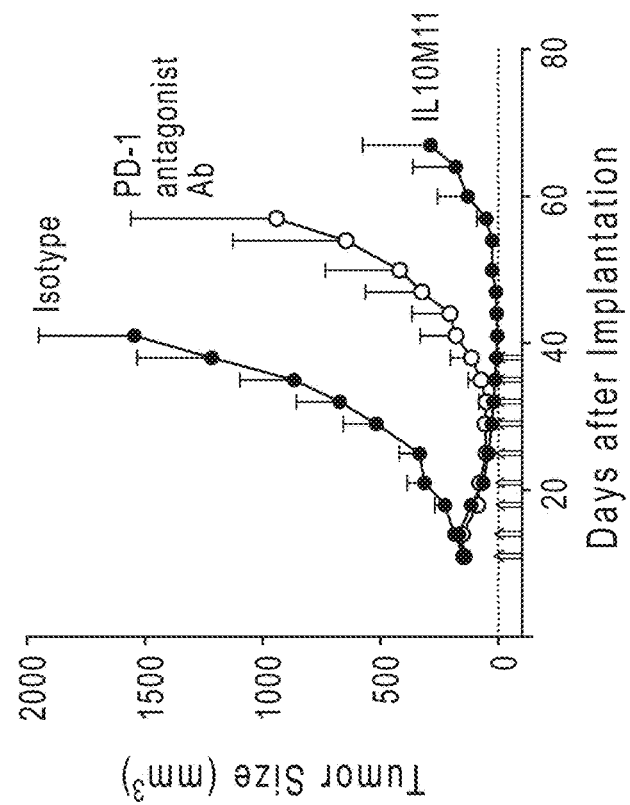
Figure 13C:
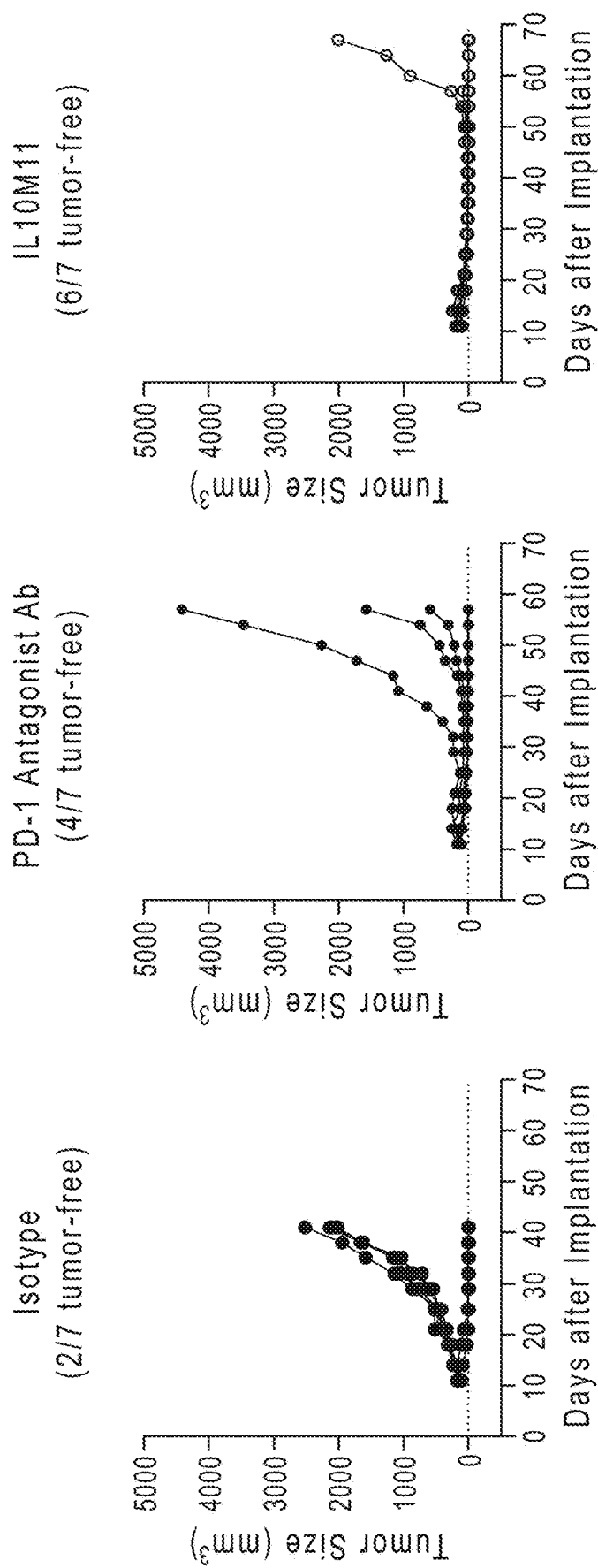

FIGS. 13A-13C illustrate the experimental design for the A20 tumor model study (FIG. 13A) and results from treatment with control, IL10M11, or a PD-1 antagonist antibody (FIGS. 13B and 13C). 150 mm$^3$ A20 B cell lymphoma responded to PD-1 Ab treatment, with significant delay of tumor growth and ~50% of tumor-free survival. IL10M11 elicited an even deeper and broader immune response against A20, with ~85% of tumor-free survival.

Figure 14A:
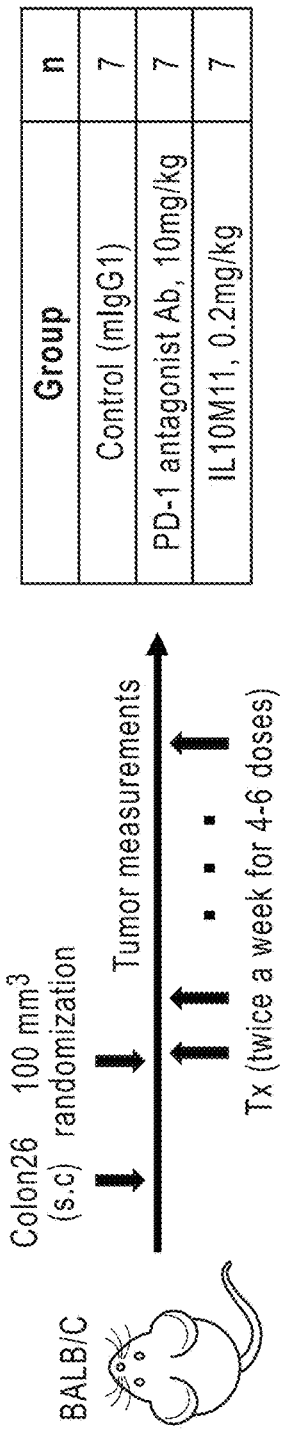
Figure 14B:
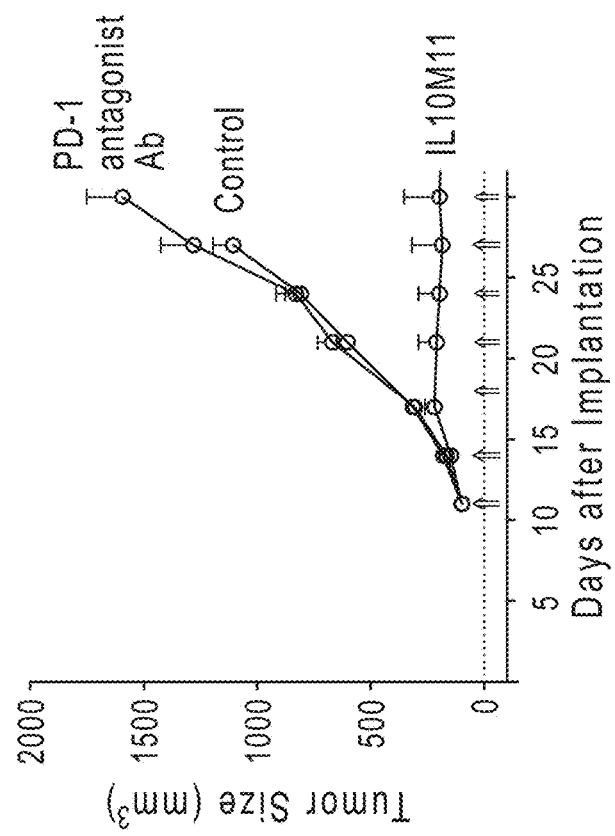
Figure 14C:
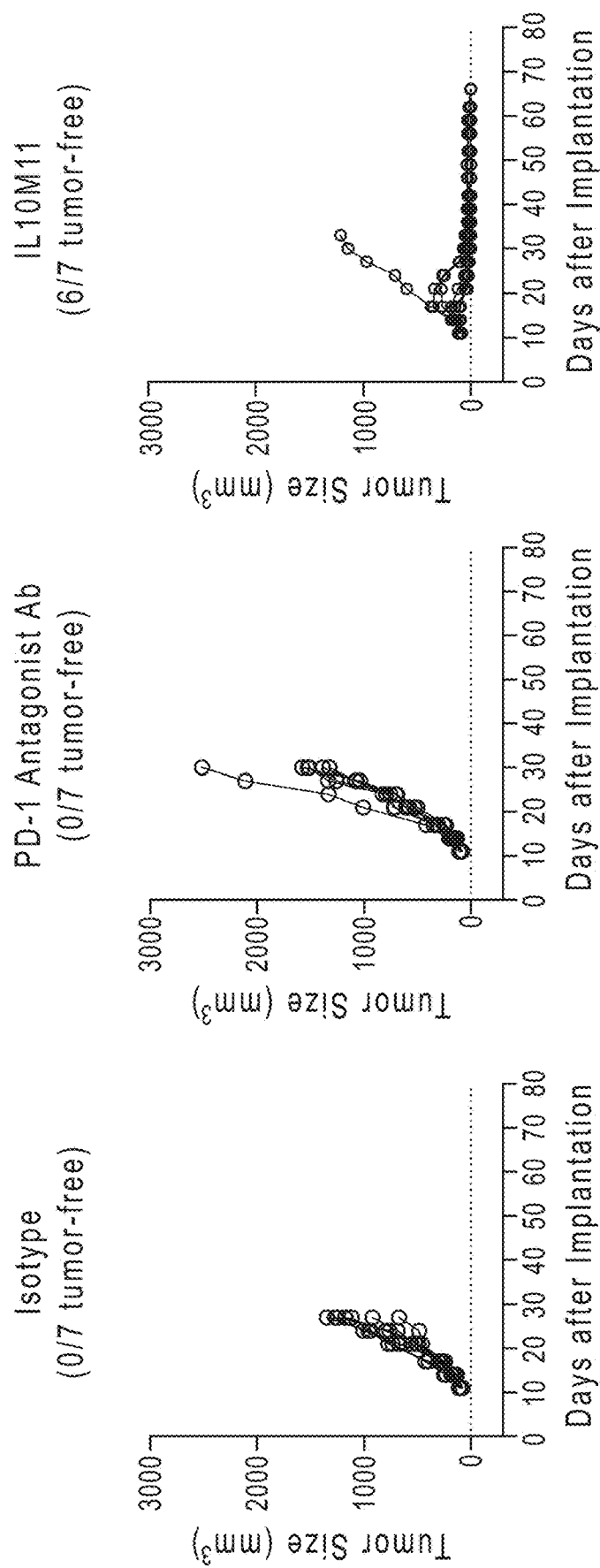

FIGS. 14A-14C illustrate the experimental design for the Colon26 tumor model study (FIG. 14A) and results from treatment with control, IL10M11, or a PD-1 antagonist antibody (FIGS. 14B and 14C). 100 mm$^3$ tumors were completely resistant to PD1 Ab treatment. Treatment with IL10M11 resulted in ~85% tumor-free survival.

Figure 15A:
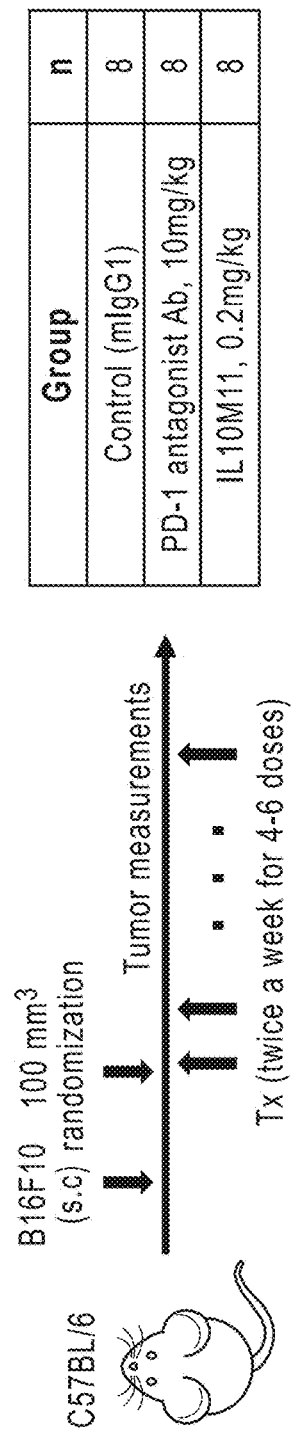
Figure 15B:
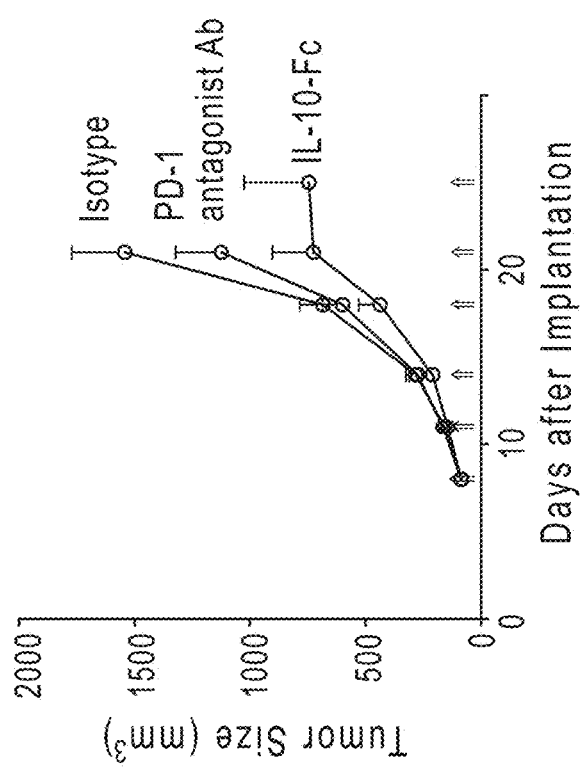
Figure 15C:
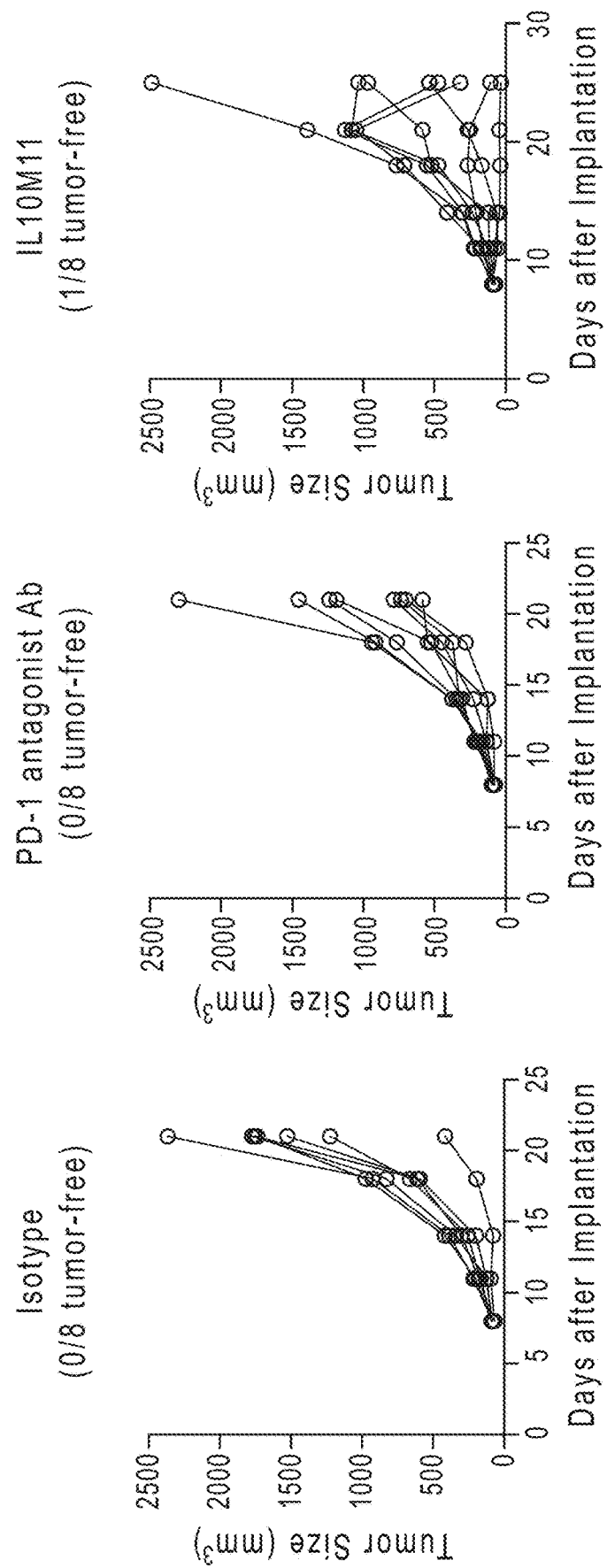

FIGS. 15A-15C illustrate the experimental design for the B16F10 tumor model study (FIG. 15A) and results from treatment with control, IL10M11, or a PD-1 antagonist antibody (FIGS. 15B and 14S). 100 mm$^3$ B16F10 tumors responded poorly to PD1 Ab. IL10M11 significantly delayed tumor growth and rendered a majority of tumors of being responsive.

Figure 16A:
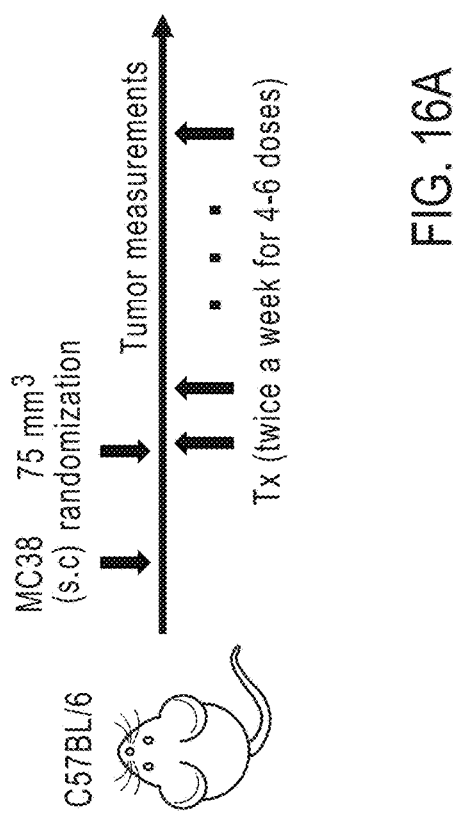
Figure 16B:
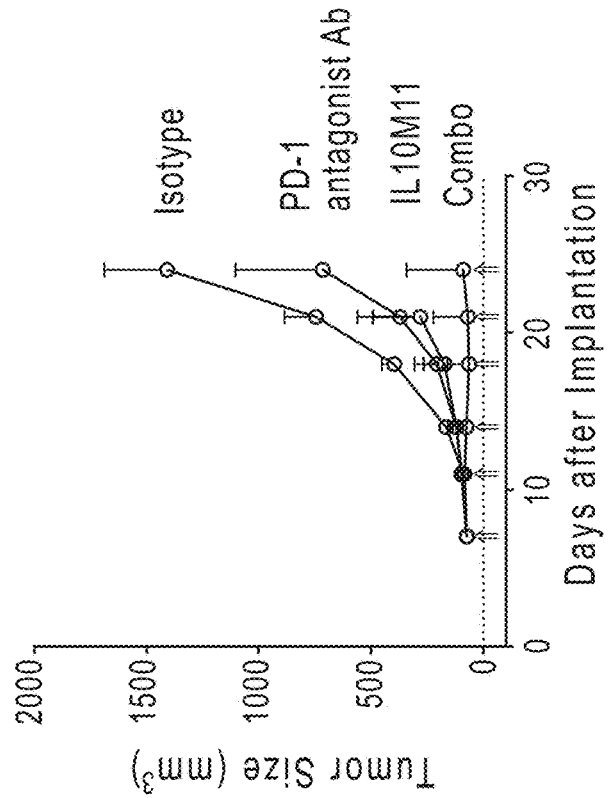
Figure 16C:
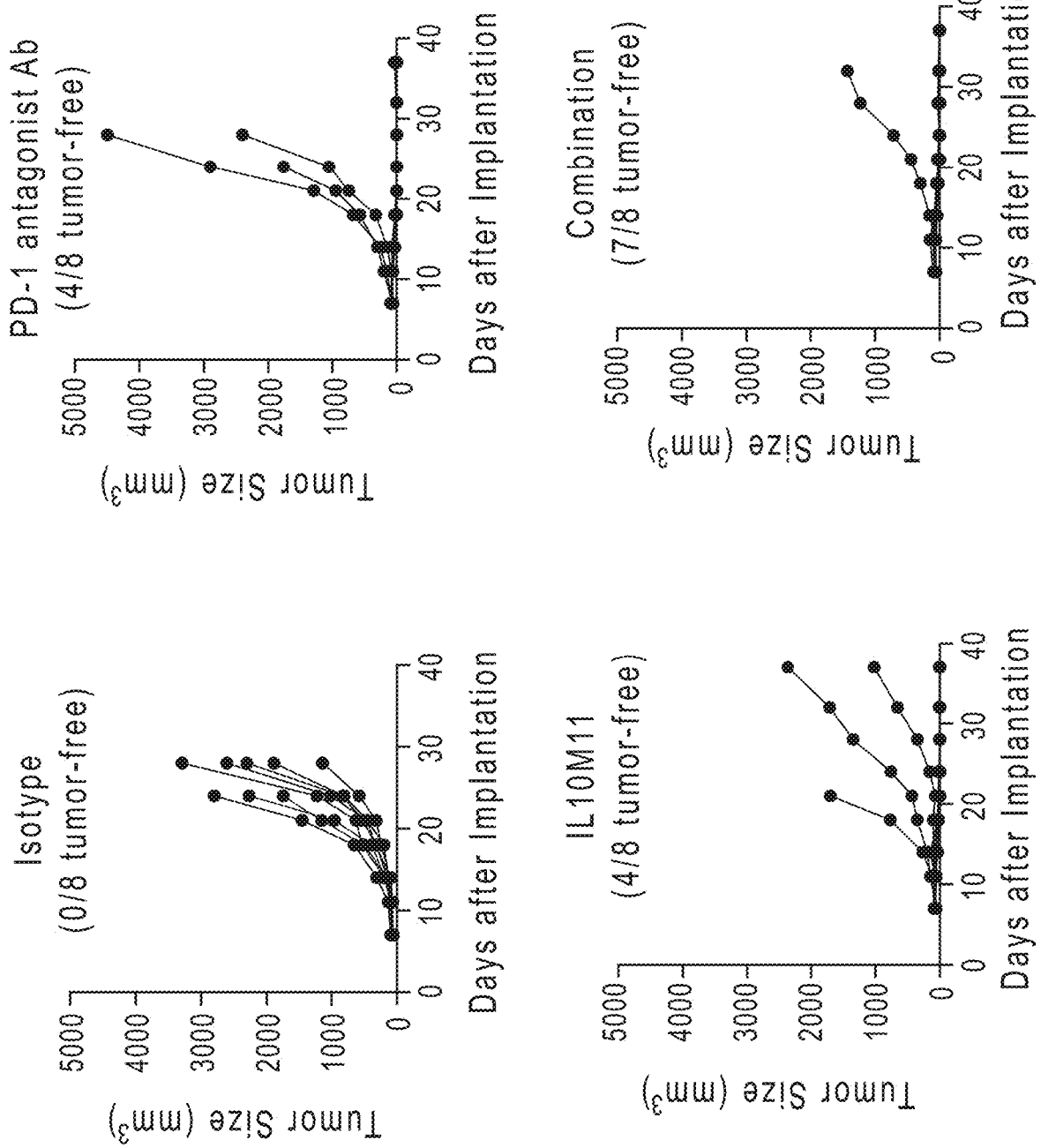
Figures 1, 17A:
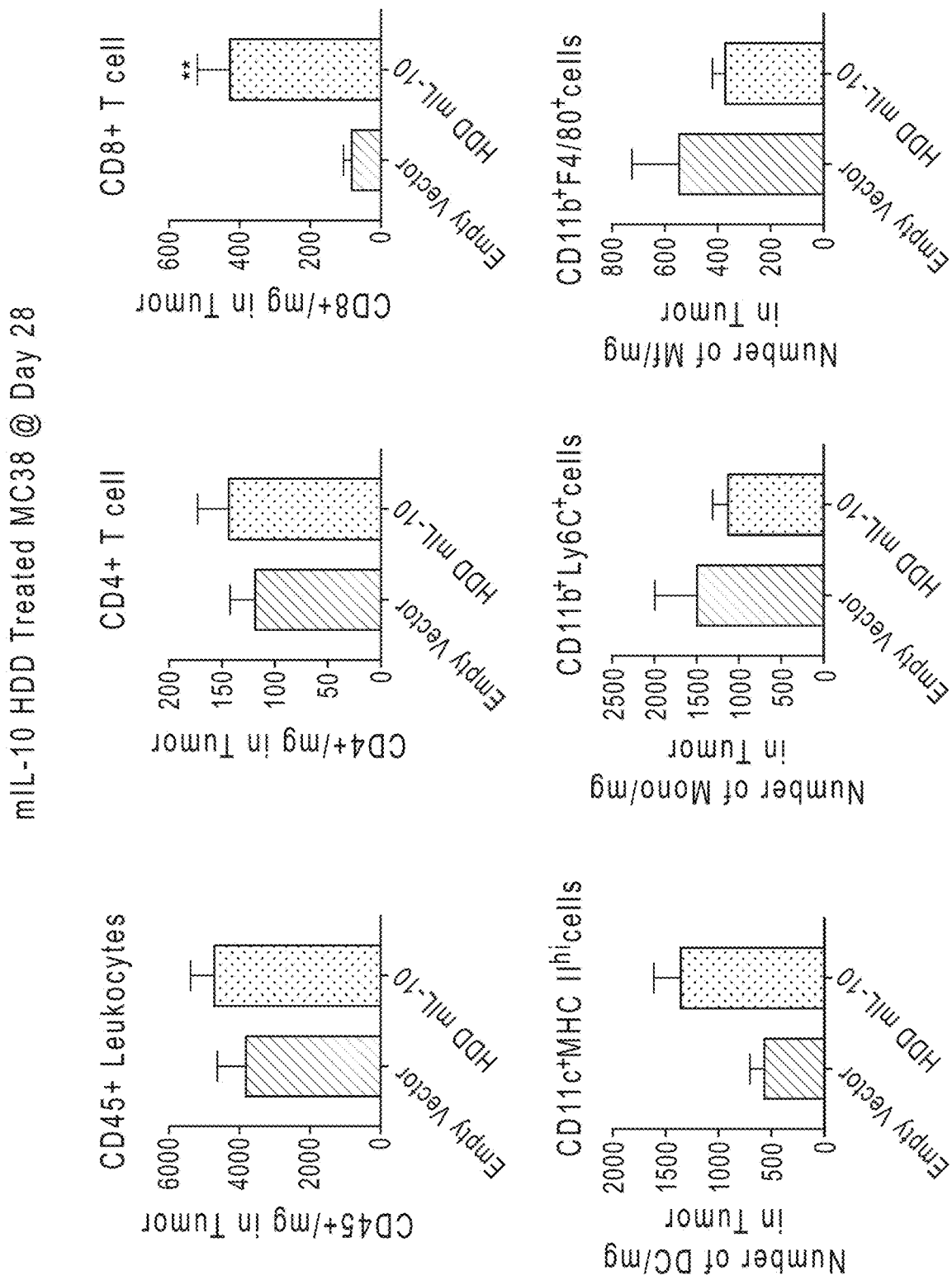
Figures 2, 17A:
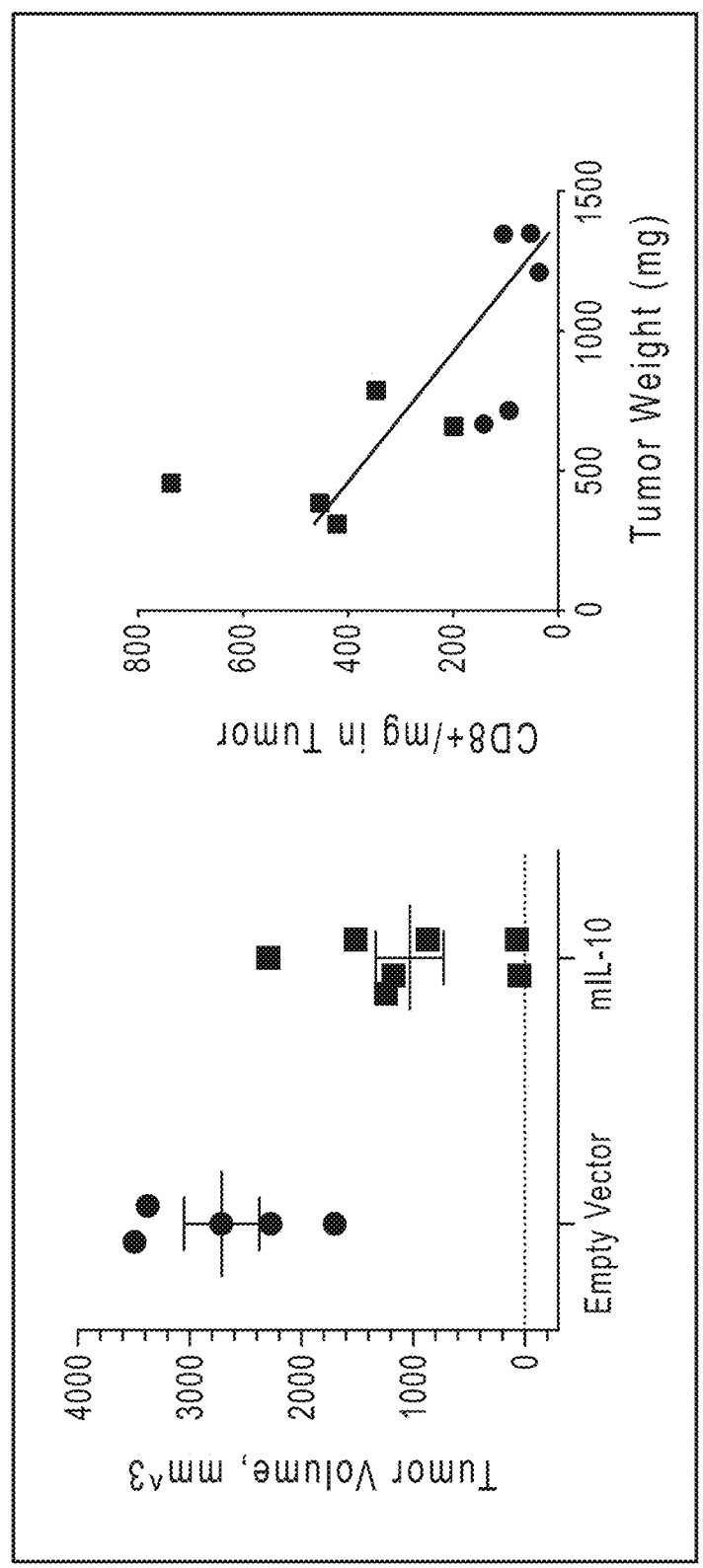
Figures 1, 17B:
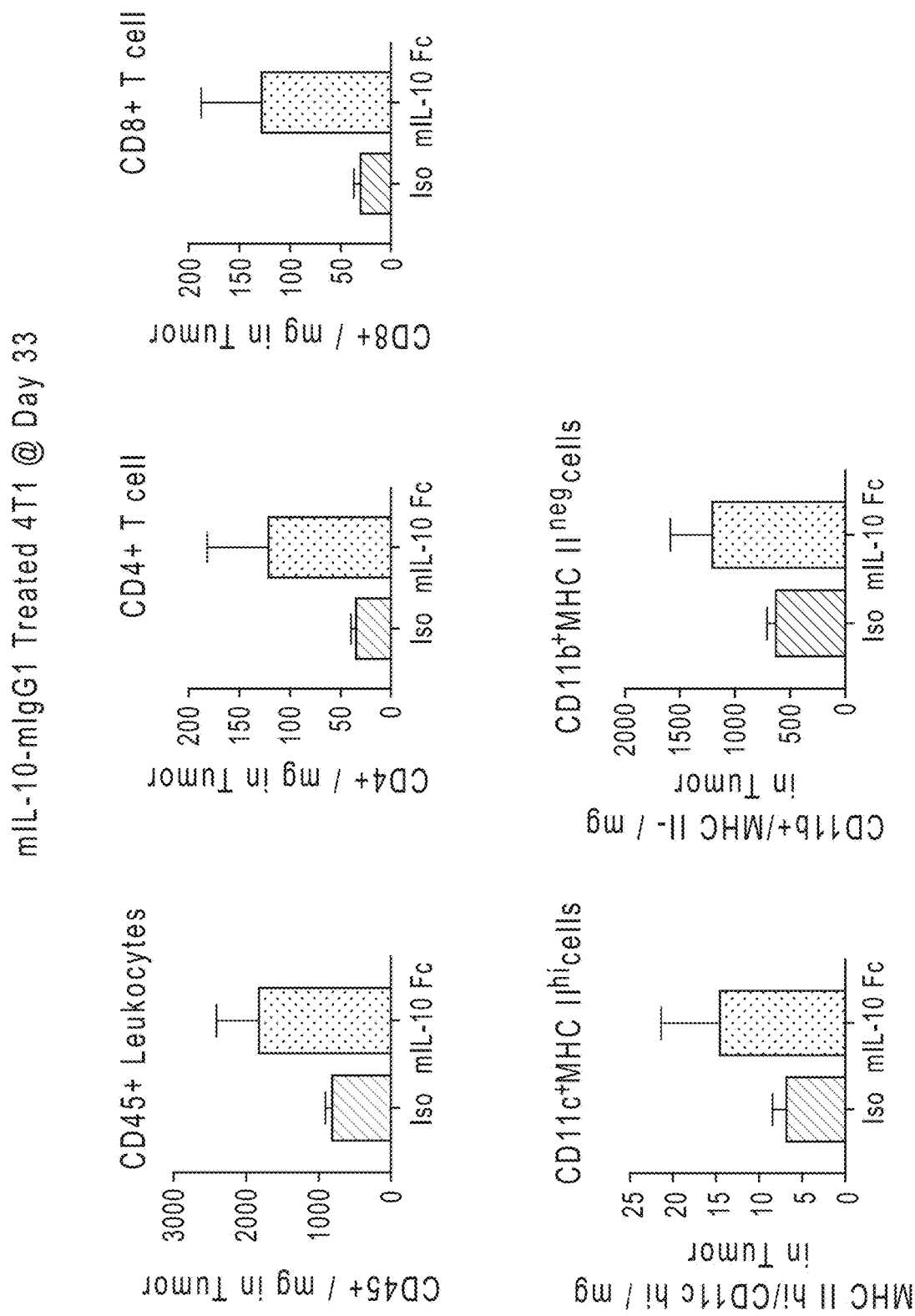
Figures 2, 17B:
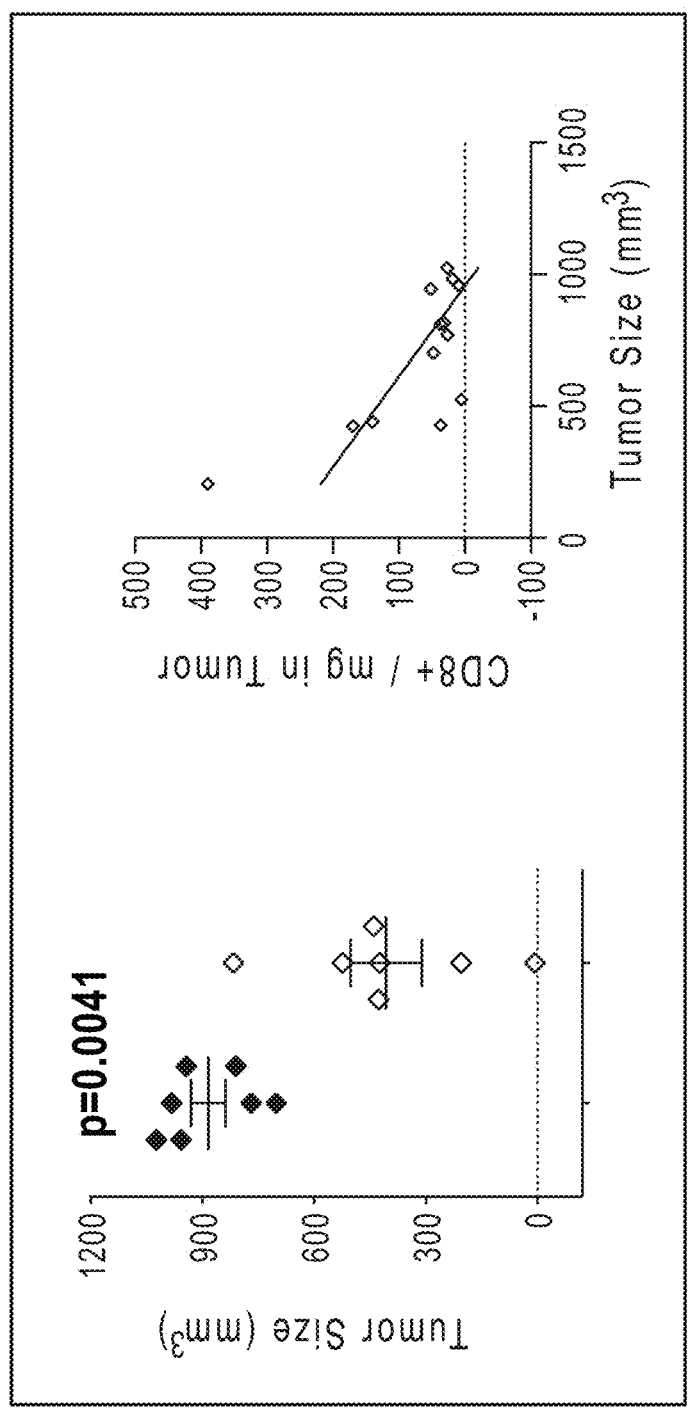

FIGS. 16A-16C illustrate the experimental design for the MC38 tumor model study (FIG. 16A) and results from treatment with control, IL10M11, a PD-1 antagonist antibody, or a combination of IL10M11 and the PD-1 antagonist antibody (FIGS. 16B and 16C). Both PD1 Ab and IL10-Fc had a similar anti-tumor effect as single agents. The combination of PD1Ab and IL10-Fc dramatically increased antitumor responses by delaying tumor growth and giving rise to higher incidence of tumor-free survival.

FIGS. 17A-1-17B-2 show the results from immune profiling of tumor microenvironment following therapy. As shown, IL10 treatment significantly increased CD8 T cell density in both the immunogenic MC38 tumor model (FIGS. 17A-1 and 17A-2) and the less immunogenic 4T1 tumor model (FIGS. 17B-1 and 17B-2), which were correlated with better prognosis in both cases.

Figure 18A:
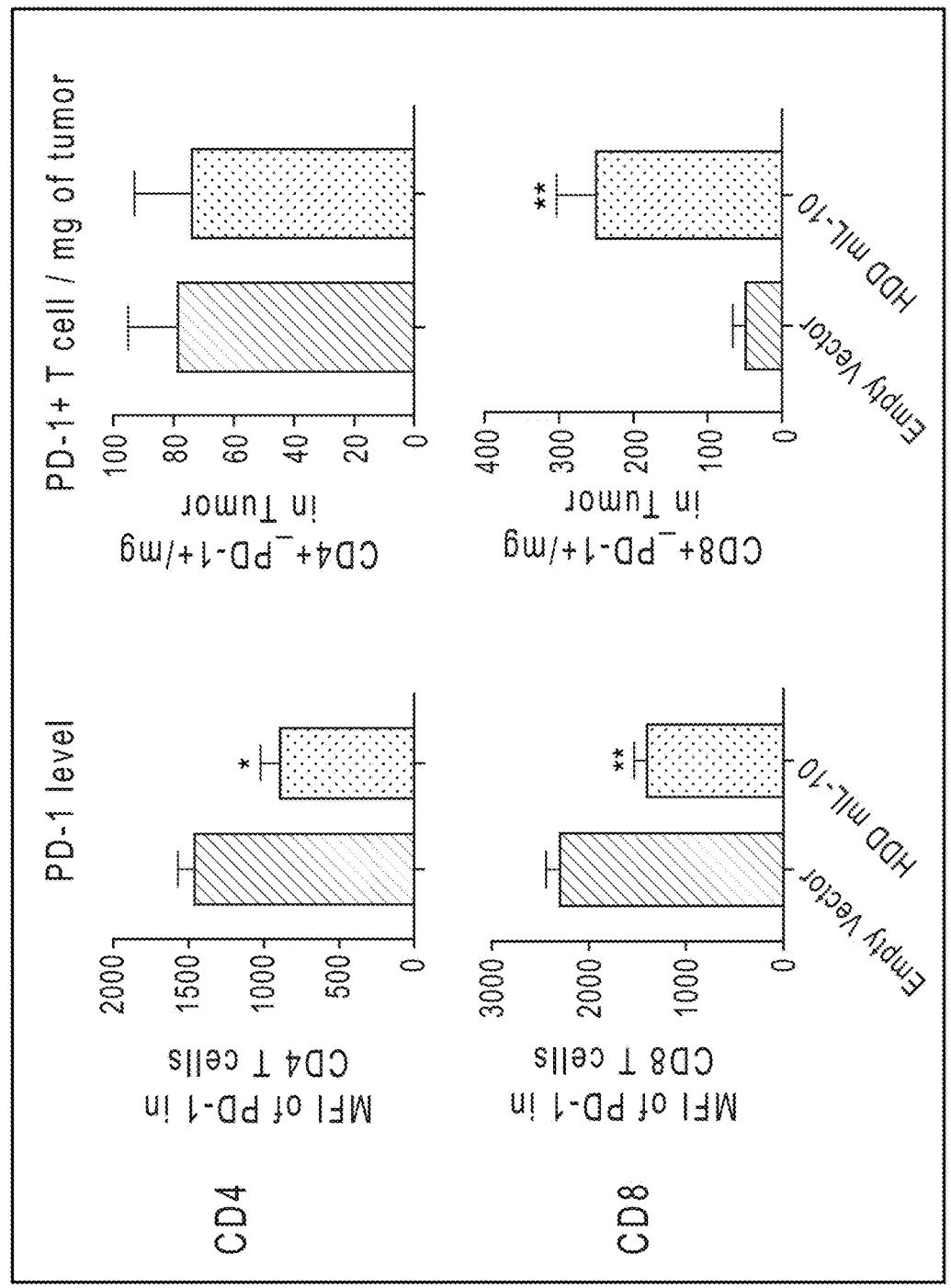
Figure 18B:
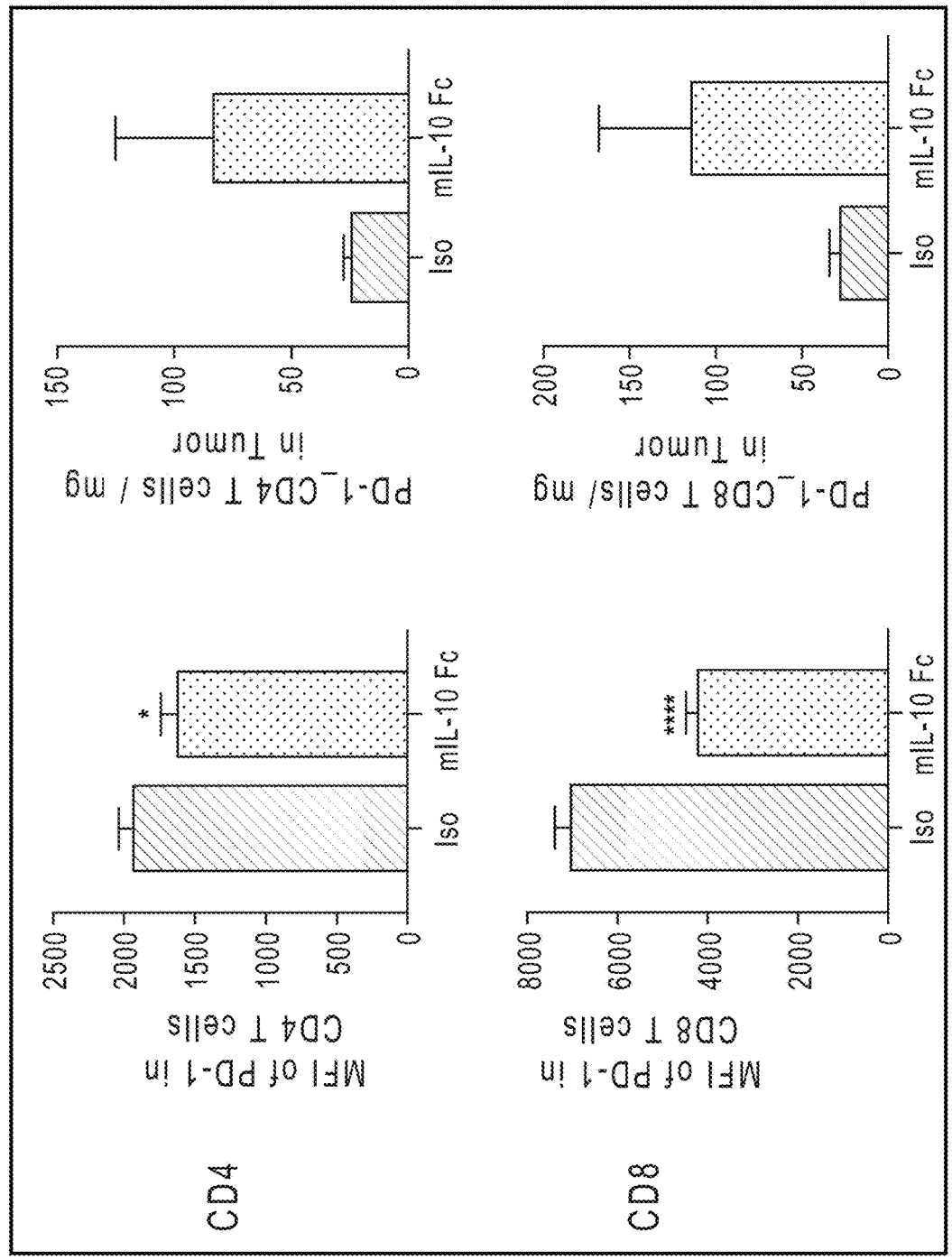

FIGS. 18A-18B show the density of PD1+CD8 T cells in MC38 tumor (FIG. 18A) and in 4T1 tumor (FIG. 18B).

Figure 19C:
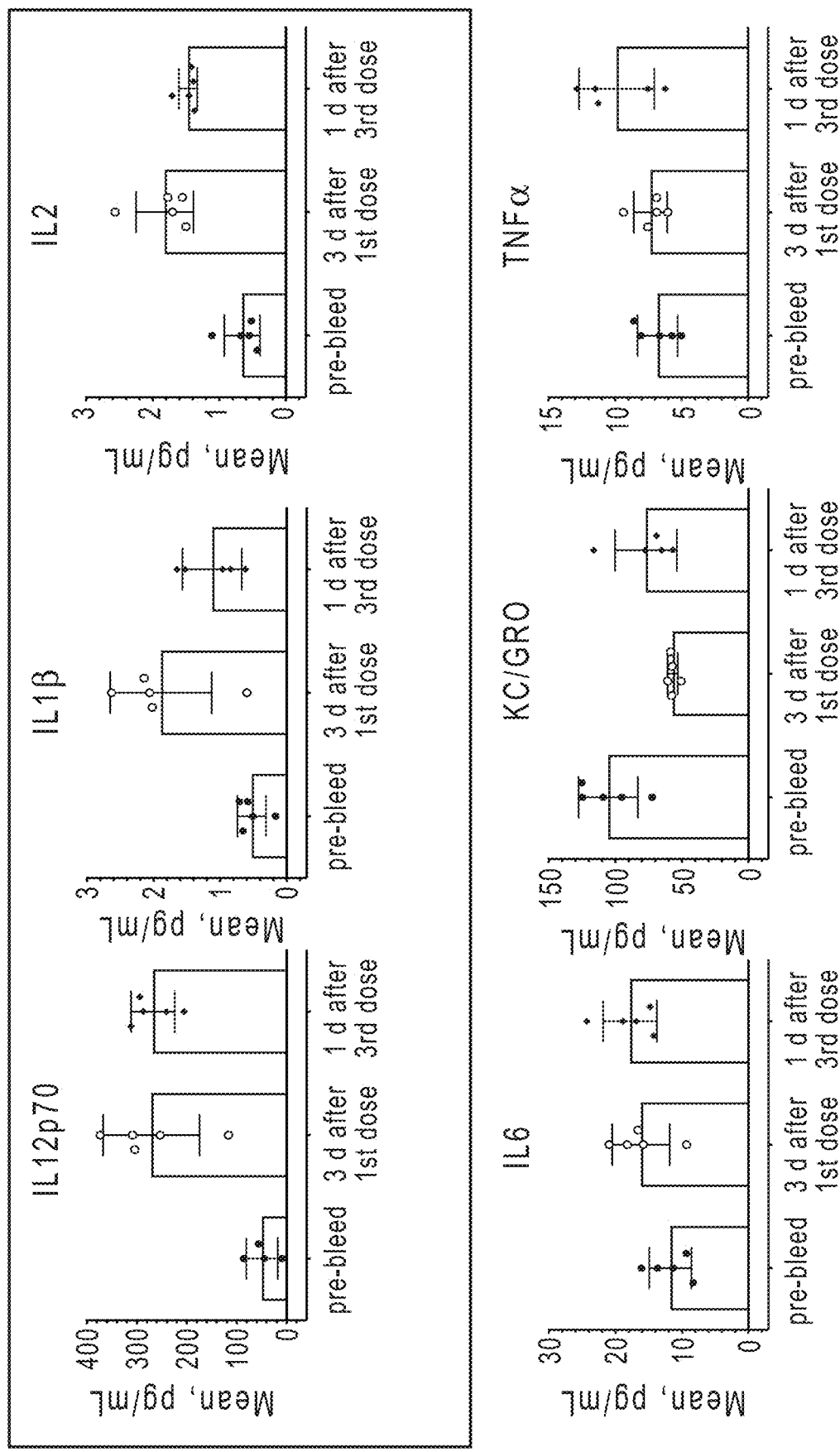

FIGS. 19A-19C illustrate the experimental design (FIG. 19A) and show serum levels of various cytokines following treatment of naïve, non-tumor bearing mice with IL10M11 (FIGS. 19B-19C).

Figure 20A:
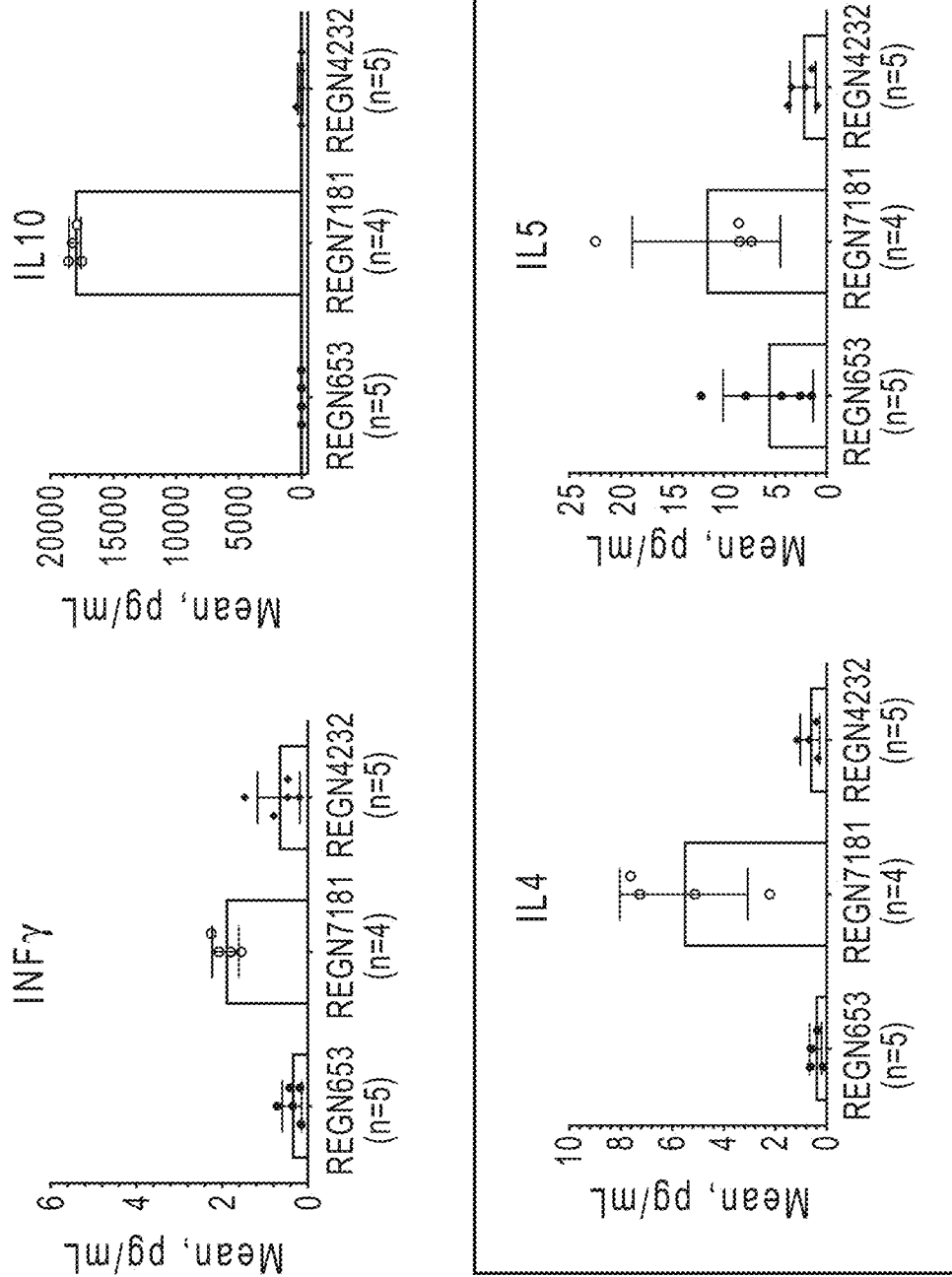
Figure 20B:
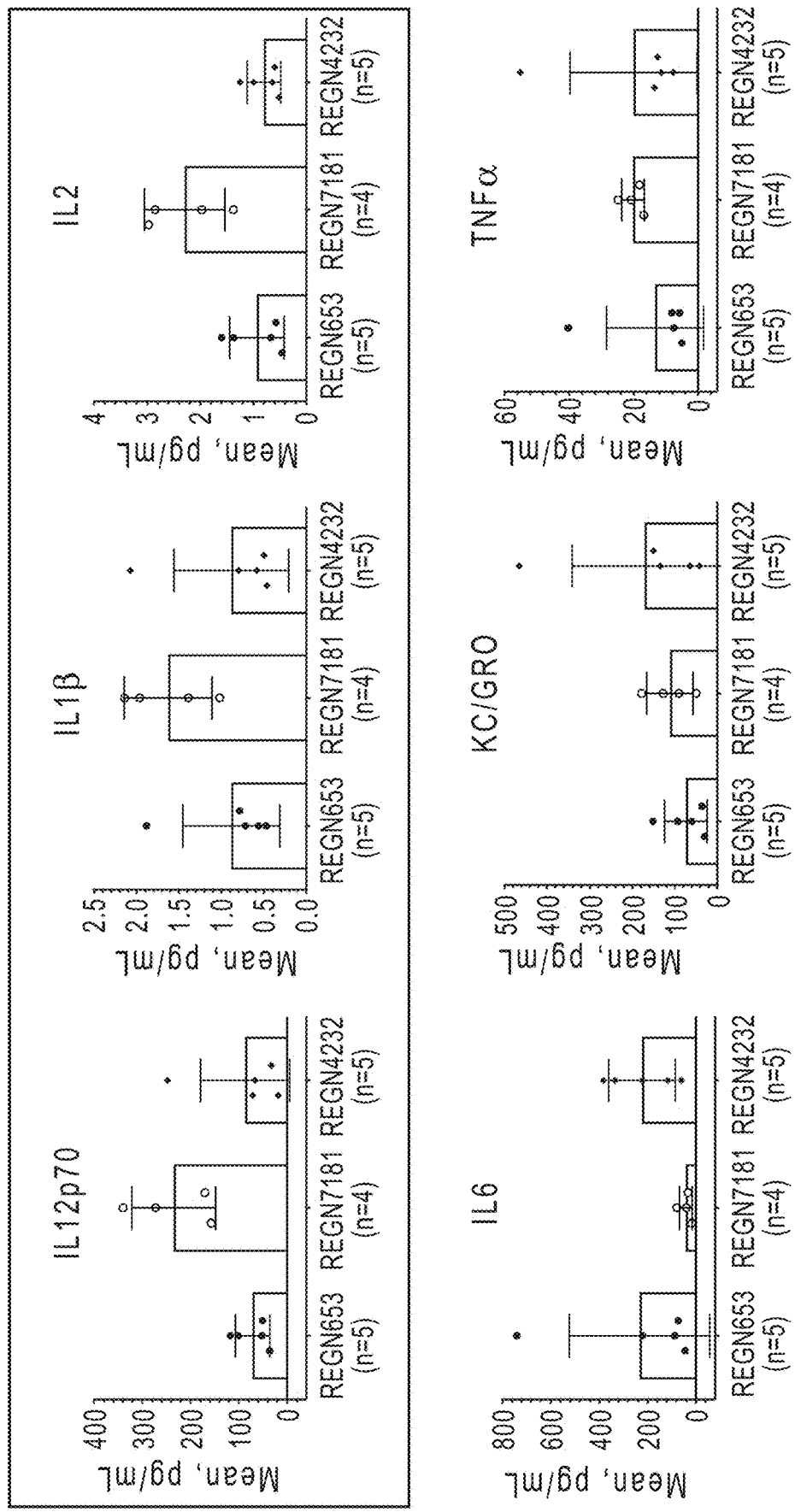

FIGS. 20A-20B show serum levels of various cytokines following treatment of B16F10 tumor bearing mice with IL10M11 IL12, IL1b, IL2, IL4, and IL5 were upregulated by IL10, but not by the PD1 antibody.

Figure 21B:
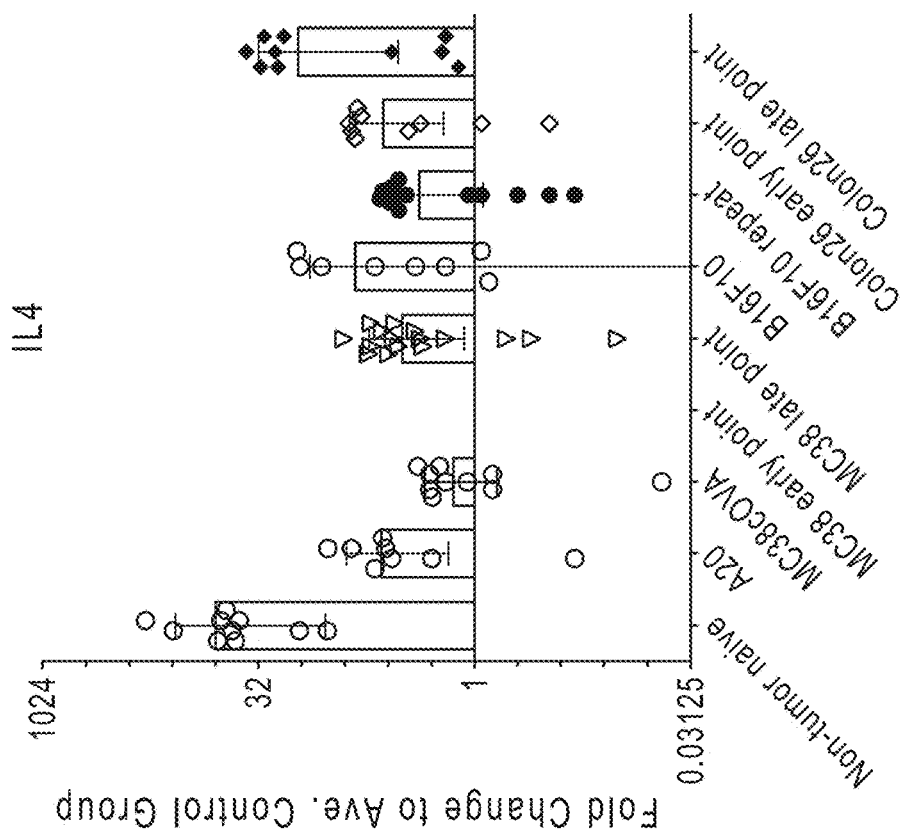
Figure 21A:
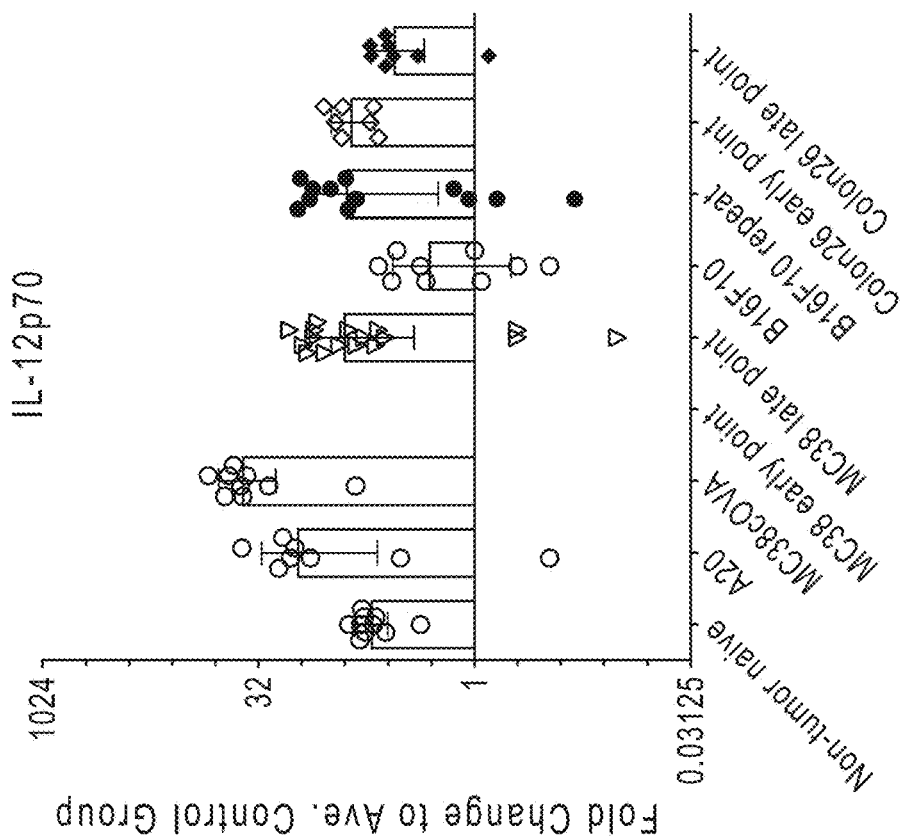

FIGS. 21A-21B shows serum levels of IL12 (FIG. 21A) and IL4 (FIG. 21B), normalized to average values in isotype control treated mice. Upregulation of IL12 and IL4 is shown across A20, MC38, MC38-cOVA, B16F10, and Colon26 tumor models.

Figures 22A, 22B:
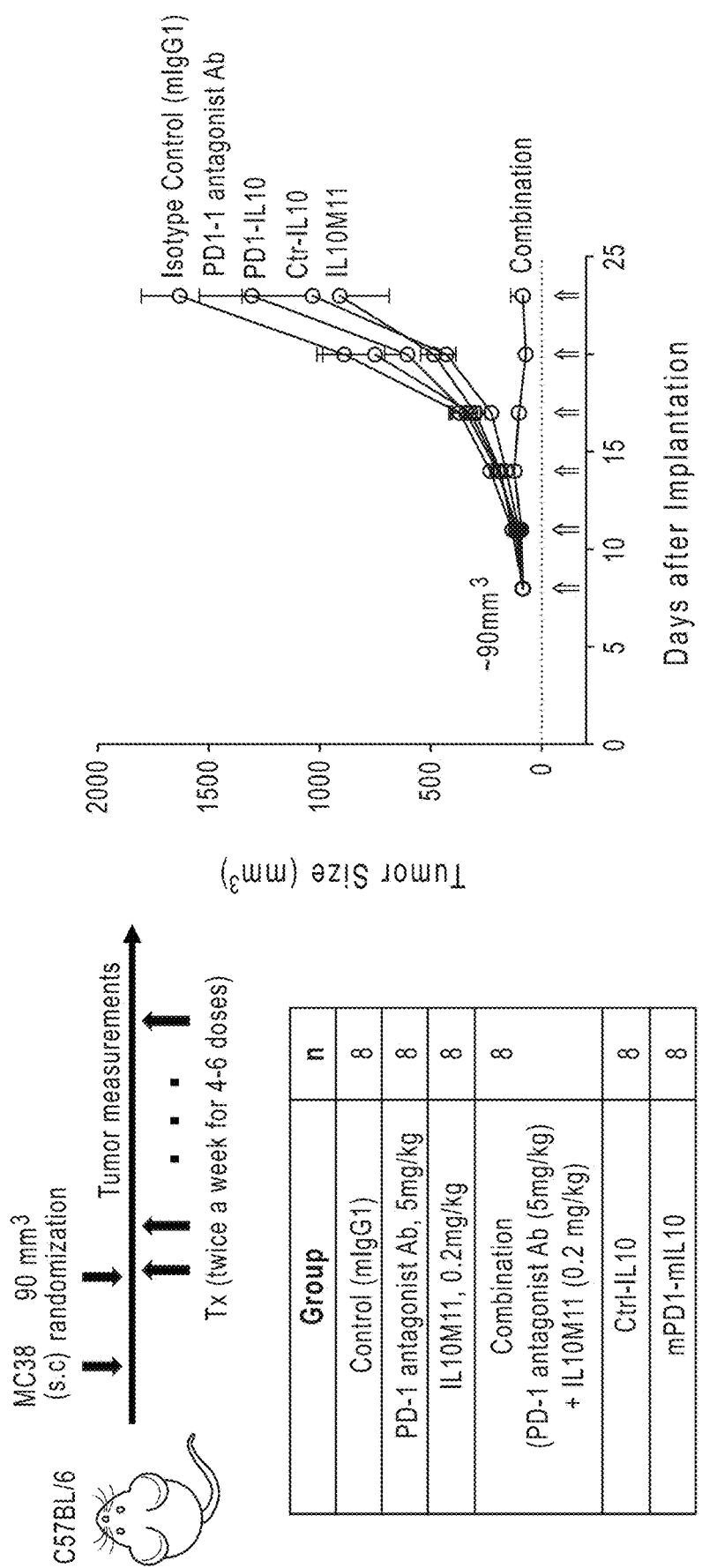

FIGS. 22A-22B illustrate the experimental design for the MC38 tumor model study (FIG. 22A) and results from treatment with control, IL10M11, a PD-1 antagonist antibody, a combination of IL10M11 and the PD-1 antagonist antibody, or IL10 linked to a PD-1 binding domain (mPD1-mIL10) (FIGS. 22B and 22C). Both PD1 Ab and IL10-Fc demonstrated anti-tumor effect as single agents (marginal effect for PD1 Ab and a moderate effect for IL10-Fc). The combination of IL10-Fc and PD-1 Ab significantly improved the efficacy. PD1-IL10-Fc did not show any difference in terms of efficacy than control Ab-IL10 or IL10-Fc.

6. DETAILED DESCRIPTION

6.1. Definitions

Associated: The term "associated" in the context of an IL10 agonist or a component thereof (e.g., a targeting moiety such as an antibody) refers to a functional relationship between two or more polypeptide chains. In particular, the term "associated" means that two or more polypeptides are associated with one another, e.g., non-covalently through molecular interactions or covalently through one or more disulfide bridges or chemical cross-linkages, so as to produce a functional IL10 agonist. Examples of associations that might be present in an IL10 agonist of the disclosure include (but are not limited to) associations between homodimeric or heterodimeric Fc domains in an Fc region, associations between VH and VL regions in a Fab or scFv, associations between CH1 and CL in a Fab, and associations between CH3 and CH3 in a domain substituted Fab.

Cancer: The term "cancer" refers to a disease characterized by the uncontrolled (and often rapid) growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, adrenal gland cancer, autonomic ganglial cancer, biliary tract cancer, bone cancer, endometrial cancer, eye cancer, fallopian tube cancer, genital tract cancers, large intestinal cancer, cancer of the meninges, oesophageal cancer, peritoneal cancer, pituitary cancer, penile cancer, placental cancer, pleura cancer, salivary gland cancer, small intestinal cancer, stomach cancer, testicular cancer, thymus cancer, thyroid cancer, upper aerodigestive cancers, urinary tract cancer, vaginal cancer, vulva cancer, lymphoma, leukemia, lung cancer and the like.

Complementarity Determining Region or CDR: The terms "complementarity determining region" or "CDR," as used herein, refer to the sequences of amino acids within antibody variable regions which confer antigen specificity and binding affinity. In general, there are three CDRs in each heavy chain variable region (CDR-H1, CDR-H2, HCDR-H3) and three CDRs in each light chain variable region (CDR1-L1, CDR-L2, CDR-L3). Exemplary conventions that can be used to identify the boundaries of CDRs include, e.g., the Kabat definition, the Chothia definition, the ABM definition and the IMGT definition. See, e.g., Kabat, 1991, "Sequences of Proteins of Immunological Interest," National Institutes of Health, Bethesda, Md. (Kabat numbering scheme); AI-Lazikani et al., 1997, J. Mol. Biol. 273:927-948 (Chothia numbering scheme); Martin et al., 1989, Proc. Natl. Acad. Sci. USA 86:9268-9272 (ABM numbering scheme); and Lefranc et al., 2003, Dev. Comp. Immunol. 27:55-77 (IMGT numbering scheme). Public databases are also available for identifying CDR sequences within an antibody.

EC50: The term "EC50" refers to the half maximal effective concentration of a molecule (such as an IL10 agonist) which induces a response halfway between the baseline and maximum after a specified exposure time. The EC50 essentially represents the concentration of an antibody or IL10 agonist where 50% of its maximal effect is observed.

In certain embodiments, the EC50 value equals the concentration of an IL10 agonist that gives half-maximal STAT3 activation in an assay as described in Section 7.1.2.

Epitope: An epitope, or antigenic determinant, is a portion of an antigen (e.g., target molecule) recognized by an antibody or other antigen-binding moiety as described herein. An epitope can be linear or conformational.

Fab: The term "Fab" in the context of a targeting moiety of the disclosure refers to a pair of polypeptide chains, the first comprising a variable heavy (VH) domain of an antibody N-terminal to a first constant domain (referred to herein as C1), and the second comprising variable light (VL) domain of an antibody N-terminal to a second constant domain (referred to herein as C2) capable of pairing with the first constant domain. In a native antibody, the VH is N-terminal to the first constant domain (CH1) of the heavy chain and the VL is N-terminal to the constant domain of the light chain (CL). The Fabs of the disclosure can be arranged according to the native orientation or include domain substitutions or swaps on that facilitate correct VH and VL pairings. For example, it is possible to replace the CH1 and CL domain pair in a Fab with a CH3-domain pair to facilitate correct modified Fab-chain pairing in heterodimeric molecules. It is also possible to reverse CH1 and CL, so that the CH1 is attached to VL and CL is attached to the VH, a configuration generally known as Crossmab.

Fc Domain and Fc Region: The term "Fc domain" refers to a portion of the heavy chain that pairs with the corresponding portion of another heavy chain. The term "Fc region" refers to the region of antibody-based binding molecules formed by association of two heavy chain Fc domains. The two Fc domains within the Fc region may be the same or different from one another. In a native antibody the Fc domains are typically identical, but one or both Fc domains might advantageously be modified to allow for heterodimerization, e.g., via a knob-in-hole interaction. Further, the Fc domains can include chimeric sequences from more than one immunoglobulin isotype.

Host cell: The term "host cell" as used herein refers to cells into which a nucleic acid of the disclosure has been introduced. The terms "host cell" and "recombinant host cell" are used interchangeably herein. It is understood that such terms refer to the particular subject cell and to the progeny or potential progeny of such a cell. Because certain modifications may occur in succeeding generations due to either mutation or environmental influences, such progeny may not, in fact, be identical to the parent cell, but are still included within the scope of the term as used herein. Typical host cells are eukaryotic host cells, such as mammalian host cells.

Exemplary eukaryotic host cells include yeast and mammalian cells, for example vertebrate cells such as a mouse, rat, monkey or human cell line, for example HKB11 cells, PER.C6 cells, HEK cells or CHO cells.

IL10 Mutein: Is a variant IL10 molecule that has IL10 activity. The variant can be an IL10 fusion protein (e.g., an IL10 fused to IL-2Ra) and/or a mutant IL10, e.g., with one or more amino acid substitutions compared to wild type IL10. An IL10 mutein can have altered function (e.g., receptor binding, affinity, cytokine activity) and/or altered pharmacokinetics as compared to wild type IL10. While in the context of the IL10 agonists of the disclosure, the term "IL10 mutein" sometimes refers to the non-targeting components of the an IL10 molecule (and associated linker moieties), and it is to be understood that the term "IL10 mutein" encompass IL10 molecules with or without a targeting moiety and with or without a multimerization moiety unless the context dictates otherwise.

Major histocompatibility complex and MHC: These terms refer to naturally occurring MHC molecules, individual chains of MHC molecules (e.g., MHC class I α (heavy) chain, β2 microglobulin, MHC class II α chain, and MHC class II β chain), individual subunits of such chains of MHC molecules (e.g., α1, α2, and/or α3 subunits of MHC class I a chain, α1-α2 subunits of MHC class II α chain, β1-β2 subunits of MHC class II β chain) as well as portions (e.g., the peptide-binding portions, e.g., the peptide-binding grooves), mutants and various derivatives thereof (including fusions proteins), wherein such portion, mutants and derivatives retain the ability to display an antigenic peptide for recognition by a T-cell receptor (TCR), e.g., an antigen-specific TCR. An MHC class I molecule comprises a peptide binding groove formed by the α1 and α2 domains of the heavy α chain that can stow a peptide of around 8-10 amino acids. Despite the fact that both classes of MHC bind a core of about 9 amino acids (e.g., 5 to 17 amino acids) within peptides, the open-ended nature of MHC class II peptide binding groove (the α1 domain of a class II MHC a polypeptide in association with the β1 domain of a class II MHC p polypeptide) allows for a wider range of peptide lengths. Peptides binding MHC class II usually vary between 13 and 17 amino acids in length, though shorter or longer lengths are not uncommon. As a result, peptides may shift within the MHC class II peptide binding groove, changing which 9-mer sits directly within the groove at any given time. Conventional identifications of particular MHC variants are used herein. The terms encompass "human leukocyte antigen" or "HLA".

Operably linked: The term "operably linked" as used herein refers to a functional relationship between two or more regions of a polypeptide chain in which the two or more regions are linked so as to produce a functional polypeptide, or two or more nucleic acid sequences, e.g., to produce an in-frame fusion of two polypeptide components or to link a regulatory sequence to a coding sequence.

Single Chain Fv or scFv: The term "single chain Fv" or "scFv" as used herein refers to a polypeptide chain comprising the VH and VL domains of antibody, where these domains are present in a single polypeptide chain.

Specifically (or selectively) binds: The term "specifically (or selectively) binds" as used herein means that a targeting moiety, e.g., an antibody, or antigen binding domain ("ABD") thereof, forms a complex with a target molecule that is relatively stable under physiologic conditions. Specific binding can be characterized by a $K_D$ of about $5 \times 10^{-2}$M or less (e.g., less than $5 \times 10^{-2}$M, less than $10^{-2}$M, less than $5 \times 10^{-3}$M, less than $10^{-3}$M, less than $5 \times 10^{-4}$M, less than $10^{-4}$M, less than $5 \times 10^{-5}$M, less than $10^{-5}$M, less than $5 \times 10^{-6}$M, less than $10^{-6}$M, less than $5 \times 10^{-7}$M, less than $10^{-7}$M, less than $5 \times 10^{-8}$M, less than $10^{-8}$M, less than $5 \times 10^{-9}$M, less than $10^{-9}$M, or less than $10^{-10}$M). Methods for determining the binding affinity of an antibody or an antibody fragment, e.g., an IL10 agonist or a component targeting moiety, to a target molecule are well known in the art and include, for example, equilibrium dialysis, surface plasmon resonance (e.g., Biacore assays), fluorescent-activated cell sorting (FACS) binding assays and the like. An IL10 agonist of the disclosure comprising a targeting moiety or an ABD thereof that specifically binds a target molecule from one species can, however, have cross-reactivity to the target molecule from one or more other species.

Subject: The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

Target Molecule: The term "target molecule" as used herein refers to any biological molecule (e.g., protein, carbohydrate, lipid or combination thereof) expressed on a cell surface or in the extracellular matrix that can be specifically bound by a targeting moiety in an IL10 agonist of the disclosure.

Targeting Moiety: The term "targeting moiety" as used herein refers to any molecule or binding portion (e.g., an immunoglobulin or an antigen binding fragment) thereof that can bind to a cell surface or extracellular matrix molecule at a site to which an IL10 agonist of the disclosure is to be localized, for example on tumor cells or on lymphocytes in the tumor microenvironment. The targeting moiety can also have a functional activity in addition to localizing an IL10 agonist to a particular site. For example, a targeting moiety that is an anti-PD1 antibody or an antigen binding portion thereof can also exhibit anti-tumor activity or enhance the anti-tumor activity by an IL10 mutein by inhibiting PD1 signaling.

Treat, Treatment, Treating: As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more IL10 agonists of the disclosure. In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating" refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

Tumor: The term "tumor" is used interchangeably with the term "cancer" herein, e.g., both terms encompass solid and liquid, e.g., diffuse or circulating, tumors. As used herein, the term "cancer" or "tumor" includes premalignant, as well as malignant cancers and tumors.

Tumor-Associated Antigen: The term "tumor-associated antigen" or "TAA" refers to a molecule (typically a protein, carbohydrate, lipid or some combination thereof) that is expressed on the surface of a cancer cell, either entirely or as a fragment (e.g., MHC/peptide), and which is useful for the preferential targeting of a pharmacological agent to the cancer cell. In some embodiments, a TAA is a marker expressed by both normal cells and cancer cells, e.g., a lineage marker, e.g., CD19 on B cells. In some embodiments, a TAA is a cell surface molecule that is overexpressed in a cancer cell in comparison to a normal cell, for instance, 1-fold over expression, 2-fold overexpression, 3-fold overexpression or more in comparison to a normal cell. In some embodiments, a TAA is a cell surface molecule that is inappropriately synthesized in the cancer cell, for instance, a molecule that contains deletions, additions or mutations in comparison to the molecule expressed on a normal cell. In some embodiments, a TAA will be expressed exclusively on the cell surface of a cancer cell, entirely or as a fragment (e.g., MHC/peptide), and not synthesized or expressed on the surface of a normal cell. Accordingly, the term "TAA"

encompasses antigens that are specific to cancer cells, sometimes known in the art as tumor-specific antigens ("TSAs").

Universal Light Chain: The term "universal light chain" as used herein in the context of a targeting moiety refers to a light chain polypeptide capable of pairing with the heavy chain region of the targeting moiety and also capable of pairing with other heavy chain regions.

Universal light chains are also known as "common light chains."

VH: The term "VH" refers to the variable region of an immunoglobulin heavy chain of an antibody, including the heavy chain of an scFv or a Fab.

VL: The term "VL" refers to the variable region of an immunoglobulin light chain, including the light chain of an scFv or a Fab.

6.2. IL10 Agonists

The present disclosure provides IL10 agonists comprising an IL10 moiety, an optional multimerization moiety, and an optional targeting moiety.

IL10, also known as human cytokine synthesis inhibitory factor (CSIF), is classified as a type(class)-2 cytokine, a set of cytokines that includes IL19, IL20, IL22, IL24 (Mda-7), and IL26, interferons (e.g., IFNγ, IFNβ, IFNγ) and interferon-like molecules (e.g., limitin, IL28A, IL-28B).

IL10 is a cytokine with pleiotropic effects in immunoregulation and inflammation. It is produced by mast cells, counteracting the inflammatory effect that these cells have at the site of an allergic reaction. While it is capable of inhibiting the synthesis of pro-inflammatory cytokines such as IFNγ, IL2, IL3, TNFα and GM-CSF, IL10 is also stimulatory towards certain T cells and mast cells and stimulates B-cell maturation, proliferation and antibody production. IL10 can block NFκB activity and is involved in the regulation of the JAK-STAT signaling pathway. It also induces the cytotoxic activity of CD8+ T-cells and antibody production by B-cells, and it suppresses macrophage activity and tumor-promoting inflammation. The regulation of CD8+ T-cells is dose-dependent, wherein higher doses induce stronger cytotoxic responses.

Human IL10 is a homodimer. Each monomer is produced as an immature molecule of 178 amino acids, the first 18 of which are a signal peptide that is cleaved upon secretion to produce a mature IL10 containing 160 amino acids. The IL10 monomers within the dimer are non-covalently associated, although each subunit contains two intra-chain disulfide bonds, between residues 12 and 108, and between residues 62 and 114. The monomers dimerize non-covalently to form a V-shaped structure, each half of which consists of a six alpha-helices, four originating from one subunit and two from the other. The IL10 agonists of the disclosure can be in monomeric or multimeric form, e.g., dimers (homo dimers or heterodimers) or high order complexes. For convenience, IL10 agonists that are homodimers (or higher order multimers of the same polypeptide) are described by their constituent monomers; however, upon recombinant expression of the component monomers in a suitable cell line a homodimeric (or higher order multimer) molecule can be produced.

Exemplary IL10 moieties suitable for use in the IL10 agonists of the disclosure are described in Section 6.2.

The IL10 agonist can be a monomer or homodimer of two polypeptide chains, each comprising an IL10 moiety, an Fc moiety (e.g., an Fc domain comprising a CH2 domain and a CH3 domain), an optional hinge moiety, an optional linker moiety, and an optional a targeting moiety.

Accordingly, the IL10 agonist can be a monomer or a homodimer or heterodimer of two polypeptide monomers. The monomer, or each monomer in a dimer, can comprise, from the amino to carboxy terminus:

i) An optional targeting moiety
ii) An optional hinge domain
iii) An Fc domain, e.g., an Fc domain comprising a CH2 domain and a CH3 domain;
iv) A linker moiety; and
v) An IL10 moiety.

The dimerization of the IL10 agonist can occur via disulfide bonds between the hinge domains of the two monomers, disulfide bonds between the Fc domains of the two monomers, non-covalent bonds between the IL10 moieties of the two monomers, or any combination of two or all three of the above. When a monomeric form of the IL10 agonist is desired, the ability of the monomers to dimerize by modifying the IL10 moiety and the Fc domain to reduce their dimerization capability, for example as described in Section 6.3 for the IL10 moiety and Section 6.4 for the Fc domain.

Exemplary Fc moieties are described in Section 6.4 and include Fc domains that confer dimerization capability to the IL10 agonist. Active IL10 is a dimeric molecule and IL10 in vivo has very poor pharmacokinetics, partly due to monomerization in the blood stream. Without being bound by theory, it is believed that the inclusion of an Fc domain and an optional hinge domain, improves serum stability and the pharmacokinetic profile of an IL10 agonist by, inter alia, stabilizing the dimeric structure of IL10.

Sometimes, for convenience, the IL10 moiety and Fc domain moiety and the optional linker between them are referred to herein as an IL10 mutein, although the term "mutein" also encompasses molecules with a targeting moiety. Exemplary targeting moieties are described in Section 6.5 and include an antigen binding domain (e.g., a scFv or Fab) that binds to a tumor associated antigen, binds to a tumor microenvironment antigen, binds to tumor lymphocytes, or binds to MHC-peptide complexes.

It was found that when the IL10 moiety is positioned at the N-terminus of the Fc domain, the resulting recombinant IL10 agonist was truncated at the N- and/or C-terminus. For example, with an N-terminal IL10 moiety, the resulting recombinant IL10 agonist lacked a C-terminal lysine or was truncated at both the N- and C-terminus, having only residues 3-402 of the 403 amino acid full-length construct. This was not observed in IL10 agonists having an IL10 moiety at the C-terminus of the Fc domain. Thus, in some embodiments, the IL10 moiety is positioned at the C-terminus of the Fc domain.

In various embodiments, the IL10 agonist does not comprise (a) a stabilizing moiety such as polyethylene glycol and/or albumin; (b) an antibody variable region (e.g., the variable region of L19, F16, G11 or F8, which are directed against splice isoforms of fibronectin and of tenascin-C; or the variable region of an anti-CD86 antibody); (c) a non-targeting antibody variable region; (d) a non-binding antibody variable region; (e) antibody CDRs; (f) an antibody CH1 domain; (g) an antibody CL domain; (h) another cytokine (e.g., IL4), (i) an Fc domain C-terminal to an IL10 moiety; or (j) any combination of two, three, four, five, six, seven, eight or all of the above. The IL10 agonist can include one or more linker sequences connecting the various components of the molecule, for example the different domains present in a fusion protein. Exemplary linkers are described in Section 6.7.

In other embodiments, the IL10 agonist does not comprise (a) a stabilizing moiety such as a hydrophilic polymer (e.g., polyethylene glycol), albumin, XTEN, PAS, carbohydrate conjugates (e.g., hydroxyethyl starch), glycans (e.g., N- and O-linked glycans), polysialic acid, and/or fatty acids; (b) an antibody variable region (e.g., the variable region of L19, F16, G11 or F8, which are directed against splice isoforms of fibronectin and of tenascin-C; the variable region of an anti-CD86 antibody; or the variable region of anti-PD1 antibody); (c) a non-targeting antibody variable region; (d) a non-binding antibody variable region; (e) antibody CDRs; (f) an antibody CH1 domain; (g) an antibody CL domain; (h) another cytokine (e.g., IL4), (i) an Fc domain C-terminal to an IL10 moiety; (j) a human serum albumin binder or binding domain; or (k) any combination of two, three, four, five, six, seven, eight, nine, or all of the above.

In certain aspects, the IL10 agonists of the disclosure, following administration to a subject (e.g., a patient with cancer or a tumor-bearing mouse), increase the ratio of CD8+ T cells to Treg cells within a tumor. In some embodiments, treatment with IL10 agonists of the disclosure causes an increase in CD8 T cell density within a tumor. The increase can be, for example, at lease a 2-fold increase, at least a 3-fold increase, or at least a 4-fold increase in CD8 T cell density in the tumor.

In certain aspects, treatment with IL10 agonists of the disclosure causes an increase in CD45+ immune cell infiltration in a tumor. The increase in CD45+ immune cell infiltration in the tumor can be, for example, at least a 10% increase. Examples of CD45+ immune cells include, for example, CD4 T cells and myeloid cells (e.g., CD45+ leukocytes).

In some aspects, treatment with IL10 agonists of the disclosure upregulates serum IL12 levels relative to a suitable control not treated with the IL10 agonist or a pharmaceutical composition including the IL10 agonist or relative to the subject's own serum IL12 levels prior to treatment with the IL10 agonist or pharmaceutical composition. Relative to a suitable control or to the subject's own serum IL12 levels prior to treatment, IL10 agonists or the disclosure can upregulate serum IL12 levels by, for example, at least 2-fold, at least 5-fold, at least 10-fold, at least 15-fold, at least 20-fold, at least 25-fold, or at least 30-fold.

In some aspects, treatment with IL10 agonists of the disclosure upregulates serum IL12 levels relative to a suitable control not treated with the IL10 agonist or a pharmaceutical composition including the IL10 agonist or relative to the subject's own serum IL4 levels prior to treatment with the IL10 agonist or pharmaceutical composition. Relative to a suitable control or to the subject's own serum IL4 levels prior to treatment, IL10 agonists or the disclosure can upregulate serum IL4 levels by, for example, at least 2-fold, at least 5-fold, at least 10-fold, at least 15-fold, at least 20-fold, at least 25-fold, or at least 30-fold.

In the IL10 agonists of the disclosure, when the targeting moiety is an antigen binding domain ("ABD") of an antibody, one or both monomers of a dimeric IL10 agonists can bear an ABD, for example in the form of a Fab or an scFv.

The Fc domains can be e.g., IgG1 or IgG4 Fc domains, with or without substitutions that reduce glycosylation and/or effector function as described in Section 6.4.1 and subsections thereof.

In certain aspects, the IL10 agonist comprises an IL10 mutein comprising the amino acid sequence of IL10M1, IL10M2, IL10M3, IL10M4, IL10M5, IL10M6, IL10M7, IL10M8, IL10M9, or IL10M10, or an amino acid sequence having at least 90% or at least 95% sequence identity thereto, with an optional targeting moiety.

Further details of the components of the IL10 agonists of the disclosure are presented below.

6.3. The IL10 Moiety

The IL10 moiety of the IL10 antagonists of the disclosure comprises a wild type or variant IL10 domain.

The IL10 moieties encompass mature human and non-human (e.g., murine, rat, porcine, non-human primate) IL10 polypeptides, including homologs, variants, and fragments thereof, as well as IL10 polypeptides having, for example, a leader sequence (e.g., the signal peptide), and modified versions of the foregoing.

In eukaryotic cells human IL10 is synthesized as a precursor polypeptide of 178 amino acids, from which 18 amino acids are removed to generate mature secreted IL10.

Accordingly, in some embodiments, the IL10 moiety of the disclosure comprises mature human IL10, corresponding to positions S19-N178 of the 178-amino acid precursor sequence, for example the mature human IL10 with the following amino acid sequence or the amino acid sequence shown in Section 7.1.1.

```
                                          (SEQ ID NO: 1)
Ser Pro Gly Gln Gly Thr Gln Ser Glu Asn Ser Cys

Thr His Phe Pro Gly Asn Leu Pro Asn Met Leu Arg

Asp Leu Arg Asp Ala Phe Ser Arg Val Lys Thr Phe

Phe Gln Met Lys Asp Gln Leu Asp Asn Leu Leu Leu

Lys Glu Ser Leu Leu Glu Asp Phe Lys Gly Tyr Leu

Gly Cys Gln Ala Leu Ser Glu Met Ile Gln Phe Tyr

Leu Glu Glu Val Met Pro Gln Ala Glu Asn Gln Asp

Pro Asp Ile Lys Ala His Val Asn Ser Leu Gly Glu

Asn Leu Lys Thr Leu Arg Leu Arg Leu Arg Arg Cys

His Arg Phe Leu Pro Cys Glu Asn Lys Ser Lys Ala

Val Glu Gln Val Lys Asn Ala Phe Asn Lys Leu Gln

Glu Lys Gly Ile Tyr Lys Ala Met Ser Glu Phe Asp

Ile Phe Ile Asn Tyr Ile Glu Ala Tyr Met Thr Met

Lys Ile Arg Asn
```

The sequences of mature murine, porcine, and rat IL10 are disclosed in FIG. 5 of Zdanov et al., 1995, Structure 3(6):591-601, which is incorporated by reference herein in its entirety.

Hence, an "IL10 moiety" encompasses a protein of substantially similar sequence as mature wild type human, murine, porcine, or rat IL10, more preferably a protein of substantially similar sequence as mature wild type human IL10. In various embodiments, the IL10 moiety comprises an amino acid sequence with at least about 90%, at least about 95%, at least about 96%, at least about 97%, at least about 98%, at least about 99% or 100% sequence identity to human, murine, porcine, or rat IL10, e.g., a mature human IL10 sequence comprising amino acid residues S19-N178 of the human IL10 precursor.

In certain embodiments, the IL10 agonists of the disclosure have one or more amino acid modifications, e.g., substitutions, deletions or insertions, in the IL10 moiety as compared to a wild type IL10. The one or more amino acid modifications can be introduced to alter one or more properties of IL10, for example its stability. A particular modified human IL10 molecule with increased stability in monomeric form, which has an insertion of a linker sequence between N116 and K117 (i.e., between helical domains D and E of IL10) that functions as a hinge, has been described by Josephson et al., 2000, J Biol Chem 275:13552-13557. In one embodiment, the sequence inserted between N116 and K117 (or the equivalent position in IL10 of non-human species) is six amino acids and/or comprises the sequence GGGSGG (SEQ ID NO: 2). In one embodiment, the IL10 moiety does not have an insertion of a linker sequence between N116 and K117 (i.e., between helical domains D and E of IL10). In some embodiments, the IL10 moiety does not have any amino acid modifications, e.g., substitutions, deletions or insertions, in the IL10 moiety as compared to a wild type IL10.

Human IL10 contains a potential N-linked glycosylation site at N116 which is located on the surface of the molecule and is preserved in non-human species. Zdanov et al., 1995, Structure 3(6):591-601. Thus, the present disclosure encompasses IL10 molecules with or without N-linked glycans at N116 or the equivalent position in IL10 of other species. This potential N-linked glycosylation site is conserved in rat, murine and porcine IL10. Murine and rat IL10 contain a second potential N-linked glycosylation site near their N terminus (N8 in mIL10 and N1 in rat IL10). The present disclosure encompasses murine or rat IL10 moieties with and without this additional N-linked glycan.

6.4. Fc Domains

The IL10 agonists of the disclosure can include an Fc region derived from any suitable species. In one embodiment the Fc region is derived from a human Fc domain. In preferred embodiments, the IL10 domain is fused to an IgG Fc region (e.g., an IgG1 or an IgG4 Fc region).

The IL10 domain may be fused to the N-terminus or the C-terminus of the IgG Fc region. As shown in the Examples, fusion to the C-terminus of the IgG Fc region maintains the IL10 domain activity to a greater extent than when fused to the N-terminus of the IgG Fc.

One embodiment of the present disclosure is directed to a dimer comprising two Fc-fusion polypeptides created by fusing an IL10 domain to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain bonds form between the Fc moieties to yield the dimer.

The Fc domain can be derived from any suitable class of antibody, including IgA (including subclasses IgA1 and IgA2), IgD, IgE, IgG (including subclasses IgG1, IgG2, IgG3 and IgG4), and IgM. In one embodiment, the Fc domain is derived from an IgG. In one embodiment, the Fc domain is derived from IgG1, IgG2, IgG3 or IgG4. In one embodiment the Fc domain is derived from IgG1. In one embodiment the Fc domain is derived from IgG4.

The two Fc domains within the Fc region can be the same or different from one another. In a native antibody the Fc domains are typically identical, but for the purpose of producing multispecific binding molecules, e.g., the IL10 agonists of the disclosure, the Fc domains might advantageously be different to allow for heterodimerization, as described in Section 6.4.1 below.

In native antibodies, the heavy chain Fc domain of IgA, IgD and IgG is composed of two heavy chain constant domains (CH2 and CH3) and that of IgE and IgM is composed of three heavy chain constant domains (CH2, CH3 and CH4). These dimerize to create an Fc region.

In IL10 agonists of the present disclosure, the Fc region, and/or the Fc domains within it, may be chimeric, combining sequences derived from more than one immunoglobulin isotype. Thus, the Fc region, and/or the Fc domains within it, can comprise heavy chain constant domains from one or more different classes of antibody, for example one, two or three different classes.

In one embodiment the Fc region comprises CH2 and CH3 domains derived from IgG1.

In one embodiment the Fc region comprises CH2 and CH3 domains derived from IgG2.

In one embodiment the Fc region comprises CH2 and CH3 domains derived from IgG3.

In one embodiment the Fc region comprises CH2 and CH3 domains derived from IgG4.

In one embodiment the Fc region comprises a CH4 domain from IgM. The IgM CH4 domain is typically located at the C-terminus of the CH3 domain.

In one embodiment the Fc region comprises CH2 and CH3 domains derived from IgG and a CH4 domain derived from IgM.

In a further embodiment, a chimeric Fc domain can comprise part or all of a CH2 sequence derived from a human IgG1, human IgG2 or human IgG4 CH2 region, and part or all of a CH3 sequence derived from a human IgG1, human IgG2 or human IgG4. A chimeric Fc domain can also contain a chimeric hinge region, as described in Section 6.7.1.1. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the IL10 muteins set forth herein comprises, from N- to C-terminus: [IgG4 CH1]-[IgG4 upper hinge]-[IgG2 lower hinge]-[IgG4 CH2]-[IgG4 CH3]. Another example of a chimeric Fc domain that can be included in any of the antigen-binding molecules set forth herein comprises, from N- to C-terminus: [IgG1 CH1]-[IgG1 upper hinge]-[IgG2 lower hinge]-[IgG4 CH2]-[IgG1 CH3]. These and other examples of chimeric Fc domains that can be included in any of the antigen-binding molecules of the present invention are described in WO 2014/121087. Chimeric Fc regions having these general structural arrangements, and variants thereof, can have altered Fc receptor binding, which in turn affects Fc effector function.

It will be appreciated that the heavy chain constant domains for use in producing an Fc region for the IL10 agonists of the present disclosure may include variants of naturally occurring constant domains. Such variants may comprise one or more amino acid variations compared to wild type constant domains. In one example the Fc region of the present disclosure comprises at least one constant domain that varies in sequence from the wild type constant domain. It will be appreciated that the variant constant domains may be longer or shorter than the wild type constant domain. Preferably the variant constant domains are at least 60% identical or similar to a wild type constant domain. In another example the variant constant domains are at least 70% identical or similar. In another example the variant constant domains are at least 80% identical or similar. In another example the variant constant domains are at least 90% identical or similar. In another example the variant constant domains are at least 95% identical or similar.

IgM and IgA occur naturally in humans as covalent multimers of the common H2L2 antibody unit. IgM occurs as a pentamer when it has incorporated a J-chain, or as a hexamer when it lacks a J-chain. IgA occurs as monomer and dimer forms. The heavy chains of IgM and IgA possess an 18 amino acid extension to the C-terminal constant domain, known as a tailpiece. The tailpiece includes a cysteine residue that forms a disulfide bond between heavy chains in the polymer, and is believed to have an important role in polymerization. The tailpiece also contains a glycosylation site. In certain embodiments, the IL10 agonists of the present disclosure do not comprise a tailpiece.

The Fc domains that are incorporated into the IL10 agonists of the present disclosure may comprise one or more modifications that alter the functional properties of the proteins, for example, binding to Fc-receptors such as FcRn or leukocyte receptors, binding to complement, modified disulfide bond architecture, or altered glycosylation patterns. Exemplary Fc modifications that alter effector function are described in Section 6.4.1.

The Fc domains can also be altered to include modifications that improve manufacturability of asymmetric IL10 agonists, for example by allowing heterodimerization, which is the preferential pairing of non-identical Fc domains over identical Fc domains. Heterodimerization permits the production of IL10 agonists in which different polypeptide components are connected to one another by an Fc region containing Fc domains that differ in sequence. Examples of heterodimerization strategies are exemplified in Section 6.4.1.1.

Alternatively, the Fc domain can be a soluble monomeric Fc domain that has a reduced ability to self-associate. See, e.g., Helm et al., 1996, J. Biol. Chem. 271: 7494-7500 and Ying et al., 2012, J Biol Chem. 287(23):19399-19408. The IL10 agonist can still dimerize through the IL10 moiety. An example of a soluble monomeric Fc domain comprises amino acid substitutions in the positions corresponding to T366 and/or Y407 in CH3, as described in U.S. Patent Publication No. 2019/0367611. In some embodiments, an IL10 agonist is not substituted at the positions corresponding to T366 and/or Y407 in CH3. The monomeric Fc domains can be of any Ig subtype and can include additional substitutions that reduce effector function, as described in Section 6.4.1.

As used herein, the term "Fc region" can include Fc domains with or without hinge sequences. In various embodiments in which the Fc region comprises a heavy chain constant region including a hinge domain, positions 233-236 within the hinge domain may be G, G, G and unoccupied; G, G, unoccupied, and unoccupied; G, unoccupied, unoccupied, and unoccupied; or all unoccupied, with positions numbered by EU numbering. Optionally, the heavy chain constant region comprises from N-terminal to C-terminal the hinge domain, a CH2 domain and a CH3 domain. Optionally, the heavy chain constant region comprises from N-terminal to C-terminal a CH1 domain, the hinge domain, a CH2 domain and a CH3 domain. Optionally, the CH1 region, if present, remainder of the hinge region, if any, CH2 region and CH3 region are the same human isotype. Optionally, the CH1 region, if present, remainder of the hinge region, if any, CH2 region and CH3 region are human IgG1. Optionally, the CH1 region, if present, remainder of the hinge region, if any, CH2 region and CH3 region are human IgG2. Optionally, the CH1 region if present, remainder of the hinge region, if any, CH2 region and CH3 region are human IgG4.

Optionally, the constant region has a CH3 domain modified to reduce binding to protein A.

These and other examples of Fc regions that can be included in any of the IL10 muteins of the present disclosure are described in WO 2016/161010. Exemplary hinge sequences are set forth in Section 6.7.1 and subsections thereof.

It will be appreciated that any of the modifications mentioned above can be combined in any suitable manner to achieve the desired functional properties and/or combined with other modifications to alter the properties of the IL10 agonists.

6.4.1. Fc Domains with Altered Effector Function

In some embodiments, the Fc domain comprises one or more amino acid substitutions that reduces binding to an Fc receptor and/or effector function.

In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of complement dependent cytotoxicity (CDC), antibody-dependent cell-mediated cytotoxicity (ADCC), antibody-dependent cellular phagocytosis (ADCP), and cytokine secretion. In a particular embodiment, the effector function is ADCC.

In one embodiment, the Fc region comprises an amino acid substitution at a position selected from the group of E233, L234, L235, N297, P331 and P329 (numberings according to Kabat EU index). In a more specific embodiment, the Fc region comprises an amino acid substitution at a position selected from the group of L234, L235 and P329 (numberings according to Kabat EU index). In some embodiments, the Fc region comprises the amino acid substitutions L234A and L235A (numberings according to Kabat EU index). In one such embodiment, the Fc region is an IgD Fc region, particularly a human IgD Fc region. In one embodiment, the Fc region comprises an amino acid substitution at position P329. In a more specific embodiment, the amino acid substitution is P329A or P329G, particularly P329G (numberings according to Kabat EU index). In one embodiment, the Fc region comprises an amino acid substitution at position P329 and a further amino acid substitution at a position selected from E233, L234, L235, N297 and P331 (numberings according to Kabat EU index). In a more specific embodiment, the further amino acid substitution is E233P, L234A, L235A, L235E, N297A, N297D or P331S. In particular embodiments, the Fc region comprises amino acid substitutions at positions P329, L234 and L235 (numberings according to Kabat EU index). In more particular embodiments, the Fc region comprises the amino acid mutations L234A, L235A and P329G ("P329G LALA", "PGLALA" or "LALAPG").

Typically, the same one or more amino acid substitution is present in each of the two Fc domains of an Fc region. Thus, in a particular embodiment, each Fc domain of the Fc region comprises the amino acid substitutions L234A, L235A and P329G (Kabat EU index numbering), i.e. in each of the first and the second Fc domains in the Fc region the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In one embodiment, the Fc domain is an IgG1 Fc domain, particularly a human IgG1 Fc In another embodiment, the Fc domain is an IgG4 Fc domain with reduced binding to Fc receptors. Exemplary IgG4 Fc domains with reduced binding to Fc receptors may comprise an amino acid sequence selected from Table 1 below. In some embodiments, the Fc domain includes only the bolded portion of the sequences shown below:

TABLE 1

| Fc Domain | Sequence | SEQ ID NO: |
|---|---|---|
| SEQ ID NO: 1 of WO2014/121087 | Asp Lys Arg Val Glu Ser Lys Tyr Gly Pro Pro Cys Pro Pro Cys Pro Ala Pro Pro Val Ala Gly Pro Ser Val Phe Leu Phe Pro Pro Lys Pro Lys Asp Thr Leu Met Ile Ser Arg Thr Pro Glu Val Thr Cys Val Val Val Asp Val Ser Gln Glu Asp Pro Glu Val Gln Phe Asn Trp Tyr Val Asp Gly Val Glu Val His Asn Ala Lys Thr Lys Pro Arg Glu Glu Gln Phe Asn Ser Thr Tyr Arg Val Val Ser Val Leu Thr Val Leu His Gln Asp Trp Leu Asn Gly Lys Glu Tyr Lys Cys Lys Val Ser Asn Lys Gly Leu Pro Ser Ser Ile Glu Lys Thr Ile Ser Lys Ala Lys Gly Gln Pro Arg Glu Pro Gln Val Tyr Thr Leu Pro Pro Ser Gln Glu Glu Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Arg Leu Thr Val Asp Lys Ser Arg Trp Gln Glu Gly Asn Val Phe Ser Cys Ser Val Met His Glu Ala Leu His Asn His Tyr Thr Gln Lys Ser Leu Ser Leu Ser Leu Gly Lys | 3 |
| SEQ ID NO: 2 of WO2014/121087 | Asp Lys Lys Val Glu Pro Lys Ser Cys Asp Lys Thr His Thr Cys Pro Pro Cys Pro Ala Pro Pro Val Ala Gly Pro Ser Val Phe Leu PhePro Pro Lys Pro Lys Asp Thr Leu Met Ile SerArg Thr Pro Glu Val Thr Cys Val Val Val AspVal Ser Gln Glu Asp Pro Glu Val Gln Phe AsnTrp Tyr Val Asp Gly Val Glu Val His Asn AlaLys Thr Lys Pro Arg Glu Glu Gln Phe Asn SerThr Tyr Arg Val Val Ser Val Leu Thr Val LeuHis Gln Asp Trp Leu Asn Gly Lys Glu Tyr LysCys Lys Val Ser Asn Lys Gly Leu Pro Ser SerIle Glu Lys Thr Ile Ser Lys Ala Lys Gly GlnPro Arg Glu Pro Gln Val Tyr Thr Leu Pro ProSer Arg Asp Glu Leu Thr Lys Asn Gln Val SerLeu Thr Cys Leu Val Lys Gly Phe Tyr Pro SerAsp Ile Ala Val Glu Trp Glu Ser Asn Gly GlnPro Glu Asn Asn Tyr Lys Thr Thr Pro Pro ValLeu Asp Ser Asp Gly Ser Phe Phe Leu Tyr SerLys Leu Thr Val Asp Lys Ser Arg Trp Gln GlnGly Asn Val Phe Ser Cys Ser Val Met His GluAla Leu His Asn His Tyr Thr Gln Lys Ser LeuSer Leu Ser Pro Gly Lys | 4 |
| SEQ ID NO: 30 of WO2014/121087 | Ala Ser Thr Lys Gly Pro Ser Val Phe Pro Leu Ala Pro Ser Ser Lys SerThr Ser Gly Gly Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Gln Thr Tyr Ile Cys Asn Val Asn His Lys Pro Ser Asn Thr Lys Val Asp Lys Lys Val Glu Pro Lys Ser Cys Asp Lys Thr His Thr Cys Pro Pro Cys Pro Ala Pro Pro Val Ala Gly Pro Ser Val Phe Leu Phe Pro Pro Lys Pro Lys Asp Thr Leu Met Ile Ser Arg Thr Pro Glu Val Thr Cys Val Val Val Asp Val Ser Gln Glu Asp Pro Glu Val Gln Phe Asn Trp Tyr Val Asp Gly Val Glu Val His Asn Ala Lys Thr Lys Pro Arg Glu Glu Gln Phe Asn Ser Thr Tyr Arg Val Val Ser Val Leu Thr Val Leu His Gln Asp Trp Leu Asn Gly Lys Glu Tyr Lys Cys Lys Val Ser Asn Lys Gly Leu Pro Ser Ser Ile Glu Lys Thr Ile Ser Lys Ala Lys Gly Gln Pro Arg Glu Pro Gln Val Tyr Thr Leu Pro Pro Ser Arg Asp Glu Leu Thr Lys Asn Gln Val Ser Leu Thr Cys Leu Val Lys Gly | 5 |

TABLE 1-continued

| Fc Domain | Sequence | SEQ ID NO: |
|---|---|---|
| | Phe Tyr Pro Ser Asp Ile Ala Val Glu Trp Glu<br>Ser Asn Gly Gln Pro Glu Asn Asn Tyr Lys Thr<br>Thr Pro Pro Val Leu Asp Ser Asp Gly Ser Phe<br>Phe Leu Tyr Ser Lys Leu Thr Val Asp Lys Ser<br>Arg Trp Gln Gln Gly Asn Val Phe Ser Cys Ser<br>Val Met His Glu Ala Leu His Asn His Tyr Thr<br>Gln Lys Ser Leu Ser Leu Ser Pro Gly Lys | |
| SEQ ID NO: 31 of<br>WO2014/121087 | Ala Ser Thr Lys Gly Pro Ser Val Phe Pro Leu<br>Ala Pro Cys Ser Arg Ser Thr Ser Glu Ser Thr<br>Ala Ala Leu Gly Cys Leu Val Lys Asp Tyr Phe<br>Pro Glu Pro Val Thr Val Ser Trp Asn Ser Gly<br>Ala Leu Thr Ser Gly Val His Thr Phe Pro Ala<br>Val Leu Gln Ser Ser Gly Leu Tyr Ser Leu Ser<br>Ser Val Val Thr Val Pro Ser Ser Ser Leu Gly<br>Thr Lys Thr Tyr Thr Cys Asn Val Asp His Lys<br>Pro Ser Asn Thr Lys Val Asp Lys Arg Val Glu<br>Ser Lys Tyr Gly Pro Pro Cys Pro Pro Cys Pro<br>Ala Pro Pro Val Ala Gly Pro Ser Val Phe Leu<br>Phe Pro Pro Lys Pro Lys Asp Thr Leu Met Ile<br>Ser Arg Thr Pro Glu Val Thr Cys Val Val Val<br>Asp Val Ser Gln Glu Asp Pro Glu Val Gln Phe<br>Asn Trp Tyr Val Asp Gly Val Glu Val His Asn<br>Ala Lys Thr Lys Pro Arg Glu Glu Gln Phe Asn<br>Ser Thr Tyr Arg Val Val Ser Val Leu Thr Val<br>Leu His Gln Asp Trp Leu Asn Gly Lys Glu Tyr<br>Lys Cys Lys Val Ser Asn Lys Gly Leu Pro Ser<br>Ser Ile Glu Lys Thr Ile Ser Lys Ala Lys Gly<br>Gln Pro Arg Glu Pro Gln Val Tyr Thr Leu Pro<br>Pro Ser Gln Glu Glu Met Thr Lys Asn Gln Val<br>Ser Leu Thr Cys Leu Val Lys Gly Phe Tyr Pro<br>Ser Asp Ile Ala Val Glu Trp Glu Ser Asn Gly<br>Gln Pro Glu Asn Asn Tyr Lys Thr Thr Pro Pro<br>Val Leu Asp Ser Asp Gly Ser Phe Phe Leu Tyr<br>Ser Arg Leu Thr Val Asp Lys Ser Arg Trp Gln<br>Glu Gly Asn Val Phe Ser Cys Ser Val Met His<br>Glu Ala Leu His Asn His Tyr Thr Gln Lys Ser<br>Leu Ser Leu Ser Leu Gly Lys | 6 |
| SEQ ID NO: 37 of<br>WO2014M21087 | Ala Ser Thr Lys Gly Pro Ser Val Phe Pro Leu<br>Ala Pro Ser Ser Lys Ser Thr Ser Gly Gly Thr<br>Ala Ala Leu Gly Cys Leu Val Lys Asp Tyr Phe<br>Pro Glu Pro Val Thr Val Ser Trp Asn Ser Gly<br>Ala Leu Thr Ser Gly Val His Thr Phe Pro Ala<br>Val Leu Gln Ser Ser Gly Leu Tyr Ser Leu Ser<br>Ser Val Val Thr Val Pro Ser Ser Ser Leu Gly<br>Thr Gln Thr Tyr Ile Cys Asn Val Asn His Lys<br>Pro Ser Asn Thr Lys Val Asp Lys Lys Val Glu<br>Pro Lys Ser Cys Asp Lys Thr His Thr Cys Pro<br>Pro Cys Pro Ala Pro Pro Val Ala gly Pro Ser<br>Val Phe Leu Phe Pro Pro Lys Pro Lys Asp Thr<br>Leu Met Ile Ser Arg Thr Pro Glu Val Thr Cys<br>Val Val Val Asp Val Ser Gln Glu Asp Pro Glu<br>Val Gln Phe Asn Trp Tyr Val Asp Gly Val Glu<br>Val His Asn Ala Lys Thr Lys Pro Arg Glu Glu<br>Gln Phe Asn Ser Thr Tyr Arg Val Val Ser Val<br>Leu Thr Val Leu His Gln Asp Trp Leu Asn Gly<br>Lys Glu Tyr Lys Cys Lys Val Ser Asn Lys Gly<br>Leu Pro Ser Ser Ile Glu Lys Thr Ile Ser Lys<br>Ala Lys Gly Gln Pro Arg Glu Pro Gln Val Tyr<br>Thr Leu Pro Pro Ser Arg Asp Glu Leu Thr Lys<br>Asn Gln Val Ser Leu Thr Cys Leu Val Lys Gly<br>Phe Tyr Pro Ser Asp Ile Ala Val Glu Trp Glu<br>Ser Asn Gly Gln Pro Glu Asn Asn Tyr Lys Thr<br>Thr Pro Pro Val Leu Asp Ser Asp Gly Ser Phe<br>Phe Leu Tyr Ser Lys Leu Thr Val Asp Lys Ser<br>Arg Trp Gln Gln Gly Asn Val Phe Ser Cys Ser<br>Val Met His Glu Ala Leu His Asn Arg Phe Thr<br>Gln Lys Ser Leu Ser Leu Ser Pro Gly Lys | 7 |
| SEQ ID NO: 38 of<br>WO2014/121087 | Ala Ser Thr Lys Gly Pro Ser Val Phe Pro Leu<br>Ala Pro Cys Ser Arg Ser Thr Ser Glu Ser Thr<br>Ala Ala Leu Gly Cys Leu Val Lys Asp Tyr Phe<br>Pro Glu Pro Val Thr Val Ser Trp Asn Ser Gly<br>Ala Leu Thr Ser Gly Val His Thr Phe Pro Ala<br>Val Leu Gln Ser Ser Gly Leu Tyr Ser Leu Ser<br>Ser Val Val Thr Val Pro Ser Ser Ser Leu Gly | 8 |

TABLE 1-continued

| Fc Domain | Sequence | SEQ ID NO: |
|---|---|---|
| | Thr Lys Thr Tyr Thr Cys Asn Val Asp His Lys<br>Pro Ser Asn Thr Lys Val Asp Lys Arg Val Glu<br>Ser Lys Tyr Gly Pro Pro Cys Pro Pro Cys Pro<br>Ala Pro Pro Val Ala Gly Pro Ser Val Phe Leu<br>Phe Pro Pro Lys Pro Lys Asp Thr Leu Met Ile<br>Ser Arg Thr Pro Glu Val Thr Cys Val Val Val<br>Asp Val Ser Gln Glu Asp Pro Glu Val Gln Phe<br>Asn Trp Tyr Val Asp Gly Val Glu Val His Asn<br>Ala Lys Thr Lys Pro Arg Glu Glu Gln Phe Asn<br>Ser Thr Tyr Arg Val Val Ser Val Leu Thr Val<br>Leu His Gln Asp Trp Leu Asn Gly Lys Glu Tyr<br>Lys Cys Lys Val Ser Asn Lys Gly Leu Pro Ser<br>Ser Ile Glu Lys Thr Ile Ser Lys Ala Lys Gly<br>Gln Pro Arg Glu Pro Gln Val Tyr Thr Leu Pro<br>Pro Ser Gln Glu Glu Met Thr Lys Asn Gln Val<br>Ser Leu Thr Cys Leu Val Lys Gly Phe Tyr Pro<br>Ser Asp Ile Ala Val Glu Trp Glu Ser Asn Gly<br>Gln Pro Glu Asn Asn Tyr Lys Thr Thr Pro Pro<br>Val Leu Asp Ser Asp Gly Ser Phe Phe Leu Tyr<br>Ser Arg Leu Thr Val Asp Lys Ser Arg Trp Gln<br>Glu Gly Asn Val Phe Ser Cys Ser Val Met His<br>Glu Ala Leu His Asn Arg Phe Thr Gln Lys Ser<br>Leu Ser Leu Ser Leu Gly Lys | |

In a particular embodiment, the IgG4 with reduced effector function comprises the bolded portion of the amino acid sequence of SEQ ID NO:31 of WO2014/121087 reproduced above (amino acids 99 to 326 of SEQ ID NO: 6, or SEQ ID NO: 31; said bolded sequence sometimes referred to herein as IgG4s), or an amino acid sequence having at least 95%, at least 96%, at least 97%, at least 98%, at least 99%, or 100% sequence identity thereto. In other embodiments, the IgG4 with reduced effector function comprises an amino acid sequence with at least 95%, at least 96%, at least 97%, at least 98%, at least 99%, or 100% sequence identity to SEQ ID NO:31 of WO 2014/121087 (SEQ ID NO: 6).

For IL10 agonists of the disclosure that are heterodimers, it is possible to incorporate a combination of the variant IgG4 Fc sequences set forth above, for example an Fc region comprising a combination of SEQ ID NO:30 (or the bolded portion thereof) and SEQ ID NO:37 (or the bolded portion thereof) or an Fc region comprising a combination of SEQ ID NO:31 (or the bolded portion thereof) and SEQ ID NO:38 (or the bolded portion thereof), in each case of WO2014/121087.

In a particular embodiment, the Fc domain comprises the amino acid sequence designated in Section 7.1.1 as hIgG4s (SEQ ID NO: 31), or an amino acid sequence having at least 95%, at least 96%, at least 97%, at least 98%, at least 99%, or 100% sequence identity thereto.

In another particular embodiment, the Fc domain comprises the amino acid sequence designated in Section 7.1.1 as hIgG1 (SEQ ID NO: 32), or an amino acid sequence having at least 95%, at least 96%, at least 97%, at least 98%, at least 99%, or 100% sequence identity thereto. hIgG1 (SEQ ID NO:32) is a variant IgG1-based Fc sequence comprising D265A, N297A mutations (EU numbering) to reduce effector function.

6.4.1.1. Fc Heterodimerization Variants

Certain IL10 agonists entail dimerization between two Fc domains that, unlike a native immunoglobulin, are operably linked to non-identical N-terminal regions, e.g., one Fc domain connected to a Fab and the other Fc domain connected to an IL10 moiety. Inadequate heterodimerization of two Fc regions to form an Fc domain has can be an obstacle for increasing the yield of desired heterodimeric molecules and represents challenges for purification. A variety of approaches available in the art can be used in for enhancing dimerization of Fc domains that might be present in the IL10 agonists of the disclosure, for example as disclosed in EP 1870459A1; U.S. Pat. Nos. 5,582,996; 5,731,168; 5,910,573; 5,932,448; 6,833,441; 7,183,076; U.S. Patent Application Publication No. 2006204493A1; and PCT Publication No. WO 2009/089004A1.

The present disclosure provides IL10 agonists comprising Fc heterodimers, i.e., Fc regions comprising heterologous, non-identical Fc domains. Typically, each Fc domain in the Fc heterodimer comprises a CH3 domain of an antibody. The CH3 domains are derived from the constant region of an antibody of any isotype, class or subclass, and preferably of IgG (IgG1, IgG2, IgG3 and IgG4) class, as described in the preceding section.

Heterodimerization of the two different heavy chains at CH3 domains give rise to the desired IL10 agonist, while homodimerization of identical heavy chains will reduce yield of the desired IL10 agonist. Thus, in a preferred embodiment, the polypeptides that associate to form an IL10 agonist of the disclosure will contain CH3 domains with modifications that favor heterodimeric association relative to unmodified Fc domains.

In a specific embodiment said modification promoting the formation of Fc heterodimers is a so-called "knob-into-hole" or "knob-in-hole" modification, comprising a "knob" modification in one of the Fc domains and a "hole" modification in the other Fc domain. The knob-into-hole technology is described e.g., in U.S. Pat. Nos. 5,731,168; 7,695,936; Ridgway et al., 1996, Prot Eng 9:617-621, and Carter, 2001, Immunol Meth 248:7-15. Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine).

Accordingly, in some embodiments, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable. Preferably said amino acid residue having a larger side chain volume is selected from the group consisting of arginine (R), phenylalanine (F), tyrosine (Y), and tryptophan (W). Preferably said amino acid residue having a smaller side chain volume is selected from the group consisting of alanine (A), serine (S), threonine (T), and valine (V). The protuberance and cavity can be made by altering the nucleic acid encoding the polypeptides, e.g., by site-specific mutagenesis, or by peptide synthesis. An exemplary substitution is Y470T.

In a specific such embodiment, in the first Fc domain the threonine residue at position 366 is replaced with a tryptophan residue (T366W), and in the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numbering according to Kabat EU index). In a further embodiment, in the first Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second Fc domain additionally the tyrosine residue at position 349 is replaced by a cysteine residue (Y349C) (numbering according to Kabat EU index). In a particular embodiment, the first Fc domain comprises the amino acid substitutions S354C and T366W, and the second Fc domain comprises the amino acid substitutions Y349C, T366S, L368A and Y407V (numbering according to Kabat EU index).

In some embodiments, electrostatic steering (e.g., as described in Gunasekaran et al., 2010, J Biol Chem 285(25): 19637-46) can be used to promote the association of the first and the second Fc domain of the Fc region.

As an alternative, or in addition, to the use of Fc domains that are modified to promote heterodimerization, an Fc domain can be modified to allow a purification strategy that enables selections of Fc heterodimers. In one such embodiment, one polypeptide comprises a modified Fc domain that abrogates its binding to Protein A, thus enabling a purification method that yields a heterodimeric protein. See, for example, U.S. Pat. No. 8,586,713. As such, the IL10 agonists comprise a first CH3 domain and a second Ig CH3 domain, wherein the first and second Ig CH3 domains differ from one another by at least one amino acid, and wherein at least one amino acid difference reduces binding of the IL10 agonist to Protein A as compared to a corresponding IL10 agonist lacking the amino acid difference. In one embodiment, the first CH3 domain binds Protein A and the second CH3 domain contains a mutation/modification that reduces or abolishes Protein A binding such as an H95R modification (by IMGT exon numbering; H435R by EU numbering). The second CH3 may further comprise a Y96F modification (by IMGT; Y436F by EU). This class of modifications is referred to herein as "star" mutations.

6.5. The Targeting Moiety

The incorporation of targeting moieties in the IL10 agonists of the disclosure permits the delivery of high concentrations of IL10 into the tumor microenvironment or to tumor reactive lymphocytes, particularly CD8+ T lymphocytes, where they can exert a localized effect.

Suitable targeting moiety formats are described in Section 6.5.2. The targeting moiety is preferably an antigen binding moiety, for example an antibody or an antigen-binding portion of an antibody, e.g., an scFv, as described in Section 6.5.2.1, or a Fab, as described in Section 6.5.2.2.

The antibodies and antigen-binding portions generally bind to specific antigenic determinants and are able to direct the IL10 agonist to a target site, for example to a specific type of tumor cell or tumor stroma that bears the antigenic determinant. Exemplary target molecules recognized by the targeting moieties of the disclosure are described in Section 6.5.1.

6.5.1. Target Molecules

The target molecules recognized by the targeting moieties of the IL10 agonists of the disclosure are generally found, for example, on the surfaces of activated T cells, on the surfaces of tumor cells, on the surfaces of virus-infected cells, on the surfaces of other diseased cells, free in blood serum, in the extracellular matrix (ECM), or immune cells present in the target site, e.g., tumor reactive lymphocytes, or peptides in a peptide-MHC complex. Where the immune cells are exogenously administered (e.g., chimeric antigen receptor ("CAR") expressing T cells), the targeting moiety can recognize the chimeric antigen receptor or another molecule found on the surface of the CAR T cells.

Exemplary target molecules are Fibroblast Activation Protein (FAP), the A1 domain of Tenascin-C (TNC A1), the A2 domain of Tenascin-C (TNC A2), the Extra Domain B of Fibronectin (EDB), the Melanoma-associated Chondroitin Sulfate Proteoglycan (MCSP), MART-1/Melan-A, gp100, Dipeptidyl peptidase IV (DPPIV), adenosine deaminase-binding protein (ADAbp), cyclophilin b, colorectal associated antigen (CRC)-C017-1A/GA733, Carcinoembryonic Antigen (CEA) and its immunogenic epitopes CAP-1 and CAP-2, etv6, amli, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p2iras, RCAS1, α-fetoprotein, E-cadherin, α-catenin, β-catenin and γ-catenin, p120ctn, gp100 Pmeli17, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, c-erbB-2, Her2, EGFR, IGF-1R, CD2 (T-cell surface antigen), CD3 (heteromultimer associated with the TCR), CD22 (B-cell receptor), CD23 (low affinity IgE receptor), CD30 (cytokine receptor), CD33 (myeloid cell surface antigen), CD40 (tumor necrosis factor receptor), IL-6R-(IL6 receptor), CD20, MCSP, PDGFpR (β-platelet-derived growth factor receptor), ErbB2 epithelial cell adhesion molecule (EpCAM), EGFR variant III (EGFRvIII), CD19, disialoganglioside GD2, ductal-epithelial mucine, gp36, TAG-72, glioma-associated antigen, β-human chorionic gonadotropin, alphafetoprotein (AFP), lectin-reactive AFP, thyroglobulin, MN-CA IX, human telomerase reverse transcriptase, RU1, RU2 (AS), intestinal carboxyl esterase, mut hsp70-2, M-CSF, prostase, prostase specific antigen (PSA), PAP, LAGA-1a, p53, prostein, PSMA, surviving and telomerase, prostate-carcinoma tumor antigen-1 (PCTA-1), ELF2M, neutrophil elastase, ephrin B2, insulin growth factor (IGF1)-I, IGF-II, IGFI receptor, 5T4, ROR1, Nkp30, NKG2D, tumor stromal antigens, the extra domain A (EDA) and extra domain B (EDB) of fibronectin and the A1 domain of tenascin-C (TnC A1).

In some embodiments, the targeting moiety binds to an MHC-peptide complex or the peptide in an MHC-peptide complex, for example a tumor neoantigen. Some tumor neoantigens are viral antigens.

Non-limiting examples of viral antigens include an EBV antigen (e.g., Epstein-Barr virus LMP-1), a hepatitis C virus antigen (e.g., hepatitis C virus E2 glycoprotein), an HIV antigen (e.g., HIV gp160, and HIV gp120); a CMV antigen; a HPV-specific antigen, or an influenza virus antigen (e.g., influenza virus hemagglutinin). Particular embodiments of tumor neoantigens that can be bound by the targeting moieties of the disclosure are LCMV derived peptide gp33-41, APF (126-134), BALF(276-284), CEA (571-579), CMV pp65 (495-503), FLU-M1 (58-66), gp100 (154-162), gp100 (209-217), HBV Core (18-27), Her2/neu (369-377; V2v9); HPV E7 (11-20), KLK4 (11-19), LMP1 (125-133), MAG-A3 (112-120), NYESO1 (157-165, C165A), NYESO1 (157-165, C165V), p54 WT (264-272), PAP-3 (136-143), PSMA (4-12), PSMA (135-145), Survivin (96-014), Tyrosinase (369-377, 371D), and WT1 (126-134).

Non-limiting examples of ECM antigens include syndecan, heparanase, integrins, osteopontin, link, cadherins, laminin, laminin type EGF, lectin, fibronectin, notch, tenascin, collagen and matrixin.

Other target molecules are cell surface molecules of tumor or viral lymphocytes, for example T-cell co-stimulatory proteins such as CD27, CD28, 4-1BB (CD137), OX40, CD30, CD40, ICOS, lymphocyte function-associated antigen-1 (LFA-1), CD2, CD7, LIGHT, NKG2C, and B7-H3.

In particular embodiments, the target molecules are checkpoint inhibitors, for example CTLA-4, PD1, PDL1, PDL2, B7-H3, B7-H4, BTLA, HVEM, TIM3, GAL9, LAG3, VISTA, KIR, 2B4, CD160, CGEN-15049, CHK1, CHK2.

In some embodiments, the IL10 agonist does not comprise a targeting moiety, such as but not limited to a targeting moiety that binds to a tumor associated antigen, binds to a tumor microenvironment antigen, binds to a cell surface molecule of tumor reactive lymphocytes, or binds to a checkpoint inhibiter.

In various embodiments, the IL10 agonist does not comprise a PD1-binding targeting domain.

6.5.2. Targeting Moiety Format

In certain aspects, the targeting moiety can be any type of antibody or fragment thereof that retains specific binding to an antigenic determinant. In one embodiment the antigen binding moiety is a full-length antibody. In one embodiment the antigen binding moiety is an immunoglobulin molecule, particularly an IgG class immunoglobulin molecule, more particularly an $IgG_1$ or $IgG_4$ immunoglobulin molecule. Antibody fragments include, but are not limited to, VH (or $V_H$) fragments, VL (or $V_L$) fragments, Fab fragments, $F(ab')_2$ fragments, scFv fragments, Fv fragments, minibodies, diabodies, triabodies, and tetrabodies. Antibody fragments can be advantageously incorporated N-terminal to the Fc domain in the IL10 agonists of the disclosure.

6.5.2.1. scFv

Single chain Fv or "scFv" antibody fragments comprise the VH and VL domains of an antibody in a single polypeptide chain, are capable of being expressed as a single chain polypeptide, and retain the specificity of the intact antibodies from which they are derived. Generally, the scFv polypeptide further comprises a polypeptide linker between the VH and VL domain that enables the scFv to form the desired structure for target binding. Examples of linkers suitable for connecting the VH and VL chains of an scFv are the linkers identified in Section 6.7.

Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The scFv can comprise VH and VL sequences from any suitable species, such as murine, human or humanized VH and VL sequences.

To create an scFv-encoding nucleic acid, the VH and VL-encoding DNA fragments are operably linked to another fragment encoding a linker, e.g., encoding any of the linkers described in Section 6.7 (typically a repeat of a sequence containing the amino acids glycine and serine, such as the amino acid sequence (Gly4~Ser)$_3$ (SEQ ID NO: 53), such that the VH and VL sequences can be expressed as a contiguous single-chain protein, with the VL and VH regions joined by the flexible linker (see, e.g., Bird et al., 1988, Science 242:423-426; Huston et al., 1988, Proc. Natl. Acad. Sci. USA 85:5879-5883; McCafferty et al., 1990, Nature 348:552-554).

6.5.2.2. Fab

Fab domains were traditionally produced from by proteolytic cleavage of immunoglobulin molecules using enzymes such as papain. In the IL10 agonists of the disclosure, the Fab domains are typically recombinantly expressed as part of the IL10 agonist.

The Fab domains can comprise constant domain and variable region sequences from any suitable species, and thus can be murine, chimeric, human or humanized.

Fab domains typically comprise a CH domain attached to a VH domain which pairs with a CL domain attached to a VL domain. In a wild-type immunoglobulin, the VH domain is paired with the VL domain to constitute the Fv region, and the CH1 domain is paired with the CL domain to further stabilize the binding module. A disulfide bond between the two constant domains can further stabilize the Fab domain.

For the IL10 agonists of the disclosure, particularly when the IL10 contains two different Fab domains and the light chain is not a common or universal light chain, it is advantageous to use Fab heterodimerization strategies to permit the correct association of Fab domains belonging to the same Fab and minimize aberrant pairing of Fab domains belonging to different Fabs. For example, the Fab heterodimerization strategies shown in Table 2 below can be used:

TABLE 2

Fab Heterodimerization Strategies

| STRATEGY | VH | CH1 | VL | CL | REFERENCE |
|---|---|---|---|---|---|
| CrossMabCH1-CL | WT | CL domain | WT | CH1 domain | Schaefer et al., 2011, Cancer Cell 2011; 20:472-86; PMID:22014573. |
| orthogonal Fab VHVRD1CH1CRD2-VLVRD1CACRD2 | 39K, 62E | H172A, F174G | 1R, 38D, (36F) | L135Y, S176W | Lewis et al., 2014, Nat Biotechnol 32:191-8 |
| orthogonal Fab VHVRD2CH1wt-VLVRD2CAwt | 39Y | WT | 38R | WT | Lewis et al., 2014, Nat Biotechnol 32:191-8 |
| TCR CαCβ | 39K | TCR Cα | 38D | TCR Cβ | Wu et al., 2015, MAbs 7:364-76 |
| CR3 | WT | T192E | WT | N137K, S114A | Golay at al., 2016, J Immunol 196:3199-211. |
| MUT4 | WT | L143Q, S188V | WT | V133T, S176V | Golay at al., 2016, J Immunol 196:3199-211. |
| DuetMab | WT | F126C | WT | S121C | Mazor et al., 2015, MAbs 7:377-89; Mazor et al., 2015, MAbs 7:461-669. |
| Domain exchanged | WT | CH3 + knob or hole mutation | WT | CH3 + hole or knob mutation | Wozniak-Knopp et al., 2018, PLoSONE13(4):e0195442 |

Accordingly, in certain embodiments, correct association between the two polypeptides of a Fab is promoted by exchanging the VL and VH domains of the Fab for each other or exchanging the CH1 and CL domains for each other, e.g., as described in WO 2009/080251.

Correct Fab pairing can also be promoted by introducing one or more amino acid modifications in the CH1 domain and one or more amino acid modifications in the CL domain of the Fab and/or one or more amino acid modifications in the VH domain and one or more amino acid modifications in the VL domain. The amino acids that are modified are typically part of the VH:VL and CH1:CL interface such that the Fab components preferentially pair with each other rather than with components of other Fabs.

In one embodiment, the one or more amino acid modifications are limited to the conserved framework residues of the variable (VH, VL) and constant (CH1, CL) domains as indicated by the Kabat numbering of residues. Almagro, 2008, Frontiers In Bioscience 13:1619-1633 provides a definition of the framework residues on the basis of Kabat, Chothia, and IMGT numbering schemes.

In one embodiment, the modifications introduced in the VH and CH1 and/or VL and CL domains are complementary to each other. Complementarity at the heavy and light chain interface can be achieved on the basis of steric and hydrophobic contacts, electrostatic/charge interactions or a combination of the variety of interactions. The complementarity between protein surfaces is broadly described in the literature in terms of lock and key fit, knob into hole, protrusion and cavity, donor and acceptor etc., all implying the nature of structural and chemical match between the two interacting surfaces.

In one embodiment, the one or more introduced modifications introduce a new hydrogen bond across the interface of the Fab components. In one embodiment, the one or more introduced modifications introduce a new salt bridge across the interface of the Fab components. Exemplary substitutions are described in WO 2014/150973 and WO 2014/082179, the contents of which are hereby incorporated by reference.

In some embodiments, the Fab domain comprises a 192E substitution in the CH1 domain and 114A and 137K substitutions in the CL domain, which introduces a salt-bridge between the CH1 and CL domains (see, e.g., Golay et al., 2016, J Immunol 196:3199-211).

In some embodiments, the Fab domain comprises a 143Q and 188V substitutions in the CH1 domain and 113T and 176V substitutions in the CL domain, which serves to swap hydrophobic and polar regions of contact between the CH1 and CL domain (see, e.g., Golay et al., 2016, J Immunol 196:3199-211).

In some embodiments, the Fab domain can comprise modifications in some or all of the VH, CH1, VL, CL domains to introduce orthogonal Fab interfaces which promote correct assembly of Fab domains (Lewis et al., 2014 Nature Biotechnology 32:191-198). In an embodiment, 39K, 62E modifications are introduced in the VH domain, H172A, F174G modifications are introduced in the CH1 domain, 1 R, 38D, (36F) modifications are introduced in the VL domain, and L135Y, S176W modifications are introduced in the CL domain. In another embodiment, a 39Y modification is introduced in the VH domain and a 38R modification is introduced in the VL domain.

Fab domains can also be modified to replace the native CH1:CL disulfide bond with an engineered disulfide bond, thereby increasing the efficiency of Fab component pairing. For example, an engineered disulfide bond can be introduced by introducing a 126C in the CH1 domain and a 121 C in the CL domain (see, e.g., Mazor et al., 2015, MAbs 7:377-89).

Fab domains can also be modified by replacing the CH1 domain and CL domain with alternative domains that promote correct assembly. For example, Wu et al., 2015, MAbs 7:364-76, describes substituting the CH1 domain with the constant domain of the a T cell receptor and substituting the CL domain with the b domain of the T cell receptor, and pairing these domain replacements with an additional charge-charge interaction between the VL and VH domains by introducing a 38D modification in the VL domain and a 39K modification in the VH domain.

In lieu of, or in addition to, the use of Fab heterodimerization strategies to promote correct VH-VL pairings, the VL of common light chain (also referred to as a universal light chain) can be used for each Fab VL region of an IL10 agonist of the disclosure. In various embodiments, employing a common light chain as described herein reduces the number of inappropriate species of IL10 agonists as compared to employing original cognate VLs. In various embodiments, the VL domains of the IL10 agonists are identified from monospecific antibodies comprising a common light chain. In various embodiments, the VH regions of the IL10 agonists comprise human heavy chain variable gene segments that are rearranged in vivo within mouse B cells that have been previously engineered to express a limited human light chain repertoire, or a single human light chain, cognate with human heavy chains and, in response to exposure with an antigen of interest, generate an antibody repertoire containing a plurality of human VHs that are cognate with one or one of two possible human VLs, wherein the antibody repertoire specific for the antigen of interest. Common light chains are those derived from a rearranged human VK1-39JK5 sequence or a rearranged human VK3-20JK1 sequence, and include somatically mutated (e.g., affinity matured) versions. See, for example, U.S. Pat. No. 10,412,940.

6.6. Stabilization Moieties

The IL10 agonists of the disclosure can comprise a stabilization moiety that can extend the molecule's serum half-life in vivo. Serum half-life is often divided into an alpha phase and a beta phase. Either or both phases may be improved significantly by addition of an appropriate stabilization moiety. For example, the stabilization moiety can increase the serum half-life of the IL10 agonist by more than 5, 10, 20, 30, 40, 50, 60, 70, 80, 90, 100, 120, 150, 200, 400, 600, 800, 1000% or more relative to a corresponding IL10 agonist not containing the stabilization moiety. For the purpose of this disclosure, serum half-life can refer to the half-life in humans or other mammals (e.g., mice or non-human primates). Further, it is recognized the inclusion of an Fc domain in an IL10 agonist extends the half-life of the IL10 moiety; in the context of this disclosure the term "stabilization moiety" refers to a moiety other than an Fc domain/Fc region.

Wild type IL10 has a serum half-life of less than 30 minutes. The IL10 agonists of the disclosure have preferably a serum half-life in humans and/or mice of at least about 2 hours, at least about 4 hours, at least about 6 hours, or at least about 8 hours. In some embodiments, the IL10 agonists of the disclosure have a serum half-life of at least 10 hours, at least 12 hours, at least 15 hours, at least 18 hours, at least 24 hours, at least 36 hours, at least 48 hours, at least 60 hours, or at least 72 hours.

Stabilization moieties, include polyoxyalkylene moieties (e.g., polyethylene glycol), sugars (e.g., sialic acid), and well-tolerated protein moieties (e.g., Fc and fragments and variants thereof, transferrin, or serum albumin).

Other stabilization moieties that can be used in the IL10 agonists of the disclosure include those described in Kontermann et al., 2011, Current Opinion in Biotechnology 22:868-76. Such Stabilization moieties include, but are not limited to, human serum albumin fusions, human serum albumin conjugates, human serum albumin binders (e.g., Adnectin PKE, AlbudAb, ABD), XTEN fusions, PAS fusions (i.e., recombinant PEG mimetics based on the three amino acids proline, alanine, and serine), carbohydrate conjugates (e.g., hydroxyethyl starch (HES)), glycosylation, polysialic acid conjugates, and fatty acid conjugates.

Accordingly, in some embodiments the disclosure provides an IL10 agonist comprising a stabilization moiety that is a polymeric sugar.

Serum albumin can also be engaged in half-life extension through modules with the capacity to non-covalently interact with albumin. Accordingly, the IL10 agonists of the disclosure can include as a stabilization moiety an albumin-binding protein. The albumin-binding protein can be either conjugated or genetically fused to one or more other components of the IL10 agonist of the disclosure. Proteins with albumin-binding activity are known from certain bacteria. For example, streptococcal protein G contains several small albumin-binding domains composed of roughly 50 amino acid residues (6 kDa). Additional examples of serum albumin binding proteins such as those described in U.S. Publication Nos. 2007/0178082 and 2007/0269422. Fusion of an albumin binding domain to a protein results in a strongly extended half-life (see Kontermann et al., 2011, Current Opinion in Biotechnology 22:868-76).

In other embodiments the stabilization moiety is human serum albumin. In other embodiments, the stabilization moiety is transferrin.

In yet other embodiments, the stabilization moiety is a polyethylene glycol moiety or another polymer, as described in Section 6.6.1 below.

The stabilization moiety can be connected to one or more other components of the IL10 agonists of the disclosure via a linker, for example as described in Section 6.7 below.

In certain embodiments, the IL10 agonist is not conjugated to polyethylene glycol, other hydrophilic polymers, albumin, a human serum albumin binder, an XTEN, a PAS, a polysialic acid, and/or a hydroxyethyl starch. In some embodiments, the IL10 agonist does not comprise an N-linked glycan and/or an O-linked glycan. In a particular embodiment, the IL10 agonist lacks any stabilizing moiety.

6.6.1. Polyethylene Glycol

In some embodiments, the IL10 agonist comprises polyethylene glycol (PEG) or another hydrophilic polymer as a stabilization moiety, for example a copolymer of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), dextran or poly(n-vinyl pyrrolidone)polyethylene glycol, a propropylene glycol homopolymer, a prolypropylene oxide/ethylene oxide co-polymer, a polyoxyethylated polyol (e.g., glycerol), polyvinyl alcohol, and mixtures thereof. The polymer may be of any molecular weight, and may be branched or unbranched.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O(CH$_2$CH$_2$O)$_n$-1CH$_2$CH$_2$OH, where n is 20 to 2300 and X is H or a terminal modification, e.g., a C$_{1-4}$ alkyl. PEG can contain further chemical groups which are necessary for binding reactions, which result from the chemical synthesis of the molecule; or which act as a spacer for optimal distance of parts of the molecule. In addition, such a PEG can consist of one or more PEG side-chains which are linked together. PEGs with more than one PEG chain are called multiarmed or branched PEGs. Branched PEGs are described in, for example, European Application No. 473084A and U.S. Pat. No. 5,932,462.

One or more PEG molecules can be attached at different positions on the IL10 agonist, and such attachment may be achieved by reaction with amines, thiols or other suitable reactive groups. The amine moiety may be, for example, a primary amine found at the N-terminus of the IL10 agonist (or a component thereof) or an amine group present in an amino acid, such as lysine or arginine.

PEGylation can be achieved by site-directed PEGylation, wherein a suitable reactive group is introduced into the protein to create a site where PEGylation preferentially occurs. In some embodiments, the IL10 agonist is modified to introduce a cysteine residue at a desired position, permitting site-directed PEGylation on the cysteine. Mutations can be introduced into the coding sequence of an IL10 agonist of the disclosure to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or three dimensional structure. The three dimensional structure of IL10 is described in, e.g., Wang et al., 2005, Science 310(5751): 1159-63, and can be used to identify surface-exposed residues that can be mutated to cysteine. The mutations can be chosen to avoid disrupting the interaction between IL10 and one or more of its receptors. PEGylation of cysteine residues may be carried out using, for example, PEG-maleimide, PEG-vinylsulfone, PEG-iodoacetamide, or PEG-orthopyridyl disulfide.

The PEG is typically activated with a suitable activating group appropriate for coupling to a desired site on the polypeptide. PEGylation methods are well-known in the art and further described in Zalipsky et al., "Use of Functionalized Poly(Ethylene Glycols) for Modification of Polypeptides" in Polyethylene Glycol Chemistry: Biotechnical and Biomedical Applications, J. M. Harris, Plenus Press, New York (1992), and in Zalipsky, 1995, Advanced Drug Reviews 16: 157-182.

PEG moieties may vary widely in molecular weight and may be branched or linear. Typically, the weight-average molecular weight of PEG is from about 100 Daltons to about 150,000 Daltons. Exemplary weight-average molecular weights for PEG include about 20,000 Daltons, about 40,000 Daltons, about 60,000 Daltons and about 80,000 Daltons. In certain embodiments, the molecular weight of PEG is 40,000 Daltons. Branched versions of PEG having a total molecular weight of any of the foregoing can also be used. In some embodiments, the PEG has two branches. In other embodiments, the PEG has four branches. In another embodiment, the PEG is a bis-PEG (NOF Corporation, DE-200MA), in which two IL10-containing polypeptide chains are conjugated.

Conventional separation and purification techniques known in the art can be used to purify PEGylated IL10 agonists, such as size exclusion (e.g., gel filtration) and ion exchange chromatography. Products can also be separated using SDS-PAGE. Products that can be separated include mono-, di-, tri-, poly- and un-PEGylated IL10 agonists, as well as free PEG. The percentage of mono-PEG conjugates can be controlled by pooling broader fractions around the elution peak to increase the percentage of mono-PEG in the composition. About 90% mono-PEG conjugates represent a good balance of yield and activity.

In some embodiments, the PEGylated IL10 agonists will preferably retain at least about 25%, 50%, 60%, 70%, 80%, 85%, 90%, 95% or 100% of the biological activity associated with the unmodified IL10 agonist. In some embodiments, biological activity refers to its ability to bind to IL10R1, as assessed by $K_D$, $k_{on}$, or $k_{off}$.

6.7. Linkers

In certain aspects, the present disclosure provides IL10 agonist in which two or more components of an IL10 agonist are connected to one another by a peptide linker. By way of example and not limitation, linkers can be used to connect (a) an IL10 moiety and an Fc domain; (b) an IL10 moiety and a targeting moiety; (c) an Fc domain and a targeting moiety (e.g., a Fab domain or an scFv); (d) different domains within a targeting moiety (e.g., the VH and VL domains in a scFv).

A peptide linker can range from 2 amino acids to 60 or more amino acids, and in certain aspects a peptide linker ranges from 3 amino acids to 50 amino acids, from 4 to 30 amino acids, from 5 to 25 amino acids, from 10 to 25 amino acids, 10 amino acids to 60 amino acids, from 12 amino acids to 20 amino acids, from 20 amino acids to 50 amino acids, or from 25 amino acids to 35 amino acids in length.

Charged (e.g., charged hydrophilic linkers) and/or flexible linkers are particularly preferred.

Examples of flexible linkers that can be used in the IL10 agonists of the disclosure include those disclosed by Chen et al., 2013, Adv Drug Deliv Rev. 65(10): 1357-1369 and Klein et al., 2014, Protein Engineering, Design & Selection 27(10): 325-330. Particularly useful flexible linkers are repeats of glycines and serines, e.g., a monomer or multimer of $G_nS$ (SEQ ID NO: 9) or $SG_n$ (SEQ ID NO: 10), where n is an integer from 1 to 10, e.g., 1 2, 3, 4, 5, 6, 7, 8, 9 or 10. In one embodiment, the linker is a monomer or multimer of repeat of $G_4S$ (SEQ ID NO: 51) e.g., $(GGGGS)_n$ (SEQ ID NO: 11).

6.7.1. Hinge Sequences

In other embodiments, the IL10 agonist of the disclosure comprise a linker that is a hinge region. In particular, where an IL10 agonist contains an immunoglobulin-based targeting moiety, the hinge can be used to connect the targeting moiety, e.g., a Fab domain, to a multimerization domain, e.g., an Fc domain. Even in the absence of a targeting moiety, a hinge sequence can be utilized to stabilize the IL10 agonist dimer The hinge region can be a native or a modified hinge region. Hinge regions are typically found at the N-termini of Fc regions.

A native hinge region is the hinge region that would normally be found between Fab and Fc domains in a naturally occurring antibody. A modified hinge region is any hinge that differs in length and/or composition from the native hinge region. Such hinges can include hinge regions from other species, such as human, mouse, rat, rabbit, shark, pig, hamster, camel, llama or goat hinge regions. Other modified hinge regions may comprise a complete hinge region derived from an antibody of a different class or subclass from that of the heavy chain Fc region. Alternatively, the modified hinge region may comprise part of a natural hinge or a repeating unit in which each unit in the repeat is derived from a natural hinge region. In a further alternative, the natural hinge region may be altered by converting one or more cysteine or other residues into neutral residues, such as serine or alanine, or by converting suitably placed residues into cysteine residues. By such means the number of cysteine residues in the hinge region may be increased or decreased. Other modified hinge regions may be entirely synthetic and may be designed to possess desired properties such as length, cysteine composition and flexibility.

A number of modified hinge regions have already been described for example, in U.S. Pat. No. 5,677,425, WO 99/15549, WO 2005/003170, WO 2005/003169, WO 2005/003170, WO 98/25971 and WO 2005/003171 and these are incorporated herein by reference.

In various embodiments, positions 233-236 within a hinge domain may be G, G, G and unoccupied; G, G, unoccupied, and unoccupied; G, unoccupied, unoccupied, and unoccupied; or all unoccupied, with positions numbered by EU numbering.

In some embodiments, the IL10 muteins of the disclosure comprise a modified hinge domain that reduces binding affinity for an Fcγ receptor relative to a wild-type hinge domain of the same isotype (e.g., human IgG1 or human IgG4).

In one embodiment, the Fc region of one or both chains of a dimeric IL10 agonist of the disclosure possesses an intact hinge region at its N-terminus.

In one embodiment the Fc region of one or both chains of a dimeric IL10 agonist of the disclosure and the hinge region are derived from IgG4 and the hinge region comprises the modified sequence CPPC. The core hinge region of human IgG4 contains the sequence CPSC compared to IgG1 which contains the sequence CPPC. The serine residue present in the IgG4 sequence leads to increased flexibility in this region, and therefore a proportion of molecules form disulfide bonds within the same protein chain (an intrachain disulfide) rather than bridging to the other heavy chain in the IgG molecule to form the interchain disulfide. (Angel et al., 1993, Mol Immunol 30(1):105-108). Changing the serine residue to a proline to give the same core sequence as IgG1 allows complete formation of inter-chain disulfides in the IgG4 hinge region, thus reducing heterogeneity in the purified product. This altered isotype is termed IgG4P.

6.7.1.1. Chimeric Hinge Sequences

The hinge region can be a chimeric hinge region.

For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region.

In particular embodiments, a chimeric hinge region comprises the amino acid sequence EPKSCDKTH-TCPPCPAPPVA (SEQ ID NO: 12) (SEQ ID NO:8 of WO2014/121087, which is incorporated by reference in its entirety herein) or ESKYGPPCPPCPAPPVA (SEQ ID NO: 13) (SEQ ID NO:9 of WO2014/121087). Such chimeric hinge sequences can be suitably linked to an IgG4 CH2 region (for example by incorporation into an IgG4 Fc domain, for example a human or murine Fc domain, which can be further modified in the CH2 and/or CH3 domain to reduce effector function, for example as described in Section 6.4.1).

6.7.1.2. Hinge Sequences with Reduced Effector Function

In further embodiments, the hinge region can be modified to reduce effector function, for example as described in WO2016161010A2, which is incorporated by reference in its entirety herein. In various embodiments, the positions 233-236 of the modified hinge region are G, G, G and unoccupied; G, G, unoccupied, and unoccupied; G, unoccupied, unoccupied, and unoccupied; or all unoccupied, with positions numbered by EU numbering (as shown in FIG. 1 of WO2016161010A2). These segments can be represented as GGG-, GG--, G--- or ---- with "-" representing an unoccupied position.

Position 236 is unoccupied in canonical human IgG2 but is occupied by in other canonical human IgG isotypes. Positions 233-235 are occupied by residues other than G in all four human isotypes (as shown in FIG. 1 of WO2016161010A2).

The hinge modification within positions 233-236 can be combined with position 228 being occupied by P. Position 228 is naturally occupied by P in human IgG1 and IgG2 but is occupied by S in human IgG4 and R in human IgG3. An S228P mutation in an IgG4 antibody is advantageous in stabilizing an IgG4 antibody and reducing exchange of heavy chain light chain pairs between exogenous and endogenous antibodies. Preferably positions 226-229 are occupied by C, P, P and C respectively.

Exemplary hinge regions have residues 226-236, sometimes referred to as middle (or core) and lower hinge, occupied by the modified hinge sequences designated GGG-(233-236), GG--(233-236), G---(233-236) and no G(233-236). Optionally, the hinge domain amino acid sequence comprises CPPCPAPGGG-GPSVF (SEQ ID NO: 14) (SEQ ID NO:1 of WO2016161010A2), CPPCPAPGG--GPSVF (SEQ ID NO: 15) (SEQ ID NO:2 of WO2016161010A2), CPPCPAPG---GPSVF (SEQ ID NO: 16) (SEQ ID NO:3 of WO2016161010A2), or CPPCPAP----GPSVF (SEQ ID NO: 17) (SEQ ID NO:4 of WO2016161010A2).

The modified hinge regions described above can be incorporated into a heavy chain constant region, which typically include CH2 and CH3 domains, and which may have an additional hinge segment (e.g., an upper hinge) flanking the designated region. Such additional constant region segments present are typically of the same isotype, preferably a human isotype, although can be hybrids of different isotypes. The isotype of such additional human constant regions segments is preferably human IgG4 but can also be human IgG1, IgG2, or IgG3 or hybrids thereof in which domains are of different isotypes. Exemplary sequences of human IgG1, IgG2 and IgG4 are shown in FIGS. 2-4 of WO2016161010A2.

In specific embodiments, the modified hinge sequences can be linked to an IgG4 CH2 region (for example by incorporation into an IgG4 Fc domain, for example a human or murine Fc domain, which can be further modified in the CH2 and/or CH3 domain to reduce effector function, for example as described in Section 6.4.1).

6.8. Nucleic Acids and Host Cells

In another aspect, the disclosure provides nucleic acids encoding the IL10 agonists of the disclosure. In some embodiments, the IL10 agonists are encoded by a single nucleic acid. In other embodiments, for example in the case of a heterodimeric molecule or a molecule comprising a targeting moiety composed of more than one polypeptide chain, the IL10 agonists can be encoded by a plurality (e.g., two, three, four or more) nucleic acids.

A single nucleic acid can encode an IL10 agonist that comprises a single polypeptide chain, an IL10 agonist that comprises two or more polypeptide chains, or a portion of an IL10 agonist that comprises more than two polypeptide chains (for example, a single nucleic acid can encode two polypeptide chains of an IL10 agonist comprising three, four or more polypeptide chains, or three polypeptide chains of an IL10 agonist comprising four or more polypeptide chains). For separate control of expression, the open reading frames encoding two or more polypeptide chains can be under the control of separate transcriptional regulatory elements (e.g., promoters and/or enhancers). The open reading frames encoding two or more polypeptides can also be controlled by the same transcriptional regulatory elements, and separated by internal ribosome entry site (IRES) sequences allowing for translation into separate polypeptides.

In some embodiments, an IL10 agonist comprising two or more polypeptide chains is encoded by two or more nucleic acids. The number of nucleic acids encoding an IL10 agonist can be equal to or less than the number of polypeptide chains in the IL10 agonist (for example, when more than one polypeptide chains are encoded by a single nucleic acid).

The nucleic acids of the disclosure can be DNA or RNA (e.g., mRNA).

In another aspect, the disclosure provides host cells and vectors containing the nucleic acids of the disclosure. The nucleic acids may be present in a single vector or separate vectors present in the same host cell or separate host cell, as described in more detail herein below.

6.8.1. Vectors

The disclosure provides vectors comprising nucleotide sequences encoding an IL10 agonist or an IL10 agonist component described herein, for example one or two of the polypeptide chains of a dimeric IL10 agonist. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes can be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by co-transformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors can be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. Methods and conditions for culturing the resulting transfected cells and for recovering the expressed polypeptides are known to those skilled in the art, and may be varied or optimized depending upon the specific expression vector and mammalian host cell employed, based upon the present description.

6.8.2. Cells

The disclosure also provides host cells comprising a nucleic acid of the disclosure.

In one embodiment, the host cells are genetically engineered to comprise one or more nucleic acids described herein.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The disclosure also provides host cells comprising the vectors described herein.

Also provided are IL10 agonists that are the product of recombinant cell expression in a mammalian cell.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

6.8.3. Production Methods

The disclosure also provides methods for producing an IL10 agonist of the disclosure.

In some embodiments, the IL10 agonist is produced by culturing the host cells described in section 6.8.2 and recovering the IL10 expressed by the host cells. In certain embodiments, the method also includes the steps a) contacting the recovered IL10 agonist with an affinity column configured to trap the IL10 agonist, b) eluting the affinity column to produce an elute, and c) performing size-exclusion chromatography on the elute.

The affinity column can be any affinity column configured to trap the IL10 agonist. For example, the affinity column can include a binding molecule (e.g., an antibody or an affinity ligand) that specifically binds to the Fc domain or the IL10 moiety of the IL10 agonist. In one embodiment, the affinity column is a protein A affinity column. Protein A is an affinity ligand that includes five regions that bind to the Fc region of IgG. Often coupled to Sepharose, these regions are free to bind IgG Fc, with one molecule of coupled protein A capable of binding at least two molecules of IgG. In another embodiment, the affinity column includes an IL10 antibody capable of specifically and reversibly binding an IL10 moiety of the IL10 agonist.

Once bound to the affinity column, the trapped IL10 agonist is eluted with an elution buffer to produce an elute comprising the IL10 agonist. Many elution buffers are known in the art, and an appropriate buffer can be selected by those skilled in the art. In some embodiments, the elution buffer is Pierce Gentle elution buffer (pH 6.6).

The elute comprising the IL10 agonist is then subjected to size-exclusion chromatography to isolate and purify those IL10 agonists that do not form an aggregate. Many size exclusion chromatography methods and columns are known in the art. Those of skill in the art can select an appropriate size exclusion chromatography method and/or column. In some embodiments, size exclusion ultra performance liquid chromatography is used. In a particular embodiment, a Superdex 200, 26/600 pg column (MilliporeSigma, St. Louis, Mo. USA) is used.

In some embodiments, the elution buffer comprising the IL10 following affinity chromatography is exchanged for another buffer prior to passing the eluted IL10 agonists through size exclusion chromatography. This can be achieved by methods known in the art, such as, for example, dialysis. Buffer exchange may be required where a size exclusion chromatography column requires use of a particular buffer. In one embodiment, the elution buffer (e.g., Pierce Gentle) is exchanged for PBS+5% glycerol prior to performing size exclusion chromatography.

With the benefit of the present disclosure, those of skill in the art can select an IL10 agonist construct having an orientation (i.e., N-terminal vs. C-terminal IL10 moiety), linker length, and purification method to achieve a desired IL10 agonist. In some embodiments, the desired IL10 agonist is minimally aggregated, and is not truncated at the N-terminus and/or C-terminus of the construct. In certain embodiments, the IL10 agonist comprises an IL10 moiety at the C-terminus of the Fc domain, a linker of a single, double, or triple repeat of $G_4S$ (SEQ ID NO:51), and is purified using a process that includes size exclusion chromatography.

Following production, the IL10 agonists of the disclosure can be formulated into pharmaceutical compositions, for example as described in Section 6.9.

6.9. Pharmaceutical Compositions

6.9.1. Pharmaceutical Compositions Comprising IL10 Agonist Polypeptide

The IL10 agonists of the disclosure, for example IL10 agonists produced by the methods described in Section 6.8.3 may be provided in the form of compositions comprising the IL10 agonist and one or more carriers, excipients and/or diluents. The compositions may be formulated for specific uses, such as for veterinary uses or pharmaceutical uses in humans. The form of the composition (e.g., dry powder, liquid formulation, etc.) and the excipients, diluents and/or carriers used will depend upon the intended uses of the IL10 agonist and, for therapeutic uses, the mode of administration.

For therapeutic uses, the compositions may be supplied as part of a sterile, pharmaceutical composition that includes a pharmaceutically acceptable carrier. This composition can be in any suitable form (depending upon the desired method of administering it to a patient). The pharmaceutical composition can be administered to a patient by a variety of routes such as orally, transdermally, subcutaneously, intranasally, intravenously, intramuscularly, intratumorally, intrathecally, topically or locally. The most suitable route for administration in any given case will depend on the particular antibody, the subject, and the nature and severity of the disease and the physical condition of the subject. Typically, the pharmaceutical composition will be administered intravenously or subcutaneously.

Pharmaceutical compositions can be conveniently presented in unit dosage forms containing a predetermined amount of an IL10 agonist of the disclosure per dose. The quantity of IL10 agonist included in a unit dose will depend on the disease being treated, as well as other factors as are well known in the art. Such unit dosages may be in the form of a lyophilized dry powder containing an amount of IL10 agonist suitable for a single administration, or in the form of a liquid. Dry powder unit dosage forms may be packaged in a kit with a syringe, a suitable quantity of diluent and/or other components useful for administration. Unit dosages in liquid form may be conveniently supplied in the form of a syringe pre-filled with a quantity of IL10 agonist suitable for a single administration.

In some embodiments, a pharmaceutical composition of the present disclosure includes at least 5 mg, at least 10 mg, at least 20 mg, or at least 50 mg of the IL10 agonist.

In certain embodiments, a pharmaceutical composition of the present disclosure includes exclusively or almost exclusively full-length IL10 agonists. For example, in some embodiments, a pharmaceutical composition does not include a detectable amount of C-terminal truncated variants of the IL10 agonist and/or a detectable amount of N-terminal truncated variants of the IL10 agonist. As provided herein, positioning the IL10 moiety at the N-terminus of the Fc domain can result in N- and/or C-terminal truncations of the recombinantly expressed IL10 agonist.

In some embodiments, a pharmaceutical composition of the present disclosure includes minimal or no IL10 agonist aggregates. As provided herein, size exclusion chromatography can be used to produce non-aggregated IL10 agonists. In some embodiments, a pharmaceutical composition includes less than 30%, less than 25%, less than 20%, less than 15%, less than 10%, or less than 5% of the IL10 agonist is present in an aggregate form, as determined by size exclusion ultra performance liquid chromatography (SE-UPLC). In some embodiments, the pharmaceutical composition does not contain a detectable amount of aggregates of the IL10 agonist, as determined by size exclusion ultra performance liquid chromatography (SE-UPLC).

The pharmaceutical compositions may also be supplied in bulk form containing quantities of IL10 agonist suitable for multiple administrations.

Pharmaceutical compositions may be prepared for storage as lyophilized formulations or aqueous solutions by mixing an IL10 agonist having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives should be nontoxic to the recipients at the dosages and concentrations employed.

Buffering agents help to maintain the pH in the range which approximates physiological conditions. They may be present at a wide variety of concentrations, but will typically be present in concentrations ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives may be added to retard microbial growth, and can be added in amounts ranging from about 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, a-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trehalose; and trisaccacharides such as raffinose; and polysaccharides such as dextran. Stabilizers may be present in amounts ranging from 0.5 to 10 wt % per wt of IL10 agonist.

Non-ionic surfactants or detergents (also known as "wetting agents") may be added to help solubilize the glycoprotein as well as to protect the glycoprotein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), and pluronic polyols. Non-ionic surfactants may be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents.

6.9.2. Pharmaceutical Compositions for Delivery of IL10 Agonist Encoding Nucleic Acids An IL10 agonist of the disclosure can be delivered by any method useful for gene therapy, for example as mRNA or through viral vectors encoding the IL10 agonist under the control of a suitable promoter.

Exemplary gene therapy vectors include adenovirus- or AAV-based therapeutics. Non-limiting examples of adenovirus-based or AAV-based therapeutics for use in the methods, uses or compositions herein include, but are not limited to: rAd-p53, which is a recombinant adenoviral vector encoding the wild-type human tumor suppressor protein p53, for example, for the use in treating a cancer (also known as Gendicine®, Genkaxin®, Qi et al., 2006, Modern Oncology, 14:1295-1297); Ad5_d11520, which is an adenovirus lacking the E1B gene for inactivating host p53 (also called H101 or ONYX-015; see, e.g., Russell et al., 2012, Nature Biotechnology 30:658-670); AD5-D24-GM-CSF, an adenovirus containing the cytokine GM-CSF, for example, for the use in treating a cancer (Cerullo et al., 2010, Cancer Res. 70:4297); rAd-HSVtk, a replication deficient adenovirus with HSV thymidine kinase gene, for example, for the treatment of cancer (developed as Cerepro®, Ark Therapeutics, see e.g. U.S. Pat. No. 6,579,855; developed as ProstAtak™ by Advantagene; International PCT Appl. No. WO2005/049094); rAd-TNFα, a replication-deficient adenoviral vector expressing human tumor necrosis factor alpha (TNFα) under the control of the chemoradiation-inducible EGR-1 promoter, for example, for the treatment of cancer (TNFerade™, GenVec; Rasmussen et al., 2002, Cancer Gene Ther. 9:951-7; Ad-IFNβ, an adenovirus serotype 5 vector from which the E1 and E3 genes have been deleted expressing the human interferon-beta gene under the direction of the cytomegalovirus (CMV) immediate-early promoter, for example for treating cancers (BG00001 and H5.110CMVhIFN-β, Biogen; Sterman et al., 2010, Mol. Ther. 18:852-860).

The nucleic acid molecule (e.g., mRNA) or virus can be formulated as the sole pharmaceutically active ingredient in a pharmaceutical composition or can be combined with other active agents for the particular disorder treated. Optionally, other medicinal agents, pharmaceutical agents, carriers, adjuvants, diluents can be included in the compositions provided herein. For example, any one or more of a wetting agents, emulsifiers and lubricants, such as sodium lauryl sulfate and magnesium stearate, as well as coloring agents, release agents, coating agents, sweetening, flavoring and perfuming agents, preservatives, antioxidants, chelating agents and inert gases also can be present in the compositions. Exemplary other agents and excipients that can be included in the compositions include, for example, water soluble antioxidants, such as ascorbic acid, cysteine hydrochloride, sodium bisulfate, sodium metabisulfite, sodium sulfite; oil-soluble antioxidants, such as ascorbyl palmitate, butylated hydroxyanisole (BHA), butylated hydroxytoluene (BHT), lecithin, propyl gallate, α-tocopherol; and metal chelating agents, such as citric acid, ethylenediamine tetraacetic acid (EDTA), sorbitol, tartaric acid and phosphoric acid.

When used as adjunct therapy for adoptive cell transfer therapies, e.g., CAR-expressing cell therapies as described in Section 6.11.1, the cell therapies, e.g., CAR-expressing cells, can be engineered to express the IL10 agonists of the disclosure. The IL10 agonist can be targeted to a specific genomic locus, e.g., the endogenous IL10 locus or another locus that is active in activated or dysfunctional lymphocytes, e.g., the PD-1 locus, or inserted into a non-specific genomic locus. Targeting a specific genomic locus can be achieved through gene editing, e.g., using zinc finger proteins, the CRISPR/Cas9 system, and the like.

6.10. Therapeutic Indications and Methods of Treatment

IL10 agonists of the disclosure are useful in treating conditions which are treatable with IL10, e.g., inflammatory- and immune-related disorders, fibrotic disorders, cancer and cancer-related disorders, or cardiovascular disorders (e.g., atherosclerosis).

In particular embodiments, the condition treated by the IL10 agonists of the disclosure is autoimmunity, transplantation rejection, post-traumatic immune response, infectious disease, or graft-versus-host disease. In particular embodiments, the conditions is an autoimmune disease, organ or bone marrow transplant rejection, graft-versus-host disease, a parasitic infection, a granuloma, Crohn's disease, colitis, pancreatitis, inflammatory lung, an allergic condition, asthma, atopic dermatitis, or rhinitis.

In other embodiments the disease to be treated is a proliferative disorder, preferably cancer, for example a solid tumor. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using an IL10 agonist of the present disclosure include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. Similarly, other cell proliferation disorders can also be treated by the IL10 agonists of the present disclosure. Examples of such cell proliferation disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other cell proliferation disease, besides neoplasia, located in an organ system listed above.

In some embodiments, the disease to be treated is resistant to treatment with an anti-PD1 antibody. In some embodiments, the disease to be treated is resistant to monotherapy with an anti-PD1 antibody. While blockade of the PD1/PD-L1 checkpoint has proven an effective treatment of a number of malignancies, it is ineffective in a significant percentage of patients with some initial responders developing resistance accompanied by relapsed disease (Nowicki et al., 2018, Cancer J. 24(1):47-53). Resistance to treatment with an anti-PD1 antibody can be primary or acquired. Mechanisms leading to both primary and acquired resistance to PD1 inhibition are known in the art, as are methods for identifying malignancies resistant to PD1 inhibition. See, e.g., Nowicki et al., supra; Shergold et al., 2019, Pharmacological Research 145:204258; and Fares et al., 2019, American Society of Clinical Oncology Educational Book 39:147-164.

The IL10 agonists of the disclosure will generally be used in an amount effective to achieve the intended purpose. For use to treat or prevent a disease condition, the IL10 agonists of the disclosure, or pharmaceutical compositions thereof, are administered or applied in a therapeutically effective amount. Determination of a therapeutically effective amount is well within the capabilities of those skilled in the art, especially in light of the detailed disclosure provided herein. A skilled artisan readily recognizes that in many cases treatment with an IL10 agonist may not provide a cure but may only provide partial benefit. In some embodiments, a physiological change having some benefit is also considered therapeutically beneficial. Thus, the terms "effective amount" and "therapeutically effective amount" encompass dosages and dosing regimens that confer a partial benefit.

In some embodiments, the IL10 agonists of the disclosure, or pharmaceutical compositions thereof, are administered or applied in an amount sufficient to increase the density of CD8 T cells in a solid tumor relative to a suitable control (see. Section 7.7 and FIGS. 18A-18B). The IL10 agonists of the disclosure, or pharmaceutical compositions thereof, can be administered or applied in an amount that increases CD45+ immune cell infiltration in a solid tumor. CD45+ immune cells include, for example, CD4 T cells and myeloid cells. Further, the IL10 agonists of the disclosure, or pharmaceutical compositions thereof, can be administered or applied in an amount sufficient to upregulate the expression of serum IL12 and/or IL4 relative to a suitable control (see. Section 7.7 and FIGS. 21A-21B). In certain aspects, the IL10 agonists of the disclosure, or pharmaceutical compositions thereof, can upregulate IL12 serum levels by at least 5-fold, at least 10-fold, at least 15-fold, at least 20-fold, at least 25-fold, or at least 30-fold relative to the control (FIG. 21A). In further aspects, the IL10 agonists of the disclosure, or pharmaceutical compositions thereof, can upregulate IL4 serum levels by at least 5-fold, at least 10-fold, at least 15-fold, or at least 20-fold relative to the control (FIG. 21A).

Suitable control samples for determination of a reference value or baseline value of IL12 and/or IL4 can be derived from individuals having the same disease condition as the individual being treated with the IL10 agonist of the disclosure or pharmaceutical composition thereof. A control sample can be age-matched with the subject undergoing treatment with the IL10 agonist of the disclosure or pharmaceutical composition thereof. Reference values or baseline values can be obtained from suitable individuals or a suitable population of individuals and used as a general reference value for multiple analysis. Alternatively, the control sample can be based on the subject's own values prior to initiation of IL10 agonist therapy. It is within in the ordinary skill of those skilled in the art to identify and select a suitable control.

The subject, patient, or individual in need of treatment is typically a mammal, more specifically a human. For the prevention or treatment of disease, the appropriate dosage of an IL10 agonist of the disclosure (when used alone or in combination with one or more other additional therapeutic agents) will depend on the type of disease to be treated, the route of administration, the body weight of the patient, the particular IL10 agonist, the severity and course of the disease, whether the antibody is administered for preventive or therapeutic purposes, previous or concurrent therapeutic interventions, the patient's clinical history and response to the IL10 agonist, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

A single administration of unconjugated IL10 can range from about 50,000 IU/kg to about 1,000,000 IU/kg or more, more typically about 600,000 IU/kg of IL10. This may be repeated several times a day (e.g., 2-3 times.), for several days (e.g., about 3-5 consecutive days) and then may be repeated one or more times following a period of rest (e.g., about 7-14 days). Thus, a therapeutically effective amount may comprise only a single administration or many administrations over a period of time (e.g., about 20-30 individual administrations of about 600,000 IU/kg of IL10 each given over about a 10-20 day period).

Similarly, the IL10 agonist is suitably administered to the patient at one time or over a series of treatments. Depending on the type and severity of the disease, about 1 µg/kg to 15 mg/kg (e.g., 0.1 mg/kg-10 mg/kg) of IL10 agonist can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the IL10 agonist would be in the range from about 0.005 mg/kg to about 10 mg/kg. In other non-limiting examples, a dose may also comprise from about 1 µg/kg/body weight, about 5 µg/kg/body weight, about 10 µg/kg/body weight, about 50 µg/kg/body weight, about 100 µg/kg/body weight, about 200 µg/kg/body weight, about 350 µg/kg/body weight, about 500 µg/kg/body weight, about 1 mg/kg/body weight, about 5 mg/kg/body weight, about 10 mg/kg/body weight, about 50 mg/kg/body weight, about 100 mg/kg/body weight, about 200 mg/kg/body weight, about 350 mg/kg/body weight, about 500 mg/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 µg/kg/body weight to about 500 mg/kg/body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g., every week or every three weeks (e.g., such that the patient receives from about two to about twenty, or e.g., about six doses of the IL10 agonist). An initial higher loading dose, followed by one or more lower doses may be administered. However, other dosage regimens may be useful. The progress of this therapy is easily monitored by conventional techniques and assays.

For systemic administration, a therapeutically effective dose can be estimated initially from in vitro assays, such as cell culture assays. A dose can then be formulated in animal models to achieve a circulating concentration range that includes the $EC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the IL10 agonists which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by ELISA HPLC.

In cases of local administration or selective uptake, the effective local concentration of the IL10 agonists may not be related to plasma concentration. One having skill in the art will be able to optimize therapeutically effective local dosages without undue experimentation.

A therapeutically effective dose of the IL10 agonists described herein will generally provide therapeutic benefit without causing substantial toxicity. Toxicity and therapeutic efficacy of an IL10 agonist can be determined by standard pharmaceutical procedures in cell culture or experimental animals (see, e.g., Examples 8 and 9). Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. IL10 agonists that exhibit large therapeutic indices are preferred. In one embodiment, the IL10 agonist according to the present disclosure exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition. (See, e.g., Fingl et al., 1975, In: The Pharmacological Basis of Therapeutics, Ch. 1, p. 1, incorporated herein by reference in its entirety).

The attending physician for patients treated with IL10 agonists of the disclosure would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

6.11. Combination Therapy

The IL10 agonists according to the disclosure may be administered in combination with one or more other additional agents in therapy. For instance, an IL10 agonist of the disclosure may be co-administered with at least one additional therapeutic agent. The term "therapeutic agent" encompasses any agent administered to treat a symptom or disease in a subject in need of such treatment. Such additional therapeutic agent may comprise any active ingredients suitable for the particular indication being treated, preferably those with complementary activities that do not adversely affect each other.

For the treatment of cancer, the IL10 agonists of the disclosure can be administered in combination with one or more anti-neoplastic agents (e.g., chemotherapeutic agents) or anti-neoplastic treatment modalities (e.g., radiation). The identity of the additional agent(s) will be largely dependent on the nature of the underlying condition being treated (e.g., the addition of an alkylating agent such as cisplatin may be appropriate in the treatment of bladder cancer). One or more additional agents (e.g., chemotherapeutic agents) administered in conjunction with an IL10 agonists are given in amounts that are effective for the purpose intended. The effective amount of such additional agents depends on the amount of IL10 agonist used, the type of disorder or treatment, and other factors discussed above.

The IL10 agonists are generally used in the same dosages and with administration routes as described herein, or about from 1 to 99% of the dosages described herein, or in any dosage and by any route that is empirically/clinically determined to be appropriate.

Examples of chemotherapeutic agents for use in combination with the IL10 agonists of the disclosure include but are not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and docetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above. The term "chemotherapeutic agents" also includes anti-hormonal agents that act to regulate or inhibit hormone action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In some embodiments, the additional agent may be one or more chemical or biological agents identified in the art as useful in the treatment of neoplastic disease, including, but not limited to, a cytokines or cytokine antagonists such as IL12, INFα, or anti-epidermal growth factor receptor, radiotherapy, antibodies against tumor antigens, a complex of a monoclonal antibody and toxin, a T-cell adjuvant, bone marrow transplant, or antigen presenting cells (e.g., dendritic cell therapy), anti-tumor vaccines, replication competent viruses, and CART cells, for example as described in Section 6.11.1.

For treatment of immune and inflammatory conditions, the IL10 agonists of the disclosure can be used in combination with immunosuppressive or immunomodulatory therapies. Non-limiting examples of immunosuppressive therapies include immunosuppressive compounds such as cyclosporin A, cyclophosphamide, FK506, tacrolimus, corticosteroids, azathioprine, mycophenolate mofetil, sirolimus, rapamycin, rapamycin analogs, deoxyspagarin, prednisone, and the like.

In some embodiments, the IL10 agonists of the disclosure can be used in combination with an anti-PD1 antibody. Examples of anti-PD1 antibodies for use in combination with the IL10 agonists of the disclosure include but are not limited to MDX-1106 (nivolumab), MK-3475 (pembrolizumab), MEDI-0680 (AMP-514), PDR001, REGN2810, or BGB-108.

Such combination therapies noted above encompass combined administration (where two or more therapeutic agents are included in the same or separate compositions), and separate administration, in which case, administration of the IL10 agonist of the disclosure can occur prior to, simultaneously, and/or following, administration of the additional therapeutic agent and/or adjuvant.

6.11.1. Combination Therapy Using IL10 Agonist Therapy and Immunotherapy

The IL10 agonists of the disclosure can be advantageously used in combination with chimeric antigen receptor ("CAR")-expressing cells, e.g., CAR-expressing T ("CAR-T") cells, for example CAR-T in the treatment of cancer or autoimmune diseases.

Conditioning or lymphodepletion therapy, e.g., a regimen of cyclophosphamide and fludarabine, can also be administered to a subject receiving CAR and IL10 agonist therapy. Such therapy is usually performed in the days prior to administration of the CAR-expressing cells to the subject. For example, cyclophosphamide can be administered for two days, e.g., at days-8 and -7 prior to infusion with CAR-expressing cells (the infusion day being zero) and fludarabine can be administered to the subject for five consecutive days from day-6 to day-2. In one embodiment, 60 mg/kg of cyclophosphamide is administered to the subject. In one embodiment, 25 mg/m$^2$ of fludarabine is administered to the subject. In one embodiment, there is a day of no treatment on day-1, the day immediately prior to the CAR-expressing cell infusion to the subject.

The CAR-expressing cells can be administered in an amount ranging from 104 to $10^9$ cells/kg body weight, preferably 105 to $10^6$ cells/kg body weight, including all integer values within those ranges. T-cell compositions may also be administered multiple times at these dosages. In some embodiments, the CAR-expressing cells are administered in doses of $1\times10^6$ to $1\times10^{11}$ cells or $1\times10^7$ to $1\times10^8$ cells.

The CAR-expressing cells can be activated with an anti-CD3 and/or anti-CD28 antibody in concert with IL10 expansion prior to administration to the human subject.

The CAR-expressing cells, e.g., T cells, are preferably autologous to the subject but can also be of allogeneic origin.

In one embodiment, the IL10 agonist is administered to the human subject by bolus infusion for four consecutive days beginning on the day of administration of the population of CAR-expressing cells.

In one embodiment, the IL10 agonist is administered to the human subject by bolus for at least five consecutive days beginning on the day of administration of the population of CAR-expressing cells.

The IL10 agonist can be administered for longer periods, for example for a week, for two weeks, for one month or longer. The dosing frequency can be reduced, e.g., after exhaustion of the CAR-expressing cells. For example, the IL10 agonist can be initially administered on a daily basis and then the dosing frequency reduced to weekly.

The initiation of IL10 therapy can begin on the same day as, or one, two, three, four, five, six days or a week after, administration of the CAR-expressing cells.

In one embodiment, the population of cells comprises T-cells obtained from the subject that have been engineered to recombinantly express the CAR.

In one embodiment, the IL10 agonist plasma level is maintained for one to two weeks following administration of the population of cells to the subject.

In one embodiment, the IL10 agonist plasma level is maintained for a month following administration of the population of cells to the subject.

6.11.1.1. CAR Components

Atypical CAR comprises an extracellular region comprising antigen binding domain, e.g., an antigen binding domain of an antibody, linked to an intracellular signaling block that includes CD3 signaling domains that induce T cell activation following antigen binding (e.g., a CD3 (signaling region of a T cell receptor). The antigen binding domain can be in the form of an scFv, as described in Section 6.5.2.1.

The antigen binding domain is typically linked to the signal domain via a linker (e.g., a linker as described in Section 6.7), an optional spacer (e.g., as described in Section 6.11.1.1.1), an optional hinge (e.g., as described in Section 6.11.1.1.2), a transmembrane domain (e.g., as described in Section 6.11.1.1.3), and an intracellular signaling block (e.g., as described in Section 6.11.1.1.4).

6.11.1.1.1. Spacer Domain

In particular embodiments, the antigen binding domain of the CAR (followed by an optional linker) is followed by one or more "spacer domains," which refers to the region that moves the antigen binding domain away from the effector cell surface to enable proper cell/cell contact, antigen binding and activation (Patel et al., 1999, Gene Therapy 6:412-419). The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

In one embodiment, the spacer domain comprises the CH2 and CH3 domains of IgG1 or IgG4.

6.11.1.1.2. Hinge Domain

The antigen binding domain of the CAR is generally followed by one or more "hinge domains" (downstream of the optional linker and/or spacer), which play a role in positioning the antigen binding domain away from the effector cell surface to enable proper cell/cell contact, antigen binding and activation. A CAR generally comprises one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region.

An "altered hinge region" refers to (a) a naturally occurring hinge region with up to 30% amino acid changes (e.g., up to 25%, 20%, 15%, 10%, or 5% amino acid substitutions or deletions), (b) a portion of a naturally occurring hinge region that is at least 10 amino acids (e.g., at least 12, 13, 14 or 15 amino acids) in length with up to 30% amino acid changes (e.g., up to 25%, 20%, 15%, 10%, or 5% amino acid substitutions or deletions), or (c) a portion of a naturally occurring hinge region that comprises the core hinge region (which may be 4, 5, 6, 7, 8, 9, 10, 11, 12, 13, 14, or 15, or at least 4, 5, 6, 7, 8, 9, 10, 11, 12, 13, 14, or 15 amino acids in length). In certain embodiments, one or more cysteine residues in a naturally occurring immunoglobulin hinge region may be substituted by one or more other amino acid residues (e.g., one or more serine residues). An altered immunoglobulin hinge region may alternatively or additionally have a proline residue of a wild type immunoglobulin hinge region substituted by another amino acid residue (e.g., a serine residue).

Other illustrative hinge domains suitable for use in the CARs described herein include the hinge region derived from the extracellular regions of type 1 membrane proteins such as CD8α, CD4, CD28 and CD7, which may be wild-type hinge regions from these molecules or may be altered. In another embodiment, the hinge domain comprises a CD8α hinge region.

6.11.1.1.3. Transmembrane (TM) Domain

The "transmembrane domain" is the portion of the CAR that fuses the extracellular binding portion and intracellular signaling domain and anchors the CAR to the plasma membrane of the immune effector cell. As used herein, the term "transmembrane domain" refers to any polypeptide structure that is thermodynamically stable in a cell membrane, preferably a eukaryotic cell membrane (e.g., a mammalian cell membrane).

The TM domain may be derived either from a natural, synthetic, semi-synthetic, or recombinant source. The TM domain may be derived from (e.g., comprise at least the transmembrane region(s) of) the alpha, beta or zeta chain of the T-cell receptor, CD3ε, CD3ζ, CD4, CD5, CD8α, CD9, CD 16, CD22, CD27, CD28, CD33, CD37, CD45, CD64, CD80, CD86, CD 134, CD137, CD152, CD 154, or PD1. In a particular embodiment, the TM domain is synthetic and predominantly comprises hydrophobic residues such as leucine and valine.

In certain embodiments, the CAR comprises a CD3ζ transmembrane domain (e.g., a transmembrane domain that comprises the amino acid sequence LCYLLDGIL-FIYGVILTALFL (SEQ ID NO: 18) or LDPKLCYLLDG-ILFIYGVILTALFLRVK (SEQ ID NO:19)), a CD28 transmembrane domain (e.g., a transmembrane domain that comprises the amino acid sequence FWVLVVVGGVLA-CYSLLVTVAFIIFWV (SEQ ID NO: 20)) or a CD8a transmembrane domain (e.g., a transmembrane domain that comprises the amino acid sequence KPTTTPAPRPPTPAPTIASQPLSLR PEACR-PAAGGAVHTRGLDFA (SEQ ID NO:21)).

The TM can be followed by a short linker, preferably 1, 2, 3, 4, 5, 6, 7, 8, 9, or 10 amino acids in length that links the TM domain and the intracellular signaling domain of the CAR. A glycine-serine based linker (e.g., a linker according to Section 6.7) provides a particularly suitable linker.

6.11.1.1.4. Intracellular Signaling Domain

CARs typically comprise an intracellular signaling domain. An "intracellular signaling domain," refers to the part of a CAR that participates in transducing the message of effective antigen binding into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain.

The term "effector function"" refers to a specialized function of an immune effector cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

It is known that signals generated through the TCR alone are insufficient for full activation of the T cell and that a secondary or co-stimulatory signal is also required. Thus, T cell activation can be said to be mediated by two distinct classes of intracellular signaling domains: primary signaling domains that initiate antigen-dependent primary activation through the TCR (e.g., a TCR/CD3 complex) and co-stimulatory signaling domains that act in an antigen-independent manner to provide a secondary or co-stimulatory signal. In preferred embodiments, a CAR contemplated herein comprises an intracellular signaling domain that comprises one or more "co-stimulatory signaling domain" and a "primary signaling domain."

Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs.

Illustrative examples of ITAM containing primary signaling domains that are of particular use in the methods of the disclosure include those derived from TCRζ, FcRγ, FcRβ, CD3γ, CD3δ, CD3ε, CD3ζ, CD22, CD79a, CD79b, and CD66d. In particular preferred embodiments, a CAR comprises a CD3ζ primary signaling domain and one or more co-stimulatory signaling domains. The intracellular primary signaling and co-stimulatory signaling domains may be linked in any order in tandem to the carboxyl terminus of the transmembrane domain.

CARs contemplated herein comprise one or more co-stimulatory signaling domains to enhance the efficacy and expansion of T cells expressing CAR receptors. As used herein, the term, "co-stimulatory signaling domain," or "co-stimulatory domain," refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules include CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70.

In some embodiments, the CD3ζ signaling region is linked to co-stimulatory endodomains of CD28, 4-1BB (also known as CD137), CD70, or OX40 (also known as CD134), or combinations thereof, or have two signaling domains of CD3ζ in tandem. These endodomains allow for robust T cell activation during TCR recognition by antigen-presenting cells (APCs), improving cytokine production and proliferation of CAR-T cells.

In another embodiment, a CAR comprises CD28 and CD137 co-stimulatory signaling domains and a CD3ζ primary signaling domain.

In yet another embodiment, a CAR comprises CD28 and CD134 co-stimulatory signaling domains and a CD3ζ primary signaling domain.

In one embodiment, a CAR comprises CD137 and CD134 co-stimulatory signaling domains and a CD3ζ primary signaling domain.

Exemplary CD3ζ signaling regions can comprise one of the following amino acid sequences:

```
                                        (SEQ ID NO: 22)
LDPKLCYLLDGILFIYGVILTALFLRVKFSRSADAPAYQQGQNQLYNELN
LGRREEYDVLDKRRGRDPEMGGKPRRKNPQEGLYNELQKDKMAEAYSEIG
MKGERRRGKGHDGLYQGLSTATKDTYDALHMQALPPR;

(SEQ ID NO: 23)
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR.
```

Exemplary CD28 signaling regions can comprise one of the following amino acid sequences:

```
                                        (SEQ ID NO: 24)
KIEVMYPPPYLDNEKSNGTIIHVKGKHLCPSPLFPGPSKPFWVLVVVGG
VLACYSLLVTVAFIIFWVRSKRSRLLHSDYMNMTPRRPGPTRKHYQPYA
PPRDFAAYRS;

(SEQ ID NO: 25)
RSKRSRLLHSDYMNMTPRRPGPTRKHYQPYAPPRDFAAYRS;

(SEQ ID NO: 26)
KIEVMYPPPYLDNEKSNGTIIHVKGKHLCPSPLFPGPSKP;

(SEQ ID NO: 20)
FWVLVVVGGVLACYSLLVTVAFIIFWV.
```

Exemplary CD137 (41BB) signaling regions can comprise the following amino acid sequence:

```
                                        (SEQ ID NO: 27)
   KRGRKKLLYIFKQPFMRPVQTTQEEDGCSCRFPEEEEGGCEL.
```

6.11.1.1.5. Tag

In some embodiments, the CAR comprises a tag used for identification of the CAR, for example a V5 epitope tag is derived from a small epitope (Pk) present on the P and V proteins of the paramyxovirus of simian virus 5 (SV5). The V5 tag is usually used with all 14 amino acids (GKPIPN-PLLGLDST (SEQ ID NO: 28)), although it has also been used with a shorter 9 amino acid sequence (IPNPLLGLD (SEQ ID NO: 29)).

6.11.1.1.6. Signal Peptide

In some embodiments, the CAR comprises a signal peptide. Signal peptides facilitate the expression of the CAR of the cell surface. Signal peptides, including signal peptides of naturally occurring proteins or synthetic, non-naturally occurring signal peptides, that are compatible for use in the CARs described herein will be evident to those of skill in the art. In some embodiments, the signal peptide is disposed N-terminus of the antigen-binding portion of the CAR. Upon expression and processing of the CAR in a cell, e.g., a T cell, the signal peptide is cleaved and is therefore typically not present in the mature molecule.

6.11.1.2. Preparation of CART Cells

For generating CART cells ex vivo, PBMC, peripheral blood lymphocytes, or T cells enriched therefrom, can be expanded prior to and/or following introduction of a nucleic encoding the CAR into the cells, for example by viral transduction.

T cells useful for generating CART cells can be isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28$^+$, CD4+, CD8+, CD45RA+, and CD45RO+ T cells, can be further isolated by positive or negative selection techniques. For example, in one embodiment, T cells are isolated by incubation with anti-CD3/anti-CD28 (e.g., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells, subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this disclosure. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. T reg cells can be also be depleted by anti-C25 conjugated beads or other similar method of selection.

In certain embodiments, for example for applications involving the treatment of autoimmune disease as described in Section 6.11.1.4, it may be desirable to enrich for or positively select for regulatory T cells which typically express CD4+, CD25+, CD62L$^{hi}$, GITR$^+$, and FoxP3+. T regs can also be induced by recombinant expression of FoxP3.

Whether prior to or after genetic modification of the T cells to express a desirable CAR, the T cells can be activated and expanded generally using methods known in the art, for example as described in U.S. Pat. Nos. 7,144,575; 7,067,318; 7,172,869; 7,232,566; or 7,175,843.

Generally, the T cells useful in the methods of the disclosure are expanded by contact with a surface having attached thereto an agent that stimulates a CD3/TCR complex associated signal and a ligand that stimulates a co-stimulatory molecule on the surface of the T cells. In particular, T cell populations may be stimulated by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For costimulation of an accessory molecule on the surface of the T cells, a ligand that binds the accessory molecule is used. For example, a population of T cells can be contacted with an anti-CD3 antibody and optionally an anti-CD28 antibody, for example on anti-CD3 and anti-CD28 bead, under conditions appropriate for stimulating proliferation of the T cells.

Prior to administration to the human subject the CAR-expressing cells can also be conditioned with IL12 (see, e.g., Emtage et al., 2003, J. Immunother. 16(2): 97-106, incorporated herein by reference).

6.11.1.3. Cancer Immunotherapy

Accordingly, the present disclosure provides methods of treating cancer in a human subject in need thereof, comprising administering to the subject an effective amount of an IL10 agonist of the disclosure and administering to the CAR-expressing cells, e.g., the CAR-expressing T cells (or "CART cells"). Particularly useful T cell subtypes for the treatment of cancer are T cells with robust CAR mediated cytotoxicity, e.g., CD3+CD8+ T cells, which can be prepared as described in 6.11.1.2 above.

For treatment of cancer, the extracellular domain of the CAR can target a tumor associated antigen, for example as described in Section 6.5.1. In certain embodiments, the tumor associated antigen is CD20, EGFR, FITC, CD19, CD22, CD33, PSMA, GD2, EGFR variants, ROR1, c-Met, HER2, CEA, mesothelin, GM2, CD7, CD10, CD30, CD34, CD38, CD41, CD44, CD74, CD123 CD133, CD171, MUC16, MUC1, CS1 (CD319), IL-13Ra2, BCMA, Lewis Y, IgG kappa chain, folate receptor-alpha, PSCA, or EpCAM. In particular embodiments:

- the CAR is designed to target CD22 to treat diffuse large B-cell lymphoma.
- the CAR is designed to target mesothelin to treat mesothelioma, pancreatic cancer, ovarian cancer, and the like.
- the CAR is designed to target CD33/IL3Rα to treat acute myelogenous leukemia and the like.
- the CAR is designed to target c-Met to treat triple negative breast cancer, non-small cell lung cancer, and the like.

the CAR is designed to target PSMA to treat prostate cancer and the like.

the CAR is designed to target Glycolipid F77 to treat prostate cancer and the like.

the CAR is designed to target EGFRvIII to treat glioblastoma and the like.

the CAR is designed to target GD-2 to treat neuroblastoma, melanoma, and the like.

the CAR is designed to target NY-ESO-1 TCR to treat myeloma, sarcoma, melanoma, and the like.

the CAR is designed to target MAGE A3 TCR to treat myeloma, sarcoma, melanoma, and the like.

Particularly useful for CAR-IL10 agonist combination therapy are IL10 agonists comprising a targeting moiety that recognizes a cell surface antigen present on the surface of the CAR-expressing lymphocytes cells.

6.11.1.4. Immunotherapy of Autoimmune Disease

Chimeric antigen receptor (CAR) T cells have become powerful treatment options for blood cancers. By using the same idea of modifying T cells to efficiently target disease calls, scientists have efficiently engineered T cells with a predetermined antigen-specificity via transfection of viral vectors encoding chimeric antigen receptors (CARs). CAR-modified T cells engineered in a non-MHC restricted manner have the advantage of widespread applications, especially in transplantation and autoimmunity.

For use in treatment of autoimmune disease, the extracellular domain of the CAR is preferably specific for a target antigen or ligand associated with the autoimmune response. Such modification causes activation of redirected Tregs at sites of inflammation to suppress the proinflammatory effector-type immune responses. Examples of autoimmune diseases targeted by CAR $T_{reg}$ therapy are multiple sclerosis, inflammatory bowel diseases (IBD), rheumatoid arthritis, systemic lupus erythematosus, Crohn's Disease, psoriasis, Type I Diabetes, Sjogren's disease, myasthenia gravis (MG), Hashimoto's thyroiditis; Graves' Disease, and uveitis.

In particular embodiments, the CART cells are engineered to express a CAR targeting an antigen or ligand specific to:

inflammatory bowel disease (IBD), wherein the antigen or ligand is one that is expressed in diseased colon or ileum;

rheumatoid arthritis, wherein the antigen or ligand is an epitope of collagen or an antigen present in joints;

Type I diabetes mellitus or autoimmune insulitis, wherein the antigen or ligand is a pancreatic p cell antigen;

multiple sclerosis, wherein the antigen or ligand is, for example, a myelin basic protein (MBP) antigen or MOG-1 or MOG2-2, or a neuronal antigen;

autoimmune thyroiditis, wherein the antigen or ligand is a thyroid antigen;

autoimmune gastritis, wherein the antigen or ligand is a gastric antigen;

autoimmune uveitis or uveoretinitis, wherein the antigen or ligand is S-antigen or another uveal or retinal antigen;

autoimmune orchitis, wherein the antigen or ligand is a testicular antigen;

autoimmune oophoritis, wherein the antigen or ligand is an ovarian antigen;

psoriasis, wherein the antigen or ligand is a keratinocyte antigen or another antigen present in dermis or epidermis;

vitiligo, where the antigen or ligand is a melanocyte antigen such as melanin or tyrosinase;

autoimmune prostatitis, wherein the antigen or ligand is a prostate antigen;

any undesired immune response, wherein the antigen or ligand is an activation antigen or other antigen expressed on T effector cells present at the site of the undesired response;

tissue rejection, wherein the antigen or ligand is the MHC specific to the transplanted tissue; or an inflammatory condition, wherein the antigen or ligand is one that is expressed on nonlymphoid cells of the hemopoietic lineage that participate in inflammation.

In one embodiment, T cells can be engineered to express chimeric autoantigen receptor (CAAR) T cells to specifically eliminate B cells that are responsible for autoimmune diseases. Accordingly, reference to CAR-expressing T cells includes reference to CAAR-expressing unless the context dictates otherwise.

7. EXAMPLES

7.1. Materials and Methods

7.1.1. Production of IL10 Agonists

Constructs encoding the IL10 and IL10 muteins (identified with an IL10M_) listed in the Table 3 below and Fc controls were generated. The IL10 mutein constructs included different configurations of murine or human IL10, an IgG1 or an IgG4 Fc domain, and linkers of different lengths from different repeats of $G_4S$ (SEQ ID NO: 51):

| | |
|---|---|
| Human IL10: | SPGQGTQSENSCTHFPGNLPNMLRDLRDAFSRVKTFF QMKDQLDNLLLKESLLEDFKGYLGCQALSEMIQFYLEE VMPQAENQDPDIKAHVNSLGENLKTLRLRLRRCHRFL PCENKSKAVEQVKNAFNKLQEKGIYKAMSEFDIFINYIE AYMTMKIRN (SEQ ID NO: 1) |
| Murine IL10 | SRGQYSREDNNCTHFPVGQSHMLLELRTAFSQVKTFF QTKDQLDNILLTDSLMQDFKGYLGCQALSEMIQFYLVE VMPQAEKHGPEIKEHLNSLGEKLKTLRMRLRRCHRFL PCENKSKAVEQVKSDFNKLQDQGVYKAMNEFDIFINCI EAYMMIKMKS (SEQ ID NO: 30) |
| hIgG4s-Fc Variant hIgG4 with IgG2-based hinge region (hIgG4E99-105 hIgG2_HingeC106- A115 hIgG4_CH2_CH3 G117-K237) | ESKYGPPCPPCPAPPVAGPSVFLFPPKPKDTLMISRTP EVTCVVVDVSQEDPEVQFNWYVDGVEVHNAKTKPRE EQFNSTYRVVSVLTVLHQDWLNGKEYKCKVSNKGLPS SIEKTISKAKGQPREPQVYTLPPSQEEMTKNQVSLTCL VKGFYPSDIAVEWESNGQPENNYKTTPPVLDSDGSFF LYSRLTVDKSRWQEGNVFSCSVMHEALHNHYTQKSL SLSLGK (SEQ ID NO: 31) |

-continued

| | |
|---|---|
| hIgG1-Fc<br>IgG1 with D265A, N297A (EU numbering) to reduce effector function | DKTHTCPPCPAPELLGGPSVFLFPPKPKDTLMISRTPE<br>VTCVVVAVSHEDPEVKFNWYVDGVEVHNAKTKPREE<br>QYASTYRVVSVLTVLHQDWLNGKEYKCKVSNKALPAP<br>IEKTISKAKGQPREPQVYTLPPSRDELTKNQVSLTCLV<br>KGFYPSDIAVEWESNGQPENNYKTTPPVLDSDGSFFL<br>YSKLTVDKSRWQQGNVFSCSVMHEALHNHYTQKSLS<br>LSPGK (SEQ ID NO: 32) |
| mIgG1-Fc<br>IgG1 with N276D, N278D | VPRDCGCKPCICTVPEVSSVFIFPPKPKDVLTITLTPKV<br>TCVVVDISKDDPEVQFSWFVDDVEVHTAQTQPREEQF<br>NSTFRSVSELPIMHQDWLNGKEFKCRVNSAAFPAPIEK<br>TISKTKGRPKAPQVYTIPPPKEQMAKDKVSLTCMITDFF<br>PEDITVEWQWNGQPAENYKNTQPIMDTDGSYFVYSKL<br>NVQKSNWEAGNTFTCSVLHEGLHNHHTEKSLSHSPG<br>K (SEQ ID NO: 33) |
| G4S: | GGGGS (SEQ ID NO: 51) |

The constructs were recombinantly expressed in a mammalian cell line and purified.

TABLE 3

| Molecule | Alternate Name | Description | Sequence | SEQ ID NO: |
|---|---|---|---|---|
| IL10 | hIL10 | Recombinant human IL10 (obtained from Peprotech, Princeton NJ, Product #200-10) | SPGQGTQSENSCTHFPGNLPNMLRDLRDAFSRVKTFFQMKD<br>QLDNLLLKESLLEDFKGYLGCQALSEMIQFYLEEVMPQAENQ<br>DPDIKAHVNSLGENLKTLRLRLRRCHRFLPCENKSKAVEQVK<br>NAFNKLQEKGIYKAMSEFDIFINYIEAYMTMKIRN | 1 |
| IL10M1 | IL10 Mutein 1 | Fc-3XG4S-hIL10<br>Fc is IgG4s | ESKYGPPCPPCPAPPVAGPSVFLFPPKPKDTLMISRTPEVTCV<br>VVDVSQEDPEVQFNWYVDGVEVHNAKTKPREEQFNSTYRVV<br>SVLTVLHQDWLNGKEYKCKVSNKGLPSSIEKTISKAKGQPRE<br>PQVYTLPPSQEEMTKNQVSLTCLVKGFYPSDIAVEWESNGQP<br>ENNYKTTPPVLDSDGSFFLYSRLTVDKSRWQEGNVFSCSVM<br>HEALHNHYTQKSLSLSLGKGGGGSGGGGSGGGGSSPGQGT<br>QSENSCTHFPGNLPNMLRDLRDAFSRVKTFFQMKDQLDNLLL<br>KESLLEDFKGYLGCQALSEMIQFYLEEVMPQAENQDPDIKAH<br>VNSLGENLKTLRLRLRRCHRFLPCENKSKAVEQVKNAFNKLQ<br>EKGIYKAMSEFDIFINYIEAYMTMKIRN | 34 |
| IL10M2 | IL10 Mutein 2 | hIL10-3XG4S-Fc<br>Fc is IgG4s | SPGQGTQSENSCTHFPGNLPNMLRDLRDAFSRVKTFFQMKD<br>QLDNLLLKESLLEDFKGYLGCQALSEMIQFYLEEVMPQAENQ<br>DPDIKAHVNSLGENLKTLRLRLRRCHRFLPCENKSKAVEQVK<br>NAFNKLQEKGIYKAMSEFDIFINYIEAYMTMKIRNGGGGSGGG<br>GSGGGGSESKYGPPCPPCPAPPVAGPSVFLFPPKPKDTLMIS<br>RTPEVTCVVVDVSQEDPEVQFNWYVDGVEVHNAKTKPREEQ<br>FNSTYRVVSVLTVLHQDWLNGKEYKCKVSNKGLPSSIEKTISK<br>AKGQPREPQVYTLPPSQEEMTKNQVSLTCLVKGFYPSDIAVE<br>WESNGQPENNYKTTPPVLDSDGSFFLYSRLTVDKSRWQEGN<br>VFSCSVMHEALHNHYTQKSLSLSLGK | 35 |
| IL10M3 | IL10 Mutein 3 | hIL10-1XG4S-Fc<br>Fc is murine IgG1 | SPGQGTQSENSCTHFPGNLPNMLRDLRDAFSRVKTFFQMKD<br>QLDNLLLKESLLEDFKGYLGCQALSEMIQFYLEEVMPQAENQ<br>DPDIKAHVNSLGENLKTLRLRLRRCHRFLPCENKSKAVEQVK<br>NAFNKLQEKGIYKAMSEFDIFINYIEAYMTMKIRNGGGGSVPR<br>DCGCKPCICTVPEVSSVFIFPPKPKDVLTITLTPKVTCVVVDISK<br>DDPEVQFSWFVDDVEVHTAQTQPREEQFNSTFRSVSELPIM<br>HQDWLNGKEFKCRVNSAAFPAPIEKTISKTKGRPKAPQVYTIP<br>PPKEQMAKDKVSLTCMITDFFPEDITVEWQWNGQPAENYKN<br>TQPIMDTDGSYFVYSKLNVQKSNWEAGNTFTCSVLHEGLHN<br>HHTEKSLSHSPGK | 36 |
| IL10M4 | IL10 Mutein 4 | Fc-2XG4S-hIL10<br>Fc is IgG4s | ESKYGPPCPPCPAPPVAGPSVFLFPPKPKDTLMISRTPEVTCV<br>VVDVSQEDPEVQFNWYVDGVEVHNAKTKPREEQFNSTYRVV<br>SVLTVLHQDWLNGKEYKCKVSNKGLPSSIEKTISKAKGQPRE<br>PQVYTLPPSQEEMTKNQVSLTCLVKGFYPSDIAVEWESNGQP<br>ENNYKTTPPVLDSDGSFFLYSRLTVDKSRWQEGNVFSCSVM<br>HEALHNHYTQKSLSLSLGKGGGGSGGGGSSPGQGTQSENS<br>CTHFPGNLPNMLRDLRDAFSRVKTFFQMKDQLDNLLLKESLL<br>EDFKGYLGCQALSEMIQFYLEEVMPQAENQDPDIKAHVNSLG<br>ENLKTLRLRLRRCHRFLPCENKSKAVEQVKNAFNKLQEKGIYK<br>AMSEFDIFINYIEAYMTMKIRN | 37 |

TABLE 3-continued

| Molecule | Alternate Name | Description | Sequence | SEQ ID NO: |
|---|---|---|---|---|
| IL10M5 | IL10 Mutein 5 | Fc-1XG4S-hIL10 Fc is IgG4s | ESKYGPPCPPCPAPPVAGPSVFLFPPKPKDTLMISRTPEVTCV VVDVSQEDPEVQFNWYVDGVEVHNAKTKPREEQFNSTYRVV SVLTVLHQDWLNGKEYKCKVSNKGLPSSIEKTISKAKGQPRE PQVYTLPPSQEEMTKNQVSLTCLVKGFYPSDIAVEWESNGQP ENNYKTTPPVLDSDGSFFLYSRLTVDKSRWQEGNVFSCSVM HEALHNHYTQKSLSLSLGKGGGGSSPGQGTQSENSCTHFPG NLPNMLRDLRDAFSRVKTFFQMKDQLDNLLLKESLLEDFKGY LGCQALSEMIQFYLEEVMPQAENQDPDIKAHVNSLGENLKTL RLRLRRCHRFLPCENKSKAVEQVKNAFNKLQEKGIYKAMSEF DIFINYIEAYMTMKIRN | 38 |
| IL10M6 | IL10 Mutein 6 | hIL10-2XG4S-Fc Fc is IgG4s | SPGQGTQSENSCTHFPGNLPNMLRDLRDAFSRVKTFFQMKD QLDNLLLKESLLEDFKGYLGCQALSEMIQFYLEEVMPQAENQ DPDIKAHVNSLGENLKTLRLRLRRCHRFLPCENKSKAVEQVK NAFNKLQEKGIYKAMSEFDIFINYIEAYMTMKIRNGGGGSGGG GSESKYGPPCPPCPAPPVAGPSVFLFPPKPKDTLMISRTPEV TCVVVDVSQEDPEVQFNWYVDGVEVHNAKTKPREEQFNSTY RVVSVLTVLHQDWLNGKEYKCKVSNKGLPSSIEKTISKAKGQ PREPQVYTLPPSQEEMTKNQVSLTCLVKGFYPSDIAVEWESN GQPENNYKTTPPVLDSDGSFFLYSRLTVDKSRWQEGNVFSC SVMHEALHNHYTQKSLSLSLGK | 39 |
| IL10M7 | IL10 Mutein 7 | hIL10-1XG4S-Fc Fc is IgG4s | SPGQGTQSENSCTHFPGNLPNMLRDLRDAFSRVKTFFQMKD QLDNLLLKESLLEDFKGYLGCQALSEMIQFYLEEVMPQAENQ DPDIKAHVNSLGENLKTLRLRLRRCHRFLPCENKSKAVEQVK NAFNKLQEKGIYKAMSEFDIFINYIEAYMTMKIRNGGGGSESK YGPPCPPCPAPPVAGPSVFLFPPKPKDTLMISRTPEVTCVVV DVSQEDPEVQFNWYVDGVEVHNAKTKPREEQFNSTYRVVSV LTVLHQDWLNGKEYKCKVSNKGLPSSIEKTISKAKGQPREPQ VYTLPPSQEEMTKNQVSLTCLVKGFYPSDIAVEWESNGQPEN NYKTTPPVLDSDGSFFLYSRLTVDKSRWQEGNVFSCSVMHE ALHNHYTQKSLSLSLGK | 40 |
| IL10M8 | IL10 Mutein 8 | hIL10-Fc Fc is IgG4s | SPGQGTQSENSCTHFPGNLPNMLRDLRDAFSRVKTFFQMKD QLDNLLLKESLLEDFKGYLGCQALSEMIQFYLEEVMPQAENQ DPDIKAHVNSLGENLKTLRLRLRRCHRFLPCENKSKAVEQVK NAFNKLQEKGIYKAMSEFDIFINYIEAYMTMKIRNESKYGPPCP PCPAPPVAGPSVFLFPPKPKDTLMISRTPEVTCVVVDVSQED PEVQFNWYVDGVEVHNAKTKPREEQFNSTYRVVSVLTVLHQ DWLNGKEYKCKVSNKGLPSSIEKTISKAKGQPREPQVYTLPP SQEEMTKNQVSLTCLVKGFYPSDIAVEWESNGQPENNYKTTP PVLDSDGSFFLYSRLTVDKSRWQEGNVFSCSVMHEALHNHY TQKSLSLSLGK | 41 |
| IL10M9 | IL10 Mutein 9 | hIL10-1XG4S-Fc Fc is an IgG1 with D265A, N297A mutations | SPGQGTQSENSCTHFPGNLPNMLRDLRDAFSRVKTFFQMKD QLDNLLLKESLLEDFKGYLGCQALSEMIQFYLEEVMPQAENQ DPDIKAHVNSLGENLKTLRLRLRRCHRFLPCENKSKAVEQVK NAFNKLQEKGIYKAMSEFDIFINYIEAYMTMKIRNGGGGSDKT HTCPPCPAPELLGGPSVFLFPPKPKDTLMISRTPEVTCVVVAV SHEDPEVKFNWYVDGVEVHNAKTKPREEQYASTYRVVSVLT VLHQDWLNGKEYKCKVSNKALPAPIEKTISKAKGQPREPQVY TLPPSRDELTKNQVSLTCLVKGFYPSDIAVEWESNGQPENNY KTTPPVLDSDGSFFLYSKLTVDKSRWQQGNVFSCSVMHEAL HNHYTQKSLSLSPGK | 42 |
| IL10M10 | IL10 Mutein 10 | hIL10-Fc Fc is an IgG1 with D265A, N297A mutations | SPGQGTQSENSCTHFPGNLPNMLRDLRDAFSRVKTFFQMKD QLDNLLLKESLLEDFKGYLGCQALSEMIQFYLEEVMPQAENQ DPDIKAHVNSLGENLKTLRLRLRRCHRFLPCENKSKAVEQVK NAFNKLQEKGIYKAMSEFDIFINYIEAYMTMKIRNDKTHTCPPC PAPELLGGPSVFLFPPKPKDTLMISRTPEVTCVVVAVSHEDPE VKFNWYVDGVEVHNAKTKPREEQYASTYRVVSVLTVLHQDW LNGKEYKCKVSNKALPAPIEKTISKAKGQPREPQVYTLPPSRD ELTKNQVSLTCLVKGFYPSDIAVEWESNGQPENNYKTTPPVL DSDGSFFLYSKLTVDKSRWQQGNVFSCSVMHEALHNHYTQK S | 43 |
| IL10M11 | IL10 Mutein 11 | mIL10-1XG4S-Fc Fc is a murine IgG1 | SRGQYSREDNNCTHFPVGQSHMLLELRTAFSQVKTFFQTKD QLDNILLTDSLMQDFKGYLGCQALSEMIQFYLVEVMPQAEKH GPEIKEHLNSLGEKLKTLRMRLRRCHRFLPCENKSKAVEQVK SDFNKLQDQGVYKAMNEFDIFINCIEAYMMIKMKSGGGGSVP RDCGCKPCICTVPEVSSVFIFPPKPKDVLTITLTPKVTCVVVDIS KDDPEVQFSWFVDDVEVHTAQTQPREEQFNSTFRSVSELPIM HQDWLNGKEFKCRVNSAAFPAPIEKTISKTKGRPKAPQVYTIP PPKEQMAKDKVSLTCMITDFFPEDITVEWQWNGQPAENYKN TQPIMDTDGSYFVYSKLNVQKSNWEAGNTFTCSVLHEGLHN HHTEKSLSHSPGK | 44 |

TABLE 3-continued

| Molecule | Alternate Name | Description | Sequence | SEQ ID NO: |
|---|---|---|---|---|
| mIgG1 | N/A (control antibody with murine IgG1 sequence) | Murine IgG1 Fc isotype control | Heavy Chain; Variable Region (VR) + mIgG1: QVQLQESGPGLVAPSQSLSITCTVSGFSLTTFGVHWVRQSPG KGLEWLGVIWADETTNYNSALMSRLSISKDNSKSQVFLKMNG LRTDDTAIYSCARSKVSYYFDYWGRGTTLTVSSAKTTPPSVY PLAPGSAAQTNSMVTLGCLVKGYFPEPVTVTWNSGSLSSGV HTFPAVLQSDLYTLSSSVTVPSSTWPSETVTCNVAHPASSTK VDKKIVPRDCGCKPCICTVPEVSSVFIFPPKPKDVLTITLTPKVT CVVVDISKDDPEVQFSWFVDDVEVHTAQTQPREEQFNSTFR SVSELPIMHQDWLNGKEFKCRVNSAAFPAPIEKTISKTKGRPK APQVYTIPPPKEQMAKDKVSLTCMITDFFPEDITVEWQWNGQ PAENYKNTQPIMDTDGSYFVYSKLNVQKSNWEAGNTFTCSVL HEGLHNHHTEKSLSHSPGK | 45 |
| | | | Light Chain; VR + mouse Kappa NIMMTQSPSSLPVSPGEKVTMNCKSSRSVLYSLNQKNYLAW YQQKPGQSPKLLIYWASTRESGVPDRFTGSGSGTDFSLTISS VQAEDLAVYYCHQYLSSWTFGGGTKLEIKRADAAPTVSIFPPS SEQLTSGGASVVCFLNNFYPKDINVKWKIDGSERQNGVLNSW TDQDSKDSTYSMSSTLTLTKDEYERHNSYTCEATHKTSTSPIV KSFNRGEC | 46 |
| hIgG4s | N/A (control antibody with hIgG4s sequence) | Human IgG4 Fc isotype control. Fc is IgG4s | Heavy Chain VR + hIgG4s EVQLVESGGGLVQPGGSLRLSCAASGFTLSTYAMTWVRQAP GKGLEWVSAINYRAANTWYADSVKGRFTISRDNSKNTLYLQM NSLRDEDTAVYYCAQDRVIIKDYYVMDVWGQGTTVTVSSAST KGPSVFPLAPCSRSTSESTAALGCLVKDYFPEPVTVSWNSGA LTSGVHTFPAVLQSSGLYSLSSVVTVPSSSLGTKTYTCNVDHK PSNTKVDKRVESKYGPPCPPCPAPPVAGPSVFLFPPKPKDTL MISRTPEVTCVVVDVSQEDPEVQFNWYVDGVEVHNAKTKPR EEQFNSTYRVVSVLTVLHQDWLNGKEYKCKVSNKGLPSSIEK TISKAKGQPREPQVYTLPPSQEEMTKNQVSLTCLVKGFYPSDI AVEWESNGQPENNYKTTPPVLDSDGSFFLYSRLTVDKSRWQ EGNVFSCSVMHEALHNHYTQKSLSLSLGK | 47 |
| | | | Light Chain VR + human Kappa DIQMTQSPSSLSASVGDRVTITCRASQSISSYLNWYQQKPGK APKLLIYAASSLQSGVPSRFSGSGSGTDFTLTISSLQPEDFATY YCQQSYSTPPITFGQGTRLEIKRTVAAPSVFIFPPSDEQLKSG TASVVCLLNNFYPREAKVQWKVDNALQSGNSQESVTEQDSK DSTYSLSSTLTLSKADYEKHKVYACEVTHQGLSSPVTKSFNR GEC | 48 |
| hIgG1 | N/A (control antibody with hIgG1 sequence) | Anti-FelD1 human IgG1 Fc isotype control | Heavy Chain QVQLQESGPGLVKPSETLSLTCTVSGGSISSYYWSWIRQPPG KGLEWIGYIYYSGRTNYNPSLKSRVTISVDTSKNQFSLKLSSV TAADTAIYYCARHRVTRTADSFDYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSNT KVDKKVEPKSCDKTHTCPPCPAPELLGGPSVFLFPPKPKDTL MISRTPEVTCVVVDVSHEDPEVKFNWYVDGVEVHNAKTKPR EEQYNSTYRVVSVLTVLHQDWLNGKEYKCKVSNKALPAPIEK TISKAKGQPREPQVYTLPPSRDELTKNQVSLTCLVKGFYPSDI AVEWESNGQPENNYKTTPPVLDSDGSFFLYSKLTVDKSRWQ QGNVFSCSVMHEALHNHYTQKSLSLSPGK | 49 |
| | | | Light Chain DIQMTQSPSSLSASVGDRVTITCQASQDINNYLNWYQQKTGK APKFLIYDASNLETGVSSRFSGSGSGTDFTFTISSLQPEDVGT YYCHQYGDLPYTFGQGTKLEIKRTVAAPSVFIFPPSDEQLKSG TASVVCLLNNFYPREAKVQWKVDNALQSGNSQESVTEQDSK DSTYSLSSTLTLSKADYEKHKVYACEVTHQGLSSPVTKSFNR GEC | 50 |

7.1.2. STAT3 Reporter Assay

A STAT3 driven luciferase-based reporter assay was developed to evaluate the ability of IL10 and IL10 muteins to activate STAT3-mediated transcription in two cell lines, TF-1 and Ramos, previously reported to express the IL10 receptor (Tan et al., 1993, J Biol Chem. 268(28):21053-9).

7.1.2.1. Engineering of reporter TF-1 cells

TF-1 cells (ATCC, #CRL-2003) were transduced with lentiviral particles harboring a STAT3 luciferase reporter construct (Cignal STAT3-Luc lenti reporter, SA Biosciences, CLS-6028L-8) in the presence of 5 µg/mL polybrene. Puromycin resistant cells (TF-1/STAT3-Luc) were selected and maintained in RPMI+10% FBS+P/S/G+2 ng/mL GM-CSF+1 µg/mL puromycin.

7.1.2.2. Engineering of Reporter Ramos cells

Ramos.2G6.4C10 cells (ATCC, #CRL-1923) were transduced with lentiviral particles harboring a STAT3 luciferase reporter construct (Cignal STAT3-Luc lenti reporter, SA Biosciences, CLS-6028L-8) in the presence of 5 µg/mL polybrene. Puromycin resistant cells (Ramos/STAT3-Luc) were selected and maintained in RPMI+10% FBS+P/S/G+1 µg/mL puromycin.

7.1.2.3. IL10 Stimulation of Reporter Cells

In this experiment, engineered reporter cells are stimulated via either recombinant IL10 or IL10 muteins. The cytokine, through binding to the IL10 receptor subunit alpha (IL10Ra), recruits the beta subunit (IL10Rb) permitting the assembly of the signaling complex and inducing STAT3 phosphorylation (Yoon et al., 2006, J Biol Chem. 281(46): 35088-96). STAT3 phosphorylation leads to enhanced transcriptional activity of the STAT3 response elements driving the production of the reporter gene, luciferase.

7.1.2.4. Luciferase Assay Set Up

RPMI1640 supplemented with 10% FBS and P/S/G was used as assay medium to prepare cell suspensions and antibody dilutions.

A day prior to screening, engineered reporter cells were diluted 1:3. The day of the assay cells were spun down and resuspended in assay medium at $1\times10^6$/mL. IL10, IL10 muteins and controls were diluted 1:5 following an 11-point dilution, ranging from 100 nM to 10 fM with the 12th point containing no recombinant protein. $5\times10^4$ reporter cells were added to 96 well white flat bottom plates and incubated with serially diluted IL10, IL10 mutein, or control proteins. Plates were incubated for 5 hours and 30 min at 37° C./5% $CO_2$, before the addition of 100 μL ONE-Glo™ (Promega) reagent to lyse cells and detect luciferase activity. The emitted light was captured in relative light units (RLU) on a multilabel plate reader Envision (PerkinElmer). All serial dilutions were tested in duplicates.

For determination of EC50 values, points leading to a hook effect, whereby concentrations of the protein higher than the max signal lead to a dose dependent decrease in signal, were excluded. The EC50 values of the antibodies were determined using the GraphPad Prism™ software from a four-parameter logistic equation over a 12-point dose-response curve where the 12th dilution point contained no recombinant protein. Fold induction was calculated using the following equation:

$$\text{Fold induction} = \frac{\text{Highest mean } (RLU) \text{ value with in tested dose range}}{\text{Mean } RLU \text{ values of no protein control}}$$

7.1.3. Characterization of Human IL10 Muteins in Cell-Based Assays Using Primary Human Immune Cells A primary mixed T-cell/allogeneic PBMC functional assay was developed to evaluate the effect of IL10 stimulation on IL2, TNFα and IFNγ release during T cell activation.

7.1.3.1. Human Primary PBMC Isolation

Human peripheral blood mononuclear cells (PBMCs) were isolated from a healthy donor leukopak (donor 123). PBMC isolation was accomplished by density gradient centrifugation using 50 mL SepMate™ tubes following the manufacturer's recommended protocol. Briefly, the leukopak was diluted 1:2 with D-PBS and 30 ml layered over 15 mL of Ficoll that was added to 50 mL SepMate tubes. Subsequent steps were followed according to SepMate manufacturer's protocol. Isolated PBMC were frozen in FBS supplemented with 10% DMSO.

7.1.3.2. Human Primary T Cell Isolation

T cells were isolated from 2 healthy donors leukopaks (donors 5500Y and 6900M). T cell isolation was accomplished using RosetteSep Human T cell enrichment cocktail (StemCell) in agreement with the manufacturer protocol. T cells were separated by density gradient centrifugation using 50 mL SepMate™ tubes following the manufacturer's recommended protocol. Isolated T-cells were in FBS supplemented with 10% DMSO.

7.1.3.3. Cytokine Release from Primary T-Cells Co-Incubated with IL10 and Allogeneic PBMC In this experiment, primary T-cells are stimulated via a 3 day coculture with allogeneic PBMC which were mitomycin C treated to arrest PBMC growth. A titration of IL10 or IL10 muteins were added during the coculture and their impact on T-cell activity was determined by measuring the release of IL2, TNFα and IFNγ in the cell culture supernatant using homogenous, no wash, AlphaLISA kits (Perkin Elmer, AL208F, AL217S, AL221F).

Previously isolated and frozen human T-cells from donor 5500Y and 6900M were thawed the day of the assay in stimulation media (X-VIVO 15 cell culture media supplemented with 10% FBS, HEPES, NaPyr, NEAA, and 0.01 mM BME) containing 50 U/ml benzonase nuclease. Cells were centrifuged at 1200 rpm for 10 minutes, resuspended in stimulation media and plated out into 96-well round bottom plates at a concentration of $1\times10^5$ cells/well. Previously isolated and frozen human PBMC from donor 123 were thawed the day of the assay in stimulation media containing 50 U/ml benzonase nuclease. Cells were centrifuged at 1200 rpm for 10 minutes and resuspended in stimulation media containing 50 μg/mL mitomycin C at a concentration of $1\times10^7$ cells/mL. After incubation for 1 hour at 37° C., the PBMCs were washed 3 times with D-PBS containing 2% FBS, resuspended in stimulation media and added to the wells containing T-cells at a final concentration of $1.5\times10^5$ cells per well. Subsequently, IL10, IL10 muteins and controls were diluted 1:5 following an 9-point dilution, ranging for IL10 from 500 nM to 1.28 pM and for IL10 muteins or control antibodies from 100 nM to 0.256 pM, with the 10th dilution point containing no recombinant protein.

The serial diluted proteins were added to wells, and the plates were incubated for 72 hours at 37° C./5% CO2. The plates were then centrifuged to pellet the cells, and 50 μL of supernatant was collected. From this, 5 μL of supernatant was taken and tested in human IL-2, TNFα and IFNγ AlphaLISA assays according to the manufacturer's protocols. The measurements were acquired on the multilabel plate reader Envision. Standard curves of known IL-2, TNFα and IFNγ concentrations were generated in order to extrapolate the pg/mL of each cytokine released in the assay wells. All serial dilutions were tested in duplicates.

The IC50 values of the cytokines were determined using the GraphPad Prism™ software from a four-parameter logistic equation over a 10-point dose-response curve, where the 10th dilution point contained no recombinant protein. Percent inhibition was calculated using the following equation:

$$\text{Percent inhibition} = 100 \times \frac{(\text{mean pg/ml of no protein control}) - (\text{lowest mean pg/ml with in tested dose range})}{(\text{mean pg/ml of no protein control})}$$

7.1.4. Activity of IL10 Muteins in Syngeneic Tumor Allograft Model 7.1.4.1. Implantation of Tumors and Allocation of Dosing Groups Female BALB/c mice (the Jackson Laboratory, Bar Harbor, Me.) were implanted with tumor cells subcutaneously. $1\times10^6$ tumor cells were implanted subcutaneously into the right flank of 6 to 8-week-old female BALB/c mice (the Jackson Laboratory, Bar Harbor, Me.).

The therapeutic intervention or isotype control was administered intraperitoneally for 3 weeks. Mice received intraperitoneal injections of test articles twice a week for 3 weeks, and tumor volumes and body weights were monitored twice a week throughout the study.

7.1.4.2. Calculation of Tumor Size and Growth Inhibition

Average and median tumor size, as well as percent tumor growth inhibition relative to the control treated group, were calculated for each group. Tumors length and width were measured with calipers twice a week and tumor volume was calculated using the formula (length×width$^2$)/2. Measurements were performed until the average tumor size of the control group reached 4000 mm$^3$, or until any mouse in any group needed to be euthanized due to ulceration or body weight loss of more than 20%. Tumor growth inhibition was calculated according to the following formula: $[1-(T_{final}-T_{initial})/(C_{final}-C_{initial})]*100$, where T (treated group) and C (control group) represent the mean tumor mass on the day when all mice were alive. Observations were extended to Day 54 (3 weeks after the last treatment) to determine the frequency of tumor-free mice.

7.2. Example 1: Activity of IL10 Muteins in STAT3 Reporter Assay

The ability of recombinant IL10 muteins to stimulate IL10 receptor was assessed in a STAT3-reporter cell-based bioassay as described in Section 7.1.2.

Activation curves are shown in FIGS. 3A-3F, EC50 and fold induction values are summarized in Table 4 for engineered reporter cells, Ramos/STAT3-Luc or TF-1/STAT3-Luc cells, incubated with recombinant human IL10, IL10 muteins, the human IgG4s isotype control or the murine IgG1 isotype control.

When reporter cells were treated with control proteins, no increase in luciferase activity was detected. In contrast, incubation of the reporter cells Ramos/STAT3-Luc and TF-1/STAT3-Luc, with human IL10 induced luciferase activity (4.5 and 5.9-fold respectively). Incubation of the Ramos/STAT3-Luc and TF-1/STAT3-Luc with IL10 muteins also induced luciferase activity (Ramos/STAT3: IL10M1: 3.7 fold, IL10M2: 3.6 fold, IL10M3: 3.2 fold; TF-1/STAT3-Luc, IL10M1: 4.8 fold, IL10M2: 4.1 fold, IL10M3: 3.4 fold) with sub-nanomolar EC50 values as shown in Table 4 and FIGS. 3A-3F.

TABLE 4

Tabulated EC$_{50}$ values of luciferase activity in engineered reporter cells incubated with IL10 or IL10 muteins

| Protein | Construct | Ramos/STAT3-Luc EC$_{50}$ [M] | Fold induction | TF-1/STAT3-Luc EC$_{50}$ [M] | Fold induction |
|---|---|---|---|---|---|
| hIL10 | Recombinant human IL10 purchased from Peprotech | 5.074E−11 | 4.5 | 7.051E−11 | 5.9 |
| IL10M1 | hIgG4s-3XG$_4$S-hIL10 | 1.185E−10 | 3.7 | 1.184E−10 | 4.8 |
| IL10M2 | hIL10-3XG$_4$S-hIgG4s | 2.126E−10 | 3.6 | 5.145E−10 | 4.1 |
| IL10M3 | hIL10-1XG$_4$S-mIgG1 | 2.195E−10 | 3.2 | 4.511E−10 | 3.4 |
| mIgG1 Control | mIgG1 Iso | ND | 1.1 | ND | 1.1 |
| hIgG4 Control | hIgG4s Iso | ND | 1.0 | ND | 1.4 |

Abbreviations:
NC: Not calculated because the data did not fit a 4-parameter logistic equation.
ND: Not determined because a concentration-dependent response was not observed.

7.3. Example 2: Activity of IL10 Muteins on Cytokine Release in Primary Human T-Cells The ability of IL10 to inhibit T-cell stimulation was assessed in a functional primary T-cell assay measuring IL2, TNFα and IFNγ cytokine production.

Data for cytokine release are shown in FIGS. 4A-4I and FIGS. 5A-5I (for donor 5500Y and 6900M respectively), IC50 and percentage inhibition values are summarized in Tables 5 and 6 (for donor 5500Y and donor 6900M respectively) for T-cells co-incubated with allogeneic mitomycin C treated PBMC with a titration of either H4sH10154P3 (human IgG4 stealth isotype control), mIgG$_1$ (mouse IgG1 isotype control), human IL10 or IL10 muteins.

Co-incubation of T cells from 2 donors (FIGS. 4A-4I: donor 5500Y and FIGS. 5A-5I: donor 6900M) with allogeneic mitomycin C treated PBMC led to measurable IL2 (A) TNFα (B) and IFNγ release (C). Addition of a titration of human IL10 or IL10 Fc muteins during the T cells/PBMC co-incubation lowered IL2, TNFα, and IFNγ release in a dose dependent manner (Donor 5500Y: Table 5 and FIGS. 4A-4I; Donor 6900M: Table 6 and FIGS. 5A-5I).

TABLE 5

IC$_{50}$ and fold inhibition results for donor 5500Y T cell supression in presence of IL10 and IL10 Muteins

| Protein | Construct | IL2 IC$_{50}$ [M] | IL2 % inhibition | TNFα IC$_{50}$ [M] | TNFα % inhibition | IFNγ IC$_{50}$ [M] | IFNγ % inhibition |
|---|---|---|---|---|---|---|---|
| hIL10 | Purchased from Peptrotech | 2.659E−11 | 82.8 | NC | 69.5 | 1.640E−11 | 81.5 |
| IL10M1 | hIgG$_4$s-3XG$_4$S-hIL10 | 5.590E−11 | 78.5 | 1.134E−11 | 70.0 | 3.163E−12 | 84.2 |
| IL10M2 | hIL10-3XG$_4$S-hIgG$_4$s | NC | 75.7 | 1.921E−11 | 63.6 | NC | 84.4 |
| IL10M3 | hIL10-1XG$_4$S-mIgG$_1$ | 9.609E−11 | 66.7 | 1.890E−11 | 54.6 | 1.210E−11 | 78.2 |
| mIgG$_1$ | mIgG1 Iso | ND | 17.2 | ND | 6.1 | ND | 18.8 |
| hIgG$_4$ | hIgG4s Iso | ND | 24.3 | ND | 20.4 | ND | 31.4 |

Abbreviations:
NC: Not calculated because the data did not fit a 4-parameter logistic equation.
ND: Not determined because a concentration-dependent response was not observed

TABLE 6

IC$_{50}$ and fold inhibition results for donor 6900M T cell supression in presence of IL10 and IL10 Muteins

| Protein | Construct | IL2 IC$_{50}$ [M] | IL2 % inhibition | TNFα IC$_{50}$ [M] | TNFα % inhibition | IFNγ IC$_{50}$ [M] | IFNγ % inhibition |
|---|---|---|---|---|---|---|---|
| hIL10 |  | 1.496E−11 | 80.7 | 1.607E−11 | 82.3 | 9.985E−12 | 90.8 |
| IL10M1 | hIgG$_4$s-3XG$_4$S-hIL10 | 5.971E−11 | 76.3 | 2.592E−11 | 77.1 | 6.561E−12 | 91.1 |
| IL10M2 | hIL10-3XG$_4$S-hIgG$_4$s | 1.489E−10 | 65.4 | 2.976E−11 | 72.7 | 8.791E−12 | 89.1 |
| IL10M3 | hIL10-1XG$_4$S-mIgG$_1$ | 8.911E−11 | 63.6 | 1.351E−11 | 66.3 | 2.900E−12 | 84.3 |
| mIgG$_1$ | mIgG1 Iso | ND | 15.3 | ND | 6.6 | ND | 8.0 |
| hIgG$_4$ | hIgG4s Iso | ND | 36.5 | ND | 13.7 | ND | −0.3 |

Abbreviations:
NC: Not calculated because the data did not fit a 4-parameter logistic equation.
ND: Not determined because a concentration-dependent response was not observed

7.4. Example 3: Anti-Tumor Activity of IL10 Muteins

The activity of IL10 muteins in a syngeneic tumor allograft model was evaluated. Colon 26 tumor cells were implanted into BALB-C mice as described in Section 7.1.4. Once tumors had reached an average volume of 110 mm$^3$ on day 11 (ranging from 80 to 140 mm$^3$) mice were randomized into groups (n=7/group) and dosed with either hIgG4s isotype control, IL10M1, or IL10M2 in equivalent molar amounts of isotype control (0.167 mg/kg) or IL10 mutein (0.1 mg/kg).

Figure 1A:
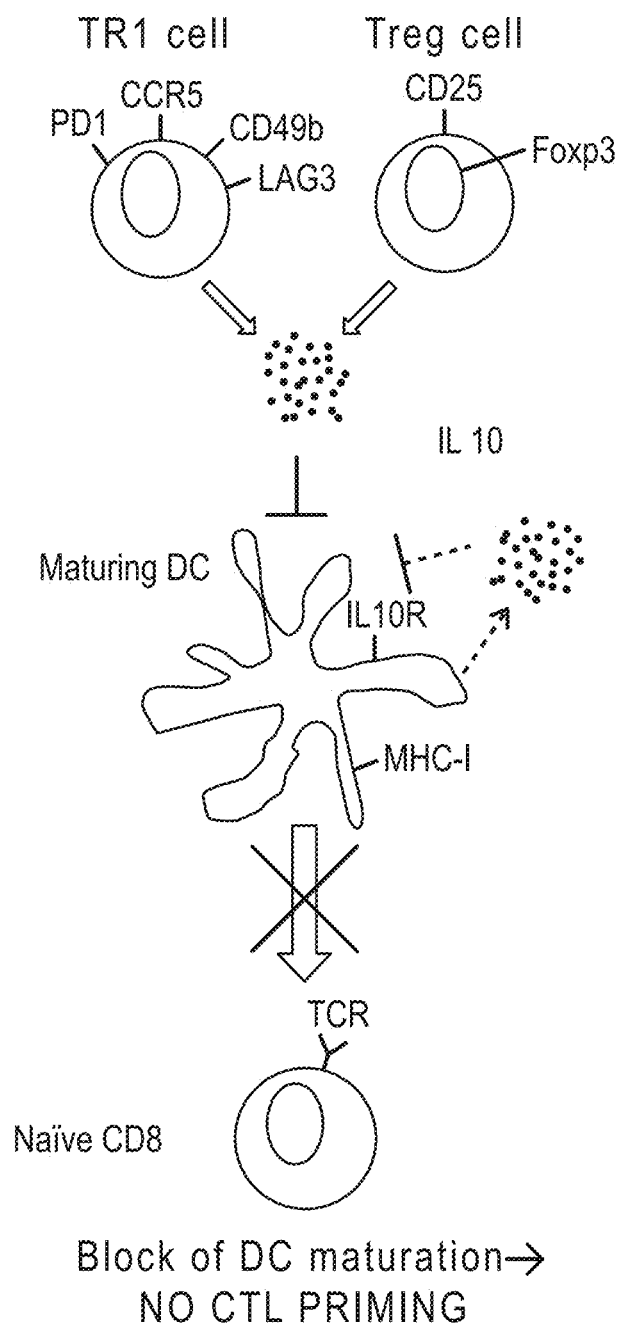
Figure 1B:
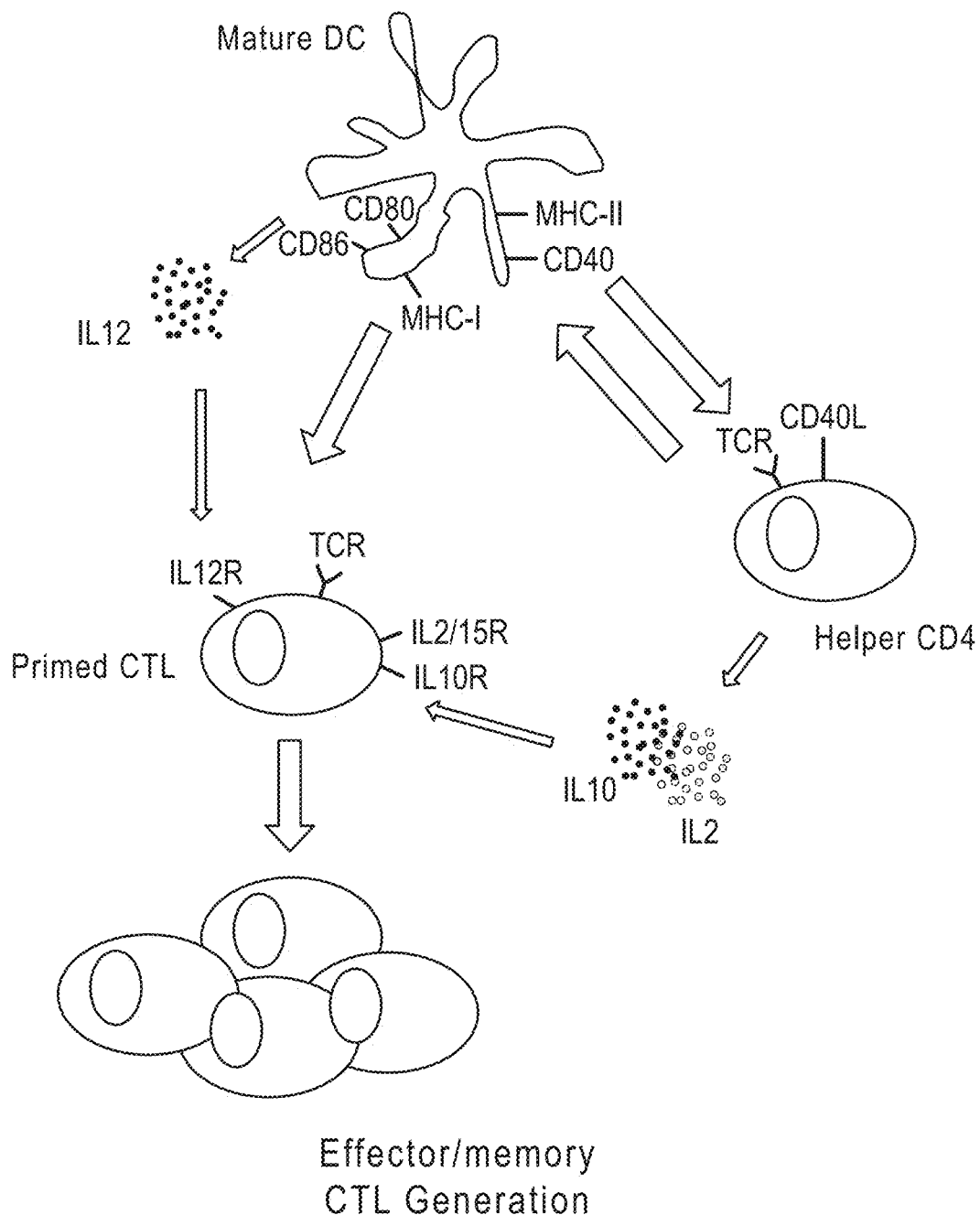
Figure 2A:
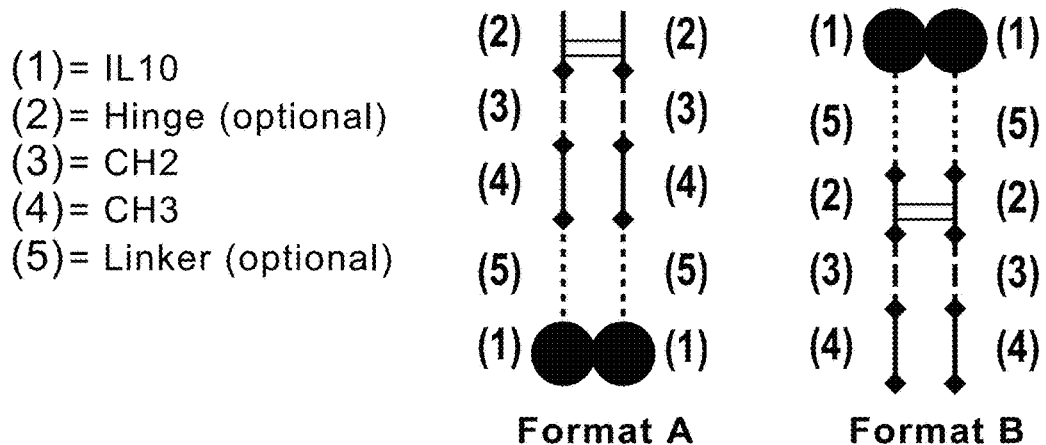
Figure 2B:
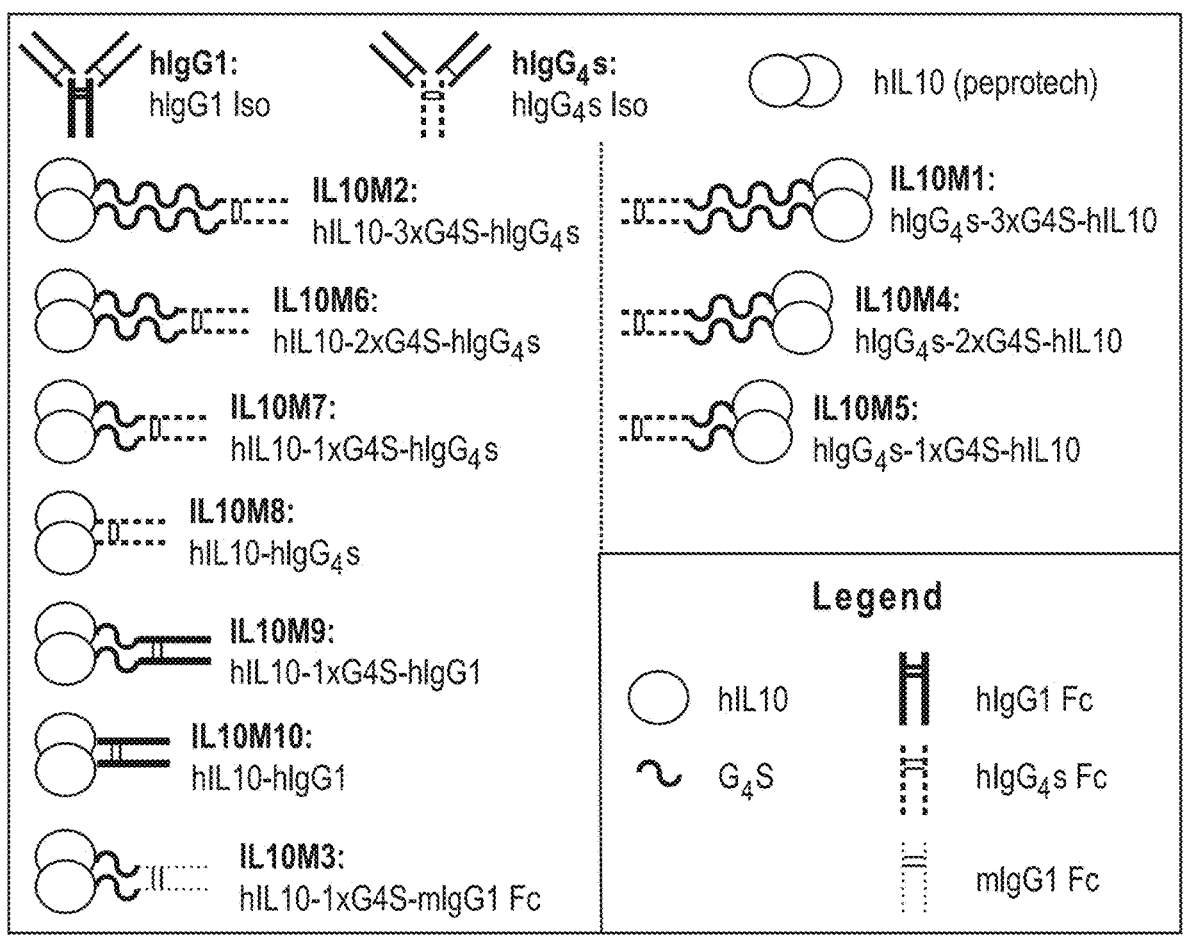
Figure 3D:
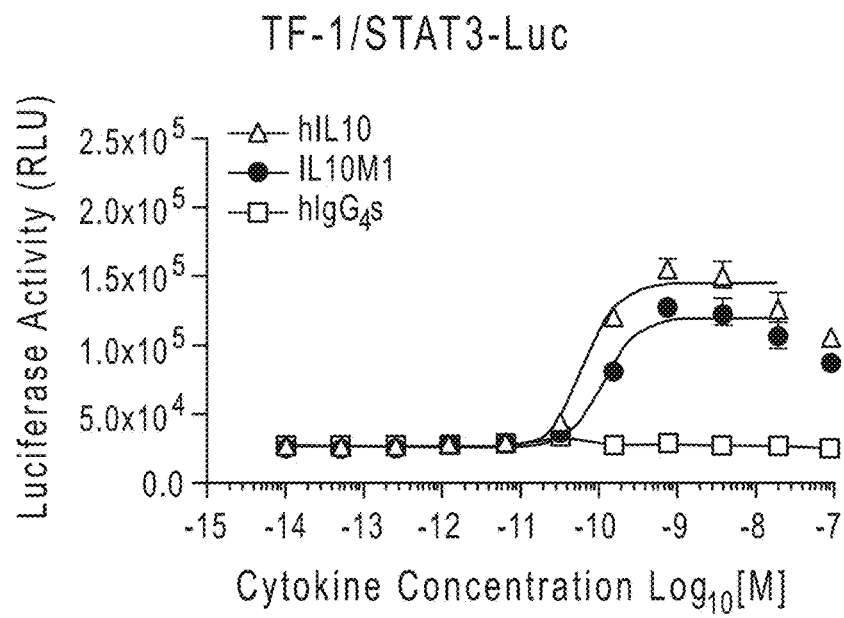
Figure 3E:
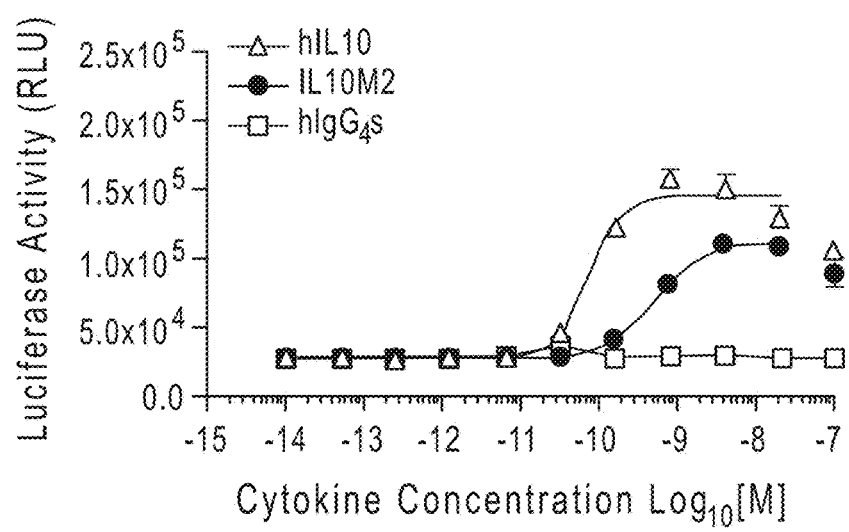
Figure 3F:
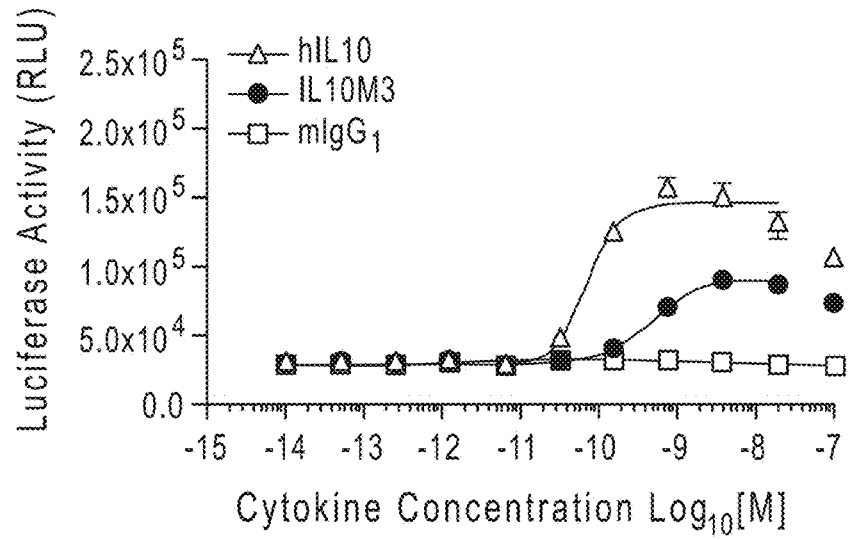
Figure 4A:
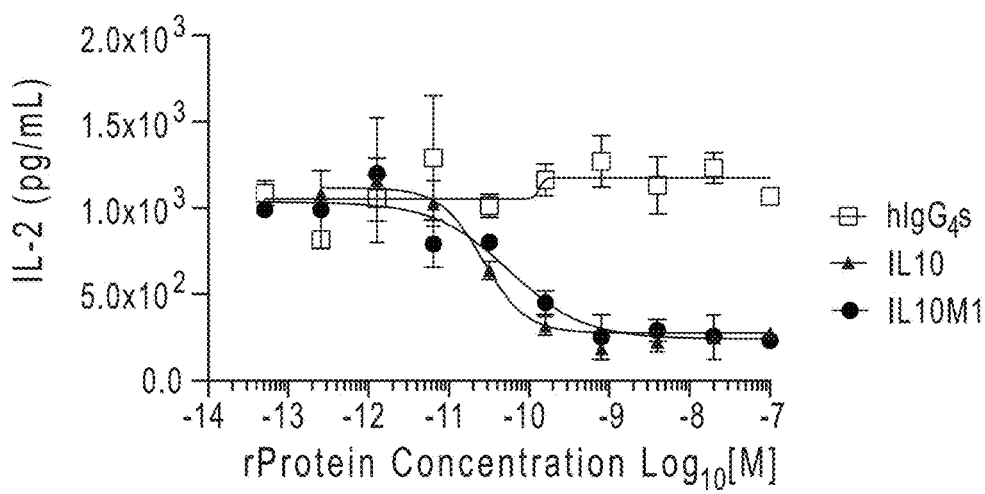
Figure 4B:
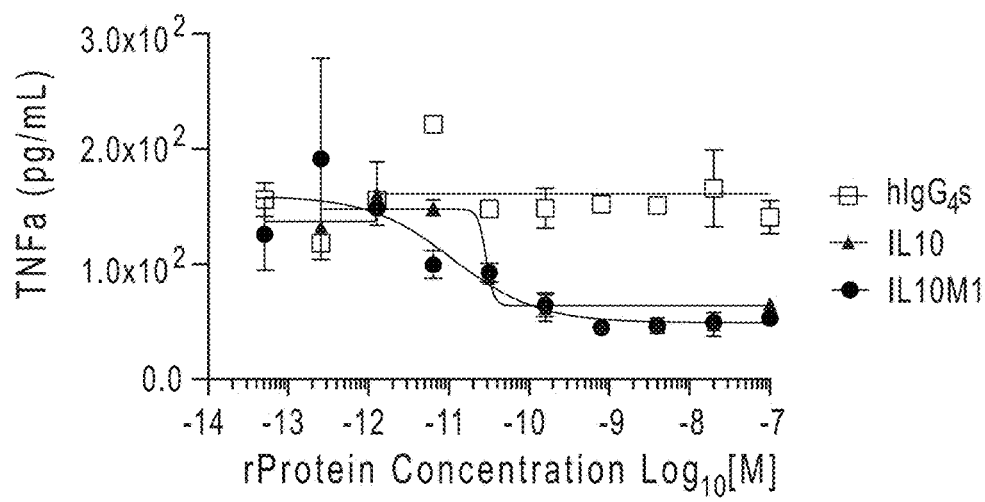
Figure 4C:
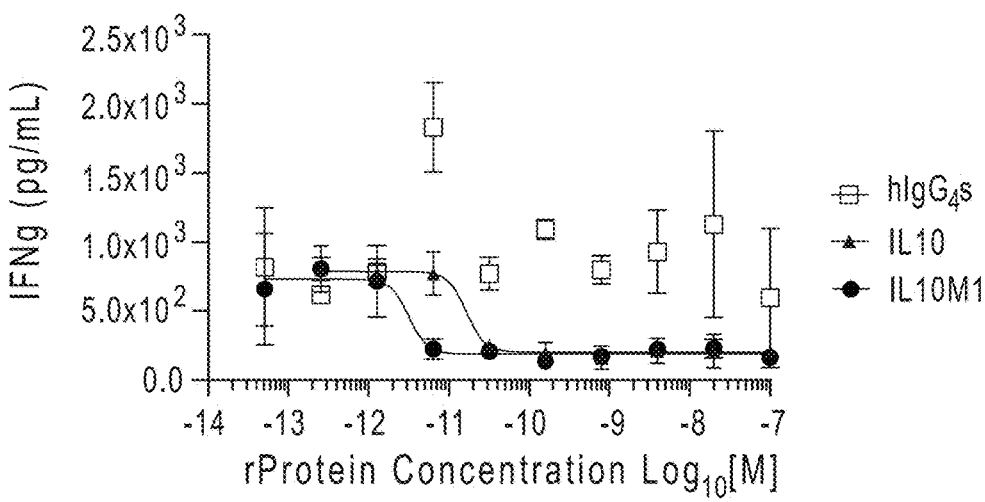
Figure 4D:
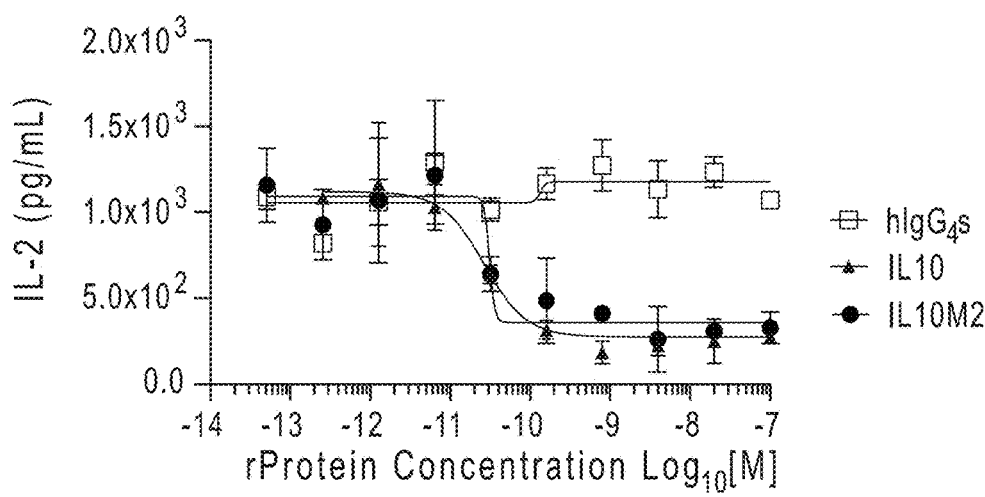
Figure 4E:
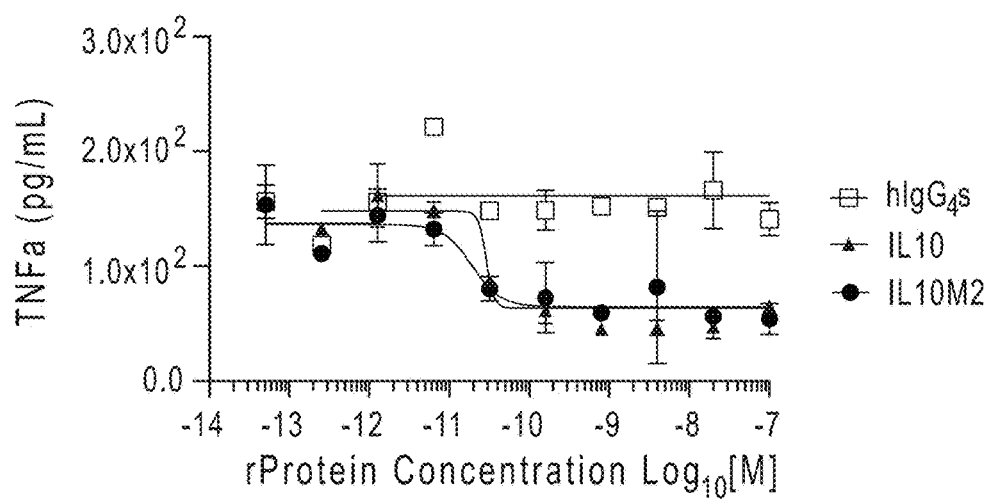
Figure 4F:
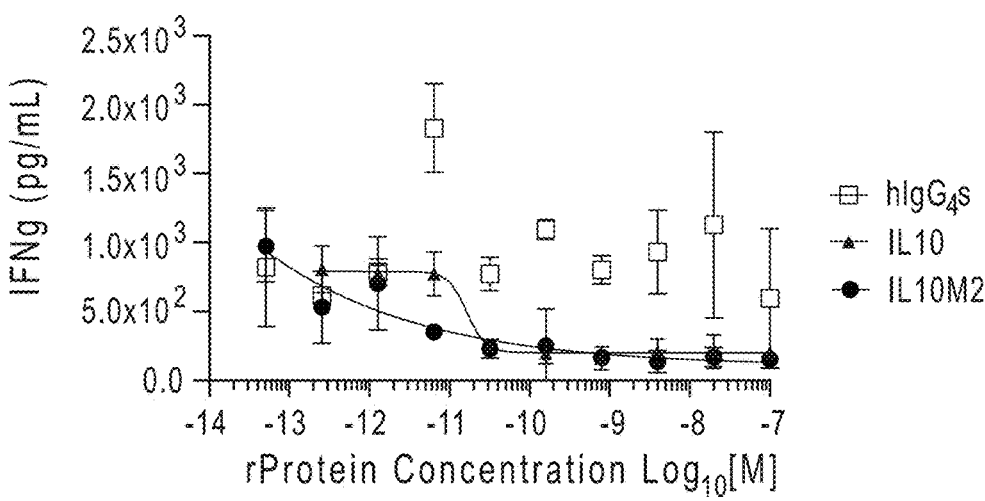
Figure 4G:
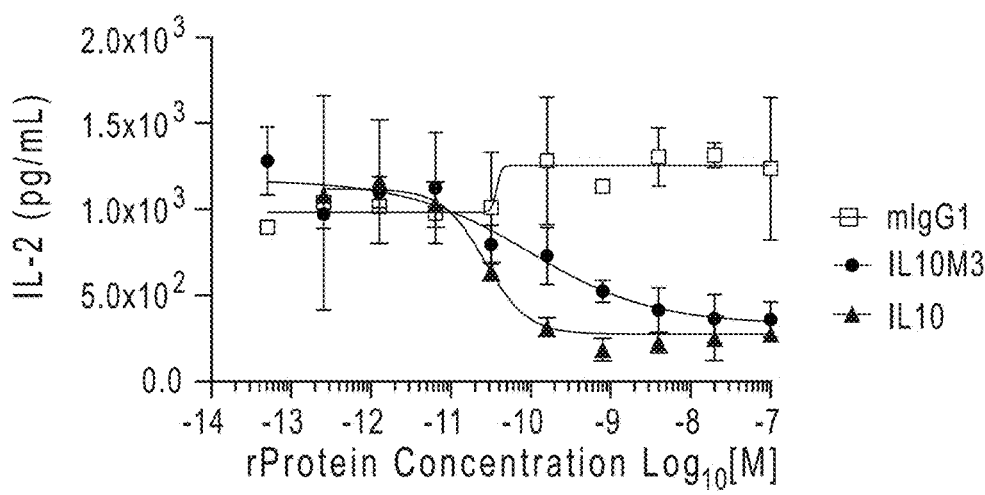
Figure 4H:
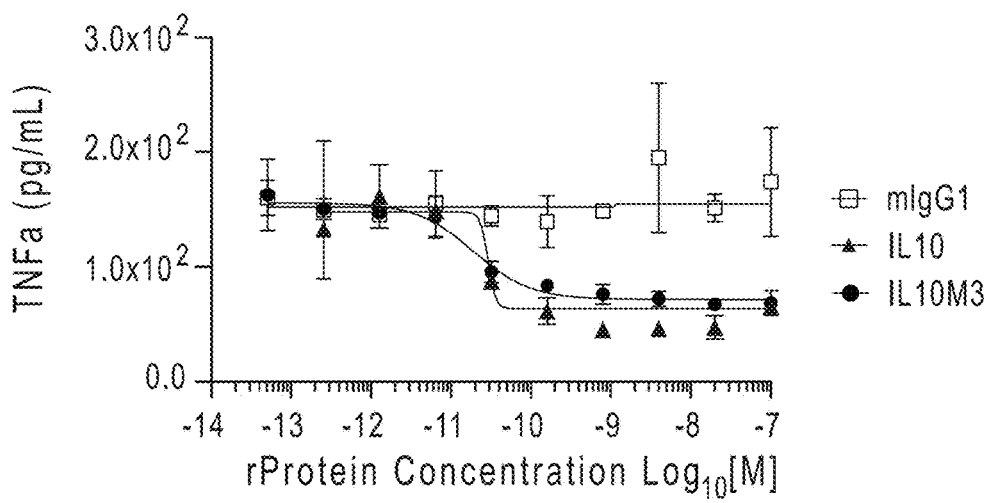
Figure 4I:
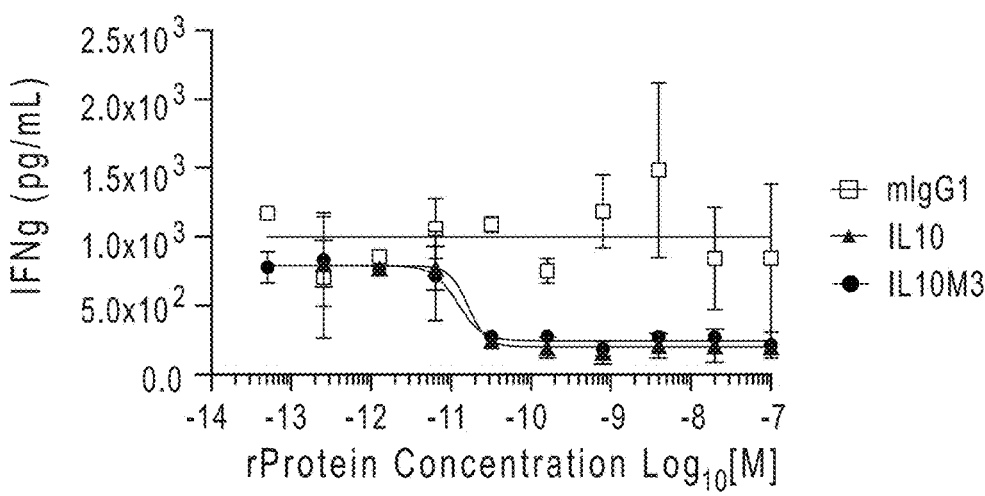
Figure 5A:
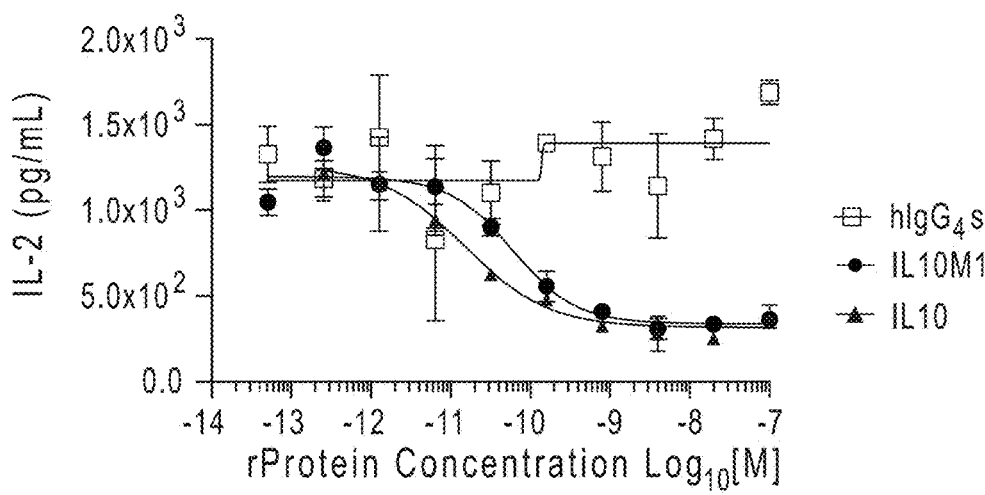
Figure 5B:
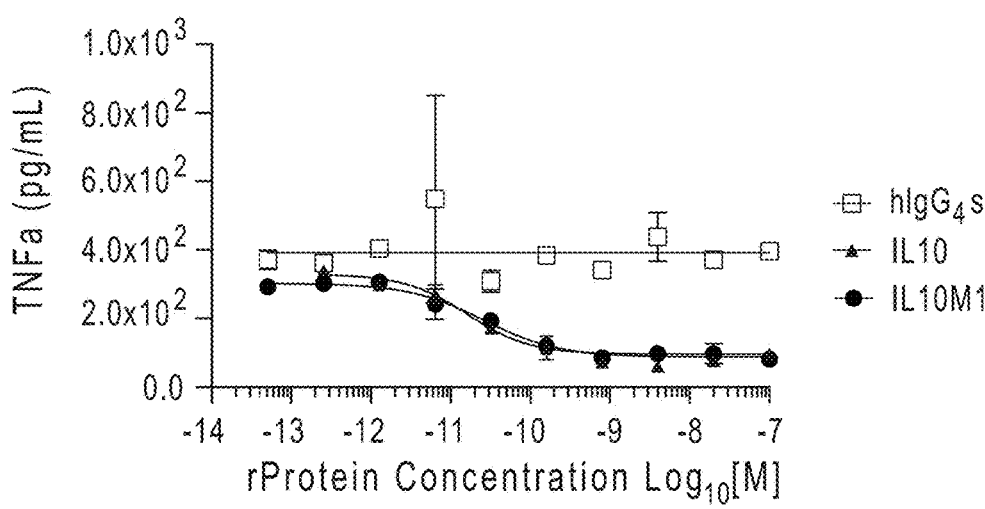
Figure 5C:
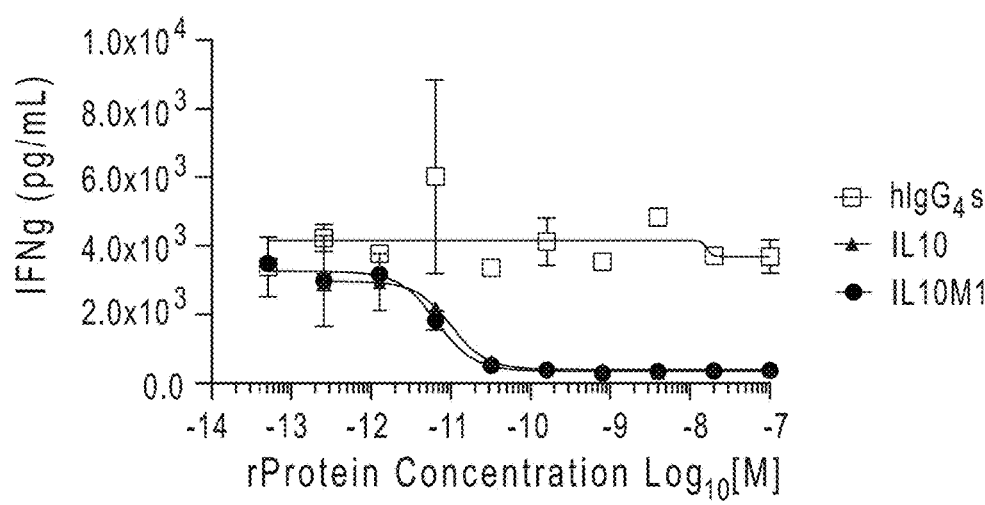
Figure 5D:
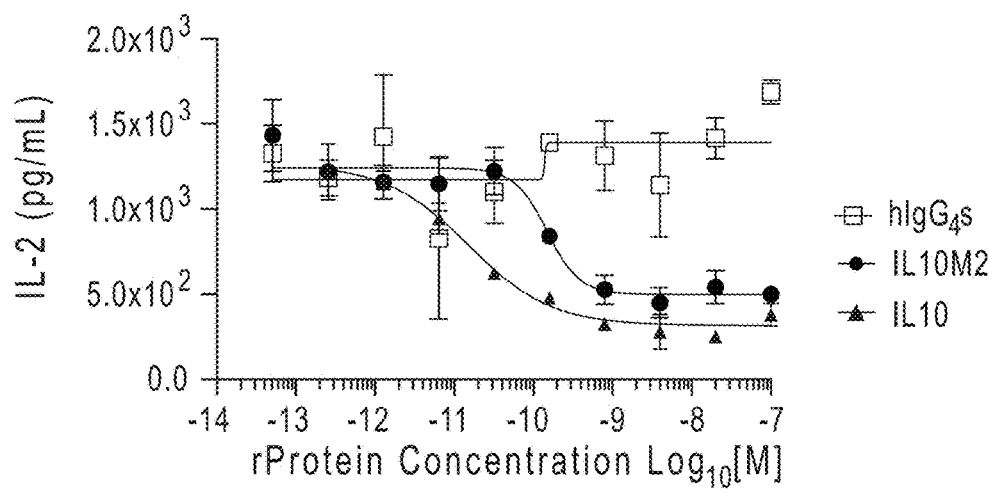
Figure 5E:
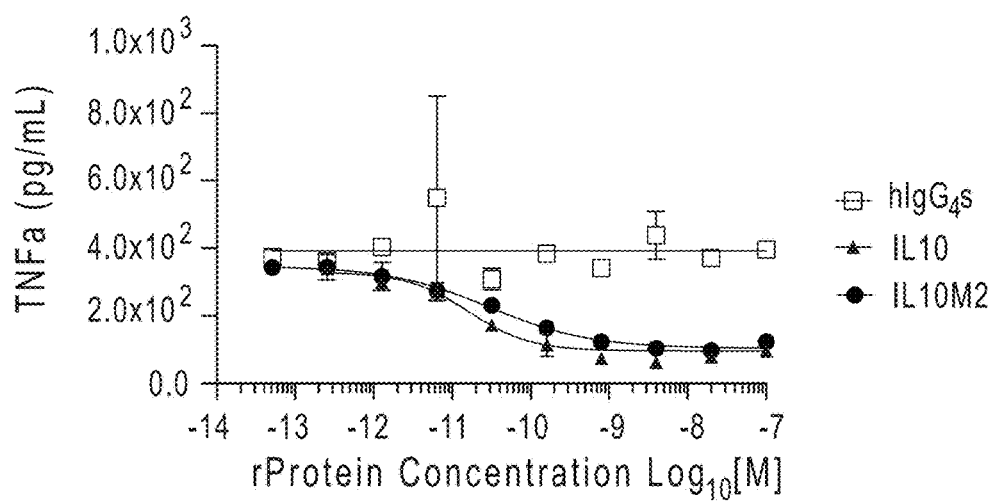
Figure 5F:
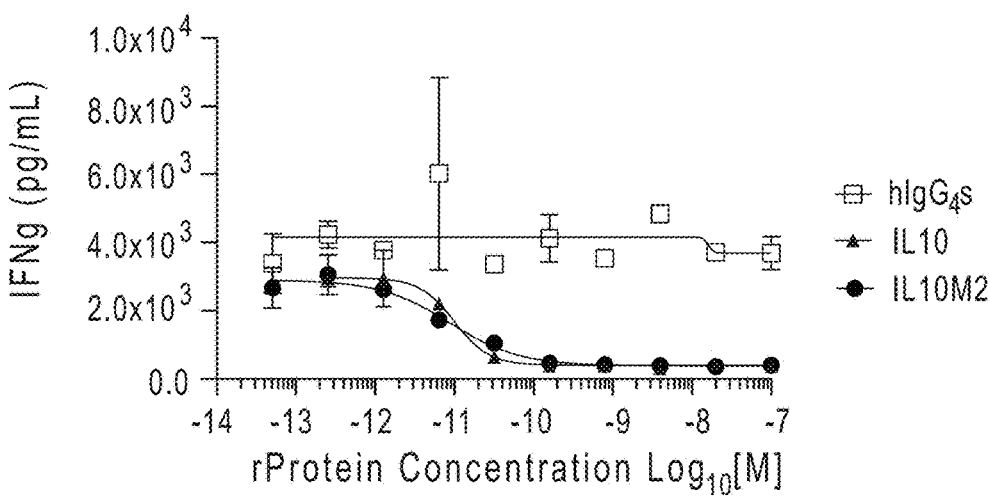
Figure 5G:
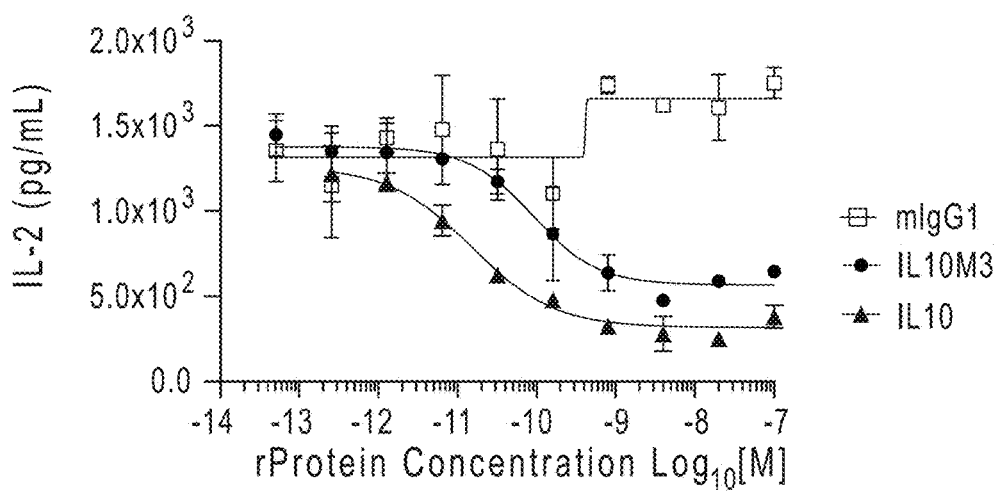
Figure 5H:
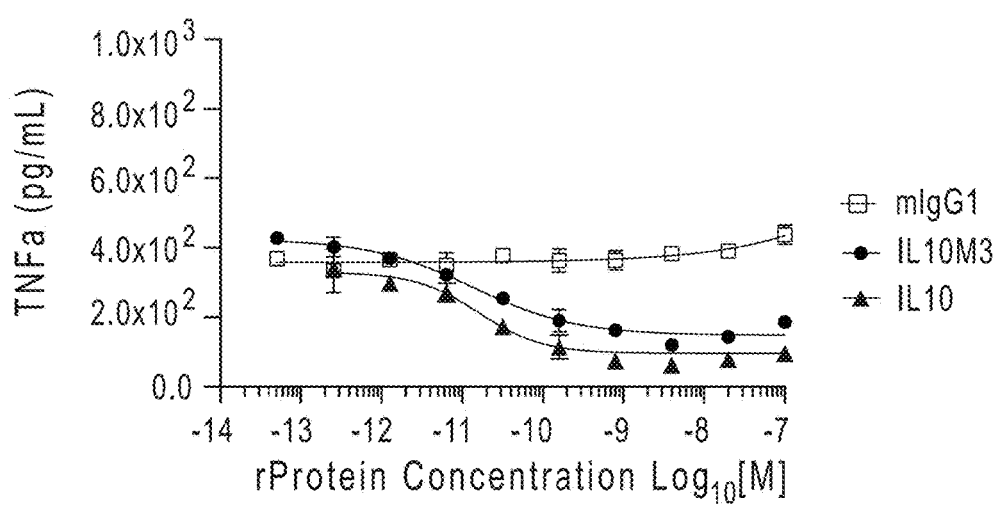
Figure 5I:
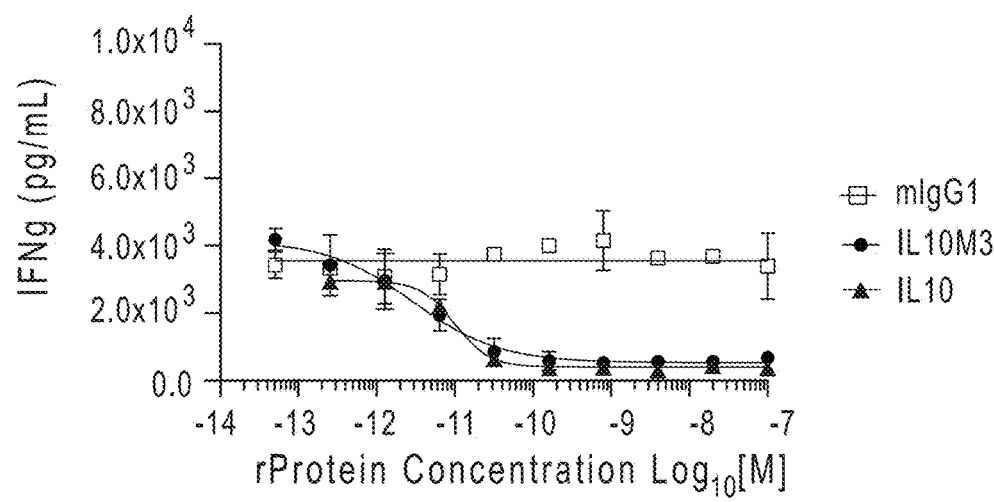
Figure 6A:
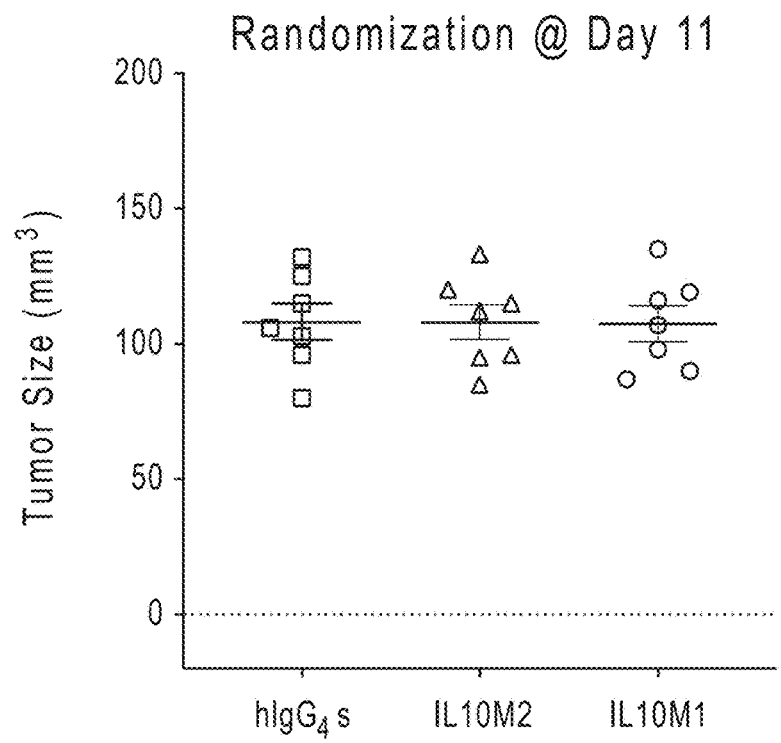
FIGS. 6A-6B show the anti-tumor activity of IL10 muteins as compared to an isotype control in a syngeneic mouse model. Tumor volume is shown on Day 11 (FIG. 6A) and Day 32 (FIG. 6B).
Figure 6B:
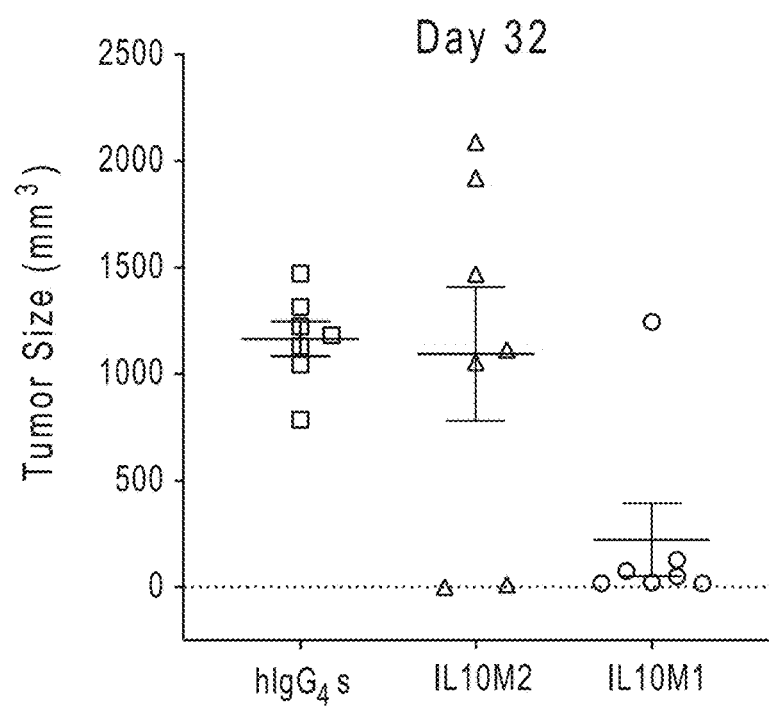
Figure 7A:
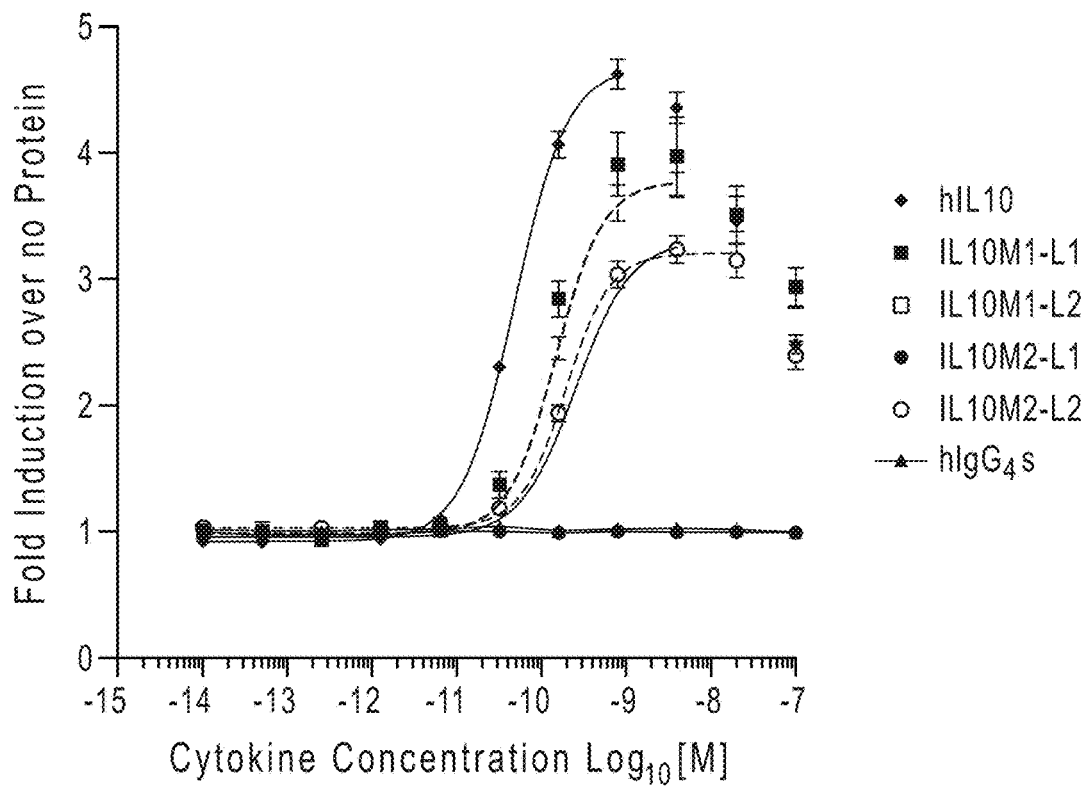
FIGS. 7A-7F show the activity of different IL10 muteins in a STAT3 luciferase assay.
Figure 7B:
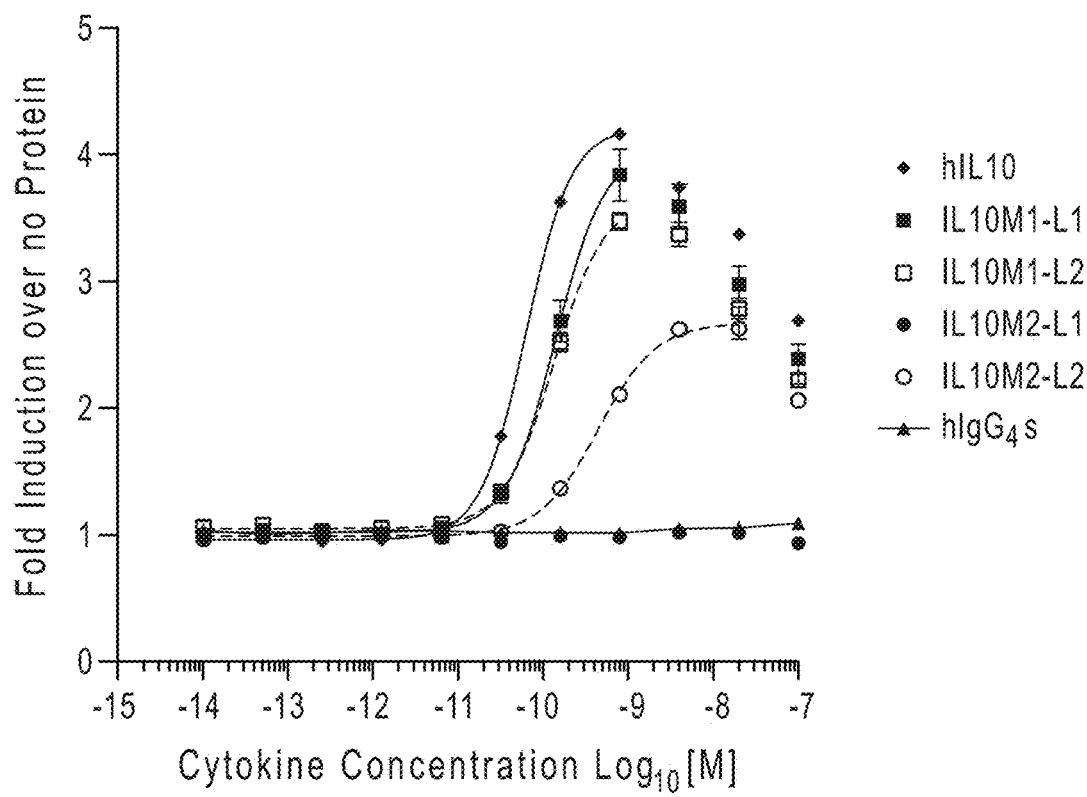
Figure 7C:
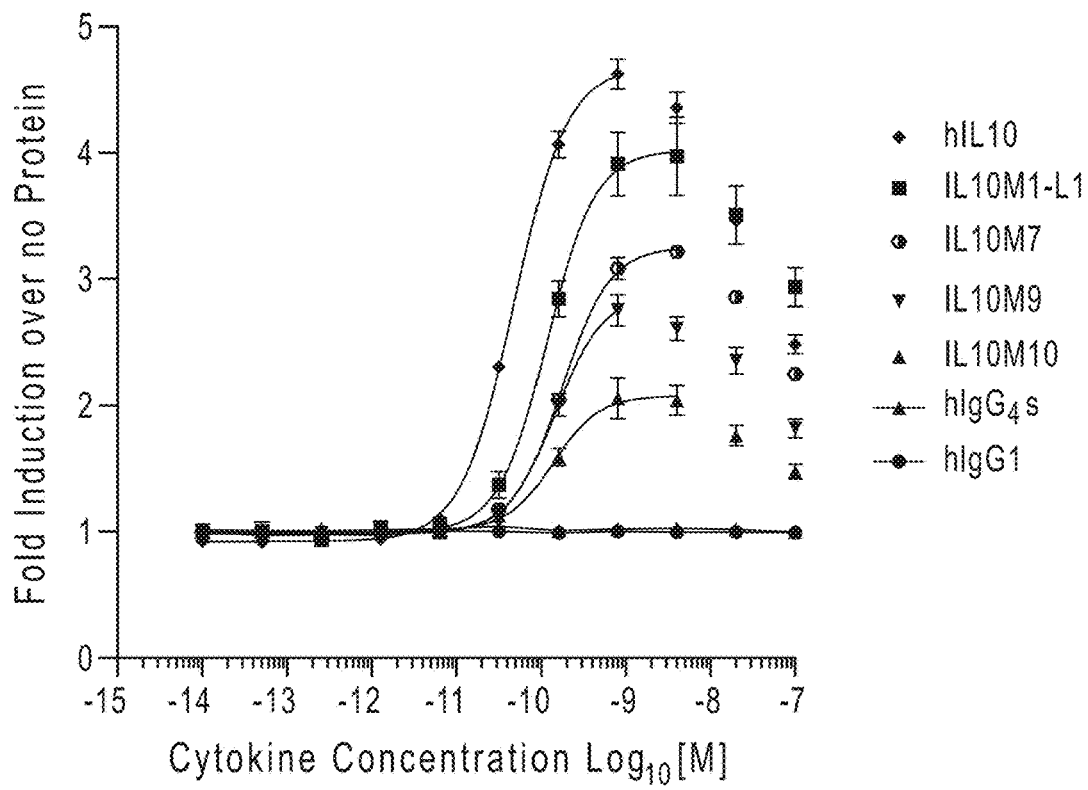
Figure 7D:
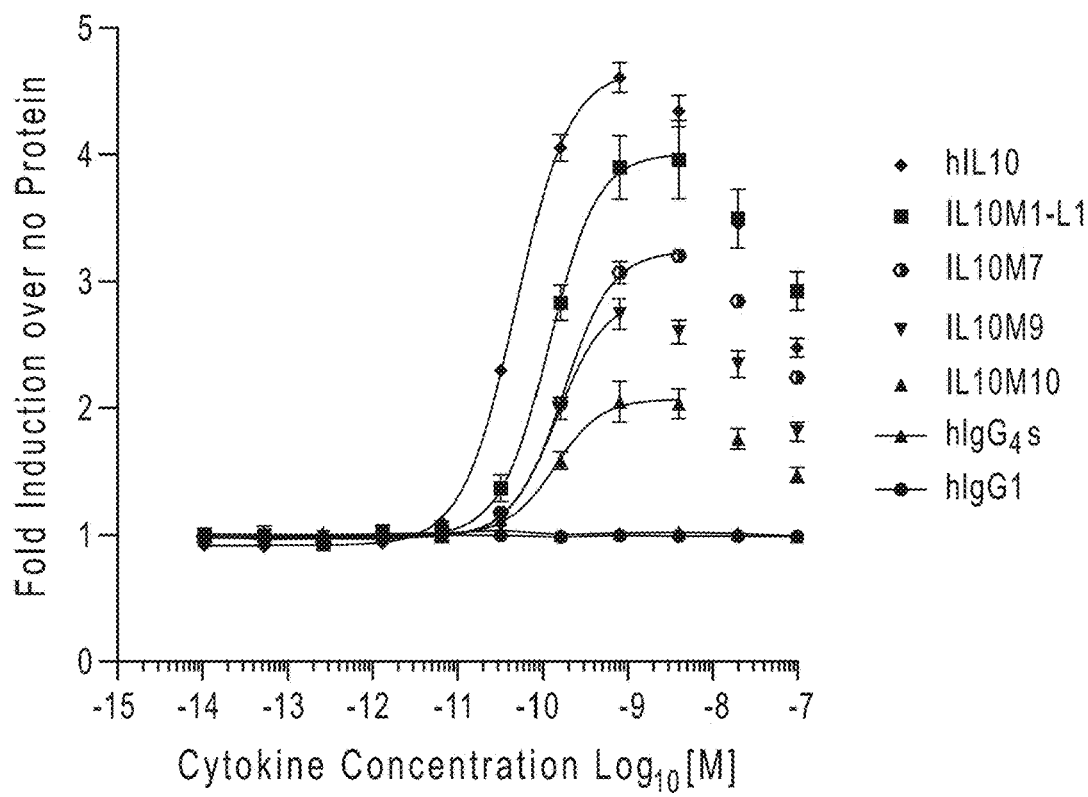
Figure 7E:
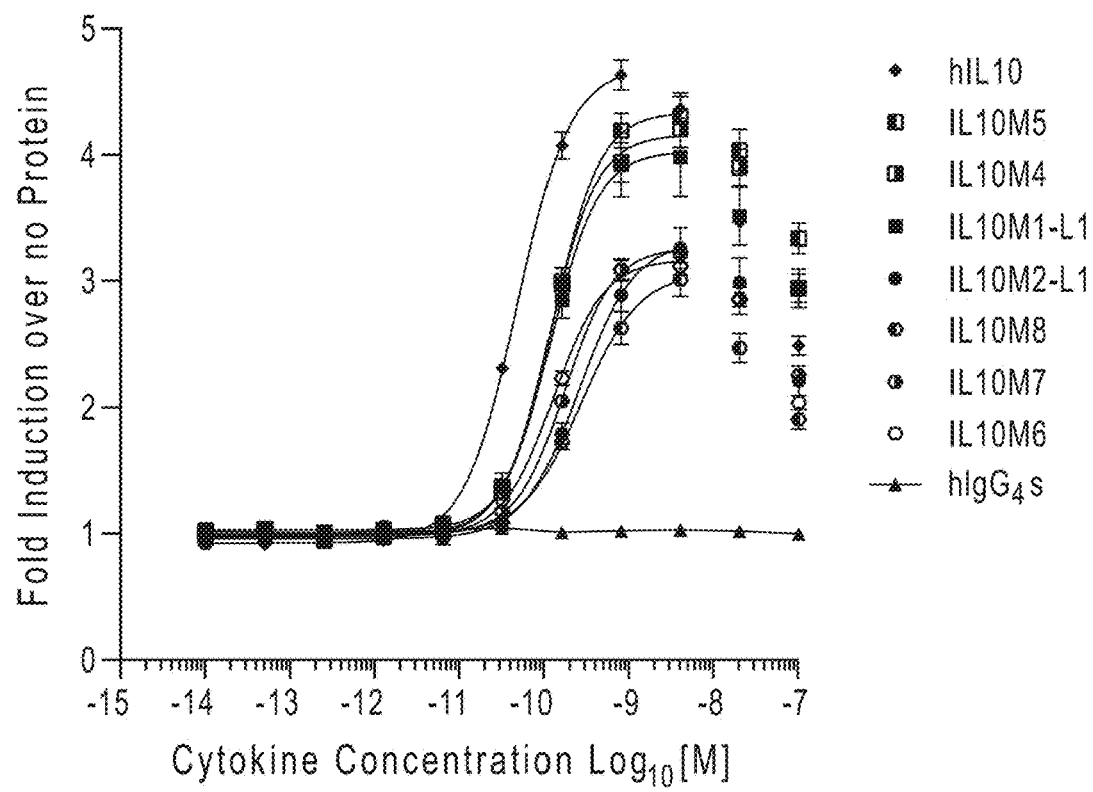
Figure 7F:
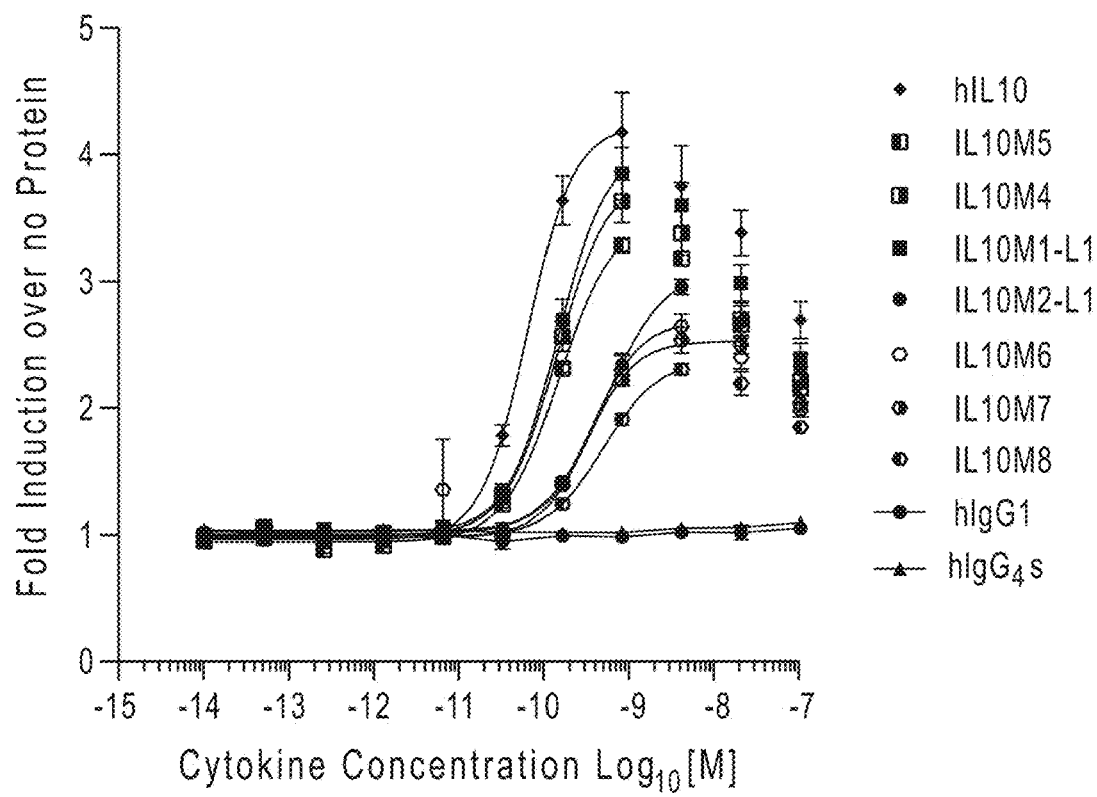

The results are summarized in Table 7 and shown in FIGS. 6A-6B.

TABLE 7

Anti-tumor activity of IL10 muteins in syngeneic tumor model

| Protein | Tumor size @ Day 11, mm$^3$ (mean ± SEM; median) | Tumor size @ Day 32, mm$^3$ (mean ± SEM; median) | Average inhibition of tumor growth (%) |
|---|---|---|---|
| hIgG4s | 108 ± 6.7; 106 | 1165 ± 81.9; 1183 | — |
| IL10M2 | 108 ± 6.3; 112 | 1094 ± 315.6; 1115 | 6.7% |
| IL10M1 | 107 ± 6.5; 107 | 223 ± 171.2; 51 | 89% |

On Day 32 when all mice were alive, treatment with 6 doses of IL10M1 resulted in ~90% tumor growth inhibition, whereas treatment with IL10M2 had minimal effect (~7% of tumor growth inhibition) when compared to the isotype control treatment group. Extended observation further revealed that in the IL10M1 treated group, 4 out of 7 mice became tumor-free, compared to only 2 out of 7 tumor-free mice in the IL10M2 treated group, and no tumor-free mice in the control group. These data support the conclusion that IL10 fused to the C-terminus of hIgG4s-Fc (IL10M1) demonstrates superior efficacy compared to the N-terminus Fc-IL-10 fusion protein (IL10M2) in a Colon 26 in vivo tumor model.

7.5. Example 4: Effect of Linker Length on IL10 Mutein Activity

The activity of IL10 muteins with different linker lengths (including two different lots of each of IL10M1 and IL10M2, referred to as lot 1 and lot 2 or L1 and L2, respectively) were evaluated in a Ramos/STAT3-Luc and TF-1/STAT3-Luc assay as described in Section 7.1.2. Cells were collected, spun, resuspended in assay media (Jurkat media) and plated in white bottom/side flat bottom dish at 5×10$^5$ cells/well in a volume of 50 μl, then 50 μl of media containing a titration of IL10 or IL10 muteins was added.

Cells were incubated for 5.5 hours, followed by the addition of 100 μL ONE-Glo luciferase agent (Promega Corporation, Madison Wis.). The plate was incubated in the presence of ONE-Glo for 3 minutes and activity read on an Envision fluorescence plate reader (Perkin Elmer, Waltham, Mass.).

The fold induction and EC50 were determined as set forth in Section 7.1.2.4. Results are summarized in Tables 8-1 and 8-2 and shown in FIGS. 7A-7F.

TABLE 8-1

Tabulated EC$_{50}$ values of luciferase activity in engineered reporter cells incubated with IL10 or IL10 muteins

|  |  | hIL10 | hIgG1 | hIgG4s | IL10M1 L1 | IL10M1 L2 | IL10M2 L1 | IL10M2 L2 |
|---|---|---|---|---|---|---|---|---|
| Ramos/Stat3-Luc | EC50 | 4.82 × 10$^{-11}$ | ND | ND | 1.17 × 10$^{-10}$ | 1.48 × 10$^{-10}$ | 2.54 × 10$^{-10}$ | 1.92 × 10$^{-10}$ |
|  | Fold Induction | 5.16 | 1.01 | 1.01 | 4.11 | 3.66 | 3.42 | 3.06 |
| TF-1/Stat3-Luc | EC50 | 6.295 × 10$^{-11}$ | ND | ND | 1.394 × 10$^{-10}$ | 1.337 × 10$^{-10}$ | 5.072 × 10$^{-10}$ | 4.502 × 10$^{-10}$ |
|  | Fold Induction | 4.02 | 1.00 | 0.99 | 4.12 | 3.4 | 2.85 | 2.68 |

TABLE 8-2

Tabulated EC$_{50}$ values of luciferase activity in engineered reporter cells incubated with IL10 or IL10 muteins (continued)

|  |  | IL10M10 | IL10M9 | IL10M8 | IL10M7 | IL10M6 | IL10M5 | IL10M4 |
|---|---|---|---|---|---|---|---|---|
| Ramos/Stat3-Luc | EC50 | 1.38 × 10$^{-10}$ | 1.45 × 10$^{-10}$ | 2.68 × 10$^{-10}$ | 1.72 × 10$^{-10}$ | 1.27 × 10$^{-10}$ | 1.27 × 10$^{-10}$ | 1.15 × 10$^{-10}$ |
|  | Fold Induction | 2.09 | 2.77 | 3.20 | 2.88 | 3.02 | 3.81 | 4.06 |
| TF-1/Stat3-Luc | EC50 | 5.03 × 10$^{-10}$ | 7.004 × 10$^{-10}$ | 4.841 × 10$^{-10}$ | 4.841 × 10$^{-10}$ | 3.186 × 10$^{-10}$ | 1.457 × 10$^{-10}$ | 1.378 × 10$^{-10}$ |
|  | Fold Induction | 2.16 | 2.55 | 2.34 | 2.36 | 2.66 | 3.40 | 3.78 |

These results show that the IL10 muteins in which the IL10 moiety is C-terminal to the Fc moiety have higher activity and lower $EC_{50}$ than IL10 muteins in which the IL10 moiety is N-terminal to the Fc moiety. Further, while the G4S (SEQ ID NO: 51) linker length has only a small impact on fold induction and $EC_{50}$, the absence of a linker altogether from IL10 muteins in which the IL10 moiety is C-terminal to the Fc moiety results in a larger reduction of activity.

7.6. Example 5: Mechanism of Action of IL10 Anti-Tumor Activity

Syngeneic tumor allograft models were used to evaluate in vivo anti-tumor efficacy of mouse IL-10 fused to mouse Fc (IL10M11) either in the prophylactic or the therapeutic settings.

Briefly, female mice (the Jackson Laboratory, Bar Harbor, Me.) were subcutaneously implanted with strain-matched tumor cells (Tissue Culture Core, Regeneron Pharmaceuticals, Inc.): C57BL/6 syngeneic tumor cells MC38-cOVA (MC38 colon carcinoma cells engineered to over-express chicken ovalbumin); BALB/c syngeneic tumor cells Colon26 (colon carcinoma), A20 (B cell lymphoma), 4T1 breast carcinoma), or RENCA (renal cell carcinoma)

In the prophylactic setting, treatments were initiated 2 days before MC38-cOVA tumor implantation and continued twice a week. In the therapeutic setting, mice were randomized into treatment groups (n=7-9) based on average tumor volumes (typically 60~120 mm3). Treatments were initiated after tumor randomization and continued twice a week.

IL10M11 or isotype control were administered at equimolar doses intraperitoneally (6-9 doses per mouse). In IL10M11 titration studies, the doses of isotype control were equal to the highest molar doses of IL10M11.

Tumor sizes and mouse body weights were measured twice a week. To study the mechanism of action of IL10 anti-tumor activity, IL10M11 was evaluated in a tumor allograft model both prophylactically and therapeutically. Tumor cells were implanted into BALB-C or C57BL/6 mice as described in Section 7.1.4 and IL10M11 was administered either prophylactically (before tumor implantation) or therapeutically (7 days after tumor implantation) to mice. Results are shown in FIGS. 8A-8D.

7.6.1. Materials & Methods

Implantation of tumors and allocation of dosing groups: For MC38-cOVA, Colon26, and RENCA syngeneic tumor models, $1 \times 10^6$ tumor cells (the Tissue Culture Core at Regeneron Pharmaceuticals, Inc.) were respectively implanted subcutaneously into the right flank of 6 to 8-week-old female C57BL/6 or BALB/c mice (the Jackson Laboratory, Bar Harbor, Me.). For A20 and 4T1 syngeneic tumor models, $1 \times 10^7$ or $1 \times 10^5$ tumor cells (the Tissue Culture Core at Regeneron Pharmaceuticals, Inc.) were respectively implanted subcutaneously into the right flank of 6 to 8-week-old female BALB/c mice (the Jackson Laboratory, Bar Harbor, Me.). Once tumors had reached average volumes of 60-120 mm³ (depending on each unique tumor model), mice were randomized into groups (n=7-9/group) and dosed with IL10M11, CD40, PD-1, control reagents, or sometimes combinations. Mice received intraperitoneal injections of test articles twice a week for 6-9 doses, and tumor volumes and body weights were monitored twice a week throughout the study. When testing anti-tumor memory responses, mice that rejected primary Colon26 tumor challenge received $5 \times 10^6$ Colon26 tumor cells, compared to naïve mice receiving only $1 \times 10^6$ Colon26 tumor cells.

Calculation of tumor size and growth inhibition: Average and median tumor size, as well as percent tumor growth inhibition relative to the control treated group were calculated for each group. Tumor length and width were measured with calipers twice a week and tumor volumes were calculated using the formula (length x width²)/2. Measurements were performed until the average tumor size of the control group reached 4000 mm³, or until any mouse in any group needed to be euthanized due to ulceration or body weight loss of more than 20%. The percentage of tumor growth inhibition was calculated according to the following formula: $[1-(T_{final}-T_{initial})/(C_{final}-C_{initial})]*100\%$, where T (treated group) and C (control group) represent the mean tumor mass on the day when all mice were alive.

7.6.2. Results

The prophylactic treatment of MC38-cOVA tumors with the highest tested dose of IL10M11 (0.1 mg/kg) showed marginal anti-tumor efficacy with ~30% tumor growth inhibition (TGI) and 1 out of 8 tumor-free mice (FIG. 8A). IL10M11 at lower doses (0.005 or 0.0003 mg/kg) had no anti-tumor effect. By contrast, the treatment of established MC38-cOVA tumors with IL10M11 (0.1 mg/kg) resulted in ~65% TGI and 4 out 7 tumor-free mice (FIG. 8B).

The therapeutic efficacy of IL10M11 was further tested in Colon26, A20 and 4T1 tumor models. The treatment elicited 100% overall response rate (ORR), 100% TGI and nearly 100% tumor-free survival rate in both Colon26 and A20 models (FIG. 8C and FIG. 8D). Significant TGI was also observed in 4T1 tumor model, including the growth control of large established tumors exceeding 100 mm3; however, no tumor-free survival was achieved (FIGS. 8E-1-8E-3).

4T1 tumors collected at the end of the study were disassociated and subjected to the flow cytometric analysis of immune cell compositions and function. Analyses of tumor-infiltrating lymphocytes from IL10M11-treated mice revealed increased frequencies, densities, and mean fluorescence intensity (MFI) of IFNγ/TNFα-producing CD4 and CD8 T cells (FIG. 8F and FIG. 8G).

Mice that survived the primary Colon26 or A20 tumor challenge were re-challenged by bilateral implantation of either Colon26 and RENCA (FIG. 8H), or A20 and Colon26 (FIG. 8I) tumor pairs respectively. Both positive control Colon26 and RENCA, or A20 and Colon26 bilateral tumors grew aggressively when implanted into naïve mice. However, mice that completely rejected primary tumors upon IL10M11 therapy elicited long-term anti-tumor memory response and rejected the secondary challenge with the same, but not with irrelevant tumor types (FIGS. 8H and 8I).

Lastly, the anti-tumor effects of IL10M11 in combinations with CD40 agonist Ab or with PD-1 antagonist Ab were determined. IL10M11, CD40 Ab, and PD-1 Ab each demonstrated an anti-tumor response as single agents (FIG. 9A). The combinations of any two therapeutic modalities further enhanced their anti-tumor efficacies (FIG. 9A) and increased tumor-free survival (FIG. 9B).

7.7. Example 6: IL10 Anti-Tumor Activity in Anti-PD-1 Ab Sensitive and Responsive Tumors Multiple syngeneic tumor allograft models were used to evaluate the immune infiltrates in tumor microenvironment before any treatment as baseline and also used to compare the in vivo anti-tumor efficacy of mouse IL-10 fused to mouse IgG1 (IL10M11) vs anti-PD-1 antagonist Ab (mouse IgG1) in the therapeutic setting.

Briefly, female mice (the Jackson Laboratory, Bar Harbor, Me.) were subcutaneously implanted with strain-matched tumor cells: C57BL/6 mice with MC38 colon carcinoma cells and B16F10 melanoma cells, or BALB/c mice with Colon26 colon carcinoma cells and A20 B cell lymphoma cells (all cells from the Tissue Culture Core at Regeneron Pharmaceuticals, Inc.). When tumor sizes reached about 100 mm$^3$, tumors were removed and subjected to a standard protocol for immune profiling of CD45+ immune cells and listed subsets within CD45 gate. In some cases, spleen and draining lymph nodes, together with tumors, were also subjected to analysis of surface expression of IL10R1, PD1 or PD-L1 on immune cells/tumor cells. In the therapeutic setting, treatments were administered several days after tumor implantation, typically at the time when tumor size reached an average volume of 75-150 mm$^3$ (depending on tumor type) and mice were randomized into different treatment groups (n=7-8/group). Mice were dosed with either mIgG1 isotype control, IL10M11, or anti-mouse PD1 Ab. Treatments and measurements of tumor sizes and body weights were performed twice per week.

7.7.1. Materials & Methods

Implantation of tumors and allocation of dosing groups: For the B16F10, MC38, MC38-cOVA, Colon 26, and A20 syngeneic tumor models, 0.5-10×10$^6$ tumor cells (the Tissue Culture Core at Regeneron Pharmaceuticals, Inc.) were respectively implanted subcutaneously into the right flank of 6 to 8-week-old female C57BL/6 or BALB/c mice (the Jackson Laboratory, Bar Harbor, Me.). Once tumors had reached an average volume of 75-150 mm3 (depending on each unique tumor model), mice were randomized into groups (n=7-8/group) and dosed with IL10M11, PD1 Ab, PD1-IL10 (, control reagents, or sometimes combinations. Mice received intraperitoneal injections of test articles twice a week for 6-9 doses, and tumor volumes and body weights were monitored twice a week throughout the study Calculation of tumor size and growth inhibition: Average and median tumor size, as well as percent tumor growth inhibition relative to the control treated group were calculated for each group. Tumor length and width were measured with calipers twice per week and tumor volume was calculated using the formula (length x width$^2$)/2. Measurements were performed until the average tumor size of the control group reached 4000 mm$^3$, or until any mouse in any group needed to be euthanized due to ulceration or body weight loss of more than 20%. Tumor growth inhibition was calculated according to the following formula: $[1-(T_{final}-T_{initial})/(C_{final}-C_{initial})]*100$, where T (treated group) and C (control group) represent the mean tumor mass on the day when all mice were alive. Observations were extended to Day 54 (3 weeks after the last treatment) to determine the frequency of tumor-free mice.

MSD multiplexing of cytokine in serum was performed according to the standard protocol of MSD (Meso Scale Diagnostics, Rockville, Md., U.S.A).

7.7.2. Results

As shown in FIGS. 10A-10E, the density of total CD45+ immune cells, as well as all the analyzed immune cell subsets in A20, Colon26 and MC38 tumors were much higher than counterparts in B16F10 tumors. Further analysis also showed that B16F10 tumors had less Ki67 proliferating CD4 and CD8 T cells and of memory phenotype.

As expected, IL10R1 was constitutively and broadly expressed by a wide variety of myeloid cells in both spleens and tumors. Strikingly, expression of IL10R1 on T cells, CD8 T cells in particular, was very much restricted to tumor-infiltrating CD8 T cells, with little expression on T cells of secondary lymphoid tissues, such as spleen and draining LNs of MC38-cOVA and Colon26 (see FIGS. 11A-1-11I). The studies further revealed that almost all the IL10R1+CD8 T cells expressed PD1 molecules. This data suggested that: 1) those IL10R1+PD1+CD8 T cells could be tumor antigen specific; 2) the highly restricted expression pattern of IL10R1 on a subset of T cells in tumors, may represents the biological reason behind the good safety profile of IL10M11 in mice; and 3) the combination of IL10-Fc with PD-1 antagonistic Ab is a conceivable strategy to boost anti-tumor responses.

The expression of PD-L1 was variable among the four different tumor types tested (FIGS. 12A-12G). Next, the response of each tumor type to treatment of PD1 antagonistic Ab vs IL10M11 was determined. As shown in FIGS. 13A-13C, 150 mm$^3$ A20 B cell lymphoma responded to PD-1 Ab treatment very well, with significant delay of tumor growth and ~50% of tumor-free survival. However, IL10M11 elicited an even deeper and broader immune response against A20, with ~85% of tumor-free survival. In Colon26 tumor model (FIGS. 14A-14C), 100 mm$^3$ tumors were completely resistant to PD1 Ab treatment. In contrast, IL10M11 again showed ~85% of tumor-free survival. B16F10 is known to be less immunogenic with much less immune cell infiltrates, which was confirmed in our studies (FIGS. 10A-10E). 100 mm$^3$ B16F10 tumors responded poorly to PD1 Ab. Yet IL10M11 significantly delayed tumor growth and rendered a majority of tumors of being responsive (FIGS. 15A-15C). Giving the observation that 90-100 mm$^3$ MC38 tumors responded poorly to PD1 Ab (see FIGS. 22A-22B), 75 mm$^3$ of MC38 colon carcinoma was tested. In this study, while both PD1Ab and IL10-Fc had a similar anti-tumor effect as a single agent, the combination of both dramatically increased antitumor responses by delaying tumor growth and giving rise to higher incidence of tumor-free survival (FIGS. 16A-16C).

To delineate the related mechanism(s) of action by IL10-Fc (e.g., IL10M11), immune profiling of tumor microenvironment after therapies were performed. IL10 treatment significantly increased CD8 T cell density in both the immunogenic MC38 tumor model (FIGS. 17A-1-17A-2) and the less immunogenic 4T1 tumor model (FIG. 17B-1-17B-2), which were correlated with better prognosis in both cases. Further studies showed that IL10 increased PD1+CD8 T cell density, suggesting those CD8 T cells were likely to be once activated tumor-specific CD8 T cells (FIGS. 18A-18B). IL10M11 tended to increase the overall CD45 immune infiltrates, including CD4 T cells and myeloid cells, in addition to CD8 T cells in 4T1 tumor model (FIGS. 17A-1-17B-2 and 18A-18B), providing a plausible explanation why IL10 worked in less immunogenic tumor models, such as 4T1 and B16F10.

To identify potential pharmacodynamic (PD) markers for IL10-Fc, serum levels of various cytokines were analyzed using commercial multiplex MSD platform. In both naïve, non tumor-bearing mice (FIGS. 19A-19C) and B16F10 tumor-bearing mice (FIGS. 20A-20B), a signature panel of cytokines (IL12, IL1b, IL2, IL4, and IL5) were uniquely upregulated by IL10, but not by PD1 Ab. When normalized to average values in isotype control treated mice, very clear trends of multi-fold upregulation of IL12 and IL4 were observed across multiple tumor models, such as A20, MC38, MC38-cOVA, B16F10 and Colon26 (FIGS. 21A-21B).

Some of samples were collected from the same tumor model at different time points (MC38 and Colon26), yet still showed the consistent trends.

Based on previous findings of co-expression of PD1 with IL10R1 and enhanced anti-tumor efficacy by the combination of IL10-Fc and PD-1 antagonistic Ab, the possibility of PD1-targeted IL10 as a therapeutic was explored. It has been reported that higher doses of Pagilodecakin (pegylated IL10) showed some toxicities in clinical trials. It is reasonable to normalize IL10 molar amounts, rather than PD1 molar amounts, of different treat modalities (IL10-Fc, control Ab-IL10, PD1-IL10, and PD1 Ab). As shown in FIGS. 22A-22B, both PD1 Ab and IL10-Fc had their respectively expected anti-tumor effect as a single agent (a very marginal effect for PD1 Ab and a moderate effect for IL10-Fc). Whereas IL10-Fc and PD-1 Ab combination significantly improved the efficacy, PD1-IL10-Fc did not show any difference in terms of efficacy than control Ab-IL10 or IL10-Fc.

7.8. Example 8: Purification of IL10 Agonists

Multiple iterations of the IL10 agonist (i.e., IL10M1 to IL10M11) were evaluated to determine their ability to be recombinantly expressed and recovered. IL10 agonists having an IL10 moiety positioned at the N-terminus or the C-terminus of the Fc domain were recoverable, although both configurations resulted in a significant amount of aggregated IL10 agonist. A purification method was developed to produce non-aggregated IL10 agonist.

7.8.1. Materials & Methods

Constructs encoding IL10 muteins were generated and recombinantly expressed in a mammalian cell line and purified, as described in section 7.1. Cells were lysed, and the cell lysate in PBS buffer was applied to a PrismA Protein A affinity column at a flow rate of 0.4 ml/min. The affinity column was eluted with Pierce Gentle elution buffer, pH 6.6. The buffer was then exchanged by dialysis against 1×TBS+ 5% glycerol, then 2× PBS+5% glycerol. The buffer exchanged elute was then subjected to size-exclusion chromatography using a Superdex 200, 26/600 pg column (MilliporeSigma, St. Louis, Mo. USA). A fraction including non-aggregated IL10 agonists was collected.

7.8.2. Results

With IL10 agonists having an IL10 moiety at the C-terminus of the Fc domain, the purification protocol produced intact, non-aggregated IL10 agonist having no unusual peaks observed with size exclusion ultra performance liquid chromatography. IL10 agonists having an IL10 moiety at the N-terminus of the Fc domain were also recovered but were not intact, missing either a C-terminal lysine or recovered as fragment having amino acids 3 to 402, wherein the full-length construct has residues 1 to 403.

Purified, non-aggregated IL10 agonists can be formulated into a pharmaceutical composition with an excipient, with the formulated pharmaceutical composition having minimal aggregates of the IL10 agonist.

8. SPECIFIC EMBODIMENTS, CITATION OF REFERENCES

While various specific embodiments have been illustrated and described, it will be appreciated that various changes can be made without departing from the spirit and scope of the disclosure(s). The present disclosure is exemplified by the numbered embodiments set forth below.

In preferred aspects of the numbered embodiments below and the claims which follow, the IL10 domains, Fc domains, and the variants thereof preferably comprise the amino acid sequences of human IL10, human Fc domains, and variants thereof, for example variants with at least about 90%, at least about 95%, at least about 96%, at least about 97%, at least about 98%, at least about 99% or 100% sequence identity to such human sequence.

1. An IL10 agonist comprising:
   (a) an Fc domain;
   (b) a linker; and
   (c) an IL10 moiety.

2. The IL10 agonist of embodiment 1, which further comprises a hinge domain N-terminal to the Fc domain.

3. The IL10 agonist of embodiment 1 or embodiment 2, wherein the Fc domain is an IgG Fc domain.

4. The IL10 agonist of any one of embodiments 1 to 3, wherein the Fc domain is an IgG1, IgG2, IgG3 or IgG4 Fc domain 5. The IL10 agonist of any one of embodiments 1 to 4, wherein the Fc domain comprises CH2 and Ch3 domains from an IgG1, IgG2, IgG3, IgG4, or a combination thereof.

6. The IL10 agonist of any one of embodiments 1 to 5, wherein the Fc domain is an IgG1.

7. The IL10 agonist of any one of embodiments 1 to 6, wherein the IgG1 is a human IgG1.

8. The IL10 agonist of any one of embodiments 1 to 6, wherein the IgG1 is a murine IgG1.

9. The IL10 agonist of any one of embodiments 1 to 5, wherein the Fc domain is an IgG4.

10. The IL10 agonist of embodiment 9, wherein the IgG1 is a human IgG4.

11. The IL10 agonist of embodiment 9, wherein the IgG1 is a murine IgG4.

12. The IL10 agonist of any one of embodiments 1 to 4 and 9, wherein the Fc domain comprises an amino acid sequence having at least 95% sequence identity to SEQ ID NO:31.

13. The IL10 agonist of any one of embodiments 1 to 4, 9, and 12 wherein the Fc domain comprises an amino acid sequence having at least 96% sequence identity to SEQ ID NO:31.

14. The IL10 agonist of any one of embodiments 1 to 4, 9, 12, and 13, wherein the Fc domain comprises an amino acid sequence having at least 97% sequence identity to SEQ ID NO:31.

15. The IL10 agonist of any one of embodiments 1 to 4, 9, and 12 to 14, wherein the Fc domain comprises an amino acid sequence having at least 98% sequence identity to SEQ ID NO:31.

16. The IL10 agonist of any one of embodiments 1 to 4, 9, and 12 to 15, wherein the Fc domain comprises an amino acid sequence having at least 99% sequence identity to SEQ ID NO:31.

17. The IL10 agonist of any one of embodiments 1 to 4, 9, and 12 to 16, wherein the Fc domain comprises the amino acid sequence of SEQ ID NO:31.

18. The IL10 agonist of any one of embodiments 1 to 7, wherein the Fc domain comprises an amino acid sequence having at least 95% sequence identity to SEQ ID NO: 33.

19. The IL10 agonist of any one of embodiments 1 to 7 and 18, wherein the Fc domain comprises an amino acid sequence having at least 96% sequence identity to SEQ ID NO: 33.

20. The IL10 agonist of any one of embodiments 1 to 7, 18, and 19, wherein the Fc domain comprises an amino acid sequence having at least 97% sequence identity to SEQ ID NO: 33.

21. The IL10 agonist of any one of embodiments 1 to 7 and 18 to 20, wherein the Fc domain comprises an amino acid sequence having at least 98% sequence identity to SEQ ID NO: 33.

22. The IL10 agonist of any one of embodiments 1 to 7 and 18 to 21, wherein the Fc domain comprises an amino acid sequence having at least 99% sequence identity to SEQ ID NO: 33.

23. The IL10 agonist of any one of embodiments 1 to 7 and 18 to 22, wherein the Fc domain comprises the amino acid sequence of SEQ ID NO: 33.

24. The IL10 agonist of any one of embodiments 1 to 17, wherein the Fc domain has reduced effector function.

25. The IL10 agonist of any one of embodiments 5 to 24, wherein the hinge domain is derived from the same IgG as the CH2 and/or CH3 domains.

26. The IL10 agonist of any one of embodiments 5 to 24, wherein the hinge domain is derived from a different IgG as the CH2 and/or CH3 domains.

27. The IL10 agonist of any one of embodiments 2 to 26, wherein the hinge domain comprises a chimeric hinge sequence.

28. The IL10 agonist of any one of embodiments 2 to 27, wherein the hinge domain comprises the amino acid sequence of SEQ ID NO: 12.

29. The IL10 agonist of any one of embodiments 2 to 27, wherein the hinge domain comprises the amino acid sequence of SEQ ID NO: 13.

30. The IL10 agonist of any one of embodiments 1 to 18, wherein the linker is 10 amino acids to 60 amino acid residues in length.

31. The IL10 agonist of any one of embodiments 1 to 18, wherein the linker is 15 amino acids to 25 amino acid residues in length.

32. The IL10 agonist of any one of embodiments 1 to 18, wherein the linker is 15 to 20 amino acid residues in length.

33. The IL10 agonist of any one of embodiments 1 to 32, wherein the linker comprises a monomer or multimer of $G_nS$ (SEQ ID NO: 9) or $SG_n$ (SEQ ID NO: 10), optionally where n is an integer from 1 to 7.

34. The IL10 agonist of embodiment 33, wherein the linker comprises a monomer or multimer of $G_4S$ (SEQ ID NO: 51).

35. The IL10 agonist of embodiment 34, wherein the linker comprises 1 to 6 repeats of $G_4S$.

36. The IL10 agonist of embodiment 35, wherein linker comprises $(G_4S)_1$ (SEQ ID NO: 51).

37. The IL10 agonist of embodiment 35, wherein linker comprises $(G_4S)_2$ (SEQ ID NO: 52).

38. The IL10 agonist of embodiment 35, wherein linker comprises $(G_4S)_3$ (SEQ ID NO: 53).

39. The IL10 agonist of embodiment 35, wherein linker comprises $(G_4S)_4$ (SEQ ID NO: 54).

40. The IL10 agonist of embodiment 35, wherein linker comprises $(G_4S)_5$ (SEQ ID NO: 55).

41. The IL10 agonist of embodiment 35, wherein linker comprises $(G_4S)_6$ (SEQ ID NO: 56).

42. The IL10 agonist of any one of embodiments 1 to 41, wherein the linker connects the Fc domain and the IL10 moiety.

43. The IL10 agonist of any one of embodiments 1 to 41, wherein the IL10 moiety is C-terminal to the Fc domain.

44. The IL10 agonist of any one of embodiments 1 to 41, wherein the IL10 moiety is N-terminal to the Fc domain.

45. The IL10 agonist of any one of embodiments 1 to 41, wherein the IL10 moiety comprises an amino acid sequence having at least 95% sequence identity to the sequence of mature human IL10 (e.g., an IL10 having the amino acid sequence of SEQ ID NO: 1).

46. The IL10 agonist of any one of embodiments 1 to 42, wherein the IL10 moiety comprises an amino acid sequence having at least 96% sequence identity to the sequence of mature human IL10 (e.g., an IL10 having the amino acid sequence of SEQ ID NO: 1).

47. The IL10 agonist of any one of embodiments 1 to 43, wherein the IL10 moiety comprises an amino acid sequence having at least 97% sequence identity to the sequence of mature human IL10 (e.g., an IL10 having the amino acid sequence of SEQ ID NO: 1).

48. The IL10 agonist of any one of embodiments 1 to 44, wherein the IL10 moiety comprises an amino acid sequence having at least 98% sequence identity to the sequence of mature human IL10 (e.g., an IL10 having the amino acid sequence of SEQ ID NO: 1).

49. The IL10 agonist of any one of embodiments 1 to 45, wherein the IL10 moiety comprises an amino acid sequence having at least 99% sequence to the sequence of mature human IL10 (e.g., an IL10 having the amino acid sequence of SEQ ID NO: 1).

50. The IL10 agonist of any one of embodiments 1 to 49, wherein the IL10 moiety comprises the amino acid sequence of mature human IL10 (e.g., an IL10 having the amino acid sequence of SEQ ID NO: 1).

51. The IL10 agonist of any one of embodiments 1 to 41, wherein the IL10 moiety comprises an amino acid sequence having at least 95% sequence identity to the sequence of mature murine IL10 (e.g., an IL10 having the amino acid sequence of SEQ ID NO: 30).

52. The IL10 agonist of any one of embodiments 1 to 41 and 51, wherein the IL10 moiety comprises an amino acid sequence having at least 96% sequence identity to the sequence of mature murine IL10 (e.g., an IL10 having the amino acid sequence of SEQ ID NO: 30).

53. The IL10 agonist of any one of embodiments 1 to 41, 51, and 52 wherein the IL10 moiety comprises an amino acid sequence having at least 97% sequence identity to the sequence of mature murine IL10 (e.g., an IL10 having the amino acid sequence of SEQ ID NO: 30).

54. The IL10 agonist of any one of embodiments 1 to 41 and 51 to 53, wherein the IL10 moiety comprises an amino acid sequence having at least 98% sequence identity to the sequence of mature murine IL10 (e.g., an IL10 having the amino acid sequence of SEQ ID NO: 30).

55. The IL10 agonist of any one of embodiments 1 to 41 and 51 to 54, wherein the IL10 moiety comprises an amino acid sequence having at least 99% sequence identity to the sequence of mature murine IL10 (e.g., an IL10 having the amino acid sequence of SEQ ID NO: 30).

56. The IL10 agonist of any one of embodiments 1 to 41 and 51 to 55, wherein the IL10 moiety comprises the amino acid sequence of mature murine IL10 (e.g., an IL10 having the amino acid sequence of SEQ ID NO: 30).

57. The IL10 agonist of any one of embodiments 1 to 56, which is a monomer, optionally wherein the monomer has an insertion of a linker sequence between N116 and K117 of the IL10 moiety and/or the Fc has a reduced ability to self-associate such as by virtue of one or more substitutions in the positions corresponding to T366 and/or Y407 in CH3.

58. The IL10 agonist of any one of embodiments 1 to 56, which is a monomer, wherein the monomer lacks an insertion of a linker sequence between N116 and K117 of the IL10 moiety.

59. The IL10 agonist of any one of embodiments 1 to 56 and 58, which is a monomer, wherein the monomer is not substituted at the positions corresponding to T366 and/or Y407 in CH3.

60. The IL10 agonist of any one of embodiments 1 to 56, which is a homodimer.

61. The IL10 agonist of embodiment 58, which comprises two Fc domains.

62. The IL10 agonist of embodiment 61, which is dimerized through the Fc domains.

63. The IL10 agonist of embodiment 62, wherein the Fc domains comprise the amino acid sequence designated as hIgG4-Fc (e.g., an Fc having the amino acid sequence of amino acids 18 to 228 of SEQ ID SEQ ID NO: 31).

64. The IL10 agonist of embodiment 62, wherein the Fc domains comprise the amino acid sequence designated as hIgG4s-Fc (e.g., an Fc having the amino acid sequence of SEQ ID SEQ ID NO: 31).

65. The IL10 agonist of embodiment 62, wherein the Fc domains comprise the amino acid sequence designated as mIgG1-Fc (e.g., an Fc having the amino acid sequence of SEQ ID SEQ ID NO: 33).

66. The IL10 agonist of embodiment 61, wherein the Fc domains are non-dimerizing.

67. The IL10 agonist of any one of embodiments 58 to 67, which comprises two IL10 moieties.

68. The IL10 agonist of embodiment 67, which is dimerized through the IL10 moieties.

69. The IL10 agonist of embodiment 67, wherein the IL10 moieties are non-dimerizing.

70. The IL10 agonist of any one of embodiments 1 to 56, which is a heterodimer.

71. The IL10 agonist of clam 70, which comprises two Fc domains.

72. The IL10 agonist of embodiment 71, which is dimerized through the Fc domains.

73. The IL10 agonist of embodiment 71, wherein the Fc domains are non-dimerizing.

74. The IL10 agonist of any one of embodiments 70 through 73, which comprises two IL10 moieties.

75. The IL10 agonist of embodiment 74, which is dimerized through the IL10 moieties.

76. The IL10 agonist of embodiment 74, wherein the IL10 moieties are non-dimerizing.

77. The IL10 agonist of any one of embodiments 70 through 73, which comprises a single IL10 moiety.

78. An IL10 agonist which comprises an amino acid sequence having at least 95% sequence identity to the amino acid sequence of IL10M1 (i.e., an IL10 agonist having the amino acid sequence of SEQ ID NO: 34).

79. The IL10 agonist of embodiment 78 which comprises an amino acid sequence having at least 96% sequence identity to the amino acid sequence of IL10M1.

80. The IL10 agonist of embodiment 78 or embodiment 79 which comprises an amino acid sequence having at least 97% sequence identity to the amino acid sequence of IL10M1.

81. The IL10 agonist of any one of embodiments 78 to 80 which comprises an amino acid sequence having at least 98% sequence identity to the amino acid sequence of IL10M1.

82. The IL10 agonist of any one of embodiments 78 to 81 which comprises an amino acid sequence having at least 99% sequence identity to the amino acid sequence of IL10M1.

83. The IL10 agonist of any one of embodiments 78 to 82 which comprises the amino acid sequence of IL10M1.

84. An IL10 agonist which comprises an amino acid sequence having at least 95% sequence identity to the amino acid sequence of IL10M2 (i.e., an IL10 agonist having the amino acid sequence of SEQ ID NO: 35).

85. The IL10 agonist of embodiment 84 which comprises an amino acid sequence having at least 96% sequence identity to the amino acid sequence of IL10M2.

86. The IL10 agonist of embodiment 84 or embodiment 85 which comprises an amino acid sequence having at least 97% sequence identity to the amino acid sequence of IL10M2.

87. The IL10 agonist of any one of embodiments 84 to 86 which comprises an amino acid sequence having at least 98% sequence identity to the amino acid sequence of IL10M2.

88. The IL10 agonist of any one of embodiments 84 to 87 which comprises an amino acid sequence having at least 99% sequence identity to the amino acid sequence of IL10M2.

89. The IL10 agonist of any one of embodiments 84 to 88 which comprises the amino acid sequence of IL10M2.

90. An IL10 agonist which comprises an amino acid sequence having at least 95% sequence identity to the amino acid sequence of IL10M3 (i.e., an IL10 agonist having the amino acid sequence of SEQ ID NO: 36).

91. The IL10 agonist of embodiment 90 which comprises an amino acid sequence having at least 96% sequence identity to the amino acid sequence of IL10M3.

92. The IL10 agonist of embodiment 90 or embodiment 91 which comprises an amino acid sequence having at least 97% sequence identity to the amino acid sequence of IL10M3.

93. The IL10 agonist of any one of embodiments 90 to 92 which comprises an amino acid sequence having at least 98% sequence identity to the amino acid sequence of IL10M3.

94. The IL10 agonist of any one of embodiments 90 to 93 which comprises an amino acid sequence having at least 99% sequence identity to the amino acid sequence of IL10M3.

95. An IL10 agonist of any one of embodiments 90 to 94 which comprises the amino acid sequence of IL10M3.

96. An IL10 agonist which comprises an amino acid sequence having at least 95% sequence identity to the amino acid sequence of IL10M4 (i.e., an IL10 agonist having the amino acid sequence of SEQ ID NO: 37).

97. The IL10 agonist of embodiment 96 which comprises an amino acid sequence having at least 96% sequence identity to the amino acid sequence of IL10M4.

98. The IL10 agonist of embodiment 96 or embodiment 97 which comprises an amino acid sequence having at least 97% sequence identity to the amino acid sequence of IL10M4.

99. The IL10 agonist of any one of embodiments 96 to 98 which comprises an amino acid sequence having at least 98% sequence identity to the amino acid sequence of IL10M4.

100. The IL10 agonist of any one of embodiments 96 to 99 which comprises an amino acid sequence having at least 99% sequence identity to the amino acid sequence of IL10M4.

101. An IL10 agonist of any one of embodiments 96 to 100 which comprises the amino acid sequence of IL10M4.

102. An IL10 agonist which comprises an amino acid sequence having at least 95% sequence identity to the amino acid sequence of IL10M5 (i.e., an IL10 agonist having the amino acid sequence of SEQ ID NO: 38).

103. The IL10 agonist of embodiment 102 which comprises an amino acid sequence having at least 96% sequence identity to the amino acid sequence of IL10M5.

104. The IL10 agonist of embodiment 102 or embodiment 103 which comprises an amino acid sequence having at least 97% sequence identity to the amino acid sequence of IL10M5.

105. The IL10 agonist of any one of embodiments 102 to 104 which comprises an amino acid sequence having at least 98% sequence identity to the amino acid sequence of IL10M5.

106. The IL10 agonist of any one of embodiments 102 to 105 which comprises an amino acid sequence having at least 99% sequence identity to the amino acid sequence of IL10M5.

107. An IL10 agonist of any one of embodiments 102 to 106 which comprises the amino acid sequence of IL10M5.

108. An IL10 agonist which comprises an amino acid sequence having at least 95% sequence identity to the amino acid sequence of IL10M6 (i.e., an IL10 agonist having the amino acid sequence of SEQ ID NO: 39).

109. The IL10 agonist of embodiment 108 which comprises an amino acid sequence having at least 96% sequence identity to the amino acid sequence of IL10M6.

110. The IL10 agonist of embodiment 108 or embodiment 109 which comprises an amino acid sequence having at least 97% sequence identity to the amino acid sequence of IL10M6.

111. The IL10 agonist of any one of embodiments 108 to 110 which comprises an amino acid sequence having at least 98% sequence identity to the amino acid sequence of IL10M6.

112. The IL10 agonist of any one of embodiments 108 to 111 which comprises an amino acid sequence having at least 99% sequence identity to the amino acid sequence of IL10M6.

113. An IL10 agonist of any one of embodiments 108 to 112 which comprises the amino acid sequence of IL10M6.

114. An IL10 agonist which comprises an amino acid sequence having at least 95% sequence identity to the amino acid sequence of IL10M7 (i.e., an IL10 agonist having the amino acid sequence of SEQ ID NO: 40).

115. The IL10 agonist of embodiment 114 which comprises an amino acid sequence having at least 96% sequence identity to the amino acid sequence of IL10M7.

116. The IL10 agonist of embodiment 114 or embodiment 115 which comprises an amino acid sequence having at least 97% sequence identity to the amino acid sequence of IL10M7.

117. The IL10 agonist of any one of embodiments 114 to 116 which comprises an amino acid sequence having at least 98% sequence identity to the amino acid sequence of IL10M7.

118. The IL10 agonist of any one of embodiments 114 to 117 which comprises an amino acid sequence having at least 99% sequence identity to the amino acid sequence of IL10M7.

119. An IL10 agonist of any one of embodiments 114 to 118 which comprises the amino acid sequence of IL10M7.

120. An IL agonist which comprises an amino acid sequence having at least 95% sequence identity to the amino acid sequence of IL10M8 (i.e., an IL10 agonist having the amino acid sequence of SEQ ID NO: 41).

121. The IL10 agonist of embodiment 120 which comprises an amino acid sequence having at least 96% sequence identity to the amino acid sequence of IL10M8.

122. The IL10 agonist of embodiment 120 or embodiment 121 which comprises an amino acid sequence having at least 97% sequence identity to the amino acid sequence of IL10M8.

123. The IL10 agonist of any one of embodiments 120 to 122 which comprises an amino acid sequence having at least 98% sequence identity to the amino acid sequence of IL10M8.

124. The IL10 agonist of any one of embodiments 120 to 123 which comprises an amino acid sequence having at least 99% sequence identity to the amino acid sequence of IL10M8.

125. An IL10 agonist of any one of embodiments 120 to 124 which comprises the amino acid sequence of IL10M8.

126. An IL10 agonist which comprises an amino acid sequence having at least 95% sequence identity to the amino acid sequence of IL10M9 (i.e., an IL10 agonist having the amino acid sequence of SEQ ID NO: 42).

127. The IL10 agonist of embodiment 126 which comprises an amino acid sequence having at least 96% sequence identity to the amino acid sequence of IL10M9.

128. The IL10 agonist of embodiment 126 or embodiment 127 which comprises an amino acid sequence having at least 97% sequence identity to the amino acid sequence of IL10M9.

129. The IL10 agonist of any one of embodiments 126 to 128 which comprises an amino acid sequence having at least 98% sequence identity to the amino acid sequence of IL10M9.

130. The IL10 agonist of any one of embodiments 126 to 129 which comprises an amino acid sequence having at least 99% sequence identity to the amino acid sequence of IL10M9.

131. An IL10 agonist of any one of embodiments 126 to 130 which comprises the amino acid sequence of IL10M9.

132. An IL10 agonist which comprises an amino acid sequence having at least 95% sequence identity to the amino acid sequence of IL10M10 (i.e., an IL10 agonist having the amino acid sequence of SEQ ID NO: 43).

133. The IL10 agonist of embodiment 132 which comprises an amino acid sequence having at least 96% sequence identity to the amino acid sequence of IL10M10.

134. The IL10 agonist of embodiment 132 or embodiment 133 which comprises an amino acid sequence having at least 97% sequence identity to the amino acid sequence of IL10M10.

135. The IL10 agonist of any one of embodiments 132 to 134 which comprises an amino acid sequence having at least 98% sequence identity to the amino acid sequence of IL10M10.

136. The IL10 agonist of any one of embodiments 132 to 135 which comprises an amino acid sequence having at least 99% sequence identity to the amino acid sequence of IL10M10.

137. An IL10 agonist of any one of embodiments 132 to 136 which comprises the amino acid sequence of IL10M10.

138. An IL10 agonist which comprises an amino acid sequence having at least 95% sequence identity to the amino acid sequence of IL10M11 (i.e., an IL10 agonist having the amino acid sequence of SEQ ID NO: 44).

139. The IL10 agonist of embodiment 138 which comprises an amino acid sequence having at least 96% sequence identity to the amino acid sequence of IL10M11.

140. The IL10 agonist of embodiment 138 or embodiment 139 which comprises an amino acid sequence having at least 97% sequence identity to the amino acid sequence of IL10M11.

141. The IL10 agonist of any one of embodiments 138 to 140 which comprises an amino acid sequence having at least 98% sequence identity to the amino acid sequence of IL10M11.

142. The IL10 agonist of any one of embodiments 138 to 141 which comprises an amino acid sequence having at least 99% sequence identity to the amino acid sequence of IL10M11.

143. An IL10 agonist of any one of embodiments 138 to 142 which comprises the amino acid sequence of IL10M11.

144. The IL10 agonist of any one of embodiments 1 to 143 which further comprises a targeting moiety.

145. The IL10 agonist of embodiment 144, wherein the targeting moiety is N-terminal to the Fc domain and, if a hinge domain is present, N-terminal to the hinge domain.

146. The IL10 agonist of embodiment 144 or embodiment 145, wherein the targeting moiety:
(a) binds to a tumor associated antigen;
(b) binds to a tumor microenvironment antigen;
(c) binds to a cell surface molecule of tumor reactive lymphocytes; or
(d) binds to a checkpoint inhibitor.

147. The IL10 agonist of embodiment 146, wherein the targeting moiety binds to a tumor associated antigen.

148. The IL10 agonist of embodiment 147, wherein the tumor associated antigen is Fibroblast Activation Protein (FAP), the A1 domain of Tenascin-C (TNC A1), the A2 domain of Tenascin-C (TNC A2), the Extra Domain B of Fibronectin (EDB), the Melanoma-associated Chondroitin Sulfate Proteoglycan (MCSP), MART-1/Melan-A, gp100, Dipeptidyl peptidase IV (DPPIV), adenosine deaminase-binding protein (ADAbp), cyclophilin b, colorectal associated antigen (CRC)-C017-1A/GA733, Carcinoembryonic Antigen (CEA) and its immunogenic epitopes CAP-1 and CAP-2, etv6, amli, Prostate Specific Antigen (PSA) or an immunogenic epitopes thereoPSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p2iras, RCAS1, α-fetoprotein, E-cadherin, α-catenin, β-catenin and γ-catenin, p120ctn, gp100 Pmeli17, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, c-erbB-2, Her2, EGFR, IGF-1R, CD2 (T-cell surface antigen), CD3 (heteromultimer associated with the TCR), CD22 (B-cell receptor), CD23 (low binding affinity IgE receptor), CD30 (cytokine receptor), CD33 (myeloid cell surface antigen), CD40 (tumor necrosis factor receptor), IL-6R-(IL6 receptor), CD20, MCSP, PDGFPR (β-platelet-derived growth factor receptor), ErbB2 epithelial cell adhesion molecule (EpCAM), EGFR variant III (EGFRvIII), CD19, disialoganglioside GD2, ductal-epithelial mucine, gp36, TAG-72, glioma-associated antigen, β-human chorionic gonadotropin, alphafetoprotein (AFP), lectin-reactive AFP, thyroglobulin, MN-CA IX, human telomerase reverse transcriptase, RU1, RU2 (AS), intestinal carboxyl esterase, mut hsp70-2, M-CSF, prostase, prostase specific antigen (PSA), PAP, LAGA-1a, p53, prostein, PSMA, surviving and telomerase, prostate-carcinoma tumor antigen-1 (PCTA-1), ELF2M, neutrophil elastase, ephrin B2, insulin growth factor (IGF1)-I, IGF-II, IGFI receptor, 5T4, ROR1, Nkp30, NKG2D, tumor stromal antigens, the extra domain A (EDA) or extra domain B (EDB) of fibronectin, or the A1 domain of tenascin-C (TnC A1).

149. The IL10 agonist of embodiment 147, wherein the tumor associated antigen is a viral antigen.

150. The IL10 agonist of embodiment 149, wherein the viral antigen is Epstein-Barr virus LMP-1, hepatitis C virus E2 glycoprotein, HIV gp160, or HIV gp120, HPV E6, HPV E7, CMV early membrane antigen (EMA) or CMV late membrane antigen (LMA).

151. The IL10 agonist of embodiment 146, wherein the targeting moiety binds to a tumor microenvironment antigen.

152. The IL10 agonist of embodiment 151, wherein the tumor microenvironment antigen is an extracellular matrix protein.

153. The IL10 agonist of embodiment 152, wherein the extracellular matrix protein is syndecan, heparanase, integrins, osteopontin, link, a cadherin, laminin, laminin type EGF, lectin, fibronectin, notch, tenascin, collagen or matrixin.

154. The IL10 agonist of embodiment 146, wherein the targeting moiety binds to a cell surface molecule of tumor reactive lymphocytes.

155. The IL10 agonist of embodiment 154, wherein the cell surface molecule is CD27, CD28, 4-1BB (CD137), OX40, CD30, CD40, PD1, ICOS, lymphocyte function-associated antigen-1 (LFA-1), CD2, CD7, LIGHT, NKG2C, LAG3, TIM3, or B7-H3.

156. The IL10 agonist of embodiment 146, wherein the targeting moiety binds to a checkpoint inhibitor.

157. The IL10 agonist of embodiment 156, wherein the checkpoint inhibitor is CTLA-4, PD1, PDL1, PDL2, PD1, B7-H3, B7-H4, BTLA, HVEM, TIM3, GAL9, LAG3, VISTA, KIR, 2B4, CD160, CGEN-15049, CHK1, VISTA, PSGL1, or CHK2.

158. The IL10 agonist of embodiment 157, wherein the checkpoint inhibitor is PD1.

159. The IL10 agonist of embodiment 144 or embodiment 145, wherein the targeting moiety binds to an MHC-peptide complex.

160. The IL10 agonist of embodiment 159, wherein the peptide in the peptide-MHC complex comprises a tumor neoantigen.

161. The IL10 agonist of embodiment 160, wherein the tumor neoantigen is LCMV derived peptide gp33-41, APF (126-134), BALF(276-284), CEA (571-579), CMV pp65 (495-503), FLU-M1 (58-66), gp100 (154-162), gp100 (209-217), HBV Core (18-27), Her2/neu (369-377; V2v9); HPV E7 (11-20), KLK4 (11-19), LMP1 (125-133), MAG-A3 (112-120), NYESO1 (157-165, C165A), NYESO1 (157-165, C165V), p54 WT (264-272), PAP-3 (136-143), PSMA (4-12), PSMA (135-145), Survivin (96-014), Tyrosinase (369-377, 371D), or WT1 (126-134).

162. The IL10 agonist of any one of embodiments 144 to 161, wherein the targeting moiety is an antibody or antigen binding fragment thereof.

163. The IL10 agonist of embodiment 162, wherein the targeting moiety is a Fab.

164. The IL10 agonist of embodiment 162, wherein the targeting moiety is a scFv.

165. The IL10 agonist of any one of embodiments 144 to 164, wherein the targeting moiety does not bind to a checkpoint inhibitor, optionally wherein the checkpoint inhibitor is PD1.

166. The IL10 agonist of any one of embodiments 1 to 164, which lacks a targeting domain that binds to a checkpoint inhibitor, optionally wherein the checkpoint inhibitor is PD1.

167. The IL10 agonist of any one of embodiments 1 to 139, which lacks a targeting moiety.

168. The IL10 agonist of any one of embodiments 1 to 99 and 167, which lacks a targeting moiety, such as but not limited to a targeting moiety that:
(a) binds to a tumor associated antigen;
(b) binds to a tumor microenvironment antigen;
(c) binds to a cell surface molecule of tumor reactive lymphocytes; or
(d) binds to a checkpoint inhibitor.

169. The IL agonist of embodiment 168, which lacks a targeting moiety that binds PD1.

170. The IL10 agonist of any one of embodiments 1 to 139 and 165, which lacks a CH1 domain.

171. The IL10 agonist of any one of embodiments 1 to 139, 165 and 168 which lacks a CL domain.

172. The IL10 agonist of any one of embodiments 1 to 139 and 165 to 171 which lacks an antibody variable region.

173. The IL10 agonist of any one of embodiments 1 to 172 which further comprises a hydrophilic polymer.

174. The IL10 agonist of embodiment 173, wherein the hydrophilic polymer is polyethylene glycol ("PEG").

175. The IL10 agonist of embodiment 174, wherein the PEG has a molecular weight ranging from about 7.5 kDa to about 80 kDa.

176. The IL10 agonist of embodiment 175, wherein the PEG has a molecular weight ranging from about 30 kDa to about 60 kDa, optionally wherein the molecular weight is about 50 kDa.

177. The IL10 agonist of any one of embodiments 1 to 172, which comprises a stabilization moiety.

178. The IL10 agonist of embodiment 177, wherein the stabilization moiety is albumin, a human serum albumin binder, an XTEN, a PAS, a hydrophilic polymer, a polysialic acid or a fatty acid.

179. The IL10 agonist of any one of embodiments 1 to 172 which is not conjugated to polyethylene glycol.

180. The IL 10 agonist of any one of embodiments 1 to 172 and 179 which is not conjugated to albumin.

181. The IL 10 agonist of any one of embodiments 1 to 172, 179, and 180 which is not conjugated to a human serum albumin binder.

182. The IL10 agonist of any one of embodiments 1 to 172 and 179 to 181 which is not conjugated to an XTEN.

183. The IL10 agonist of any one of embodiments 1 to 172 and 179 to 182 which is not conjugated to a PAS.

184. The IL10 agonist of any one of embodiments 1 to 172 and 179 to 183 which is not conjugated to a hydrophilic polymer.

185. The IL10 agonist of any one of embodiments 1 to 172 and 179 to 184 which is not conjugated to a polysialic acid.

186. The IL10 agonist of any one of embodiments 1 to 172 and 179 to 185 which is not conjugated to a hydroxyethyl starch.

187. The IL10 agonist of any one of embodiments 1 to 172 and 179 to 186 which is not conjugated to a fatty acid.

188. The IL10 agonist of any one of embodiments 1 to 172 and 179 to 187 which does not include an N-linked glycan.

189. The IL10 agonist of any one of embodiments 1 to 172 and 179 to 187 which does not include an O-linked glycan.

190. The IL10 agonist of any one of embodiments 1 to 172 and 179 to 189, which lacks a stabilizing moiety.

191. The IL10 agonist of any one of embodiments 1 to 180 which does not contain IL4.

192. The IL10 agonist of any one of embodiments 1 to 191 which does not contain any cytokine other than IL10.

193. The IL10 agonist of any one of embodiments 1 to 192 which does not contain an Fc domain C-terminal to an IL10 moiety.

194. The IL10 agonist of any one of embodiments 1 to 193, which is the product of recombinant cell expression in a mammalian cell.

195. The IL10 agonist of embodiment 194, wherein the mammalian cell is of a mouse cell line.

196. The IL10 agonist of embodiment 194, wherein the mammalian cell is of a rat cell line.

197. The IL10 agonist of embodiment 194, wherein the mammalian cell is of a monkey cell line.

198. The IL10 agonist of embodiment 194, wherein the mammalian cell is of a human cell line.

199. A nucleic acid or plurality of nucleic acids encoding the IL10 agonist of any one of embodiments 1 to 198.

200. A host cell engineered to express the IL10 agonist of any one of embodiments 1 to 198 or the nucleic acid of embodiment 194.

201. The host cell of embodiment 200, wherein the host cell is of a mouse cell line.

202. The IL10 agonist of embodiment 200, wherein the mammalian cell is of a rat cell line.

203. The IL10 agonist of embodiment 200, wherein the mammalian cell is of a monkey cell line.

204. The IL10 agonist of embodiment 200, wherein the mammalian cell is of a human cell line.

205. A method of producing the IL10 agonist of any one of embodiments 1 to 198, comprising culturing the host cell of any one of embodiments 200 to 204 and recovering the IL10 agonist expressed thereby.

206. The method of embodiment 205, further comprising:
(a) contacting the recovered IL10 agonist with an affinity column configured to trap the IL10 agonist;
(b) eluting the affinity column to produce an elute; and
(c) performing size-exclusion chromatography on the elute.

207. The method of embodiment 206, wherein the affinity column is a Protein A affinity column.

208. An IL10 agonist produced by a method comprising:
(a) culturing the host cell of any one of embodiments 200 to 204; and
(b) recovering the IL10 agonist expressed thereby.

209. The IL10 agonist of embodiment 208, wherein the method further comprises:
(a) contacting the recovered IL10 agonist with an affinity column configured to trap the IL10 agonist;

(b) eluting the affinity column to produce an elute; and (c) performing size-exclusion chromatography on the elute.

210. A method of preparing a pharmaceutical composition, comprising formulating an IL10 agonist prepared by the method of any one of embodiments 205 to 207 with an excipient.

211. A pharmaceutical composition comprising the IL10 agonist of any one of embodiments 1 to 198 and an excipient.

212. A pharmaceutical composition obtained by the method of embodiment 210.

213. The pharmaceutical composition of embodiment 210 or embodiment 211 which comprises at least 10 mg of the IL10 agonist.

214. The pharmaceutical composition of embodiment 210 or embodiment 211 which comprises at least 20 mg of the IL10 agonist.

215. The pharmaceutical composition of embodiment 210 or embodiment 211 which comprises at least 50 mg of the IL10 agonist.

216. The pharmaceutical composition of any one of embodiments 211 to 215 in which less than 30% of the IL10 agonist is present in an aggregate form, as determined by as determined by size exclusion ultra performance liquid chromatography (SE-UPLC).

217. The pharmaceutical composition of any one of embodiments 211 to 216 in which less than 25% of the IL10 agonist is present in an aggregate form, as determined by as determined by size exclusion ultra performance liquid chromatography (SE-UPLC).

218. The pharmaceutical composition of any one of embodiments 211 to 217 in which less than 20% of the IL10 agonist is present in an aggregate form, as determined by as determined by size exclusion ultra performance liquid chromatography (SE-UPLC).

219. The pharmaceutical composition of any one of embodiments 211 to 218 in which less than 15% of the IL10 agonist is present in an aggregate form, as determined by as determined by size exclusion ultra performance liquid chromatography (SE-UPLC).

220. The pharmaceutical composition of any one of embodiments 211 to 219 in which less than 10% of the IL10 agonist is present in an aggregate form, as determined by as determined by size exclusion ultra performance liquid chromatography (SE-UPLC).

221. The pharmaceutical composition of any one of embodiments 211 to 220 in which less than 5% of the IL10 agonist is present in an aggregate form, as determined by as determined by size exclusion ultra performance liquid chromatography (SE-UPLC).

222. The pharmaceutical composition of any one of embodiments 211 to 215 which does not contain a detectable amount of aggregates of the IL10 agonist as determined by as determined by size exclusion ultra performance liquid chromatography (SE-UPLC).

223. The pharmaceutical composition of any one of embodiments 211 to 222 which does not contain a detectable amount of C-terminal truncated variants of the IL10 agonist.

224. A method of treating an inflammatory condition, an immune-related disorder, fibrotic disorder or cancer, comprising administering to a subject in need thereof the IL10 agonist of any one of embodiments 1 to 198 or the pharmaceutical composition of any one of embodiments 211 to 223.

225. The method of embodiment 224, which is a method of treating cancer and wherein the cancer is a solid tumor.

226. The method of embodiment 225, wherein the solid tumor is colon cancer.

227. The method of embodiment 225, wherein the solid tumor is melanoma.

228. The method of embodiment 225, wherein the solid tumor is squamous cell carcinoma.

229. The method of embodiment 225, wherein the solid tumor is lymphoma.

230. The method of embodiment 225, wherein the solid tumor is a tumor of the pancreas.

231. The method of embodiment 225, wherein the solid tumor is a tumor of the lung.

232. The method of any one of embodiments 224 to 231, wherein the IL10 agonist or pharmaceutical composition is administered in combination with 5-fluorouracil, folinic acid, and a platinum coordination complex.

233. The method of any one of embodiments 224 to 231, wherein the IL10 agonist or pharmaceutical composition is administered subcutaneously.

234. The method of any one of embodiments 224 to 231, wherein the IL10 agonist or pharmaceutical composition is administered intravenously.

235. The method of any one of embodiments 224 to 234, wherein the solid tumor is resistant to treatment with an anti-PD1 antibody.

236. The method of any one of embodiments 224 to 235, wherein the solid tumor is resistant to treatment with an anti-PD1 antibody monotherapy.

237. The method of any one of embodiments 224 to 236, which further comprises administering an anti-PD1 antibody to the subject.

238. The method of any one of embodiments 235 to 237, wherein the anti-PD1 antibody is MDX-1106 (nivolumab), MK-3475 (pembrolizumab), MEDI-0680 (AMP-514), PDR001, REGN2810, or BGB-108.

239. The method of any one of embodiments 225 to 238, which results in an increase in CD8 T cell density in the solid tumor.

240. The method of embodiment 239, wherein the increase in CD8 T cell density in the solid tumor is at least a 2-fold increase.

241. The method of embodiment 239, wherein the increase in CD8 T cell density in the solid tumor is at least a 3-fold increase.

242. The method of embodiment 239, wherein the increase in CD8 T cell density in the solid tumor is at least a 4-fold increase.

243. The method of any one of embodiments 225 to 242, which results in an increase in CD45+ immune cell infiltration in the solid tumor.

244. The method of embodiment 243, wherein the increase in CD45+ immune cell infiltration in the solid tumor is a 5% increase.

245. The method of embodiment 243, wherein the increase in CD45+ immune cell infiltration in the solid tumor is a 10% increase.

246. The method of embodiment 243, wherein the increase in CD45+ immune cell infiltration in the solid tumor is a 15% increase.

247. The method of embodiment 243, wherein the increase in CD45+ immune cell infiltration in the solid tumor is a 20% increase.

248. The method of any one of embodiments 243 to 247, wherein CD45+ immune cells comprise CD4 T cells, myeloid cells, or both CD4 T cells and myeloid cells.

249. The method of any one of embodiments 225 to 248, wherein the method upregulates serum IL12 relative to a suitable control not treated with the IL10 agonist or pharmaceutical composition or relative to the subject's own serum IL12 levels prior to treatment with the IL10 agonist or pharmaceutical composition.

250. The method of embodiment 249, wherein the method upregulates serum IL12 levels at least 2-fold relative to the control or relative to the subject's own serum IL12 levels prior to treatment with the IL10 agonist or pharmaceutical composition.

251. The method of embodiment 249, wherein the method upregulates serum IL12 levels at least 5-fold relative to the control or relative to the subject's own serum IL12 levels prior to treatment with the IL10 agonist or pharmaceutical composition.

252. The method of embodiment 249, wherein the method upregulates serum IL12 levels at least 10-fold relative to the control or relative to the subject's own serum IL12 levels prior to treatment with the IL10 agonist or pharmaceutical composition.

253. The method of embodiment 249, wherein the method upregulates serum IL12 levels at least 15-fold relative to the control or relative to the subject's own serum IL12 levels prior to treatment with the IL10 agonist or pharmaceutical composition.

254. The method of embodiment 249, wherein the method upregulates serum IL12 levels at least 20-fold relative to the control or relative to the subject's own serum IL12 levels prior to treatment with the IL10 agonist or pharmaceutical composition.

255. The method of embodiment 249, wherein the method upregulates serum IL12 levels at least 25-fold relative to the control or relative to the subject's own serum IL12 levels prior to treatment with the IL10 agonist or pharmaceutical composition.

256. The method of embodiment 249, wherein the method upregulates serum IL12 levels at least 30-fold relative to the control or relative to the subject's own serum IL12 levels prior to treatment with the IL10 agonist or pharmaceutical composition.

257. The method of any one of embodiments 225 to 256, wherein the method upregulates serum IL4 levels relative to a suitable control not treated with the IL10 agonist or pharmaceutical composition or relative to the subject's own serum IL4 levels prior to treatment with the IL10 agonist or pharmaceutical composition.

258. The method of embodiment 257, wherein the method upregulates serum IL4 levels at least 2-fold relative to the control or relative to the subject's own serum IL4 levels prior to treatment with the IL10 agonist or pharmaceutical composition.

259. The method of embodiment 257, wherein the method upregulates serum IL4 levels at least 5-fold relative to the control or relative to the subject's own serum IL4 levels prior to treatment with the IL10 agonist or pharmaceutical composition.

260. The method of embodiment 257, wherein the method upregulates serum IL4 levels at least 10-fold relative to the control or relative to the subject's own serum IL4 levels prior to treatment with the IL10 agonist or pharmaceutical composition.

261. The method of embodiment 257, wherein the method upregulates serum IL4 levels at least 15-fold relative to the control or relative to the subject's own serum IL4 levels prior to treatment with the IL10 agonist or pharmaceutical composition.

262. The method of embodiment 257, wherein the method upregulates serum IL4 levels at least 20-fold relative to the control or relative to the subject's own serum IL4 levels prior to treatment with the IL10 agonist or pharmaceutical composition.

263. A method of treating cancer, comprising administering to a subject in need thereof:
(a) chimeric antigen receptor ("CAR")-expressing CD8+ T cells ("CART cells"); and
(b) the IL10 agonist any one of embodiments 1 to 198.

264. The method of embodiment 263, wherein the IL10 agonist is administered to the subject within one week of administration of the CART cells.

265. The method of embodiment 264, wherein the wherein the IL10 agonist is administered to the subject on the same day as the administration of the CART cells.

266. The method of any one of embodiments 263 to 265, which comprises dosing the subject with the IL10 agonist for a period of at least two weeks.

267. The method of embodiment 266, wherein the IL10 agonist is dosed by continuous infusion.

268. The method of embodiment 266, wherein the IL10 agonist is dosed by daily administration for at least a portion of the at least two-week period.

269. The method of embodiment 266, wherein the IL10 agonist is dosed according to a split dosing regimen, comprising:
(a) administering the IL10 agonist at a first dosing frequency in the initial part of the at least two-week period; and
(b) administering IL10 agonist at a second dosing frequency in a subsequent portion of the at least two-week period.

270. The method of embodiment 269, wherein the first dosing frequency is daily.

271. The method of embodiment 269 or embodiment 270, wherein the second dosing frequency is less frequent than the first dosing frequency.

272. The method of embodiment 271, wherein the second dosing frequency is weekly.

273. The method of any one of embodiments 269 to 272, wherein the subject is transitioned from the first dosing frequency to the second dosing frequency concurrently with or after exhaustion of the CART cells.

274. The method of any one of embodiments 263 to 273, wherein the cancer is resistant to treatment with an anti-PD1 antibody.

275. The method of any one of embodiments 263 to 274, wherein the cancer is resistant to treatment with an anti-PD1 antibody monotherapy.

276. The method of any one of embodiments 263 to 275, which further comprises administering an anti-PD1 antibody to the subject.

277. The method of any one of embodiments 274 to 276, wherein the anti-PD1 antibody is MDX-1106 (nivolumab), MK-3475 (pembrolizumab), MEDI-0680 (AMP-514), PDR001, REGN2810, or BGB-108.

278. The method of any one of embodiments 263 to 277, wherein the CAR is designed to target 5T4, alphafetoprotein, B cell maturation antigen (BCMA), CA-125, carcinoembryonic antigen, CD19, CD20, CD22, CD23, CD30, CD33, CD56, CD123, CD138, c-Met, CSPG4, C-type lectin-like molecule 1 (CLL-1), EGFRvIII, epithelial tumor antigen, ERBB2, FLT3, folate binding protein, GD2, GD3, HER1-HER2 in combination, HER2-HER3 in combination, HER2/Neu, HERV-K, HIV-1 envelope glycoprotein gp41, HIV-1 envelope glycoprotein gp120, IL-IIRalpha, kappa chain, lambda chain, melanoma-associated antigen, mesothelin, MUC-1, mutated p53, mutated ras, prostate-specific antigen, ROR1, or VEGFR2, or a combination thereof.

279. The method of any one of embodiments 263 to 278, wherein the CAR is configured according to Section 6.11.1 and subsections thereof.

280. The method of any one of embodiments 263 to 279, wherein the IL10 agonist is in the form of a pharmaceutical composition according to any one of embodiments 211 to 223.

281. The method of any one of embodiments 263 to 280, which results in an increase in CD8 T cell density in the solid tumor.

282. The method of embodiment 281, wherein the increase in CD8 T cell density in the solid tumor is at least a 2-fold increase.

283. The method of embodiment 281, wherein the increase in CD8 T cell density in the solid tumor is at least a 3-fold increase.

284. The method of embodiment 281, wherein the increase in CD8 T cell density in the solid tumor is at least a 4-fold increase.

285. The method of any one of embodiments 263 to 281, which results in an increase in CD45+ immune cell infiltration in the solid tumor, optionally wherein the increase is at least a 10% increase.

286. The method of embodiment 285, wherein the increase in CD45+ immune cell infiltration in the solid tumor is a 5% increase.

287. The method of embodiment 285, wherein the increase in CD45+ immune cell infiltration in the solid tumor is a 10% increase.

288. The method of embodiment 285, wherein the increase in CD45+ immune cell infiltration in the solid tumor is a 15% increase.

289. The method of embodiment 285, wherein the increase in CD45+ immune cell infiltration in the solid tumor is a 20% increase.

290. The method of any one of embodiments 285 to 289, wherein CD45+ immune cells comprise CD4 T cells and myeloid cells.

291. The method of any one of embodiments 263 to 286, wherein the method upregulates serum IL12 levels relative to a suitable control not treated with the IL10 or pharmaceutical composition.

292. The method of embodiment 291, wherein the method upregulates serum IL12 levels at least 2-fold relative to the control or relative to the subject's own serum IL12 levels prior to treatment with the IL10 agonist or pharmaceutical composition.

293. The method of embodiment 291, wherein the method upregulates serum IL12 levels at least 5-fold relative to the control or relative to the subject's own serum IL12 levels prior to treatment with the IL10 agonist or pharmaceutical composition.

294. The method of embodiment 291, wherein the method upregulates serum IL12 levels at least 10-fold relative to the control or relative to the subject's own serum IL12 levels prior to treatment with the IL10 agonist or pharmaceutical composition.

295. The method of embodiment 291, wherein the method upregulates serum IL12 levels at least 15-fold relative to the control or relative to the subject's own serum IL12 levels prior to treatment with the IL10 agonist or pharmaceutical composition.

296. The method of embodiment 291, wherein the method upregulates serum IL12 levels at least 20-fold relative to the control or relative to the subject's own serum IL12 levels prior to treatment with the IL10 agonist or pharmaceutical composition.

297. The method of embodiment 291, wherein the method upregulates serum IL12 levels at least 25-fold relative to the control or relative to the subject's own serum IL12 levels prior to treatment with the IL10 agonist or pharmaceutical composition.

298. The method of embodiment 291, wherein the method upregulates serum IL12 levels at least 30-fold relative to the control or relative to the subject's own serum IL12 levels prior to treatment with the IL10 agonist or pharmaceutical composition.

299. The method of any one of embodiments 263 to 298, wherein the method upregulates serum IL4 levels relative to a suitable control not treated with the IL10 or pharmaceutical composition.

300. The method of embodiment 299, wherein the method upregulates serum 1L4 levels at least 2-fold relative to the control or relative to the subject's own serum IL4 levels prior to treatment with the IL10 agonist or pharmaceutical composition.

301. The method of embodiment 299, wherein the method upregulates serum 1L4 levels at least 5-fold relative to the control or relative to the subject's own serum IL4 levels prior to treatment with the IL10 agonist or pharmaceutical composition.

302. The method of embodiment 299, wherein the method upregulates serum 1L4 levels at least 10-fold relative to the control or relative to the subject's own serum IL4 levels prior to treatment with the IL10 agonist or pharmaceutical composition.

303. The method of embodiment 299, wherein the method upregulates serum 1L4 levels at least 15-fold relative to the control or relative to the subject's own serum IL4 levels prior to treatment with the IL10 agonist or pharmaceutical composition.

304. The method of embodiment 299, wherein the method upregulates serum IL4 levels at least 20-fold relative to the control or relative to the subject's own serum IL4 levels prior to treatment with the IL10 agonist or pharmaceutical composition.

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

What is claimed is:

1. A method of treating a solid tumor resistant to treatment with an anti-PD1 antibody, the method comprising administering to a subject in need thereof an IL10 agonist comprising, from amino to carboxy terminus:
   (a) an IgG Fc domain;
   (b) a linker moiety; and
   (c) an IL10 moiety.

2. The method of claim 1, wherein the Fc domain comprises CH2 and CH3 domains from an IgG1.

3. The method of claim 1, wherein the Fc domain comprises CH2 and CH3 domains from an IgG4.

4. The method of claim 1, wherein the IL10 agonist further comprises a hinge domain at the N-terminus of the Fc domain.

5. The method of claim 4, wherein the hinge domain comprises a chimeric hinge sequence.

6. The method of claim 1, wherein the linker moiety comprises or consists of a monomer or multimer of $G_nS$ (SEQ ID NO: 9) or $SG_n$ (SEQ ID NO: 10), wherein n is an integer from 1 to 7.

7. The method of claim 1, wherein the IL10 moiety comprises or consists of an amino acid sequence having at least 95% sequence identity to mature human IL10 (SEQ NO: 1).

8. The method of claim 1, wherein the IL10 moiety comprises or consists of an amino acid sequence having at least 95% sequence identity to mature murine IL10 (SEQ NO: 30).

9. The method of claim 1, wherein the IL10 agonist is a homodimer.

10. The method of claim 1, wherein the IL10 agonist is a heterodimer.

11. The method of claim 1, wherein the IL10 agonist comprises two Fc domains.

12. The method of claim 1, wherein the IL10 agonist comprises or consists of an amino acid sequence having at least 95% sequence identity to the sequence of IL10M1 (SEQ ID NO: 34).

13. The method of claim 1, wherein the IL10 agonist comprises or consists of an amino acid sequence having at least 95% sequence identity to the sequence of IL10M4 (SEQ ID NO: 37).

14. The method of claim 1, wherein the IL10 agonist comprises or consists of an amino acid sequence having at least 95% sequence identity to the sequence of IL10M5 (SEQ ID NO: 38).

15. The method of claim 1, wherein the IL10 agonist is the product of recombinant expression in a mammalian cell.

16. The method of claim 1, wherein the IL10 agonist is in the form of a pharmaceutical composition comprising the IL10 agonist and an excipient.

17. The method of claim 16 in which less than 30% of the IL10 agonist is present in the pharmaceutical composition in an aggregate form, as determined by size exclusion ultra performance liquid chromatography (SE-UPLC).

18. The method of claim 1, wherein the cancer is a solid tumor resistant to treatment with an anti-PD1 antibody monotherapy.

19. The method of claim 1 which further comprises administering an anti-PD1 antibody to the subject.

20. The method of claim 19, wherein the anti-PD1 antibody is administered to the subject prior to administration of the IL10 agonist.

21. The method of claim 19, wherein the anti-PD1 antibody is administered to the subject following administration of the IL10 agonist.

22. The method of claim 19, wherein the anti-PD1 antibody is administered to the subject simultaneously with administration of the IL10 agonist.

23. The method of claim 1, wherein the method upregulates serum IL12 relative to the subject's own serum IL12 levels prior to treatment with the IL10 agonist.

24. The method of claim 1, wherein the method upregulates serum IL4 relative to the subject's own serum IL4 levels prior to treatment with the IL10 agonist.

* * * * *

SEQUENCE LISTING

<160> NUMBER OF SEQ ID NOS: 59

<210> SEQ ID NO 1
<211> LENGTH: 160
<212> TYPE: PRT
<213> ORGANISM: Homo sapiens

<400> SEQUENCE: 1

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
130                 135                 140

Ile Phe Ile Asn Tyr Ile Glu Ala Tyr Met Thr Met Lys Ile Arg Asn
145                 150                 155                 160
```

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

```
Gly Gly Gly Ser Gly Gly
1               5
```

<210> SEQ ID NO 3
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Asp Lys Arg Val Glu Ser Lys Tyr Gly Pro Pro Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser Gln Glu Asp Pro Glu Val Gln Phe Asn Trp Tyr Val
50                  55                  60

Asp Gly Val Glu Val His Asn Ala Lys Thr Lys Pro Arg Glu Glu Gln
65                  70                  75                  80

Phe Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Gly
            100                 105                 110
```

Leu Pro Ser Ser Ile Glu Lys Thr Ile Ser Lys Ala Lys Gly Gln Pro
            115                 120                 125

Arg Glu Pro Gln Val Tyr Thr Leu Pro Pro Ser Gln Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Arg Leu Thr Val Asp Lys Ser Arg Trp Gln Glu Gly Asn Val Phe
        195                 200                 205

Ser Cys Ser Val Met His Glu Ala Leu His Asn His Tyr Thr Gln Lys
    210                 215                 220

Ser Leu Ser Leu Ser Leu Gly Lys
225                 230

<210> SEQ ID NO 4
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Lys Lys Val Glu Pro Lys Ser Cys Asp Lys Thr His Thr Cys Pro
1               5                   10                  15

Pro Cys Pro Ala Pro Pro Val Ala Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser Gln Glu Asp Pro Glu Val Gln Phe Asn
    50                  55                  60

Trp Tyr Val Asp Gly Val Glu Val His Asn Ala Lys Thr Lys Pro Arg
65                  70                  75                  80

Glu Glu Gln Phe Asn Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Gly Leu Pro Ser Ser Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Lys
225                 230                 235

-continued

```
<210> SEQ ID NO 5
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 6
<211> LENGTH: 326
<212> TYPE: PRT
<213> ORGANISM: Artificial Sequence
```

<220> FEATURE:
<223> OTHER INFORMATION: Description of Artificial Sequence: Synthetic
     polypeptide

<400> SEQUENCE: 6

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Leu Gly Lys
                325
```

<210> SEQ ID NO 7
<211> LENGTH: 329
<212> TYPE: PRT
<213> ORGANISM: Artificial Sequence
<220> FEATURE:
<223> OTHER INFORMATION: Description of Artificial Sequence: Synthetic
     polypeptide

```
<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn Arg Phe Thr Gln
305                 310                 315                 320

Lys Ser Leu Ser Leu Ser Pro Gly Lys
                325

<210> SEQ ID NO 8
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 8

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn Arg Phe Thr Gln Lys Ser Leu
305                 310                 315                 320

Ser Leu Ser Leu Gly Lys
                325

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(10)
<223> OTHER INFORMATION: This region can include 1-10 residues
```

-continued

```
<400> SEQUENCE: 9

Gly Gly Gly Gly Gly Gly Gly Gly Gly Ser
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (2)..(11)
<223> OTHER INFORMATION: This region can include 1-10 residues

<400> SEQUENCE: 10

Ser Gly Gly Gly Gly Gly Gly Gly Gly Gly
1               5                   10

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 11

Gly Gly Gly Gly Ser
1               5

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Pro Lys Ser Cys Asp Lys Thr His Thr Cys Pro Pro Cys Pro Ala
1               5                   10                  15

Pro Pro Val Ala
            20

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Ser Lys Tyr Gly Pro Pro Cys Pro Pro Cys Pro Ala Pro Pro Val
1               5                   10                  15

Ala

<210> SEQ ID NO 14
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 14

Cys Pro Pro Cys Pro Ala Pro Gly Gly Gly Gly Pro Ser Val Phe
1               5                   10                  15

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Pro Pro Cys Pro Ala Pro Gly Gly Gly Pro Ser Val Phe
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Pro Pro Cys Pro Ala Pro Gly Gly Pro Ser Val Phe
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Pro Pro Cys Pro Ala Pro Gly Pro Ser Val Phe
1               5                   10

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 19

Leu Asp Pro Lys Leu Cys Tyr Leu Leu Asp Gly Ile Leu Phe Ile Tyr
1               5                   10                  15

Gly Val Ile Leu Thr Ala Leu Phe Leu Arg Val Lys
            20                  25

<210> SEQ ID NO 20
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Trp Val Leu Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 21
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala
        35                  40                  45

<210> SEQ ID NO 22
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Leu Asp Pro Lys Leu Cys Tyr Leu Leu Asp Gly Ile Leu Phe Ile Tyr
1               5                   10                  15

Gly Val Ile Leu Thr Ala Leu Phe Leu Arg Val Lys Phe Ser Arg Ser
            20                  25                  30

Ala Asp Ala Pro Ala Tyr Gln Gln Gly Gln Asn Gln Leu Tyr Asn Glu
        35                  40                  45

Leu Asn Leu Gly Arg Arg Glu Glu Tyr Asp Val Leu Asp Lys Arg Arg
    50                  55                  60

Gly Arg Asp Pro Glu Met Gly Gly Lys Pro Arg Arg Lys Asn Pro Gln
65                  70                  75                  80

Glu Gly Leu Tyr Asn Glu Leu Gln Lys Asp Lys Met Ala Glu Ala Tyr
                85                  90                  95

Ser Glu Ile Gly Met Lys Gly Glu Arg Arg Arg Gly Lys Gly His Asp
            100                 105                 110
```

```
Gly Leu Tyr Gln Gly Leu Ser Thr Ala Thr Lys Asp Thr Tyr Asp Ala
            115                 120                 125

Leu His Met Gln Ala Leu Pro Pro Arg
    130                 135

<210> SEQ ID NO 23
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Lys Ile Glu Val Met Tyr Pro Pro Pro Tyr Leu Asp Asn Glu Lys Ser
1               5                   10                  15

Asn Gly Thr Ile Ile His Val Lys Gly Lys His Leu Cys Pro Ser Pro
            20                  25                  30

Leu Phe Pro Gly Pro Ser Lys Pro Phe Trp Val Leu Val Val Val Gly
        35                  40                  45

Gly Val Leu Ala Cys Tyr Ser Leu Leu Val Thr Val Ala Phe Ile Ile
    50                  55                  60

Phe Trp Val Arg Ser Lys Arg Ser Arg Leu Leu His Ser Asp Tyr Met
65                  70                  75                  80

Asn Met Thr Pro Arg Arg Pro Gly Pro Thr Arg Lys His Tyr Gln Pro
                85                  90                  95

Tyr Ala Pro Pro Arg Asp Phe Ala Ala Tyr Arg Ser
            100                 105

<210> SEQ ID NO 25
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 25

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 26
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Lys Ile Glu Val Met Tyr Pro Pro Pro Tyr Leu Asp Asn Glu Lys Ser
1               5                   10                  15

Asn Gly Thr Ile Ile His Val Lys Gly Lys His Leu Cys Pro Ser Pro
            20                  25                  30

Leu Phe Pro Gly Pro Ser Lys Pro
        35                  40

<210> SEQ ID NO 27
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Lys Pro Ile Pro Asn Pro Leu Leu Gly Leu Asp Ser Thr
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ile Pro Asn Pro Leu Leu Gly Leu Asp
1               5
```

<210> SEQ ID NO 30
<211> LENGTH: 160
<212> TYPE: PRT
<213> ORGANISM: Mus sp.

<400> SEQUENCE: 30

Ser Arg Gly Gln Tyr Ser Arg Glu Asp Asn Asn Cys Thr His Phe Pro
1               5                   10                  15

Val Gly Gln Ser His Met Leu Leu Glu Leu Arg Thr Ala Phe Ser Gln
            20                  25                  30

Val Lys Thr Phe Phe Gln Thr Lys Asp Gln Leu Asp Asn Ile Leu Leu
        35                  40                  45

Thr Asp Ser Leu Met Gln Asp Phe Lys Gly Tyr Leu Gly Cys Gln Ala
    50                  55                  60

Leu Ser Glu Met Ile Gln Phe Tyr Leu Val Glu Val Met Pro Gln Ala
65                  70                  75                  80

Glu Lys His Gly Pro Glu Ile Lys Glu His Leu Asn Ser Leu Gly Glu
                85                  90                  95

Lys Leu Lys Thr Leu Arg Met Arg Leu Arg Arg Cys His Arg Phe Leu
            100                 105                 110

Pro Cys Glu Asn Lys Ser Lys Ala Val Glu Gln Val Lys Ser Asp Phe
        115                 120                 125

Asn Lys Leu Gln Asp Gln Gly Val Tyr Lys Ala Met Asn Glu Phe Asp
    130                 135                 140

Ile Phe Ile Asn Cys Ile Glu Ala Tyr Met Met Ile Lys Met Lys Ser
145                 150                 155                 160

<210> SEQ ID NO 31
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

```
Glu Trp Glu Ser Asn Gly Gln Pro Glu Asn Asn Tyr Lys Thr Thr Pro
            165                 170                 175

Pro Val Leu Asp Ser Asp Gly Ser Phe Phe Leu Tyr Ser Arg Leu Thr
        180                 185                 190

Val Asp Lys Ser Arg Trp Gln Glu Gly Asn Val Phe Ser Cys Ser Val
    195                 200                 205

Met His Glu Ala Leu His Asn His Tyr Thr Gln Lys Ser Leu Ser Leu
210                 215                 220

Ser Leu Gly Lys
225

<210> SEQ ID NO 32
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Ala Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Tyr Ser Lys Leu Thr Val
        180                 185                 190

Asp Lys Ser Arg Trp Gln Gln Gly Asn Val Phe Ser Cys Ser Val Met
    195                 200                 205

His Glu Ala Leu His Asn His Tyr Thr Gln Lys Ser Leu Ser Leu Ser
210                 215                 220

Pro Gly Lys
225

<210> SEQ ID NO 33
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 33

Val Pro Arg Asp Cys Gly Cys Lys Pro Cys Ile Cys Thr Val Pro Glu
1               5                   10                  15

Val Ser Ser Val Phe Ile Phe Pro Pro Lys Pro Lys Asp Val Leu Thr
            20                  25                  30

Ile Thr Leu Thr Pro Lys Val Thr Cys Val Val Val Asp Ile Ser Lys
        35                  40                  45

Asp Asp Pro Glu Val Gln Phe Ser Trp Phe Val Asp Asp Val Glu Val
    50                  55                  60

His Thr Ala Gln Thr Gln Pro Arg Glu Glu Gln Phe Asn Ser Thr Phe
65                  70                  75                  80

Arg Ser Val Ser Glu Leu Pro Ile Met His Gln Asp Trp Leu Asn Gly
                85                  90                  95

Lys Glu Phe Lys Cys Arg Val Asn Ser Ala Ala Phe Pro Ala Pro Ile
            100                 105                 110

Glu Lys Thr Ile Ser Lys Thr Lys Gly Arg Pro Lys Ala Pro Gln Val
        115                 120                 125

Tyr Thr Ile Pro Pro Lys Glu Gln Met Ala Lys Asp Lys Val Ser
    130                 135                 140

Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175

Ile Met Asp Thr Asp Gly Ser Tyr Phe Val Tyr Ser Lys Leu Asn Val
            180                 185                 190

Gln Lys Ser Asn Trp Glu Ala Gly Asn Thr Phe Thr Cys Ser Val Leu
        195                 200                 205

His Glu Gly Leu His Asn His His Thr Glu Lys Ser Leu Ser His Ser
    210                 215                 220

Pro Gly Lys
225

<210> SEQ ID NO 34
<211> LENGTH: 403
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110
```

```
Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Leu Tyr Ser Arg Leu Thr
            180                 185                 190

Val Asp Lys Ser Arg Trp Gln Glu Gly Asn Val Phe Ser Cys Ser Val
    195                 200                 205

Met His Glu Ala Leu His Asn His Tyr Thr Gln Lys Ser Leu Ser Leu
    210                 215                 220

Ser Leu Gly Lys Gly Gly Gly Ser Gly Gly Gly Ser Gly Gly
225                 230                 235                 240

Gly Gly Ser Ser Pro Gly Gln Gly Thr Gln Ser Glu Asn Ser Cys Thr
                245                 250                 255

His Phe Pro Gly Asn Leu Pro Asn Met Leu Arg Asp Leu Arg Asp Ala
                260                 265                 270

Phe Ser Arg Val Lys Thr Phe Phe Gln Met Lys Asp Gln Leu Asp Asn
    275                 280                 285

Leu Leu Leu Lys Glu Ser Leu Leu Glu Asp Phe Lys Gly Tyr Leu Gly
    290                 295                 300

Cys Gln Ala Leu Ser Glu Met Ile Gln Phe Tyr Leu Glu Glu Val Met
305                 310                 315                 320

Pro Gln Ala Glu Asn Gln Asp Pro Asp Ile Lys Ala His Val Asn Ser
                325                 330                 335

Leu Gly Glu Asn Leu Lys Thr Leu Arg Leu Arg Leu Arg Arg Cys His
                340                 345                 350

Arg Phe Leu Pro Cys Glu Asn Lys Ser Lys Ala Val Glu Gln Val Lys
                355                 360                 365

Asn Ala Phe Asn Lys Leu Gln Glu Lys Gly Ile Tyr Lys Ala Met Ser
    370                 375                 380

Glu Phe Asp Ile Phe Ile Asn Tyr Ile Glu Ala Tyr Met Thr Met Lys
385                 390                 395                 400

Ile Arg Asn

<210> SEQ ID NO 35
<211> LENGTH: 403
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60
```

Leu Ser Glu Met Ile Gln Phe Tyr Leu Glu Val Met Pro Gln Ala
 65                  70                  75                  80

Glu Asn Gln Asp Pro Asp Ile Lys Ala His Val Asn Ser Leu Gly Glu
                 85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Gly Gly Ser Gly Gly Gly Ser Gly Gly Gly Gly Ser Glu
                165                 170                 175

Ser Lys Tyr Gly Pro Pro Cys Pro Pro Cys Pro Ala Pro Pro Val Ala
                180                 185                 190

Gly Pro Ser Val Phe Leu Phe Pro Pro Lys Pro Lys Asp Thr Leu Met
            195                 200                 205

Ile Ser Arg Thr Pro Glu Val Thr Cys Val Val Val Asp Val Ser Gln
        210                 215                 220

Glu Asp Pro Glu Val Gln Phe Asn Trp Tyr Val Asp Gly Val Glu Val
225                 230                 235                 240

His Asn Ala Lys Thr Lys Pro Arg Glu Glu Gln Phe Asn Ser Thr Tyr
                245                 250                 255

Arg Val Val Ser Val Leu Thr Val Leu His Gln Asp Trp Leu Asn Gly
                260                 265                 270

Lys Glu Tyr Lys Cys Lys Val Ser Asn Lys Gly Leu Pro Ser Ser Ile
            275                 280                 285

Glu Lys Thr Ile Ser Lys Ala Lys Gly Gln Pro Arg Glu Pro Gln Val
        290                 295                 300

Tyr Thr Leu Pro Pro Ser Gln Glu Glu Met Thr Lys Asn Gln Val Ser
305                 310                 315                 320

Leu Thr Cys Leu Val Lys Gly Phe Tyr Pro Ser Asp Ile Ala Val Glu
                325                 330                 335

Trp Glu Ser Asn Gly Gln Pro Glu Asn Asn Tyr Lys Thr Thr Pro Pro
                340                 345                 350

Val Leu Asp Ser Asp Gly Ser Phe Phe Leu Tyr Ser Arg Leu Thr Val
            355                 360                 365

Asp Lys Ser Arg Trp Gln Glu Gly Asn Val Phe Ser Cys Ser Val Met
        370                 375                 380

His Glu Ala Leu His Asn His Tyr Thr Gln Lys Ser Leu Ser Leu Ser
385                 390                 395                 400

Leu Gly Lys

<210> SEQ ID NO 36
<211> LENGTH: 392
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 36

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Gly Gly Ser Val Pro Arg Asp Cys Gly Cys Lys Pro Cys Ile
                165                 170                 175

Cys Thr Val Pro Glu Val Ser Ser Val Phe Ile Phe Pro Pro Lys Pro
        180                 185                 190

Lys Asp Val Leu Thr Ile Thr Leu Thr Pro Lys Val Thr Cys Val Val
    195                 200                 205

Val Asp Ile Ser Lys Asp Asp Pro Glu Val Gln Phe Ser Trp Phe Val
210                 215                 220

Asp Asp Val Glu Val His Thr Ala Gln Thr Gln Pro Arg Glu Glu Gln
225                 230                 235                 240

Phe Asn Ser Thr Phe Arg Ser Val Ser Glu Leu Pro Ile Met His Gln
                245                 250                 255

Asp Trp Leu Asn Gly Lys Glu Phe Lys Cys Arg Val Asn Ser Ala Ala
        260                 265                 270

Phe Pro Ala Pro Ile Glu Lys Thr Ile Ser Lys Thr Lys Gly Arg Pro
    275                 280                 285

Lys Ala Pro Gln Val Tyr Thr Ile Pro Pro Pro Lys Glu Gln Met Ala
290                 295                 300

Lys Asp Lys Val Ser Leu Thr Cys Met Ile Thr Asp Phe Phe Pro Glu
305                 310                 315                 320

Asp Ile Thr Val Glu Trp Gln Trp Asn Gly Gln Pro Ala Glu Asn Tyr
                325                 330                 335

Lys Asn Thr Gln Pro Ile Met Asp Thr Asp Gly Ser Tyr Phe Val Tyr
        340                 345                 350

Ser Lys Leu Asn Val Gln Lys Ser Asn Trp Glu Ala Gly Asn Thr Phe
    355                 360                 365

Thr Cys Ser Val Leu His Glu Gly Leu His Asn His His Thr Glu Lys
370                 375                 380

Ser Leu Ser His Ser Pro Gly Lys
385                 390
```

-continued

```
<210> SEQ ID NO 37
<211> LENGTH: 398
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys Gly Gly Gly Ser Gly Gly Gly Ser Ser Pro
225                 230                 235                 240

Gly Gln Gly Thr Gln Ser Glu Asn Ser Cys Thr His Phe Pro Gly Asn
                245                 250                 255

Leu Pro Asn Met Leu Arg Asp Leu Arg Asp Ala Phe Ser Arg Val Lys
            260                 265                 270

Thr Phe Phe Gln Met Lys Asp Gln Leu Asp Asn Leu Leu Leu Lys Glu
        275                 280                 285

Ser Leu Leu Glu Asp Phe Lys Gly Tyr Leu Gly Cys Gln Ala Leu Ser
    290                 295                 300

Glu Met Ile Gln Phe Tyr Leu Glu Glu Val Met Pro Gln Ala Glu Asn
305                 310                 315                 320

Gln Asp Pro Asp Ile Lys Ala His Val Asn Ser Leu Gly Glu Asn Leu
                325                 330                 335

Lys Thr Leu Arg Leu Arg Leu Arg Arg Cys His Arg Phe Leu Pro Cys
            340                 345                 350

Glu Asn Lys Ser Lys Ala Val Glu Gln Val Lys Asn Ala Phe Asn Lys
        355                 360                 365
```

-continued

```
Leu Gln Glu Lys Gly Ile Tyr Lys Ala Met Ser Glu Phe Asp Ile Phe
    370                 375                 380

Ile Asn Tyr Ile Glu Ala Tyr Met Thr Met Lys Ile Arg Asn
385                 390                 395

<210> SEQ ID NO 38
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

Gln Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Gln Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
                180                 185                 190

Val Asp Lys Ser Arg Trp Gln Glu Gly Asn Val Phe Ser Cys Ser Val
            195                 200                 205

Met His Glu Ala Leu His Asn His Tyr Thr Gln Lys Ser Leu Ser Leu
        210                 215                 220

Ser Leu Gly Lys Gly Gly Gly Gly Ser Pro Gly Gln Gly Thr Gln
225                 230                 235                 240

Ser Glu Asn Ser Cys Thr His Phe Pro Gly Asn Leu Pro Asn Met Leu
                245                 250                 255

Arg Asp Leu Arg Asp Ala Phe Ser Arg Val Lys Thr Phe Phe Gln Met
                260                 265                 270

Lys Asp Gln Leu Asp Asn Leu Leu Leu Lys Glu Ser Leu Leu Glu Asp
            275                 280                 285

Phe Lys Gly Tyr Leu Gly Cys Gln Ala Leu Ser Glu Met Ile Gln Phe
        290                 295                 300

Tyr Leu Glu Glu Val Met Pro Gln Ala Glu Asn Gln Asp Pro Asp Ile
305                 310                 315                 320

Lys Ala His Val Asn Ser Leu Gly Glu Asn Leu Lys Thr Leu Arg Leu
                325                 330                 335
```

```
Arg Leu Arg Arg Cys His Arg Phe Leu Pro Cys Glu Asn Lys Ser Lys
            340                 345                 350

Ala Val Glu Gln Val Lys Asn Ala Phe Asn Lys Leu Gln Glu Lys Gly
        355                 360                 365

Ile Tyr Lys Ala Met Ser Glu Phe Asp Ile Phe Ile Asn Tyr Ile Glu
    370                 375                 380

Ala Tyr Met Thr Met Lys Ile Arg Asn
385                 390

<210> SEQ ID NO 39
<211> LENGTH: 398
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
            85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
130                 135                 140

Ile Phe Ile Asn Tyr Ile Glu Ala Tyr Met Thr Met Lys Ile Arg Asn
145                 150                 155                 160

Gly Gly Gly Gly Ser Gly Gly Gly Ser Glu Ser Lys Tyr Gly Pro
                165                 170                 175

Pro Cys Pro Pro Cys Pro Ala Pro Pro Val Ala Gly Pro Ser Val Phe
            180                 185                 190

Leu Phe Pro Pro Lys Pro Lys Asp Thr Leu Met Ile Ser Arg Thr Pro
        195                 200                 205

Glu Val Thr Cys Val Val Val Asp Val Ser Gln Glu Asp Pro Glu Val
210                 215                 220

Gln Phe Asn Trp Tyr Val Asp Gly Val Glu Val His Asn Ala Lys Thr
225                 230                 235                 240

Lys Pro Arg Glu Glu Gln Phe Asn Ser Thr Tyr Arg Val Val Ser Val
            245                 250                 255

Leu Thr Val Leu His Gln Asp Trp Leu Asn Gly Lys Glu Tyr Lys Cys
        260                 265                 270

Lys Val Ser Asn Lys Gly Leu Pro Ser Ser Ile Glu Lys Thr Ile Ser
            275                 280                 285

Lys Ala Lys Gly Gln Pro Arg Glu Pro Gln Val Tyr Thr Leu Pro Pro
290                 295                 300
```

```
Ser Gln Glu Glu Met Thr Lys Asn Gln Val Ser Leu Thr Cys Leu Val
305                 310                 315                 320

Lys Gly Phe Tyr Pro Ser Asp Ile Ala Val Glu Trp Glu Ser Asn Gly
                325                 330                 335

Gln Pro Glu Asn Asn Tyr Lys Thr Thr Pro Pro Val Leu Asp Ser Asp
            340                 345                 350

Gly Ser Phe Phe Leu Tyr Ser Arg Leu Thr Val Asp Lys Ser Arg Trp
        355                 360                 365

Gln Glu Gly Asn Val Phe Ser Cys Ser Val Met His Glu Ala Leu His
    370                 375                 380

Asn His Tyr Thr Gln Lys Ser Leu Ser Leu Ser Leu Gly Lys
385                 390                 395
```

<210> SEQ ID NO 40
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Gly Gly Ser Glu Ser Lys Tyr Gly Pro Pro Cys Pro Pro Cys
                165                 170                 175

Pro Ala Pro Pro Val Ala Gly Pro Ser Val Phe Leu Phe Pro Pro Lys
            180                 185                 190

Pro Lys Asp Thr Leu Met Ile Ser Arg Thr Pro Glu Val Thr Cys Val
        195                 200                 205

Val Val Asp Val Ser Gln Glu Asp Pro Glu Val Gln Phe Asn Trp Tyr
    210                 215                 220

Val Asp Gly Val Glu Val His Asn Ala Lys Thr Lys Pro Arg Glu Glu
225                 230                 235                 240

Gln Phe Asn Ser Thr Tyr Arg Val Val Ser Val Leu Thr Val Leu His
                245                 250                 255

Gln Asp Trp Leu Asn Gly Lys Glu Tyr Lys Cys Lys Val Ser Asn Lys
            260                 265                 270
```

```
Gly Leu Pro Ser Ser Ile Glu Lys Thr Ile Ser Lys Ala Lys Gly Gln
            275                 280                 285

Pro Arg Glu Pro Gln Val Tyr Thr Leu Pro Pro Ser Gln Glu Glu Met
        290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
                325                 330                 335

Tyr Lys Thr Thr Pro Pro Val Leu Asp Ser Asp Gly Ser Phe Phe Leu
            340                 345                 350

Tyr Ser Arg Leu Thr Val Asp Lys Ser Arg Trp Gln Glu Gly Asn Val
        355                 360                 365

Phe Ser Cys Ser Val Met His Glu Ala Leu His Asn His Tyr Thr Gln
370                 375                 380

Lys Ser Leu Ser Leu Ser Leu Gly Lys
385                 390

<210> SEQ ID NO 41
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Glu Ser Lys Tyr Gly Pro Pro Cys Pro Pro Cys Pro Ala Pro Pro Val
                165                 170                 175

Ala Gly Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser
        195                 200                 205

Gln Glu Asp Pro Glu Val Gln Phe Asn Trp Tyr Val Asp Gly Val Glu
    210                 215                 220

Val His Asn Ala Lys Thr Lys Pro Arg Glu Glu Gln Phe Asn Ser Thr
225                 230                 235                 240
```

```
Tyr Arg Val Val Ser Val Leu Thr Val Leu His Gln Asp Trp Leu Asn
            245                 250                 255

Gly Lys Glu Tyr Lys Cys Lys Val Ser Asn Lys Gly Leu Pro Ser Ser
        260                 265                 270

Ile Glu Lys Thr Ile Ser Lys Ala Lys Gly Gln Pro Arg Glu Pro Gln
    275                 280                 285

Val Tyr Thr Leu Pro Pro Ser Gln Glu Glu Met Thr Lys Asn Gln Val
290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
            325                 330                 335

Pro Val Leu Asp Ser Asp Gly Ser Phe Phe Leu Tyr Ser Arg Leu Thr
        340                 345                 350

Val Asp Lys Ser Arg Trp Gln Glu Gly Asn Val Phe Ser Cys Ser Val
    355                 360                 365

Met His Glu Ala Leu His Asn His Tyr Thr Gln Lys Ser Leu Ser Leu
370                 375                 380

Ser Leu Gly Lys
385

<210> SEQ ID NO 42
<211> LENGTH: 392
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
            85                  90                  95

Asn Leu Lys Thr Leu Arg Leu Arg Leu Arg Arg Cys His Arg Phe Leu
        100                 105                 110

Pro Cys Glu Asn Lys Ser Lys Ala Val Glu Gln Val Lys Asn Ala Phe
    115                 120                 125

Asn Lys Leu Gln Glu Lys Gly Ile Tyr Lys Ala Met Ser Glu Phe Asp
130                 135                 140

Ile Phe Ile Asn Tyr Ile Glu Ala Tyr Met Thr Met Lys Ile Arg Asn
145                 150                 155                 160

Gly Gly Gly Gly Ser Asp Lys Thr His Thr Cys Pro Pro Cys Pro Ala
            165                 170                 175

Pro Glu Leu Leu Gly Gly Pro Ser Val Phe Leu Phe Pro Pro Lys Pro
        180                 185                 190

Lys Asp Thr Leu Met Ile Ser Arg Thr Pro Glu Val Thr Cys Val Val
    195                 200                 205
```

```
Val Ala Val Ser His Glu Asp Pro Glu Val Lys Phe Asn Trp Tyr Val
    210                 215                 220

Asp Gly Val Glu Val His Asn Ala Lys Thr Lys Pro Arg Glu Glu Gln
225                 230                 235                 240

Tyr Ala Ser Thr Tyr Arg Val Val Ser Val Leu Thr Val Leu His Gln
                245                 250                 255

Asp Trp Leu Asn Gly Lys Glu Tyr Lys Cys Lys Val Ser Asn Lys Ala
            260                 265                 270

Leu Pro Ala Pro Ile Glu Lys Thr Ile Ser Lys Ala Lys Gly Gln Pro
        275                 280                 285

Arg Glu Pro Gln Val Tyr Thr Leu Pro Pro Ser Arg Asp Glu Leu Thr
290                 295                 300

Lys Asn Gln Val Ser Leu Thr Cys Leu Val Lys Gly Phe Tyr Pro Ser
305                 310                 315                 320

Asp Ile Ala Val Glu Trp Glu Ser Asn Gly Gln Pro Glu Asn Asn Tyr
                325                 330                 335

Lys Thr Thr Pro Pro Val Leu Asp Ser Asp Gly Ser Phe Phe Leu Tyr
            340                 345                 350

Ser Lys Leu Thr Val Asp Lys Ser Arg Trp Gln Gln Gly Asn Val Phe
        355                 360                 365

Ser Cys Ser Val Met His Glu Ala Leu His Asn His Tyr Thr Gln Lys
370                 375                 380

Ser Leu Ser Leu Ser Pro Gly Lys
385                 390

<210> SEQ ID NO 43
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
130                 135                 140

Ile Phe Ile Asn Tyr Ile Glu Ala Tyr Met Thr Met Lys Ile Arg Asn
145                 150                 155                 160

Asp Lys Thr His Thr Cys Pro Pro Cys Pro Ala Pro Glu Leu Leu Gly
                165                 170                 175
```

-continued

Gly Pro Ser Val Phe Leu Phe Pro Pro Lys Pro Lys Asp Thr Leu Met
            180                 185                 190

Ile Ser Arg Thr Pro Glu Val Thr Cys Val Val Val Ala Val Ser His
        195                 200                 205

Glu Asp Pro Glu Val Lys Phe Asn Trp Tyr Val Asp Gly Val Glu Val
210                 215                 220

His Asn Ala Lys Thr Lys Pro Arg Glu Glu Gln Tyr Ala Ser Thr Tyr
225                 230                 235                 240

Arg Val Val Ser Val Leu Thr Val Leu His Gln Asp Trp Leu Asn Gly
                245                 250                 255

Lys Glu Tyr Lys Cys Lys Val Ser Asn Lys Ala Leu Pro Ala Pro Ile
            260                 265                 270

Glu Lys Thr Ile Ser Lys Ala Lys Gly Gln Pro Arg Glu Pro Gln Val
        275                 280                 285

Tyr Thr Leu Pro Pro Ser Arg Asp Glu Leu Thr Lys Asn Gln Val Ser
290                 295                 300

Leu Thr Cys Leu Val Lys Gly Phe Tyr Pro Ser Asp Ile Ala Val Glu
305                 310                 315                 320

Trp Glu Ser Asn Gly Gln Pro Glu Asn Asn Tyr Lys Thr Thr Pro Pro
                325                 330                 335

Val Leu Asp Ser Asp Gly Ser Phe Phe Leu Tyr Ser Lys Leu Thr Val
            340                 345                 350

Asp Lys Ser Arg Trp Gln Gln Gly Asn Val Phe Ser Cys Ser Val Met
        355                 360                 365

His Glu Ala Leu His Asn His Tyr Thr Gln Lys Ser
370                 375                 380

<210> SEQ ID NO 44
<211> LENGTH: 392
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ser Arg Gly Gln Tyr Ser Arg Glu Asp Asn Asn Cys Thr His Phe Pro
1               5                   10                  15

Val Gly Gln Ser His Met Leu Leu Glu Leu Arg Thr Ala Phe Ser Gln
            20                  25                  30

Val Lys Thr Phe Phe Gln Thr Lys Asp Gln Leu Asp Asn Ile Leu Leu
        35                  40                  45

Thr Asp Ser Leu Met Gln Asp Phe Lys Gly Tyr Leu Gly Cys Gln Ala
50                  55                  60

Leu Ser Glu Met Ile Gln Phe Tyr Leu Val Glu Val Met Pro Gln Ala
65                  70                  75                  80

Glu Lys His Gly Pro Glu Ile Lys Glu His Leu Asn Ser Leu Gly Glu
                85                  90                  95

Lys Leu Lys Thr Leu Arg Met Arg Leu Arg Arg Cys His Arg Phe Leu
            100                 105                 110

Pro Cys Glu Asn Lys Ser Lys Ala Val Glu Gln Val Lys Ser Asp Phe
        115                 120                 125

Asn Lys Leu Gln Asp Gln Gly Val Tyr Lys Ala Met Asn Glu Phe Asp
130                 135                 140

Ile Phe Ile Asn Cys Ile Glu Ala Tyr Met Met Ile Lys Met Lys Ser
145                 150                 155                 160

Gly Gly Gly Gly Ser Val Pro Arg Asp Cys Gly Cys Lys Pro Cys Ile
                165                 170                 175

Cys Thr Val Pro Glu Val Ser Ser Val Phe Ile Phe Pro Pro Lys Pro
            180                 185                 190

Lys Asp Val Leu Thr Ile Thr Leu Thr Pro Lys Val Thr Cys Val Val
            195                 200                 205

Val Asp Ile Ser Lys Asp Asp Pro Glu Val Gln Phe Ser Trp Phe Val
210                 215                 220

Asp Asp Val Glu Val His Thr Ala Gln Thr Gln Pro Arg Glu Glu Gln
225                 230                 235                 240

Phe Asn Ser Thr Phe Arg Ser Val Ser Glu Leu Pro Ile Met His Gln
                245                 250                 255

Asp Trp Leu Asn Gly Lys Glu Phe Lys Cys Arg Val Asn Ser Ala Ala
            260                 265                 270

Phe Pro Ala Pro Ile Glu Lys Thr Ile Ser Lys Thr Lys Gly Arg Pro
            275                 280                 285

Lys Ala Pro Gln Val Tyr Thr Ile Pro Pro Lys Glu Gln Met Ala
            290                 295                 300

Lys Asp Lys Val Ser Leu Thr Cys Met Ile Thr Asp Phe Phe Pro Glu
305                 310                 315                 320

Asp Ile Thr Val Glu Trp Gln Trp Asn Gly Gln Pro Ala Glu Asn Tyr
                325                 330                 335

Lys Asn Thr Gln Pro Ile Met Asp Thr Asp Gly Ser Tyr Phe Val Tyr
            340                 345                 350

Ser Lys Leu Asn Val Gln Lys Ser Asn Trp Glu Ala Gly Asn Thr Phe
            355                 360                 365

Thr Cys Ser Val Leu His Glu Gly Leu His Asn His His Thr Glu Lys
            370                 375                 380

Ser Leu Ser His Ser Pro Gly Lys
385                 390

<210> SEQ ID NO 45
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Thr Phe
            20                  25                  30

Gly Val His Trp Val Arg Gln Ser Pro Gly Lys Gly Leu Glu Trp Leu
        35                  40                  45

Gly Val Ile Trp Ala Asp Glu Thr Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Gly Leu Arg Thr Asp Asp Thr Ala Ile Tyr Ser Cys Ala
                85                  90                  95

Arg Ser Lys Val Ser Tyr Tyr Phe Asp Tyr Trp Gly Arg Gly Thr Thr
            100                 105                 110

Leu Thr Val Ser Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
        130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Val Thr Val Pro Ser Ser Thr Trp
            180                 185                 190

Pro Ser Glu Thr Val Thr Cys Asn Val Ala His Pro Ala Ser Ser Thr
        195                 200                 205

Lys Val Asp Lys Lys Ile Val Pro Arg Asp Cys Gly Cys Lys Pro Cys
    210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
                245                 250                 255

Val Val Asp Ile Ser Lys Asp Asp Pro Glu Val Gln Phe Ser Trp Phe
            260                 265                 270

Val Asp Asp Val Glu Val His Thr Ala Gln Thr Gln Pro Arg Glu Glu
        275                 280                 285

Gln Phe Asn Ser Thr Phe Arg Ser Val Ser Glu Leu Pro Ile Met His
    290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Lys Glu Gln Met
            340                 345                 350

Ala Lys Asp Lys Val Ser Leu Thr Cys Met Ile Thr Asp Phe Phe Pro
        355                 360                 365

Glu Asp Ile Thr Val Glu Trp Gln Trp Asn Gly Gln Pro Ala Glu Asn
    370                 375                 380

Tyr Lys Asn Thr Gln Pro Ile Met Asp Thr Asp Gly Ser Tyr Phe Val
385                 390                 395                 400

Tyr Ser Lys Leu Asn Val Gln Lys Ser Asn Trp Glu Ala Gly Asn Thr
                405                 410                 415

Phe Thr Cys Ser Val Leu His Glu Gly Leu His Asn His His Thr Glu
            420                 425                 430

Lys Ser Leu Ser His Ser Pro Gly Lys
        435                 440

<210> SEQ ID NO 46
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asn Ile Met Met Thr Gln Ser Pro Ser Ser Leu Pro Val Ser Pro Gly
1               5                   10                  15

Glu Lys Val Thr Met Asn Cys Lys Ser Ser Arg Ser Val Leu Tyr Ser
            20                  25                  30

Leu Asn Gln Lys Asn Tyr Leu Ala Trp Tyr Gln Gln Lys Pro Gly Gln
        35                  40                  45

```
Ser Pro Lys Leu Leu Ile Tyr Trp Ala Ser Thr Arg Glu Ser Gly Val
 50                  55                  60
Pro Asp Arg Phe Thr Gly Ser Gly Ser Gly Thr Asp Phe Ser Leu Thr
 65                  70                  75                  80
Ile Ser Ser Val Gln Ala Glu Asp Leu Ala Val Tyr Tyr Cys His Gln
                 85                  90                  95
Tyr Leu Ser Ser Trp Thr Phe Gly Gly Gly Thr Lys Leu Glu Ile Lys
                100                 105                 110
Arg Ala Asp Ala Ala Pro Thr Val Ser Ile Phe Pro Pro Ser Ser Glu
            115                 120                 125
Gln Leu Thr Ser Gly Gly Ala Ser Val Val Cys Phe Leu Asn Asn Phe
130                 135                 140
Tyr Pro Lys Asp Ile Asn Val Lys Trp Lys Ile Asp Gly Ser Glu Arg
145                 150                 155                 160
Gln Asn Gly Val Leu Asn Ser Trp Thr Asp Gln Asp Ser Lys Asp Ser
                165                 170                 175
Thr Tyr Ser Met Ser Ser Thr Leu Thr Leu Thr Lys Asp Glu Tyr Glu
            180                 185                 190
Arg His Asn Ser Tyr Thr Cys Glu Ala Thr His Lys Thr Ser Thr Ser
        195                 200                 205
Pro Ile Val Lys Ser Phe Asn Arg Gly Glu Cys
210                 215

<210> SEQ ID NO 47
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Leu Ser Thr Tyr
             20                  25                  30
Ala Met Thr Trp Val Arg Gln Ala Pro Gly Lys Gly Leu Glu Trp Val
         35                  40                  45
Ser Ala Ile Asn Tyr Arg Ala Ala Asn Thr Trp Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Asp Glu Asp Thr Ala Val Tyr Tyr Cys
                 85                  90                  95
Ala Gln Asp Arg Val Ile Ile Lys Asp Tyr Tyr Val Met Asp Val Trp
            100                 105                 110
Gly Gln Gly Thr Thr Val Thr Val Ser Ser Ala Ser Thr Lys Gly Pro
        115                 120                 125
Ser Val Phe Pro Leu Ala Pro Cys Ser Arg Ser Thr Ser Glu Ser Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
```

Val Pro Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
    275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
    435                 440                 445

<210> SEQ ID NO 48
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Thr Val Ala
            100                 105                 110

```
Ala Pro Ser Val Phe Ile Phe Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 49
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Arg Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Ile Tyr Tyr Cys Ala
                85                  90                  95

Arg His Arg Val Thr Arg Thr Ala Asp Ser Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 50
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Thr Gly Lys Ala Pro Lys Phe Leu Ile
        35                  40                  45

Tyr Asp Ala Ser Asn Leu Glu Thr Gly Val Ser Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Val Gly Thr Tyr Tyr Cys His Gln Tyr Gly Asp Leu Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Gly Gly Gly Ser
1               5

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Gly Gly Gly Ser Gly Gly Gly Gly Ser
1               5                   10

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Gly Gly Gly Ser Gly Gly Gly Gly Ser Gly Gly Gly Gly Ser
1               5                   10                  15

<210> SEQ ID NO 54
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gly Gly Gly Ser Gly Gly Gly Gly Ser Gly Gly Gly Gly Ser Gly
1               5                   10                  15

Gly Gly Gly Ser
            20

<210> SEQ ID NO 55
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 55

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 56
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(7)
<223> OTHER INFORMATION: This region can include 1-7 residues

<400> SEQUENCE: 57

Gly Gly Gly Gly Gly Gly Gly Ser
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (2)..(8)
<223> OTHER INFORMATION: This region can include 1-7 residues

<400> SEQUENCE: 58

Ser Gly Gly Gly Gly Gly Gly Gly
1               5

<210> SEQ ID NO 59
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(30)
<223> OTHER INFORMATION: This sequence can include 1-6 "Gly Gly Gly Gly
      Ser" repeating units
```

```
<400> SEQUENCE: 59

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Ser
            20                  25                  30
```